(12) United States Patent
Tsunenari et al.

(10) Patent No.: US 11,660,340 B2
(45) Date of Patent: May 30, 2023

(54) COMBINATION THERAPY USING T CELL REDIRECTION ANTIGEN BINDING MOLECULE AGAINST CELL HAVING IMMUNOSUPPRESSING FUNCTION

(71) Applicant: CHUGAI SEIYAKU KABUSHIKI KAISHA, Tokyo (JP)

(72) Inventors: Toshiaki Tsunenari, Kanagawa (JP); Yutaka Matsuda, Kanagawa (JP); Taro Miyazaki, Tokyo (JP); Kenji Taniguchi, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/776,587

(22) PCT Filed: Nov. 17, 2016

(86) PCT No.: PCT/JP2016/084027
§ 371 (c)(1),
(2) Date: May 16, 2018

(87) PCT Pub. No.: WO2017/086367
PCT Pub. Date: May 26, 2017

(65) Prior Publication Data
US 2018/0326058 A1 Nov. 15, 2018

(30) Foreign Application Priority Data

Nov. 18, 2015 (JP) .............................. JP2015-225236

(51) Int. Cl.
| | | |
|---|---|---|
| *A61P 35/00* | (2006.01) | |
| *A61K 39/395* | (2006.01) | |
| *A61K 45/00* | (2006.01) | |
| *A61K 31/7068* | (2006.01) | |
| *A61K 33/243* | (2019.01) | |
| *A61K 39/00* | (2006.01) | |

(52) U.S. Cl.
CPC .... *A61K 39/39558* (2013.01); *A61K 31/7068* (2013.01); *A61K 33/243* (2019.01); *A61K 39/395* (2013.01); *A61K 45/00* (2013.01); *A61P 35/00* (2018.01); *A61K 2039/505* (2013.01); *A61K 2039/507* (2013.01)

(58) Field of Classification Search
CPC .......... A61K 31/7068; A61K 2039/507; A61K 45/00; A61K 39/395; A61K 39/39558; A61P 35/00
USPC .......................................... 424/133.1, 136.1
See application file for complete search history.

(56) References Cited

U.S. PATENT DOCUMENTS

| | | | |
|---|---|---|---|
| 5,585,097 A | 12/1996 | Bolt et al. | |
| 5,595,756 A | 1/1997 | Bally et al. | |
| 5,601,819 A | 2/1997 | Wong et al. | |
| 5,624,821 A | 4/1997 | Winter et al. | |
| 5,648,260 A | 7/1997 | Winter et al. | |
| 6,025,165 A | 2/2000 | Whitlow et al. | |
| 6,143,297 A | 11/2000 | Bluestone | |
| 6,805,869 B2 | 10/2004 | Guo | |
| 7,183,076 B2 | 2/2007 | Arathoon et al. | |
| 7,563,869 B2 | 7/2009 | Honjo et al. | |
| 7,659,384 B2 | 2/2010 | Jure-Kunkel et al. | |
| 7,728,114 B2 | 6/2010 | Mach et al. | |
| 8,080,250 B1 | 12/2011 | Govindan et al. | |
| 8,101,186 B2 | 1/2012 | Mezo et al. | |
| 8,263,073 B2 | 9/2012 | Korman et al. | |
| 8,298,801 B2 | 10/2012 | Kink et al. | |
| 8,398,956 B2 | 3/2013 | McBride et al. | |
| 8,586,713 B2 | 11/2013 | Davis et al. | |
| 8,592,562 B2 | 11/2013 | Kannan et al. | |
| 8,735,545 B2 | 5/2014 | Lazar et al. | |
| 8,796,424 B2 | 8/2014 | Croasdale et al. | |
| 8,871,912 B2 | 10/2014 | Davis et al. | |
| 9,017,676 B2 | 4/2015 | Lindhofer | |
| 9,067,986 B2 | 6/2015 | Gurney et al. | |
| 9,150,663 B2 | 10/2015 | Labrijn et al. | |
| 9,212,230 B2 | 12/2015 | Schuurman et al. | |
| 9,228,017 B2 | 1/2016 | Igawa et al. | |
| 9,315,567 B2 | 4/2016 | Chang et al. | |
| 9,481,730 B2 | 11/2016 | Bruenker et al. | |
| 9,527,926 B2 | 12/2016 | Ho et al. | |
| 9,562,109 B2 | 2/2017 | Von Kreudenstein et al. | |
| 9,587,036 B2 | 3/2017 | Kufer et al. | |

(Continued)

FOREIGN PATENT DOCUMENTS

| | | | |
|---|---|---|---|
| CA | 2819530 A1 | 6/2012 | |
| CA | 2830972 A1 | 10/2012 | |

(Continued)

OTHER PUBLICATIONS

Feucht et al. (Oncotarget. Nov. 22, 2016;7(47):76902-76919).*
Baeuerle et al (Cancer Res 2009; 69: (12):4941-4944 (Jun. 15, 2009)).*
Kohmke et al (Journal of Hematology & Oncology (2015) 8:111-115)).*
Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*

(Continued)

*Primary Examiner* — Lynn A Bristol
(74) *Attorney, Agent, or Firm* — Nixon & Vanderhye P.C.

(57) ABSTRACT

The present invention provides methods for treating or preventing cancer by administering an anticancer agent and an antigen-binding molecule comprising a domain that binds to a molecule expressed on the surface of a cell having an immune response-suppressing function and a T cell receptor complex-binding domain. The present invention also provides pharmaceutical compositions for treating or preventing cancer, each comprising a combination of the anticancer agent and the antigen-binding molecule.

2 Claims, 16 Drawing Sheets

Specification includes a Sequence Listing.

(56) References Cited

U.S. PATENT DOCUMENTS

| | | | |
|---|---|---|---|
| 9,637,557 B2 | 5/2017 | Scheer et al. | |
| 9,688,762 B2 | 6/2017 | Igawa et al. | |
| 9,834,604 B2 | 12/2017 | Zhu et al. | |
| 9,975,966 B2 | 5/2018 | Nezu et al. | |
| 10,011,858 B2 | 7/2018 | Igawa et al. | |
| 10,053,513 B2 | 8/2018 | McCarthy et al. | |
| 10,435,458 B2 | 10/2019 | Kuramochi et al. | |
| 10,759,870 B2 | 9/2020 | Teranishi et al. | |
| 11,001,643 B2 | 5/2021 | Nezu et al. | |
| 11,124,576 B2 * | 9/2021 | Igawa | C07K 16/2809 |
| 2002/0102278 A1 | 8/2002 | Guo | |
| 2003/0035798 A1 | 2/2003 | Fang et al. | |
| 2003/0078385 A1 | 4/2003 | Arathoon et al. | |
| 2003/0232049 A1 | 12/2003 | Jung | |
| 2004/0002587 A1 | 1/2004 | Watkins et al. | |
| 2005/0118174 A1 | 6/2005 | Presta | |
| 2006/0177896 A1 | 8/2006 | Mach et al. | |
| 2006/0235208 A1 | 10/2006 | Lazar et al. | |
| 2006/0275282 A1 | 12/2006 | Moore et al. | |
| 2007/0178092 A1 | 8/2007 | Bolt et al. | |
| 2007/0224188 A1 | 9/2007 | Allan et al. | |
| 2007/0231329 A1 | 10/2007 | Lazar et al. | |
| 2007/0248602 A1 | 10/2007 | Lazar et al. | |
| 2007/0254831 A1 | 11/2007 | Mezo et al. | |
| 2007/0287170 A1 | 12/2007 | Davis et al. | |
| 2008/0025979 A1 | 1/2008 | Honjo et al. | |
| 2008/0095755 A1 | 4/2008 | Kink et al. | |
| 2008/0220000 A1 | 9/2008 | Moore et al. | |
| 2008/0317758 A9 | 12/2008 | Presta | |
| 2009/0068192 A1 | 3/2009 | Jure-Kunkel et al. | |
| 2009/0274649 A1 | 11/2009 | Qu et al. | |
| 2009/0324589 A1 | 12/2009 | Igawa et al. | |
| 2010/0015133 A1 | 1/2010 | Igawa et al. | |
| 2010/0105874 A1 | 4/2010 | Schuurman et al. | |
| 2010/0178298 A1 | 7/2010 | Lindhofer | |
| 2010/0221252 A1 | 9/2010 | Bigler et al. | |
| 2010/0286374 A1 | 11/2010 | Kannan et al. | |
| 2010/0298542 A1 | 11/2010 | Igawa et al. | |
| 2010/0322935 A1 | 12/2010 | Croasdale et al. | |
| 2010/0331527 A1 | 12/2010 | Davis et al. | |
| 2011/0021755 A1 | 1/2011 | Lazar et al. | |
| 2011/0059076 A1 | 3/2011 | McDonagh et al. | |
| 2011/0081354 A1 | 4/2011 | Korman et al. | |
| 2011/0123532 A1 | 5/2011 | Gurney et al. | |
| 2011/0150892 A1 | 6/2011 | Thudium et al. | |
| 2011/0236374 A1 | 9/2011 | Shitara et al. | |
| 2011/0287009 A1 | 11/2011 | Scheer et al. | |
| 2011/0293513 A1 | 12/2011 | Govindan et al. | |
| 2012/0034228 A1 | 2/2012 | Kufer et al. | |
| 2012/0065379 A1 | 3/2012 | Igawa et al. | |
| 2012/0076727 A1 | 3/2012 | McBride et al. | |
| 2012/0100140 A1 | 4/2012 | Reyes et al. | |
| 2012/0149876 A1 | 6/2012 | Von Kreudenstein et al. | |
| 2012/0184718 A1 | 7/2012 | Bruenker et al. | |
| 2012/0213781 A1 | 8/2012 | Hilbert | |
| 2012/0269826 A1 | 10/2012 | McKee et al. | |
| 2013/0039913 A1 | 2/2013 | Labrijn et al. | |
| 2013/0058937 A1 | 3/2013 | Auer et al. | |
| 2013/0101581 A1 | 4/2013 | Kuramochi et al. | |
| 2013/0115208 A1 | 5/2013 | Ho et al. | |
| 2013/0129730 A1 | 5/2013 | Kufer et al. | |
| 2014/0050660 A1 | 2/2014 | Chang et al. | |
| 2014/0112914 A1 | 4/2014 | Nezu et al. | |
| 2014/0294759 A1 | 10/2014 | Chu et al. | |
| 2014/0302037 A1 | 10/2014 | Borges et al. | |
| 2014/0348832 A1 | 11/2014 | Zhu et al. | |
| 2014/0370020 A1 | 12/2014 | Kuramochi et al. | |
| 2015/0166661 A1 | 6/2015 | Chen et al. | |
| 2015/0337053 A1 | 11/2015 | Strohl et al. | |
| 2016/0152722 A1 | 6/2016 | Sharp et al. | |
| 2016/0229915 A1 | 8/2016 | Igawa et al. | |
| 2016/0333095 A1 | 11/2016 | Van Den Brink et al. | |
| 2017/0015758 A1 * | 1/2017 | Hammond | A61P 37/02 |
| 2017/0022287 A1 | 1/2017 | Igawa et al. | |
| 2017/0260271 A1 * | 9/2017 | Igawa | A61P 37/02 |
| 2017/0267783 A1 | 9/2017 | Nezu et al. | |
| 2018/0171017 A1 | 6/2018 | Taniguchi et al. | |
| 2018/0192623 A1 * | 7/2018 | Jishage | C07K 16/2809 |
| 2018/0244805 A1 | 8/2018 | Nezu et al. | |
| 2019/0077872 A1 * | 3/2019 | Igawa | A61P 35/00 |
| 2019/0352421 A1 | 11/2019 | Adams et al. | |
| 2020/0048361 A1 * | 2/2020 | Kinoshita | A61K 45/06 |
| 2020/0087380 A1 | 3/2020 | Kuramochi et al. | |
| 2020/0123256 A1 | 4/2020 | Hoshino et al. | |
| 2020/0190213 A1 * | 6/2020 | Preyer | C07K 16/2809 |
| 2020/0223940 A1 | 7/2020 | Teranishi et al. | |
| 2020/0354473 A1 | 11/2020 | Teranishi et al. | |
| 2021/0261669 A1 * | 8/2021 | Sakashita | C07K 16/30 |
| 2022/0041756 A1 | 2/2022 | Nezu et al. | |

FOREIGN PATENT DOCUMENTS

| | | |
|---|---|---|
| CN | 1763097 A | 4/2006 |
| CN | 1842540 A | 10/2006 |
| CN | 1763097 B | 4/2011 |
| CN | 1842540 B | 7/2012 |
| CN | 102574921 A | 7/2012 |
| CN | 102574921 B | 5/2016 |
| EP | 1378520 A | 1/2004 |
| EP | 1674111 A1 | 6/2006 |
| EP | 1870459 A1 | 12/2007 |
| EP | 2194006 A1 | 6/2010 |
| EP | 2194066 A1 | 6/2010 |
| EP | 1674111 B1 | 11/2010 |
| EP | 2270051 A2 | 1/2011 |
| EP | 2445936 A1 | 5/2012 |
| EP | 2543730 A1 | 1/2013 |
| EP | 2576621 A1 | 4/2013 |
| EP | 2647707 A1 | 10/2013 |
| EP | 2194006 B1 | 1/2014 |
| EP | 2698431 A1 | 2/2014 |
| EP | 2194066 B1 | 3/2016 |
| EP | 1870459 B1 | 6/2016 |
| EP | 3130606 A1 | 2/2017 |
| EP | 2647707 B1 | 9/2018 |
| EP | 3378488 A1 | 9/2018 |
| EP | 2543730 B1 | 10/2018 |
| EP | 2576621 B1 | 4/2019 |
| EP | 2270051 B1 | 5/2019 |
| JP | 2002521053 A | 7/2002 |
| JP | 2002540771 A | 12/2002 |
| JP | 2004508036 A | 3/2004 |
| JP | 2006151993 A | 6/2006 |
| JP | 2007532095 A | 11/2007 |
| JP | 2008523783 A | 7/2008 |
| JP | 2009526823 A | 7/2009 |
| JP | 2009527499 A | 7/2009 |
| JP | 2010532369 A | 10/2010 |
| JP | 4616838 B2 | 1/2011 |
| JP | 2012515556 A | 7/2012 |
| JP | 2012224631 A | 11/2012 |
| JP | 2012528092 A | 11/2012 |
| JP | 2012531439 A | 12/2012 |
| JP | 2013505732 A | 2/2013 |
| JP | 5171948 B2 | 3/2013 |
| JP | 2013508392 A | 3/2013 |
| JP | 2013528569 A | 7/2013 |
| JP | 5376759 B2 | 12/2013 |
| JP | 5695059 B2 | 4/2015 |
| JP | 5719354 B2 | 5/2015 |
| JP | 5816170 B2 | 11/2015 |
| JP | 2015535828 A | 12/2015 |
| JP | 2016538275 A | 12/2016 |
| JP | 2017504314 A | 2/2017 |
| JP | 6153862 B2 | 6/2017 |
| JP | 6449295 B2 | 1/2019 |
| JP | 6925278 B2 | 8/2021 |
| KR | 20080013875 A | 2/2008 |
| KR | 20130130765 A | 12/2013 |
| KR | 101374454 B1 | 3/2014 |
| MX | 2013006100 A | 7/2013 |
| MX | 349057 B | 7/2017 |
| RU | 2003130072 A | 4/2005 |
| RU | 2005137578 A | 6/2007 |

(56) References Cited

FOREIGN PATENT DOCUMENTS

| | | |
|---|---|---|
| RU | 2337107 C2 | 10/2008 |
| RU | 2355705 C2 | 5/2009 |
| WO | WO-9627011 A1 | 9/1996 |
| WO | WO-9850431 A2 | 11/1998 |
| WO | WO-9958572 A1 | 11/1999 |
| WO | WO-9961057 A2 | 12/1999 |
| WO | WO-0006605 A2 | 2/2000 |
| WO | WO-0018806 A1 | 4/2000 |
| WO | WO-0042072 A2 | 7/2000 |
| WO | WO0114424 A2 | 3/2001 |
| WO | WO-0190192 A2 | 11/2001 |
| WO | WO-0220615 A2 | 3/2002 |
| WO | WO-03035835 A1 | 5/2003 |
| WO | WO03074679 A2 | 9/2003 |
| WO | WO-2004003019 A2 | 1/2004 |
| WO | WO-2004035607 A2 | 4/2004 |
| WO | WO-2004099249 A2 | 11/2004 |
| WO | WO-2005035584 A1 | 4/2005 |
| WO | WO-2005061547 A2 | 7/2005 |
| WO | WO-2005063815 A2 | 7/2005 |
| WO | WO-2005092927 A1 | 10/2005 |
| WO | WO-2005115451 A2 | 12/2005 |
| WO | WO-2005118635 A2 | 12/2005 |
| WO | WO-2006020114 A2 | 2/2006 |
| WO | WO-2006105338 A2 | 10/2006 |
| WO | WO-2006106905 A1 | 10/2006 |
| WO | WO-2007093630 A1 | 8/2007 |
| WO | WO-2007145941 A2 | 12/2007 |
| WO | WO-2007147901 A1 | 12/2007 |
| WO | WO-2008051424 A2 | 5/2008 |
| WO | WO-2008090960 A1 | 7/2008 |
| WO | WO-2009041613 A1 | 4/2009 |
| WO | WO-2009053368 A1 | 4/2009 |
| WO | WO-2009080252 A1 | 7/2009 |
| WO | WO-2009080253 A1 | 7/2009 |
| WO | WO-2009089004 A1 | 7/2009 |
| WO | WO-2009095478 A1 | 8/2009 |
| WO | WO-2009120922 A2 | 10/2009 |
| WO | WO-2009126920 A2 | 10/2009 |
| WO | WO-2009134776 A2 | 11/2009 |
| WO | WO-2010034441 A1 | 4/2010 |
| WO | WO-2010037395 A2 | 4/2010 |
| WO | WO-2010085682 A2 | 7/2010 |
| WO | WO-2010102251 A2 | 9/2010 |
| WO | WO-2010120561 A1 | 10/2010 |
| WO | WO-2010136172 A1 | 12/2010 |
| WO | WO-2010151792 A1 | 12/2010 |
| WO | WO-2011039126 A1 | 4/2011 |
| WO | WO-2011050106 A2 | 4/2011 |
| WO | WO2011108714 A1 | 9/2011 |
| WO | WO-2011121110 A1 | 10/2011 |
| WO | WO-2011147986 A1 | 12/2011 |
| WO | WO-2012073985 A1 | 6/2012 |
| WO | WO-2012095412 A1 | 7/2012 |
| WO | WO-2012115241 A1 | 8/2012 |
| WO | WO-2012145183 A2 | 10/2012 |
| WO | WO-2012175751 A2 | 12/2012 |
| WO | WO-2013026833 A1 | 2/2013 |
| WO | WO-2013070468 A1 | 5/2013 |
| WO | WO-2013072523 A1 | 5/2013 |
| WO | WO-2013092091 A1 | 6/2013 |
| WO | WO-2014047231 A1 | 3/2014 |
| WO | WO-2014089113 A1 | 6/2014 |
| WO | WO-2014108483 A1 | 7/2014 |
| WO | WO-2014116846 A2 | 7/2014 |
| WO | WO-2014138306 A1 | 9/2014 |
| WO | WO-2014145907 A1 | 9/2014 |
| WO | WO-2014165818 A2 | 10/2014 |
| WO | WO-2015046467 A1 | 4/2015 |
| WO | WO-2015063339 A1 | 5/2015 |
| WO | WO-2015095392 A1 | 6/2015 |
| WO | WO 2015/124715 A1 | 8/2015 |
| WO | WO 2015/156268 A1 | 10/2015 |
| WO | WO-2015149077 A1 | 10/2015 |
| WO | WO 2015/174439 A1 | 11/2015 |
| WO | WO-2016194992 A1 | 12/2016 |
| WO | WO-2017086419 A1 | 5/2017 |

OTHER PUBLICATIONS

Huang et al. (Appl Microbiol Biotechnol (2010) 87:401-410).*
Ward et al. (Nature 341:544-546 (1989).*
Lutterbuese, R. et al., Proc. Natl. Acad. Sci. USA 107, 12605-12610 (2010).*
(Dan Kolker, TC1600 WRitten Description pp. 1-36 (Sep. 17, 2020).*
Ishiguro et al. (Sci. Transl. Med. 9, eaal4291 pp. 1-13 (2017) Oct. 4, 2017).*
DeCorte et al (epiInformation"AssessmentofAssertionsofSynergya saBasisforInventiveStepinCompositionsComprisingMixtures" 1:Feb. 1-12, 2019).*
Berenbaum Clin. Exp. Immunol. 28:1-18 (1977).*
Berenbaum Pharmacol. Rev. 41:93-141 (1989).*
Tallarida "Drug Synergism and Dose Effect Analysis" Ed. Chapman & Hall (2000), pp. 1-71).*
USDHHS, Guidance for Industry: "Estimating the Maximum Safe Starting Dose in Initial Clinical Trials for Therapeutics in Adult Health Volunteers" pp. 1-30, Jul. 2005.*
Häusler, S. F. M., et al., "Anti-CD39 and anti-CD73 antibodies A1 and 7G2 improve targeted therapy in ovarian cancer by blocking adenosine-dependent immune evasion," Am J Transl Res., 6(2):129-139 (2014).
International Search Report issued in PCT/JP2016/084027 dated Dec. 27, 2016.
Bates, G. J., et al., "Quantification of Regulatory T Cells Enables the Identification of High-Risk Breast Cancer Patients and Those at Risk of Late Relapse," *J Clin Oncol* 24(34):5373-5380 (2006).
Borch, T. H., et al., "Reorienting the immune system in the treatment of cancer by using anti-PD-1 and anti-PD-L1 antibodies," *Drug Discovery Today* 20(9):1127-1134 (2015).
Curiel, T. J., et al., "Specific recruitment of regulatory T cells in ovarian carcinoma fosters immune privilege and predicts reduced survival," *Nature Medicine* 10(9):942-949 (2004).
D'Arena, G., et al., "Regulatory T-cell number is increased in chronic lymphocytic leukemia patients and correlates with progressive disease," *Leukemia Research* 35:363-368 (2011).
De Vos van Steenwijk, P. J., et al., "Tumor-infiltrating CD14-positive myeloid cells and CD8-positive T-cells prolong survival in patients with cervical carcinoma," *Int J Cancer* 133:2884-2894 (2013).
Drake, C. G., "Combined Immune Checkpoint Blockade," *Semin Oncol* 42(4):656-662 (2015).
French, J. D., et al., "Tumor-Associated Lymphocytes and Increased FoxP3+ Regulatory T Cell Frequency Correlate with More Aggressive Papillary Thyroid Cancer" *J Clin Endocrinol Metab* 95(5):2325-2333 (2010).
Gajewski, T. F., et al., "Innate and adaptive immune cells in the tumor microenvironment," *Nature Immunology* 14(10):1014-1022 (2013).
Gerber, A. L., et al., "High expression of $FOXP_3$ in primary melanoma is associated with tumour progression," *British Journal of Dermatology* 170:103-109 (2014).
Gobert, M., et al., "Regulatory T Cells Recruited through CCL22/CCR4 Are Selectively Activated in Lymphoid Infiltrates Surrounding Primary Breast Tumors and Lead to an Adverse Clinical Outcome," *Cancer Res* 69(5):2000-2009 (2009).
Hiraoka, N., et al., "Prevalence of FOXP3+ Regulatory T Cells Increases During the Progression of Pancreatic Ductal Adenocarcinoma and Its Premalignant Lesions," *Clin Cancer Res* 12(18):5423-5434 (2006).
Jure-Kunkel, M., et al., "Synergy between chemotherapeutic agents and CTLA-4 blockade in preclinical tumor models," *Cancer Immunol Immunother* 62:1533-1545 (2013).
Kawaida, H., et al., "Distribution of CD4(+)$CD25^{high}$ Regulatory T-Cells in Tumor-Draining Lymph Nodes in Patients with Gastric Cancer," *Journal of Surgical Research* 124:151-157 (2005).

(56) References Cited

OTHER PUBLICATIONS

Khan, A. R., et al., "Tumor Infiltrating Regulatory T Cells: Tractable Targets for Immunotherapy," *International Reviews of Immunology* 29:461-484 (2010).
Kobayashi, N., et al., "FOXP3+ Regulatory T Cells Affect the Development and Progression of Hepatocarcinogenesis," *Clin Cancer Res* 13(3):902-911 (2007).
Kono, K., et al., "CD4(+)CD25$^{high}$ regulatory T cells increase with tumor stage in patients with gastric and esophageal cancers," *Cancer Immunol Immunother* 55:1064-1071 (2006).
Liotta, F., et al., "Frequency of regulatory T cells in peripheral blood and in tumour-infiltrating lymphocytes correlates with poor prognosis in renal cell carcinoma," *Journal Compilation, BJU Int'l* 107:1500-1506 (2010).
McDermott, D. F., et al. "PD-1 as a potential target in cancer therapy," *Cancer Medicine* 2(5):662-673 (2013).
Pavlou, A. K., et al., "The therapeutic antibodies market to 2008," *European Journal of Pharmaceutics and Biopharmaceutics* 59:389-396 (2005).
Postow, M. A., et al., "Nivolumab and Ipilimumab versus Ipilimumab in Untreated Melanoma," *N Engl J Med* 372:2006-2017 (2015).
Reichert, J. M., et al., "Monoclonal antibody successes in the clinic," *Nature Biotechnology* 23(9):1073-1078 (2005).
Sato, E., et al., "Intraepithelial CD8+ tumor-infiltrating lymphocytes and a high CD8+/regulatory T cell ratio are associated with favorable prognosis in ovarian cancer," *PNAS* 102(51): 18538-18543 (2005).
Selby, M. J., et al., "Anti-CTLA-4 Antibodies of IgG2a Isotype Enhance Antitumor Activity through Reduction of Intratumoral Regulatory T Cells," *Cancer Immunol Res* 1(1):32-42 (2013).
Simpson, T. R., et al., "Fc-dependent depletion of tumor-infiltrating regulatory T cells co-defines the efficacy of anti-CTLA-4 therapy against melanoma," *J Exp Med* 210(9):1695-1710 (2013).
Tosti, G., et al., "Anti-cytotoxic T lymphocyte antigen-4 antibodies in melanoma," *Clinical, Cosmetic and Investigational Dermatology* 3(6):245-256 (2013).
Wainwright, D. A., et al., "Targeting Tregs in malignant brain cancer: overcoming IDO," *Frontiers in Immunology* 4(116):1-17 (2013).
Wang, Y.-Y., et al., "The variation of CD4+CD25+ regulatory T cells in the periphery blood and tumor microenvironment of non-small cell lung cancer patients and the downregulation effects induced by CpG ODN," *Targ Oncol* 6:147-154 (2011).
Weiner, L. M., et al., "Monoclonal antibodies: versatile platforms for cancer immunotherapy," *Nature Reviews, Immunology* 10:317-327 (2010).
Wherry, E. J., "T cell exhaustion," *Nature Immunology* 12(6):492-499 (2011).
Yang, Z.-Z., et al., "Intratumoral CD4+CD25+ regulatory T-cell-mediated suppression of infiltrating CD4+ T cells in B-cell non-Hodgkin lymphoma," *Blood* 107(9):3639-3646 (2006).
Yang, Z.-Z., et al., "Attenuation of CD8+ T-Cell Function by CD4+CD25+ Regulatory T Cells in B-Cell Non-Hodgkin's Lymphoma," *Cancer Res* 66(20):10145-10152 (2006).
Yu, P., et al., "Simultaneous inhibition of two regulatory T-cell subsets enhanced Interleukin-15 efficacy in a prostate tumor model," *PNAS* 109(16):6187-6192 (2012).
Zalevsky, J., et al., "The impact of Fc engineering on an anti-CD19 antibody: increased Fcγ receptor affinity enhances B-cell clearing in nonhuman primates," *Blood* 113(16):3735-3743 (2009).
Zheng, J., et al., "YB-1 immunization combined with regulatory T-cell depletion induces specific T-cell responses that protect against neuroblastoma in the early stage," *Acta Biochim Biophys Sin* 44(12):1006-1014 (2012).
Zhao, H., et al., "A Bispecific Protein Capable of Engaging CTLA-4 and MHCII Protects Non-Obese Diabetic Mice from Autoimmune Diabetes," *PLoS One* 8(5):e63530 (2013).
U.S. Appl. No. 13/990,088, filed Dec. 19, 2013, Nezu.
U.S. Appl. No. 15/578,931, filed Dec 1, 2017, Taniguchi.
U.S. Appl. No. 15/776,541, filed May 16, 2018, Igawa.
U.S. Appl. No. 15/302,439, filed Oct. 6, 2016, Igawa.
U.S. Appl. No. 15/310,162, filed Nov. 10, 2016, Igawa.
Alarcon, B., et al., "The CD3-gamma and CD3-delta Subunits of the T Cell Antigen Receptor Can Be Expressed Within Distinct Functional TCR/CD3Complexes," *The EMBO Journal*, 10(4):903-912(1991).
Alignment of Fc domain sequences of catumaxomab and SEQ ID Nos. 23, 24, 25, and 26, cited in opposition of EP2647707 on May 24, 2019.
Amann, M., et al., "Therapeutic Window of an EpCAM/CD3-specific Bite Antibody in Mice is Determined by a Subpopulation of EpCAM-expressing Lymphocytes That is Absent in Humans," *Cancer Immunology, Immunotherapy*, 58(1):95-109 (2009).
An, Z., et al., "IgG2m4, an Engineered Antibody Isotype With Reduced Fc Function," *mAbs*, 1(6):572-579 (2009), cited in opposition of EP2647707.
Annex 1, submitted by the patentee during examination proceedings on Sep. 18, 2015 in Opposition filed against corresponding European Patent No. 2647707.
Armour, K.L., et al., "Recombinant Human IgG Molecules Lacking Fcgamma Receptor I Binding and Monocyte Triggering Activities," *European Journal of Immunology*, 29(8):2613-2624 (1999).
Asano, R., et al., "Highly Effective Recombinant Format of a Humanized IgG-like Bispecific Antibody for Cancer Immunotherapy With Retargeting of Lymphocytes to Tumor Cells," *The Journal of Biological Chemistry*, 282(38):27659-27665 (2007).
Aschermann, S., et al., "The Other Side of Immunoglobulin G: Suppressor of Inflammation," *Clinical and Experimental Immunology*, 160(2):161-167 (2010), cited in opposition of EP2647707.
Ascierto, P.A., et al., "Clinical Experiences With Anti-CD137 and Anti-PD1 Therapeutic Antibodies," *Seminars in Oncology*, 37(5):508-516 (2010).
Auerbach, R., et al., "Angiogenesis Assays: Problems and Pitfalls," *Cancer Metastasis Reviews*, 19(1-2):167-172 (2000).
Baeuerle, P.A and Reinhardt, C., "Bispecific T-cell Engaging Antibodies for Cancer Therapy," *Cancer Research*, 69(12):4941-4944 (2009).
Baeuerle, P. A., et al., "BiTE: Teaching antibodies to engage T-cells for cancer therapy," *Curr Opino Mol Ther.*, 11(1):22-30 (2009), submitted by Opponent 2 to European Patent Office on Feb. 18, 2021 in Opposition proceedings of EP2647707.
Barach, Y.S., et al., "T Cell Coinhibition in Prostate Cancer: New Immune Evasion Pathways and Emerging Therapeutics," *Trends in Molecular Medicine*, 17(1):47-55 (2011).
Bargou, R., et al., "Tumor Regression in Cancer Patients by Very Low Doses of a T Cell-engaging Antibody," *Science*, 321(5891):974-977 (2008).
Bastid, J., et al., "ENTPD1/CD39 is a Promising Therapeutic Target in Oncology," *Oncogene*, 32(14):1743-1751 (2013).
Bekeredjian-Ding, I. and Jego. G., "Toll-like Receptors-sentries in the B-cell Response," *Immunology*, 128(3):311-323 (2009).
Bendig, M.M., "Humanization of Rodent Monoclonal Antibodies by CDR Grafting," *Methods: A Comparison to Methods in Enzymology*, 8:83-93 (1995).
Bhatia, S., et al., "CTL44 Blockade Enhances the Anti-Tumor Activity of Therapy with an Anti-CD3-Based Bispecific Antibody," *Journal of Investigative Medicine*, 45(7):346A (1997).
Bi, Y., et al., "Treatment of hepatocellular carcinoma with a GPC3-targeted bispecific T cell engager," *Oncotarget*, 8(32):52866-52876 (2017).
Bodelon, G., et al., "Immunoglobulin Domains in *Escherichia Coli* and Other Enterobacteria: From Pathogenesis to Applications in Antibody Technologies," *FEMS Microbiology Reviews*, 37(2):204-250 (2013).
Bokemeyer, C., "Catumaxomab-trifunctional Anti-EpCAM antibody Used to Treat Malignant Ascites," *Expert Opinion on Biological Therapy*, 10(8):1259-1269 (2010).
Bolt, S., et al., "The generation of a humanized, non-mitogenic CD3 monoclonal antibody which retains in vitro immunosuppressive properties," *Eur J Immunol.*, 23:403-411 (1993), submitted by Opponents to European Patent Office in Opposition proceedings of EP2647707, EPO Communication dated Jan. 20, 2021.

(56) References Cited

OTHER PUBLICATIONS

Brandl, C., et al., "The Effect of Dexamethasone on Polyclonal T Cell Activation and Redirected Target Cell Lysis as Induced by a Cd19/cd3-bispecific Single-chain Antibody Construct," Cancer Immunology, Immunotherapy, 56(10):1551-1563 (2007).
Brennan, F.R., et al., "Safety and Immunotoxicity Assessment of Immunomodulatory Monoclonal Antibodies," mAbs, 2(3):233-255 (2010), cited in opposition of EP2647707.
Brezski, R. J., et al., "The Origins, Specificity, and Potential Biological Relevance of Human Anti-IgG Hinge Autoantibodies," The Scientific World Journal, 11:1153-1167 (2011).
Brischwein, K., et al., "MT110: A novel bispecific single-chain antibody construct with high efficacy in eradicating established tumors," Mol Immunol., 43:1129-1143 (2006), submitted by Opponent 2 to European Patent Office on Feb. 18, 2021 in Opposition proceedings of EP2647707.
Brown, M., et al., "Tolerance of Single, but Not Multiple, Amino Acid Replacements in Antibody Vh Cdr 2: a Means of Minimizing B Cell Wastage From Somatic Hypermutation?," Journal of Immunology, 156(9):3285-3291 (1996).
Bugelski, P. J., "Monoclonal antibody-induced cytokine-release syndrome," Expert Rev Clin Immunol., 5(5):499-521 (2009), submitted by Opponents to European Patent Office in Opposition proceedings of EP2647707, EPO Communication dated Jan. 20, 2021.
Buszko, M., et al., "Differential Depletion of Total T Cells and Regulatory T Cells and Prolonged Allotransplant Survival in CD3ε Humanized Mice Treated With Polyclonal Anti Human Thymocyte Globulin," PloS One, 12(3):e0173088 (2017).
Campoli, M., et al., "Immunotherapy of Malignant Disease With Tumor Antigen-specific Monoclonal Antibodies," Clinical Cancer Research, 16(1):11-20 (2010).
Carpenter, P. A., et al., "Non-Fc Receptor-Binding Humanized Anti-CD3 Antibodies Induce Apoptosis of Activated Human T Cells," J Immunol., 165:6205-6213 (2000).
Carter, P., "Bispecifc human IgG by design," J Immunol Meth., 248(1-2):7-15 (2001) submitted by Opponents to European Patent Office in Opposition proceedings of EP2647707, EPO Communication dated Jan. 20, 2021.
Carter, P. J., "Potent antibody therapeutics by design," Nat Rev Immunol., 6:343-357 (2006), submitted by Opponents to European Patent Office in Opposition proceedings of EP2647707, EPO Communication dated Jan. 20, 2021.
Chandramohan, V., et al., "Antibody, T-cell and Dendritic Cell Immunotherapy for Malignant Brain Tumors," Future Oncology, 9(7):977-990 (2013).
Chelius, D., et al., "Structural and Functional Characterization of the Trifunctional Antibody Catumaxomab," mAbs, 2(3):309-319 (2010), cited in opposition of EP2647707.
Chen, S., et al., "Bispecific Antibodies in Cancer Immunotherapy," Human Vaccines & Immunotherapeutics, 12(10):2491-2500 (2016).
Cheng, L., et al., "Interleukin-6 Induces Gr-1+CD11b+ Myeloid Cells to Suppress CD8+ T Cell-Mediated Liver Injury in Mice," PLoS One, 6(3):e17631 (2011).
Chernajovsky, Y. and Nissim, A., editors, "Historical Development of Monoclonal Antibody Therapeutics," Therapeutic Antibodies. Handbook of Experimental Pharmacology, 181, 7 pages (2008), submitted by Opponent 3 on Mar. 26, 2020 in Opposition of EP 2647707.
Christiansen, J. and Rajasekaran, A.K., "Biological Impediments to Monoclonal Antibody-based Cancer Immunotherapy," Molecular Cancer Therapeutics, 3(11):1493-1501 (2004).
Clayton, A.H., et al., "Unligated Epidermal Growth Factor Receptor Forms Higher Order Oligomers Within Microclusters on A431 Cells That Are Sensitive to Tyrosine Kinase Inhibitor Binding," Biochemistry, 46(15):4589-4597 (2007).
Dall'Acqua, W. F., et al., "Increasing the Affinity of a Human IgG1 for the Neonatal Fc Receptor: Biological Consequences," J Immunol., 169:5171-5180 (2002), submitted by Opponent 3 on Mar. 26, 2020 in Opposition of EP 2647707.
Dall'Acqua, W.F., et al., "Modulation of the Effector Functions of a Human Igg1 Through Engineering of Its Hinge Region," Journal of Immunology, 177(2):1129-1138 (2006).
Das, D and Suresh, M.R., et al., "Producing Bispecific and Bifunctional Antibodies," Methods in Molecular Medicine, 109:329-346 (2005), cited in opposition of EP2647707.
De Gast, G.C., et al., "Cd8 T Cell Activation After Intravenous Administration of Cd3×Cd19 Bispecific Antibody in Patients With Non-hodgkin Lymphoma," Cancer Immunology, Immunotherapy, 40(6):390-396 (1995).
De Luca, L.S. and Gommerman, J.L., "Fine-tuning of Dendritic Cell Biology by the TNF Superfamily," Nature Reviews. Immunology, 12(5):339-351 (2012).
Demanet, C., et al., "Treatment of Murine B Cell Lymphoma With Bispecific Monoclonal Antibodies," Journal of Immunology, 147(3):1091-1097 (1991), cited in opposition of EP2647707.
Dillon, T.M., et al., "Structural and Functional Characterization of Disulfide Isoforms of the Human IgG2 Subclass," The Journal of Biological Chemistry, 283(23):16206-16215 (2008).
Dubrot, J., et al., "Treatment With Anti-CD137 mAbs Causes Intense Accumulations of Liver T Cells Without Selective Antitumor Immunotherapeutic Effects in This Organ," Cancer Immunology, Immunotherapy, 59(8):1223-1233 (2010).
Edwards, B.M., et al., "The Remarkable Flexibility of the Human Antibody Repertoire; Isolation of Over One Thousand Different Antibodies to a Single Protein, BLyS," Journal of Molecular Biology, 334(1):103-118 (2003).
El Andaloussi, A., et al., "Prolongation of Survival Following Depletion of CD4+CD25+ Regulatory T Cells in Mice With Experimental Brain Tumors," Journal of Neurosurgery, 105(3):430-437 States (2006).
English Translation of Priority Application, JP 2010-266760 dated Nov. 30, 2010, submitted by Opponent 3 on Mar. 26, 2020 in Opposition of EP 2647707.
European Patent Office Preliminary Decision dated May 13, 2020 in opposition of EP2647707, 23 pages.
Examination Report in EP 18192844.1 dated Dec. 5, 2019, 6 pages, submitted by Opponent 3 on Mar. 26, 2020 in Opposition of EP 2647707.
English translation of European Patent Application No. 11845786 (European Patent No. 2647707) submitted on Jun. 12, 2019 in Opposition of EP2647707.
Filmus, J. and Selleck, S.B., "Glypicans: Proteoglycans With a Surprise," The Journal of Clinical Investigation, 108(4):497-501 (2001).
Fischer, N. and Leger, O., "Bispecific Antibodies: Molecules That Enable Novel Therapeutic Strategies," Pathobiology, 74(1):3-14 (2007).
Furness, A.J., et al., "Impact of Tumour Microenvironment and Fc Receptors on the Activity of Immunomodulatory Antibodies," Trends in Immunology, 35(7):290-298 (2014).
Goldstein, M.J., et al., "Adoptive Cell Therapy for Lymphoma With CD4 T Cells Depleted of CD137-expressing Regulatory T Cells," Cancer Research, 72(5):1239-1247 (2012).
Graca, L., editor, "The Immune Synapse as a Novel Target for Therapy," Progress in Inflammation Research, 59-61 (2008), cited in opposition of EP2647707.
Gunasekaran, K., et al., "Enhancing Antibody Fc Heterodimer Formation Through Electrostatic Steering Effects: Applications to Bispecific Molecules and Monovalent IgG," The Journal of Biological Chemistry, 285(25):19637-46 (2010).
Guo, H., et al., "Extracellular Domain of 4-1BBL Enhanced the Antitumoral Efficacy of Peripheral Blood Lymphocytes Mediated by Anti-CD3 x Anti-pgp Bispecific Diabody Against Human Multidrug-resistant Leukemia," Cellular Immunology, 251(2):102-108 (2008).
Gura, T., "Systems for Identifying New Drugs Are Often Faulty," Science, 278(5340):1041-1042 (1997).
Haagen, I.A., et al., "Evaluation of Fc Gamma Receptor Mediated T-cell Activation by Two Purified CD3×CD19 Bispecific Monoclonal Antibodies With Hybrid Fc Domains," Therapeutic Immunology, 1(5):279-287 (1994), cited in opposition of EP2647707.
Haagen, I.A., et al., "Interaction of Human Monocyte Fc Gamma Receptors With Rat IgG2b. A New Indicator for the Fc Gamma Rlla

(56) References Cited

OTHER PUBLICATIONS (R-H131) Polymorphism," Journal of Immunology, 154(4):1852-1860 (1995), cited in opposition of EP2647707.
Hamid, O. and Carvajal, R.D., "Anti-programmed Death-1 and Anti-programmed Death-ligand 1 Antibodies in Cancer Therapy," Expert Opinion on Biological Therapy, 13(6):847-861 (2013).
Hammond, S. A., et al., "Selective Targeting and Potent Control of Tumor Growth Using an EphA2/CD3-Bispecific Single-Chain Antibody Construct," Cancer Res., 67(8):3927-3935 (2007), submitted by Opponent 2 to European Patent Office on Feb. 18, 2021 in Opposition proceedings of EP2647707.
Hanahan, D. and Weinberg, R.A., "Hallmarks of Cancer: the Next Generation," Cell, 144(5):646-674 (2011).
Harada, A., et al., "In vitro toxicological support to establish specification limit for anti-CD3 monospecific impurity in a bispecific T cell engager drug, ERY974," Toxicology in Vitro, 66:104841 (2020), 7 pages.
Hezareh, M., et al., "Effector Function Activities of a Panel of Mutants of a Broadly Neutralizing Antibody Against Human Immunodeficiency Virus Type 1," Journal of Virology, 75(24):12161-12168 (2001), cited in opposition of EP2647707.
Hinton, P.R., et al., "An Engineered Human IgG1 Antibody With Longer Serum Half-life," Journal of Immunology, 176(1):346-356 (2006), cited in opposition of EP2647707.
Hornig, N., et al., "Combination of a Bispecific Antibody and Costimulatory Antibody-ligand Fusion Proteins for Targeted Cancer Immunotherapy," Journal of immunotherapy, 35(5):418-429 (2012).
Hornig, N., et al., "Evaluating Combinations of Costimulatory Antibody-ligand Fusion Proteins for Targeted Cancer Immunotherapy," Cancer Immunology, Immunotherapy, 62(8):1369-1380 (2013).
Hoseini, S.S., et al., "Immunotherapy of Hepatocellular Carcinoma Using Chimeric Antigen Receptors and Bispecific Antibodies," Cancer Letters, 399:44-52 (2017), cited in opposition of EP2647707.
Houot, R., et al., "Therapeutic Effect of CD137 Immunomodulation in Lymphoma and Its Enhancement by Treg Depletion," Blood, 114(16):3431-3438 (2009).
Immunoglobulin G InvivoGen Review (2011).
Ishiguro, T., et al., "An Anti-glypican 3/cd3 Bispecific T Cell-redirecting Antibody for Treatment of Solid Tumors," Science Translational Medicine, 9(410):eaal4291 (2017), cited in opposition of EP2647707.
Iwata, Y., et al., "Daily ascending dosing in cynomolgus monkeys to mitigate cytokine release syndrome induced by ERY22, surrogate for T-cell redirecting bispecific antibody ERY974 for cancer immunotherapy," Toxicology and Applied Pharmacology, 379:114657 (2019), 9 pages.
Jacobs, J.F., et al., "Dendritic Cell Vaccination in Combination With Anti-CD25 Monoclonal Antibody Treatment: a Phase I/ii Study in Metastatic Melanoma Patients," Clinical Cancer Research, 16(20):5067-5078 (2010).
Jain, R.K., "Barriers to Drug Delivery in Solid Tumors," Scientific American, 271(1):58-65 (1994).
Jefferis, R. and Lund, J., "Interaction Sites on Human IgG-fc for Fcgammar: Current Models," Immunology Letters, 82(1-2):57-65 (2002).
Kasthuri, R.S., et al., "Role of Tissue Factor in Cancer," Journal of Clinical Oncology, 27(29):4834-4838 (2009), cited in opposition of EP2647707.
Kim, J., et al., "Anti-CD137 Mab Deletes Both Donor CD4 and CD8 T Cells in Acute Graft-versus-host Disease," Immune Network, 11(6):428-430 (2011).
King, D.J., "Applications and Engineering of Monoclonal Antibodies," Celltech Therapeutics, 146-147 (2005), cited in opposition of EP2647707.
Klein, C., et al., "Progress in Overcoming the Chain Association Issue in Bispecific Heterodimeric IgG Antibodies," mAbs, 4(6):653-663 (2012).
Kontermann, R. E., "Recombinant bispecific antibodies for cancer therapy," Acta Pharmacologica Sinica, 26(1):1-9 (2005), submitted by Opponents to European Patent Office in Opposition proceedings of EP2647707, EPO Communication dated Jan. 20, 2021.
Kontermann, R. E., "Strategies to Extend Plasma Half-Lives of Recombinant Antibodies," BioDrugs, 23(2):93-109 (2009), submitted by Opponent 2 to European Patent Office on Feb. 18, 2021 in Opposition proceedings of EP2647707.
Koristka, S., et al., "Retargeting of Human Regulatory T Cells by Single-chain Bispecific Antibodies," Journal of Immunology, 188(3):1551-1558 (2012).
Kufer, P., et al., "A Revival of Bispecific Antibodies," Trends in Biotechnology, 22(5):238-244, (2004).
Kumagai, et al., "Humanized Bispecific Antibodies that Recognize Lymphocytes and Cancer Cells," Drug Delivery System, 23(5):518-525 (2008).
Kumar, S., et al., "Molecular Cloning and Expression of the Fabs of Human Autoantibodies in *Escherichia Coli*. Determination of the Heavy or Light Chain Contribution to the Anti-DNA/-cardiolipin Activity of the Fab," The Journal of Biological Chemistry, 275(45):35129-35136 (2000).
Lazar, G.A., et al., "Engineered Antibody Fc Variants With Enhanced Effector Function," PNAS, 103(11):4005-4010 (2006).
Lazar, G. A. and Chamberlain, A. K., "Recombinant Antibodies for Immunotherapy," Affirmed Therapeutics, Little, M., editor, 133-134 (2009), cited in opposition of EP2647707.
Lejeune, M., et al., "Bispecific, T-Cell-Recruiting Antibodies in B-Cell Malignancies," Frontiers in Immunology, 11(762) (2020), 20 pages.
Li, B., et al., "Construction and Characterization of a Humanized Anti-human Cd3 Monoclonal Antibody 12f6 With Effective Immunoregulation Functions," Immunology, 116(4):487-498 (2005).
Li, F. and Ravetch, J.V., "Antitumor Activities of Agonistic Anti-tnfr Antibodies Require Differential FcγRIIB Coengagement in Vivo," PNAS, 110(48):19501-19506 (2013).
Li, Y., et al., "Phosphorylated ERM is Responsible for Increased T Cell Polarization, Adhesion, and Migration in Patients With Systemic Lupus Erythematosus," Journal of immunology, 178(3):1938-1947 (2007).
Lindhofer, H., et al., "Bispecific Antibodies," Kontermann, R.E., editor, 296-298 (2011), cited in opposition of EP2647707.
Link, B.K., et al., "Anti-CD3-based Bispecific Antibody Designed for Therapy of Human B-cell Malignancy Can Induce T-cell Activation by Antigen-dependent and Antigen-independent Mechanisms," International Journal of Cancer, 77(2):251-256 (1998), cited in opposition of EP2647707.
Liu, R., et al., "Efficient Inhibition of Human B-cell Lymphoma in SCID Mice by Synergistic Antitumor Effect of Human 4-1BB Ligand/anti-CD20 Fusion Proteins and Anti-CD3/anti-CD20 Diabodies," Journal of Immunotherapy, 33(5):500-509 (2010).
Lloyd, C., et al., "Modelling the Human Immune Response: Performance of a 1011 Human Antibody Repertoire Against a Broad Panel of Therapeutically Relevant Antigens," Protein Engineering, Design & Selection, 22(3) :159-168 (2009).
Loffler, A., et al., "A Recombinant Bispecific Single-chain Antibody, CD19×CD3, Induces Rapid and High Lymphoma-directed Cytotoxicity by Unstimulated T Lymphocytes," Blood, 95(6):2098-2103 (2000).
Lutterbuese, R., et al., "Potent tumor killing and inhibition of tumor growth by CEA/CD3-bispecific single chain antibodies that are resistant to inhibition by soluble CEA," Proc Am Assoc Cancer Res., 98:abstract 4106 (2007), submitted by Opponent 2 to European Patent Office on Feb. 18, 2021 in Opposition proceedings of EP2647707.
Lutterbuese, R., et al., "Conversion of Cetuximab and Trastuzumab into T cell-engaging BiTE antibodies creates novel drug candidates with superior anti-tumor activity," Proc Am Assoc Cancer Res., 99:abstract 2402 (2008), submitted by Opponent 2 to European Patent Office on Feb. 18, 2021 in Opposition proceedings of EP2647707.
Mack, M., et al., "A Small Bispecific Antibody Construct Expressed as a Functional Single-chain Molecule With High Tumor Cell Cytotoxicity," PNAS, 92(15):7021-7025 (1995).

(56) References Cited

OTHER PUBLICATIONS

Matzku, S. and Stahel, R. A., "Antibodies in Diagnosis and Therapy: Technologies, Mechanisms and Clinical Data," Studies in Medicinal Chemistry, 3:7 (1999), cited in opposition of EP2647707.
McEarchern, J.A., et al., "Engineered Anti-CD70 Antibody With Multiple Effector Functions Exhibits in Vitro and in Vivo Antitumor Activities," Blood, 109(3):1185-1192 (2007).
Melero, I., et al., "Agonist Antibodies to TNFR Molecules That Costimulate T and NK Cells," Clinical Cancer Research, 19(5):1044-1053 (2013).
Melero, I., et al., "Multi-layered Action Mechanisms of CD137 (4-1BB)-targeted Immunotherapies," Trends in Pharmacological Sciences, 29(8):383-390 (2008).
Merchant, A.M., et al., "An Efficient Route to Human Bispecific IgG," Nature Biotechnology, 16(7):677-681 (1998).
Mezzanzanica, D., et al., "Human Ovarian Carcinoma Lysis by Cytotoxic T Cells Targeted by Bispecific Monoclonal Antibodies: Analysis of the Antibody Components," International Journal of Cancer, 41(4):609-615 (1988).
Milstein, C. and Cuello, A.C., "Hybrid Hybridomas and Their Use in Immunohistochemistry," Nature, 305(5934):537-540 (1983), cited in opposition of EP2647707.
Molhoj, M., et al., "CD19-/CD3-bispecific Antibody of the Bite Class is Far Superior to Tandem Diabody With Respect to Redirected Tumor Cell Lysis," Molecular Immunology, 44(8):1935-1943 (2007).
Mueller, J. P., et al., "Humanized Porcine VCAM-Specific Monoclonal Antibodies with Chimeric IgG2/G4 Constant Regions Block Human Leukocyte Binding to Porcine Endothelial Cells," Mol Immunol., 34(6):441-452 (1997), submitted by Opponents on Mar. 26, 2020 in Opposition of EP 2647707.
Muller, D., et al., "A Novel Antibody-4-1BBL Fusion Protein for Targeted Costimulation in Cancer Immunotherapy," Journal of Immunotherapy, 31(8):714-722 (2008).
Nakano, K., et al., "Anti-glypican 3 Antibodies Cause ADCC Against Human Hepatocellular Carcinoma Cells," Biochemical and Biophysical Research Communications, 378(2):279-284 (2009).
Natsume, A., et al., "Improving Effector Functions of Antibodies for Cancer Treatment: Enhancing ADCC and CDC," Drug Design, Development and Therapy, 3:7-16 (2009).
Nelson, D. L., and Cox, M. M., "Principles of Biochemistry," Fifth Edition, Lehninger, Editor, p. 171 (2008), cited in opposition of EP2647707.
Nimmerjahn, F. and Ravetch, J.V., "Fcgamma Receptors as Regulators of Immune Responses," Nature Reviews. Immunology, 8(1):34-47 (2008), cited in opposition of EP2647707.
Nishikawa, et al., "Perspectives on Clinical Applications of Regulatory T Cells," Inflammation & Immunology, 21(1):66-72 (2013), with English translation.
Nitta, T., et al., "Bispecific F (ab')2 Monomer Prepared With Anti-CD3 and Anti-tumor Monoclonal Antibodies is Most Potent in Induction of Cytolysis of Human T Cells," European Journal of Immunology, 19(8):1437-1441 (1989), cited in opposition of EP2647707.
Office Action dated Aug. 28, 2020 in U.S. Appl. No. 16/083,975, Kinoshita, et al.
Oganesyan, V., et al., "Structural Characterization of a Human Fc Fragment Engineered for Lack of Effector Functions," Acta Crystallographica. Section D, Biological Crystallography, 64(Pt 6):700-704 (2008), cited in opposition of EP2647707.
Palazon, A., et al., "The HIF-1a Hypoxia Response in Tumor-infiltrating T Lymphocytes Induces Functional CD137 (4-1BB) for Immunotherapy," Cancer Discovery, 2(7):608-623 (2012).
Parren, P.W., et al., "Induction of T-cell Proliferation by Recombinant Mouse and Chimeric Mouse/human Anti-CD3 Monoclonal Antibodies," Research in Immunology, 142(9):749-763, (1991), cited in opposition of EP2647707.
Pastor, F., et al., "Targeting 4-1BB Costimulation to Disseminated Tumor Lesions With Bi-specific Oligonucleotide Aptamers," Molecular Therapy, 19(10):1878-1886 (2011).

Paul, Fundamental Immunology, 3rd Edition, 8:292-295 (1993).
Percival-Alwyn, J.L., et al., "Generation of Potent Mouse Monoclonal Antibodies to Self-proteins Using T-cell Epitope "Tags"," mAbs, 7(1):129-137 (2015).
Pere, H., et al., "Comprehensive Analysis of Current Approaches to Inhibit Regulatory T Cells in Cancer," Oncoimmunology, 1(3):326-333 (2012).
Porter, D.L., et al., "Chimeric Antigen Receptor-modified T Cells in Chronic Lymphoid Leukemia," The New England Journal of Medicine, 365(8):725-733 (2011).
Presta, L.G., "Molecular Engineering and Design of Therapeutic Antibodies," Current Opinion in Immunology, 20(4):460-470 (2008).
Prieto, P.A., et al., "CTLA-4 Blockade With Ipilimumab: Long-term Follow-up of 177 Patients With Metastatic Melanoma," Clinical Cancer Research, 18(7):2039-2047 (2012).
Ravetch, J.V. and Kinet, J.P., "Fc Receptors," Annual Review of Immunology, 9:457-492, (1991), cited in opposition of EP2647707.
Remer, M., et al., "Abstract B046: Therapeutic mechanisms of anti-4-1BB antibodies in cancer: agonism versus regulatory T cell depletion," Cancer Immunol Research, 4(11 Suppl) (2016).
Representative abstracts showing long-term administration of a variety of anti-cancer antibodies in the prior art, submitted by Opponents to European Patent Office in Opposition proceedings of EP2647707, EPO Communication dated Jan. 20, 2021.
Restriction Requirement dated Jun. 16, 2020 in U.S. Appl. No. 16/083,975, Kinoshita, et al.
Ridgway, J.B., et al., "Knobs-into-holes' Engineering of Antibody CH3 Domains for Heavy Chain Heterodimerization," Protein Engineering, 9(7):617-621 (1996), cited in opposition of EP2647707.
Rother, R. P., et al., "Discovery and development of the complement inhibitor eculizumab for the treatment of paroxysmal nocturnal hemoglobinuria," Nature Biotechnol., 25(11):1256-1264 (2007), submitted by Opponents to European Patent Office in Opposition proceedings of EP2647707, EPO Communication dated Jan. 20, 2021.
Routledge, E.G., et al., "A Humanized Monovalent CD3 Antibody Which Can Activate Homologous Complement," European Journal of Immunology, 21(11):2717-2725 (1991), cited in opposition of EP2647707.
Rudikoff, S., et al., "Single Amino Acid Substitution Altering Antigen-binding Specificity," PNAS, 79(6):1979-1983 (1982).
Ruf, P. and Lindhofer, H., "Induction of a Long-lasting Antitumor Immunity by a Trifunctional Bispecific Antibody," Blood, 98(8):2526-2534 (2001).
Runcie, K., et al., "Bi-specific and tri-specific antibodies—the next big thing in solid tumor therapeutics," Molecular Medicine, 24:50 (2018), 15 pages.
Salfeld, J.G., "Isotype Selection in Antibody Engineering," Nature Biotechnology, 25(12):1369-1372 (2007).
Salnikov, A.V., et al., "Targeting of Cancer Stem Cell Marker EpCAM by Bispecific Antibody EpCAMxCD3 Inhibits Pancreatic Carcinoma," Journal of Cellular and Molecular Medicine, 13(9B):4023-4033 (2009), cited in opposition of EP2647707.
Sandin, L.C., et al., "Local CTLA4 Blockade Effectively Restrains Experimental Pancreatic Adenocarcinoma Growth in Vivo," Oncoimmunology, 3(1):e27614 (2014).
Saunders, K. O., "Conceptual Approaches to Modulating Antibody Effector Functions and Circulation Half-Life," 10(1296):1-20 (2019) ), submitted by Opponents to European Patent Office in Opposition proceedings of EP2647707, EPO Communication dated Jan. 20, 2021.
Schabowsky, R.H., et al., "A Novel Form of 4-1BBL Has Better Immunomodulatory Activity Than an Agonistic Anti-4-1BB Ab Without Ab-associated Severe Toxicity," Vaccine, 28(2):512-522 (2009).
Schlereth, B., et al., "T-cell Activation and B-cell Depletion in Chimpanzees Treated With a Bispecific Anti-CD19/anti-CD3 Single-chain Antibody Construct," Cancer Immunology, Immunotherapy, 55(5):503-514 (2006).
Schneider, M. A., et al., "In vitro and in vivo properties of a dimeric bispecific single-chain antibody IgG-fusion protein for depletion of $CCR2^+$ target cells in mice," Eur J Immunol., 35:987-995 (2005).

(56) References Cited

OTHER PUBLICATIONS

Sebastian, M., et al., "Treatment of Non-small Cell Lung Cancer Patients With the Trifunctional Monoclonal Antibody Catumaxomab (anti-EpCAM x anti-CD3): a Phase I Study," Cancer Immunology, Immunotherapy, 56(10):1637-1644 (2007).
Segal, D.M., et al., "Bispecific Antibodies in Cancer Therapy," Current Opinion in Immunology, 11(5):558-562 (1999).
Segal, D.M., et al., "Production of Bispecific Antibodies," Current Protocols in Immunology, 14(1):2.13.1-2.13.16 (1995), cited in opposition of EP2647707.
Seimetz, D., et al., "Development and Approval of the Trifunctional Antibody Catumaxomab (anti-EpCAM x anti-CD3) as a Targeted Cancer Immunotherapy," Cancer Treatment Reviews, 36(6):458-467 (2010).
Sequence alignments (comparison of heavy chain constant region), submitted to European Patent Office on Dec. 23, 2020 for Opposition in EP2647707.
Sequence alignments (cited in Oppositions filed against European Patent Application No. 2647707 on May 31, 2019 and Jun. 12, 2019).
Shields, R.L., et al., "High Resolution Mapping of the Binding Site on Human Igg1 for Fc Gamma Ri, Fc Gamma Rii, Fc Gamma Riii, and Fcrn and Design of Igg1 Variants With Improved Binding to the Fc Gamma R," The Journal of Biological Chemistry, 276(9):6591-6604 (2001).
Shiraiwa, H., et al., "Engineering a bispecific antibody with a common light chain: Identification and optimization of an anti-CD3 epsilon and anti-GPC3 bispecific antibody, ERY974," Methods, 154:10-20 (2019).
Smith-Gill, S.J., et al., "Contributions of Immunoglobulin Heavy and Light Chains to Antibody Specificity for Lysozyme and Two Haptens," Journal of Immunology, 139(12):4135-4144 (1987).
Son, J.H., et al., "Humanization of Agonistic Anti-human 4-1BB Monoclonal Antibody Using a Phage-displayed Combinatorial Library," Journal of Immunological Methods, 286(1-2):187-201 (2004).
Song, M.K., et al., "Light Chain of Natural Antibody Plays a Dominant Role in Protein Antigen Binding," Biochemical and Biophysical Research Communications, 268(2):390-394 (2000).
Sporn, M.B. and Suh, N., "Chemoprevention of Cancer," Carcinogenesis, 21(3):525-530 (2000).
Staerz, U.D. and Bevan, M.J., "Hybrid Hybridoma Producing a Bispecific Monoclonal Antibody That Can Focus Effector T-cell Activity," PNAS, 83(5):1453-1457 (1986).
Staerz, U.D., et al., "Hybrid Antibodies Can Target Sites for Attack by T Cells," Nature, 314(6012):628-631 (1985).
Strauss, G., et al., "Without Prior Stimulation, Tumor-associated Lymphocytes From Malignant Effusions Lyse Autologous Tumor Cells in the Presence of Bispecific Antibody HEA125xOKT3," Clinical Cancer Research, 5(1):171-180 (1999), cited in opposition of EP2647707.
Strohl, W.R., "Optimization of Fc-mediated Effector Functions of Monoclonal Antibodies," Current Opinion in Biotechnology, 20(6):685-691 (2009), cited in opposition of EP2647707.
Strohlein, M.A., et al., "Induction of Anti-tumor Immunity by Trifunctional Antibodies in Patients With Peritoneal Carcinomatosis," Journal of Experimental & Clinical Cancer Research, 28:18 (2009).
Sugiyama, D., et al., "Anti-CCR4 Mab Selectively Depletes Effector-type FoxP3+CD4+ Regulatory T Cells, Evoking Antitumor Immune Responses in Humans," PNAS, 110(44):17945-17950 (2013).
Suzuki, "Research and Development of Antibody Pharmaceuticals," NIBS Letter, 56(4):45-51 (2010), with English translation.
Szoor, A., et al., "T Cell-Activating Mesenchymal Stem Cells as a Biotherapeutic for HCC," Molecular Therapy: Oncolytics, 6:69-79 (2017).
Teerinen, T., et al., "Structure-based Stability Engineering of the Mouse IgG1 Fab Fragment by Modifying Constant Domains," Journal of Molecular Biology, 361(4):687-697 (2006).

Teschner, D., et al., "In Vitro Stimulation and Expansion of Human Tumour-reactive CD8+ Cytotoxic T Lymphocytes by Anti-CD3/CD28/CD137 Magnetic Beads," Scandinavian Journal of Immunology, 74(2):155-164 (2011).
Thakur, A. and Lum, L.G., "Cancer Therapy With Bispecific Antibodies: Clinical Experience," Current Opinion in Molecular Therapeutics, 12(3):340-349 (2010).
Thomas, A. K., et al., "A Cell-Based Artificial Antigen-Presenting Cell Coated with Anti-CD3 and CD28 Antibodies Enables Rapid Expansion and Long-Term Growth of CD4 T Lymphocytes," Clin Immunol., 105(3):259-272 (2002), submitted by Opponents to European Patent Office in Opposition proceedings of EP2647707, EPO Communication dated Jan. 20, 2021.
Topp, E.M., et al., "Antibody Transport in Cultured Tumor Cell Layers," Journal of Controlled Release, 53(1-3):15-23 (1998).
Vajdos, F.F., et al., "Comprehensive Functional Maps of the Antigen-binding Site of an Anti-ErbB2 Antibody Obtained With Shotgun Scanning Mutagenesis," Journal of Molecular Biology, 320(2):415-428 (2002).
Van Loghem, E., et al., "Staphylococcal Protein a and Human IgG Subclasses and Allotypes," Scandinavian Journal of Immunology, 15(3):275-278 (1982), cited in opposition of EP2647707.
Viardot, A., et al., "Treatment of Patients With Non-Hodgkin Lymphoma With CD19/CD3 Bispecific Antibody Blinatumomab (MT103)," Internet Citation, 1 (2010).
Vinay, D.S. and Kwon, B.S., "4-1BB signaling Beyond T Cells," Cellular & Molecular Immunology, 8(4):281-284 (2011).
Vinay, D.S. and Kwon, B.S., "TNF Superfamily: Costimulation and Clinical Applications," Cell Biology International, 33(4):453-465 (2009).
Waaijer, S. J. H., et al., "Preclinical PET imaging of bispecific antibody ERY974 targeting CD3 and glypican 3 reveals that tumor uptake correlates to T cell infiltrate," Journal for ImmunoTherapy of Cancer, 8:0000548 (2020), 10 pages.
Wang, J., et al., "Evidence for Segregation of Heterologous GPI-anchored Proteins into Separate Lipid Rafts within the Plasma Membrane," J Membrane Biol., 189:35-43 (2002).
Wang, X.B., et al., "A New Recombinant Single Chain Trispecific Antibody Recruits T Lymphocytes to Kill Cea (Carcinoma Embryonic Antigen) Positive Tumor Cells in Vitro Efficiently," Journal of Biochemistry, 135(4):555-565 (2004).
Ward, E.S., et al., "Binding Activities of a Repertoire of Single Immunoglobulin Variable Domains Secreted From *Escherichia Coli*," Nature, 341 (6242):544-546 (1989).
Weiner, G. J., et al., "The Role of T Cell Activation in Anti-CD3 x Antitumor Bispecific Antibody Therapy," J Immunol., 152:2385-2392 (1994), submitted by Opponents to European Patent Office in Opposition proceedings of EP2647707, Epo Communication dated Jan. 20, 2021.
Wines, B.D., et al., "The IgG Fc Contains Distinct Fc Receptor (FcR) Binding Sites: the Leukocyte Receptors Fc Gamma Ri and Fc Gamma Riia Bind to a Region in the Fc Distinct From That Recognized by Neonatal FcR and Protein A," Journal of immunology, 164(10):5313-5318 (2000).
Wing, M.G., et al., "Mechanism of First-dose Cytokine-release Syndrome by CAMPATH 1-h: Involvement of CD16 (FcgammaRIII) and CD11 a/CD18 (LFA-1) on NK Cells," The Journal of Clinical Investigation, 98(12):2819-2826 (1996).
Witte, L., et al., "Monoclonal antibodies targeting the VEGF receptor-2 (Flk1/KDR) as an anti-angiogenic therapeutic strategy," Cancer Metastasis Rev., 17:155-161 (1998).
Wolf, E., et al., "BiTEs: Bispecific Antibody Constructs With Unique Anti-tumor Activity," Drug Discovery Today, 10(18):1237-1244 (2005).
Xu, D., et al., "In Vitro Characterization of Five Humanized OKT3 Effector Function Variant Antibodies," Cellular Immunology, 200(1):16-26 (2000), cited in opposition of EP2647707.
Yamauchi, N., et al., "The Glypican 3 Oncofetal Protein is a Promising Diagnostic Marker for Hepatocellular Carcinoma," Modern Pathology, 18(12):1591-1598 (2005).

(56) References Cited

OTHER PUBLICATIONS

Yang, Z.M., et al., "Anti-CD3 scFv-B7.1 Fusion Protein Expressed on the Surface of HeLa Cells Provokes Potent T-lymphocyte Activation and Cytotoxicity," Biochemistry and Cell Biology, 85(2):196-202 (2007).
Yano, H., et al., "Ipilimumab Augments Antitumor Activity of Bispecific Antibody-armed T Cells," Journal of Translational Medicine, 12:191 (2014).
Yonezawa, A., et al., "Boosting Cancer Immunotherapy With Anti-CD137 Antibody Therapy," Clinical Cancer Research 21(14):3113-3120, Denville, United States (Jul. 2015).
Yorita, K., et al., "Prognostic Significance of Circumferential Cell Surface Immunoreactivity of Glypican-3 in Hepatocellular Carcinoma," Liver international, 31(1):120-131 (2011).
Yu, L., et al., "Interaction between Bevacizumab and Murine VEGF-A: A Reassessment," Invest Ophthalmol Vis Sci., 49:522-527 (2008).
Yu, L. and Wang, J., "T cell-redirecting bispecific antibodies in cancer immunotherapy: recent advances," Journal of Cancer Research and Clinical Oncology, 145:941-956 (2019).
Yu, L., et al., "A novel targeted GPC3/CD3 bispecific antibody for the treatment hepatocellular carcinoma," Cancer Biol Ther., 21(7):597-603 (2020).
Zeidler, R., et al., "Simultaneous Activation of T Cells and Accessory Cells by a New Class of Intact Bispecific Antibody Results in Efficient Tumor Cell Killing," Journal of Immunology, 163(3):1246-1252 (1999).
Zeidler, R., et al., "The Fc-region of a New Class of Intact Bispecific Antibody Mediates Activation of Accessory Cells and Nk Cells and Induces Direct Phagocytosis of Tumour Cells," British Journal of Cancer, 83(2):261-266 (2000).
Zhao, X., et al., "Targeting CD37-positive lymphoid malignancies with a novel engineered small modular immunopharmaceutical," Blood, 110:2569-2577 (2007), submitted by Opponents to European Patent Office in Opposition proceedings of EP2647707, EPO Communication dated Jan. 20, 2021.
Zhu, Z.W., et al., "Enhanced Glypican-3 Expression Differentiates the Majority of Hepatocellular Carcinomas From Benign Hepatic Disorders," Gut, 48(4):558-564 (2001).
U.S. Appl. No. 305,856, filed Sep. 14, 1994, Wong.
U.S. Appl. No. 988,925, 371(c) date Mar. 9, 1993, Bolt.
U.S. Appl. No. 09/216,604, filed Dec. 17, 1998, Yanjun.
U.S. Appl. No. 14/351,654, filed Apr. 14, 2014, Kuramochi.
U.S. Appl. No. 08/172,140, filed Dec. 22, 1993, Bally.
U.S. Appl. No. 08/478,825, filed Jun. 7, 1995, Winter.
U.S. Appl. No. 08/458,462, filed Jun. 2, 1995, Bluestone.
U.S. Appl. No. 08/479,752, filed Jun. 7, 1995, Winter.
U.S. Appl. No. 09/166,750, filed Nov. 5, 1998, Whitlow.
U.S. Appl. No. 10/143,437, filed May 10, 2002, Arathoon.
U.S. Appl. No. 10/370,749, filed Feb. 20, 2003, Watkins.
U.S. Appl. No. 10/543,323, 371(c) date Jul. 25, 2005, Honjo.
U.S. Appl. No. 10/982,470, filed Nov. 5, 2004, Presta.
U.S. Appl. No. 11/145,131, filed Jun. 3, 2005, Mach.
U.S. Appl. No. 11/332,619, filed Jan. 12, 2006, Moore.
U.S. Appl. No. 11/396,495, filed Mar. 31, 2006, Lazar.
U.S. Appl. No. 11/520,121, filed Sep. 13, 2006, Presta.
U.S. Appl. No. 11/572,634, filed Jan. 25, 2007, Allan.
U.S. Appl. No. 11/579,190, 371(c) date Sep. 18, 2007, Moore.
U.S. Appl. No. 11/636,655, filed Dec. 11, 2006, Bolt.
U.S. Appl. No. 11/676,148, filed Feb. 16, 2007, Mezo.
U.S. Appl. No. 11/728,048, filed Mar. 23, 2007, Davis.
U.S. Appl. No. 11/765,353, filed Jun. 19, 2007, Lazar.
U.S. Appl. No. 11/879,279, filed Jul. 17, 2007, Kink.
U.S. Appl. No. 11/903,106, filed Sep. 20, 2007, Jure-kunkel.
U.S. Appl. No. 11/910,128, filed Oct. 7, 2008, Igawa.
U.S. Appl. No. 12/224,010, filed Mar. 31, 2010, Lindhofer.
U.S. Appl. No. 12/295,039, filed Jan. 20, 2009, Igawa.
U.S. Appl. No. 12/325,632, filed Dec. 1, 2008, Nakamura.
U.S. Appl. No. 12/352,632, filed Jan. 13, 2009, Qu.
U.S. Appl. No. 12/524,215, filed Jul. 23, 2009, Shitara.
U.S. Appl. No. 12/593,759, filed Jan. 6, 2010, Schuurman.
U.S. Appl. No. 12/665,009, 371(c) date May 19, 2010, Bigler.
U.S. Appl. No. 12/680,082, filed Jun. 25, 2010, Igawa.
U.S. Appl. No. 12/757,801, filed Apr. 9, 2010, McDonagh.
U.S. Appl. No. 12/768,650, filed Apr. 27, 2010, Gurney.
U.S. Appl. No. 12/788,967, filed May 27, 2010, Croasdale.
U.S. Appl. No. 12/811,207, filed Jun. 29, 2010, Kannan.
U.S. Appl. No. 12/866,149, 371(c) date Nov. 22, 2010, Korman.
U.S. Appl. No. 12/896,610, filed Oct. 1, 2010, Lazar.
U.S. Appl. No. 13/058,492, filed Feb. 10, 2011, Thudium.
U.S. Appl. No. 13/092,708, filed Apr. 22, 2011, Scheer.
U.S. Appl. No. 13/122,242, 371 (c) date Jul. 14, 2011, Kufer.
U.S. Appl. No. 13/145,994, filed Dec. 5, 2011, Reyes.
U.S. Appl. No. 13/164,275, filed Jun. 20, 2011, Govindan.
U.S. Appl. No. 13/257,112, filed Nov. 22, 2011, Igawa.
U.S. Appl. No. 13/289,934, filed Nov. 4, 2011, Spreter Von Kreudenstein.
U.S. Appl. No. 13/309,714, filed Dec. 2, 2011, McBride.
U.S. Appl. No. 13/371,379, filed Feb. 10, 2012, Hilbert.
U.S. Appl. No. 13/498,390, 371(c) date Mar. 27, 2012, Bruenker.
U.S. Appl. No. 13/502,618, filed Jul. 9, 2011, McKee.
U.S. Appl. No. 13/638,223, filed Jan. 17, 2013, Kufer.
U.S. Appl. No. 13/642,253, filed Oct. 24, 2012, Labrijn.
U.S. Appl. No. 13/697,683, filed Jan. 17, 2013, Ho.
U.S. Appl. No. 13/966,450, filed Aug. 14, 2013, Chang.
U.S. Appl. No. 13/990,088, filed Dec. 19, 2013, Nezu, related application.
U.S. Appl. No. 14/128,461, filed Aug. 13, 2014, Zhu.
U.S. Appl. No. 14/217,166, filed Mar. 17, 2014, Chu.
U.S. Appl. No. 14/574,132, filed Dec. 17, 2014, Chen.
U.S. Appl. No. 14/818,864, filed Aug. 5, 2015, McCarthy.
U.S. Appl. No. 15/024,063, 371(c) date Mar. 23, 2016, Igawa.
U.S. Appl. No. 15/110,414, filed Jul. 8, 2016, Van Den Brink.
U.S. Appl. No. 15/578,931, filed Dec. 1, 2017, Taniguchi, related application.
U.S. Appl. No. 15/776,541, filed May 16, 2018, Igawa, related application.
U.S. Appl. No. 15/302,439, filed Oct. 6, 2016, Igawa, related application.
U.S. Appl. No. 15/310,162, filed Nov. 10, 2016, Igawa, related application.
Baudler, S., et al., "Insulin-Like Growth Factor-1 Controls Type 2 T Cell-Independent B Cell Response," J Immunol., 174:5516-5525 (2005).
Bruhns, P., et al., "Specificity and affinity of human Fcγ receptors and their polymorphic variants for human IgG subclasses," Blood, 113:3716-3725 (2009).
Chan, F. K.-M., "The pre-ligand binding assembly domain: a potential target of inhibition of tumour necrosis factor receptor function," Am Rheum Dis., 59(supp I):i50-i53 (2000).
Clinical Trials, History of Changes for Study: NCT01307267: A Study of PF-05082566 as a Single Agent and In Combination With Rituximab, Submitted: Mar. 3, 2014 (v26).
Final Office Action dated Jun. 2, 2020 in U.S. Appl. No. 15/776,541, 371(c) date May 16, 2018, Igawa et al.
Final Office Action dated Jan. 11, 2021 in U.S. Appl. No. 16/083,975, 371(c) date Sep. 11, 2018, Kinoshita et al.
Fisher, T. S., et al., "Targeting of 4-1BB by monoclonal antibody PF-05082566 enhances T-cell function and promotes anti-tumor activity," Cancer Immunol Immunother., 61:1721-1733 (2012).
GenBank NCBI Reference Sequence: NP_001070977.1, murine CD137/TNFRSF9 precursor, Mar. 23, 2014, 3 pages.
GenBank NCBI Reference Sequence: NP_001552.2, human CD137/TNFRSF9 precursor, Mar. 16, 2014, 3 pages.
Ho, M. and Kim, H., "Glypican-3: A new target for cancer immunotherapy," Eur J Cancer, 47:333-338 (2011).
International Search Report dated Mar. 26, 2019 in International Application No. PCT/JP2018/048409, 4 pages.
Office Action dated Sep. 27, 2019 in U.S. Appl. No. 15/776,541, 371(c) date May 16, 2018, Igawa et al.
Office Action dated Apr. 15, 2021 in U.S. Appl. No. 15/776,541, 371(c) date May 16, 2018, Igawa et al.
Restriction Requirement dated Jun. 11, 2019 in U.S. Appl. No. 15/776,541, 371(c) date May 16, 2018, Igawa et al.

(56) References Cited

OTHER PUBLICATIONS

Shao, Z., et al., "Characterisation of soluble murine CD137 and its association with systemic lupus," Mol Immunol., 45:3990-3999 (2008).
U.S. Appl. No. 12/823,838, filed Jun. 25, 2010, Davis et al.
U.S. Appl. No. 13/582,073, 371(c) date Dec. 20, 2012, Kuramochi et al.
U.S. Appl. No. 14/210,178, filed Mar. 13, 2014, Borges et al.
U.S. Appl. No. 15/113,189, 371(c) date Jul. 21, 2016, Hammond et al.
U.S. Appl. No. 15/467,654, filed Mar. 23, 2017, Nezu et al.
U.S. Appl. No. 15/963,221, filed Apr. 26, 2018, Nezu et al.
U.S. Appl. No. 16/099,341, 371(c) date Nov. 6, 2018, Teranishi et al.
U.S. Appl. No. 16/412,701, filed May 15, 2019, Adams et al.
U.S. Appl. No. 16/605,556, 371 (c) date Oct. 16, 2019, Hoshino et al.
U.S. Appl. No. 16/692,676, filed Nov. 22, 2019, Kuramochi et al.
U.S. Appl. No. 16/715,621, filed Dec. 16, 2019, Preyer et al.
U.S. Appl. No. 16/936,575, filed Jul. 23, 2020, Teranishi et al.
Chen, H., et al., "Anti-CTLA-4 therapy results in higher CD4+ ICOShi T cell frequency and IFN-y levels in both nonmalignant and malignant prostate tissues," PNAS, 106(8):2729-2734 (2009).
Final Office Action dated Nov. 4, 2021 in U.S. Appl. No. 15/776,541, Igawa, filed May 16, 2018.
Hessell, A. J., et al., "Fc receptor but not complement binding is important in antibody protection against HIV," Nature, 449:101-104 (2007).
Ishii, et al., "A receptor involved in the regulation of the pharmacokinetics of antibody-based pharmaceuticals: FcRn," Folia Pharmacol Jpn. 136(5):280-284 (2010).
Kraft, S. and Bieber, T., "FcεRI-Mediated Activation of Transcription Factors in Antigen-Presenting Cells," 125:9-15 (2001).
Labrijn, A. F., et al., "Efficient generation of stable bispecific IgG1 by controlled Fab-arm exchange," PNAS, 110(13):5145-5150 (2013).
Lund, J., et al., "Multiple Interactions of IgG with Its Core Oligosaccharide Can Modulate Recognition by Complement and Human FcY Receptor I and Influence the Synthesis of Its Oligosaccharide Chains," J Immunol., 157:4963-4969 (1996).
Marme, A., et al., "Intraperitoneal Bispecific Antibody (HEA125XOKT3) Therapy Inhibits Malignant Ascites Production in Advanced Ovarian Carcinoma," Int J Cancer, 101:183-189 (2002).
Swain, S. L., et al., "Expanding roles for CD4+ T cells in immunity to viruses," Nat Rev Immunol., 12:136-148 (2012).
Wu, H., et al., "Humanization of a Murine Monoclonal Antibody by Simultaneous Optimization of Framework and CDR Residues," J Mol Biol., 294:151-162 (1999).
U.S. Appl. No. 17/367,909, filed Jul. 6, 2021, Nezu et al., related application.
U.S. Appl. No. 17/933,879, filed Sep. 21, 2022, Igawa et al., related application.
U.S. Appl. No. 17/367,909, filed Jul. 6, 2021, Nezu et al.
U.S. Appl. No. 17/933,879, filed Sep. 21, 2022, Igawa et al.

\* cited by examiner

COMBINATION THERAPY USING T CELL REDIRECTION ANTIGEN BINDING MOLECULE AGAINST CELL HAVING IMMUNOSUPPRESSING FUNCTION

CROSS-REFERENCE TO RELATED APPLICATIONS

This application is a U.S. National Phase of PCT Application No. PCT/JP2016/084027, filed Nov. 17, 2016, which claims the benefit of Japanese Patent Application No. 2015-225236, filed Nov. 18, 2015, each of which is incorporated herein by reference in its entirety.

REFERENCE TO SEQUENCE LISTING SUBMITTED ELECTRONICALLY

The content of the electronically submitted sequence listing (Name: 6663_0070_Sequence_Listing.txt; Size: 98 kilobytes; and Date of Creation: May 8, 2018) filed with the application is incorporated herein by reference in its entirety.

TECHNICAL FIELD

The present invention relates to T cell-redirecting antigen-binding molecules that enable the treatment of various types of cancers by damaging cells having an immune response-suppressing function; and combination therapies that use the T cell-redirecting antigen-binding molecules.

BACKGROUND ART

Antibodies are drawing attention as pharmaceuticals since they are highly stable in plasma and have few side effects. In particular, a number of IgG-type antibody pharmaceuticals are available on the market and many antibody pharmaceuticals are currently being developed (Non-patent Documents 1 and 2).

As cancer therapeutic agents using antibody pharmaceuticals, Rittman against the CD20 antigen, Cetuximab against the EGFR antigen, Herceptin against the HER2 antigen, and such have been approved so far (Non-patent Document 3). These antibody molecules bind to antigens expressed on cancer cells, and exhibit cytotoxic activity against cancer cells through ADCC and such.

Apart from such antibody pharmaceuticals that exhibit cytotoxic activities directly against cancer cells, Ipilimumab which is an IgG1-type antibody against CTLA4 was recently confirmed to be effective against metastatic melanoma, and received FDA approval in 2011. In solid cancer microenvironments, effector T cells that recognize tumors are known to be suppressed by various factors in the cancer microenvironment (Non-patent Document 4). Among them, CTLA4 which is an immune checkpoint molecule is known to have the function of suppressing T cell activation, and is strongly expressed in activated effector T cells and regulatory T cells. In cancer microenvironments, tumor-recognizing effector T cells are considered to be suppressed by CTLA4. Ipilimumab is a neutralizing antibody against CTLA4, and it is considered to exhibit antitumor effects by inhibiting the suppression of effector T cell-activation and activating the tumor-recognizing effector T cells (Non-patent Document 5). Similarly, nivolumab which is a neutralizing antibody against the immune checkpoint molecule PD1 has been recently reported to be also highly effective against metastatic melanoma by the activation of tumor-recognizing effector T cells that are suppressed by PD1 (Non-patent Document 6).

Recently, clinical trials of combined use of -antibody drugs blocking different immune checkpoint molecules have been performed on various tumors (Non-patent Document 7), and combined use of an IgG1-type anti-CTLA4 antibody, Ipilimumab and an anti-PD1 antibody against the immune checkpoint molecule PD1 have been tested in clinical trials targeting multiple types of cancers (Non-patent Documents 8 and 9). Furthermore, in experiments using tumor-bearing mouse models, synergistic anti-tumor effects have been confirmed when administering an anti-CTLA4 antibody in combination with a plurality of chemotherapeutic agents (Non-patent Document 10).

Furthermore, not only regulatory T cells but also exhausted T cells are known to be present in the cancer microenvironment, and the exhausted T cells are known to not only lack cytotoxic activity (antitumor activity) but also to contribute on immunosuppression in tumors (Non-patent Document 11).

Thus, it was thought that antibody pharmaceuticals against immune checkpoint molecules exert antitumor effects by inhibiting T-cell-suppressing effects of immune checkpoint molecules. However, it has been recently reported that for exhibiting antitumor effects of anti-CTLA4 antibodies such as ipilimumab, not only the neutralizing effects on CTLA4, but the antibody-dependent cytotoxic activity (ADCC activity) against CTLA4-expressing cells is also important (Non-patent Documents 12 and 13). Regulatory T cells and exhausted T cells in the tumor microenvironment are known to strongly express CTLA4, and anti-CTLA4 antibodies having ADCC activity are thought to be able to kill the regulatory T cells and exhausted T cells. In Non-patent Documents 12 and 13, while anti-CTLA4 antibodies having ADCC activity could eliminate regulatory T cells in tumors and exert strong antitumor effects in mice, anti-CTLA4 antibodies whose ADCC activity has been removed by amino acid substitutions could not eliminate regulatory T cells in tumors and could not exert antitumor effects.

Thus, it has been found that ADCC activity plays an important role in antitumor effects of anti-CTLA4 antibodies, and that the killing of regulatory T cells by ADCC activity is an important mechanism of action.

On the other hand, ADCC activity of an antibody is exhibited by binding of its Fc region to an Fcγ receptor. For example, substituting (modifying) amino acids of the Fc region of an IgG1 antibody to increase binding to the Fcγ receptor has been reported to enable enhancement of ADCC activity (Non-Patent Document 14). In fact, an anti-CD19 antibody with enhanced ADCC activity due to modification of the Fc region exerted stronger antitumor effects than natural anti-CD19 antibodies (Non-patent Document 14).

PRIOR ART DOCUMENTS

Non-Patent Documents

[Non-patent Document 1] Janice M Reichert, Clark J Rosensweig, Laura B Faden & Matthew C Dewitz, Monoclonal antibody successes in the clinic. Nat. Biotechnol. (2005) 23, 1073-1078

[Non-patent Document 2] Pavlou A K, Belsey M J., The therapeutic antibodies market to 2008., Eur J Pharm Biopharm. (2005) 59 (3), 389-396

[Non-patent Document 3] Monoclonal antibodies: versatile platforms for cancer immunotherapy. Weiner L M, Surana R, Wang S. Nat Rev Immunol. 2010 May; 10(5):317-27.

[Non-patent Document 4] Innate and adaptive immune cells in the tumor microenvironment, Thomas F Gajewski, Hans Schreiber & Yang-Xin Fu. Nature Immunology 14, 1014-1022 (2013)

[Non-patent Document 5] Anti-cytotoxic T lymphocyte antigen-4 antibodies in melanoma. Tosti G, Cocorocchio E, Pennacchioli E. Clin Cosmet Investig Dermatol. 2013 Oct. 17; 6:245-56

[Non-patent Document 6] PD-1 as a potential target in cancer therapy. McDermott D F, Atkins M B. Cancer Med. 2013 October; 2(5):662-73.

[Non-patent Document 7] Combined Immune Checkpoint Blockade. Charles G. Drake. Semin Oncol. 2015 August; 42(4):656-62

[Non-patent Document 8] Reorienting the immune system in the treatment of cancer by using anti-PD-1 and anti-PD-L1 antibodies. Troels H. Borch, Marco Donia, Mads H. Andersen, Inge M. Svane. Drug Discov Today. 2015 September; 20(9):1127-34

[Non-patent Document 9] Nivolumab and ipilimumab versus ipilimumab in untreated melanoma. Postow M A, Chesney J, Pavlick A C, Robert C, Grossmann K, McDermott D, Linette G P, Meyer N, Giguere J K, Agarwala S S, Shaheen M, Ernstoff M S, Minor D, Salama A K, Taylor M, Ott P A, Rollin L M, Horak C, Gagnier P, Wolchok J D, Hodi F S. N Engl J Med. 2015 May 21; 372(21):2006-17

[Non-patent Document 10] Synergy between chemotherapeutic agents and CTLA-4 blockade in preclinical tumor models. Jure-Kunkel M, Masters G, Girit E, Dito G, Lee F, Hunt J T, Humphrey R. Cancer Immunol Immunother. 2013 September; 62(9):1533-45

[Non-patent Document 11] T cell exhaustion. E John Wherry. Nature Immunology, VOLUME 12 NUMBER 6 Jun. 2011:492-499.

[Non-patent Document 12] Fc-dependent depletion of tumor-infiltrating regulatory T cells co-defines the efficacy of anti-CTLA-4 therapy against melanoma. Simpson TR1, Li F, Montalvo-Ortiz W, Sepulveda M A, Bergerhoff K, Arce F, Roddie C, Henry J Y, Yagita H, Wolchok J D, Peggs K S, Ravetch J V, Allison J P, Quezada S A. J Exp Med. 2013 Aug. 26; 210(9):1695-710.

[Non-patent Document 13] Anti-CTLA-4 Antibodies of IgG2a Isotype Enhance Antitumor Activity through Reduction of Intratumoral Regulatory T Cells, Mark J. Selby, John J. Engelhardt, Michael Quigley, Karla A. Henning, Timothy Chen, Mohan Srinivasan, and Alan J. Korman, Cancer Immunol Res; 1(1); 1-11.

[Non-patent Document 14] The impact of Fc engineering on an anti-CD19 antibody: increased Fcgamma receptor affinity enhances B-cell clearing in nonhuman primates. Zalevsky J, Leung I W, Karki S, Chu S Y, Zhukovsky E A, Desjarlais J R, Carmichael D F, Lawrence C E. Blood. 2009 Apr. 16; 113(16):3735-43.

[Non-patent Document 15] Curiel, T. J. et al. Specific recruitment of regulatory T cells in ovarian carcinoma fosters immune privilege and predicts reduced survival. Nature medicine 10, 942-949, doi:10.1038/nm1093 (2004).

[Non-patent Document 16] Sato, E. et al. Intraepithelial CD8+ tumor-infiltrating lymphocytes and a high CD8+/regulatory T cell ratio are associated with favorable prognosis in ovarian cancer. Proceedings of the National Academy of Sciences of the United States of America 102, 18538-18543, doi:10.1073/pnas.0509182102 (2005).

[Non-patent Document 17] Kawaida, H. et al. Distribution of $CD4^+CD25^{high}$ regulatory T-cells in tumor-draining lymph nodes in patients with gastric cancer. The Journal of surgical research 124, 151-157, doi:10.1016/j.jss.2004.10.004 (2005).

[Non-patent Document 18] Kono, K. et al. $CD4^+CD25^{high}$ regulatory T cells increase with tumor stage in patients with gastric and esophageal cancers. Cancer immunology, immunotherapy: CII 55, 1064-1071, doi:10.1007/s00262-005-0092-8 (2006).

[Non-patent Document 19] Hiraoka, N., Onozato, K., Kosuge, T. & Hirohashi, S. Prevalence of $FOXP3^+$ regulatory T cells increases during the progression of pancreatic ductal adenocarcinoma and its premalignant lesions. Clinical cancer research: an official journal of the American Association for Cancer Research 12, 5423-5434, doi:10.1158/1078-0432.CCR-06-0369 (2006).

[Non-patent Document 20] Liotta, F. et al. Frequency of regulatory T cells in peripheral blood and in tumour-infiltrating lymphocytes correlates with poor prognosis in renal cell carcinoma. BJU international 107, 1500-1506, doi:10.1111/j.1464-410X.2010.09555.x (2011).

[Non-patent Document 21] Kobayashi, N. et al. $FOXP3^+$ regulatory T cells affect the development and progression of hepatocarcinogenesis. Clinical cancer research: an official journal of the American Association for Cancer Research 13, 902-911, doi:10.1158/1078-0432.CCR-06-2363 (2007).

[Non-patent Document 22] Gobert, M. et al. Regulatory T cells recruited through CCL22/CCR4 are selectively activated in lymphoid infiltrates surrounding primary breast tumors and lead to an adverse clinical outcome. Cancer research 69, 2000-2009, doi:10.1158/0008-5472.CAN-08-2360 (2009).

[Non-patent Document 23] Bates, G. J. et al. Quantification of regulatory T cells enables the identification of high-risk breast cancer patients and those at risk of late relapse. Journal of clinical oncology: official journal of the American Society of Clinical Oncology 24, 5373-5380, doi:10.1200/JCO.2006.05.9584 (2006).

[Non-patent Document 24] Gerber, A. L. et al. High expression of FOXP3 in primary melanoma is associated with tumour progression. The British journal of dermatology 170, 103-109, doi:10.1111/bjd.12641 (2014).

[Non-patent Document 25] Wang, Y. Y., He, X. Y., Cai, Y. Y., Wang, Z. J. & Lu, S. H. The variation of $CD4^+CD25^+$ regulatory T cells in the periphery blood and tumor microenvironment of non-small cell lung cancer patients and the downregulation effects induced by CpG ODN. Targeted oncology 6, 147-154, doi:10.1007/s11523-011-0182-9 (2011).

[Non-patent Document 26] de Vos van Steenwijk, P. J. et al. Tumor-infiltrating CD14-positive myeloid cells and CD8-positive T-cells prolong survival in patients with cervical carcinoma. International journal of cancer. Journal international du cancer 133, 2884-2894, doi:10.1002/ijc.28309 (2013).

[Non-patent Document 27] Wainwright, D. A., Dey, M., Chang, A. & Lesniak, M. S. Targeting Tregs in Malignant Brain Cancer: Overcoming IDO. Frontiers in immunology 4, 116, doi:10.3389/fimmu.2013.00116 (2013).

[Non-patent Document 28] Yu, P. et al. Simultaneous inhibition of two regulatory T-cell subsets enhanced Interleukin-15 efficacy in a prostate tumor model. Proceedings of the National Academy of Sciences of the United States of America 109, 6187-6192, doi:10.1073/pnas.1203479109 (2012).

[Non-patent Document 29] Zheng, J., Liu, P. & Yang, X. YB-1 immunization combined with regulatory T-cell depletion induces specific T-cell responses that protect against neuroblastoma in the early stage. Acta biochimica et biophysica *Sinica* 44, 1006-1014, doi:10.1093/abbs/gms089 (2012).

[Non-patent Document 30] D'Arena, G. et al. Regulatory T-cell number is increased in chronic lymphocytic leukemia patients and correlates with progressive disease. Leukemia research 35, 363-368, doi:10.1016/j.leukres.2010.08.010 (2011).

[Non-patent Document 31] French, J. D. et al. Tumor-associated lymphocytes and increased FoxP3$^+$ regulatory T cell frequency correlate with more aggressive papillary thyroid cancer. The Journal of clinical endocrinology and metabolism 95, 2325-2333, doi:10.1210/jc.2009-2564 (2010).

[Non-patent Document 32] Khan, A. R., Dovedi, S. J., Wilkinson, R. W. & Pritchard, D. I. Tumor infiltrating regulatory T cells: tractable targets for immunotherapy. International reviews of immunology 29, 461-484, doi: 10.3109/08830185.2010.508854 (2010).

[Non-patent Document 33] Yang, Z. Z., Novak, A. J., Ziesmer, S. C., Witzig, T. E. & Ansell, S. M. Attenuation of CD8$^+$ T-cell function by CD4$^+$CD25$^+$ regulatory T cells in B-cell non-Hodgkin's lymphoma. Cancer research 66, 10145-10152, doi:10.1158/0008-5472.CAN-06-1822 (2006).

[Non-patent Document 34] Yang, Z. Z., Novak, A. J., Stenson, M. J., Witzig, T. E. & Ansell, S. M. Intratumoral CD4$^+$CD25$^+$ regulatory T-cell-mediated suppression of infiltrating CD4$^+$ T cells in B-cell non-Hodgkin lymphoma. Blood 107, 3639-3646, doi:10.1182/blood-2005-08-3376 (2006).

SUMMARY OF THE INVENTION

Problems to be Solved by the Invention

The present invention was achieved in view of the above circumstances. The present invention provides T cell-redirecting antigen-binding molecules that exhibit excellent antitumor effects by damaging cells having an immune response-suppressing function; and combination therapies that use the T cell-redirecting antigen-binding molecules.

Means for Solving the Problems

The present inventors discovered that T cell-redirecting antigen-binding molecules comprising a domain that binds to a molecule expressed on the surface of cells having immune response-suppressing functions and a domain that binds to a T-cell receptor (TCR) complex, damage the cells having immune response-suppressing functions and exhibit more superior antitumor activity than conventional T cell-redirecting antigen-binding molecules that bind to molecules expressed on the surfaces of regulatory T cells and exhausted T cells and that also have ADCC activity. Furthermore, the present inventors discovered methods for treating or preventing cancer by combined use of the T cell-redirecting antigen-binding molecule and an anticancer agent; and T cell-redirecting antigen-binding molecules, anticancer agents, or pharmaceutical compositions comprising a combination of a T cell-redirecting antigen-binding molecule and an anticancer agent, each of which is used in the combination therapies.

More specifically, the present invention provides the following:

[1] a pharmaceutical composition comprising as an active ingredient a first antigen-binding molecule that comprises:
  (1) a domain that binds to a molecule expressed on the surface of a cell having an immune response-suppressing function; and
  (2) a T cell receptor complex-binding domain, and inhibits the immune response-suppressing activity of the cell having an immune response-suppressing function, wherein the pharmaceutical composition is for use in combination with an anticancer agent;

[2] the pharmaceutical composition of [1], wherein the first antigen-binding molecule is administered simultaneously with the anticancer agent;

[3] the pharmaceutical composition of [1], wherein the first antigen-binding molecule is administered before or after administration of the anticancer agent;

[4] the pharmaceutical composition of any one of [1] to [3], wherein the first antigen-binding molecule further comprises an FcRn-binding domain;

[5] the pharmaceutical composition of [4], wherein the FcRn-binding domain is an antibody Fc region having decreased Fcγ receptor-binding activity;

[6] the pharmaceutical composition of any one of [1] to [5], wherein the first antigen-binding molecule is a multispecific antibody;

[7] the pharmaceutical composition of any one of [1] to [6], wherein the cell having an immune response-suppressing function is a regulatory T cell or an exhausted T cell;

[8] the pharmaceutical composition of any one of [1] to [7], wherein the molecule expressed on the surface of the cell having an immune response-suppressing function is any molecule selected from among CTLA4, PD1, TIM3, LAG3, CD244 (2B4), CD160, GARP, OX40, CD137 (4-1BB), CD25, VISTA, BTLA, TNFR25, CD57, KLRG1, CCR2, CCR5, CCR6, CD39, CD73, CD4, CD18, CD49b, CD1d, CD5, CD21, TIM1, CD19, CD20, CD23, CD24, CD38, CD93, IgM, B220 (CD45R), CD317, PD-L1, CD11b, Ly6G, ICAM-1, FAP, PDGFR, Podoplanin, and TIGIT;

[9] the pharmaceutical composition of any one of [1] to [8], wherein the T cell receptor complex-binding domain is a T cell receptor-binding domain or a CD3-binding domain;

[10] the pharmaceutical composition of any one of [1] to [9], wherein the anticancer agent is an alkylating agent, an antimetabolite, a plant alkaloid, an antibiotic, a platinum compound, methylhydrazine, a kinase inhibitor, an enzyme, a histone deacetylase inhibitor, a retinoid, an antibody, or an immune checkpoint inhibitor;

[11] the pharmaceutical composition of any one of [1] to [9], wherein the anticancer agent is a second antigen-binding molecule comprising:
  (1) a cancer-specific antigen-binding domain; and
  (2) a tumor necrosis factor (TNF) superfamily-binding domain or tumor necrosis factor (TNF) receptor superfamily-binding domain;

[12] the pharmaceutical composition of any one of [1] to [9], wherein the anticancer agent is a third antigen-binding molecule comprising:

(1) a cancer-specific antigen-binding domain; and
(2) a T cell receptor complex-binding domain;

[13] the pharmaceutical composition of [11] or [12], wherein the second antigen-binding molecule and/or the third antigen-binding molecule further comprises an FcRn-binding domain;

[14] the pharmaceutical composition of [13], wherein the FcRn-binding domain of the second antigen-binding molecule and/or the third antigen-binding molecule is an antibody Fc region having decreased Fcγ receptor-binding activity;

[15] the pharmaceutical composition of any one of [11] to [14], wherein the second antigen-binding molecule and/or the third antigen-binding molecule is a bispecific antibody;

[16] the pharmaceutical composition of any one of [11] to [15], wherein the cancer-specific antigen-binding domain of the second antigen-binding molecule and/or the third antigen-binding molecule is a GPC3-binding domain;

[17] the pharmaceutical composition of any one of [11] and [13] to [16], wherein the TNF superfamily-binding domain or the TNF receptor superfamily-binding domain of the second antigen-binding molecule is a CD137-binding domain or a CD40-binding domain;

[18] the pharmaceutical composition of any one of [12] to [17], wherein the T cell receptor complex-binding domain of the third antigen-binding molecule is a T cell receptor-binding domain or a CD3-binding domain;

[19] the pharmaceutical composition of any one of [1] to [18], which is a pharmaceutical composition for treating or preventing any cancer selected from the group consisting of ovarian cancer, gastric cancer, esophageal cancer, pancreatic cancer, renal cell carcinoma, hepatocellular carcinoma, breast cancer, malignant melanoma, non-small-cell lung cancer, cervical cancer, glioblastoma, prostate cancer, neuroblastoma, chronic lymphocytic leukemia, papillary thyroid cancer, colorectal cancer, and B-cell non-Hodgkin's lymphoma; and

[20] an agent for inducing cytotoxicity, an agent for suppressing cell proliferation, an agent for inhibiting cell proliferation, an agent for activating an immune response, an agent for treating cancer, or an agent for preventing cancer, each of which comprises the pharmaceutical composition of any one of [1] to [19].

Furthermore, the following inventions are also provided:

[21] a pharmaceutical composition comprising an anticancer agent as an active ingredient, wherein the pharmaceutical composition is for use in combination with a first antigen-binding molecule that comprises:
(1) a domain that binds to a molecule expressed on the surface of a cell having an immune response-suppressing function; and
(2) a T cell receptor complex-binding domain, and
inhibits the immune response-suppressing activity of the cell having an immune response-suppressing function;

[22] the pharmaceutical composition of [21], wherein the anticancer agent is administered simultaneously with the first antigen-binding molecule;

[23] the pharmaceutical composition of [21], wherein the anticancer agent is administered before or after administration of the first antigen-binding molecule;

[24] a pharmaceutical composition for treating or preventing cancer, the composition comprising a combination of an anticancer agent and a first antigen-binding molecule that comprises:
(1) a domain that binds to a molecule expressed on the surface of a cell having an immune response-suppressing function; and
(2) a T cell receptor complex-binding domain, and
inhibits the immune response-suppressing activity of the cell having an immune response-suppressing function;

[25] the pharmaceutical composition of [24], which is a combination preparation;

[26] the pharmaceutical composition of [24], wherein the first antigen-binding molecule and the anticancer agent are administered separately;

[27] the pharmaceutical composition of [26], wherein the first antigen-binding molecule and the anticancer agent are administered simultaneously or sequentially;

[28] the pharmaceutical composition of any one of [21] to [27], wherein the first antigen-binding molecule further comprises an FcRn-binding domain;

[29] the pharmaceutical composition of [28] wherein the FcRn-binding domain is an antibody Fc region having decreased Fcγ receptor-binding activity;

[30] the pharmaceutical composition of any one of [21] to [29], wherein the first antigen-binding molecule is a multispecific antibody;

[31] the pharmaceutical composition of any one of [21] to [30], wherein the cell having an immune response-suppressing function is a regulatory T cell or an exhausted T cell;

[32] the pharmaceutical composition of any one of [21] to [31], wherein the molecule expressed on the surface of the cell having an immune response-suppressing function is any molecule selected from among CTLA4, PD1, TIM3, LAG3, CD244 (2B4), CD160, GARP, OX40, CD137 (4-1BB), CD25, VISTA, BTLA, TNFR25, CD57, KLRG1, CCR2, CCR5, CCR6, CD39, CD73, CD4, CD18, CD49b, CD1d, CD5, CD21, TIM1, CD19, CD20, CD23, CD24, CD38, CD93, IgM, B220 (CD45R), CD317, PD-L1, CD11b, Ly6G, ICAM-1, FAP, PDGFR, Podoplanin, and TIGIT;

[33] the pharmaceutical composition of any one of [21] to [32], wherein the T cell receptor complex-binding domain is a T cell receptor-binding domain or a CD3-binding domain;

[34] the pharmaceutical composition of any one of [21] to [33], wherein the anticancer agent is an alkylating agent, an antimetabolite, a plant alkaloid, an antibiotic, a platinum compound, methylhydrazine, a kinase inhibitor, an enzyme, a histone deacetylase inhibitor, a retinoid, an antibody, or an immune checkpoint inhibitor;

[35] the pharmaceutical composition of any one of [21] to [34], wherein the anticancer agent is a second antigen-binding molecule comprising:
(1) a cancer-specific antigen-binding domain; and
(2) a tumor necrosis factor (TNF) superfamily-binding domain or a tumor necrosis factor (TNF) receptor superfamily-binding domain;

[36] the pharmaceutical composition of any one of [21] to [35], wherein the anticancer agent is a third antigen-binding molecule comprising:
(1) a cancer-specific antigen-binding domain; and
(2) a T cell receptor complex-binding domain;

[37] the pharmaceutical composition of [35] or [36], wherein the second antigen-binding molecule and/or the third antigen-binding molecule further comprises an FcRn-binding domain;

[38] the pharmaceutical composition of [37], wherein the FcRn-binding domain of the second antigen-binding molecule and/or the third antigen-binding molecule is an antibody Fc region having decreased Fcγ receptor-binding activity;

[39] the pharmaceutical composition of any one of [35] to [38], wherein the second antigen-binding molecule and/or the third antigen-binding molecule is a bispecific antibody;

[40] the pharmaceutical composition of any one of [35] to [39], wherein the cancer-specific antigen-binding domain of the second antigen-binding molecule and/or the third antigen-binding molecule is a GPC3-binding domain;

[41] the pharmaceutical composition of any one of [35] and [37] to [40], wherein the TNF superfamily-binding domain or the TNF receptor superfamily-binding domain of the second antigen-binding molecule is a CD137-binding domain or a CD40-binding domain;

[42] the pharmaceutical composition of any one of [36] to [41], wherein the T cell receptor complex-binding domain of the third antigen-binding molecule is a T cell receptor-binding domain or a CD3-binding domain;

[43] the pharmaceutical composition of any one of [21] to [42], which is a pharmaceutical composition for treating or preventing any cancer selected from the group consisting of ovarian cancer, gastric cancer, esophageal cancer, pancreatic cancer, renal cell carcinoma, hepatocellular carcinoma, breast cancer, malignant melanoma, non-small-cell lung cancer, cervical cancer, glioblastoma, prostate cancer, neuroblastoma, chronic lymphocytic leukemia, papillary thyroid cancer, colorectal cancer, and B-cell non-Hodgkin's lymphoma; and

[44] an agent for inducing cytotoxicity, an agent for suppressing cell proliferation, an agent for inhibiting cell proliferation, an agent for activating immune response, an agent for treating cancer, or an agent for preventing cancer, each of which comprises the pharmaceutical composition of any one of [21] to [43].

Furthermore, the following inventions are also provided:

[45] a combination of an anticancer agent and a first antigen-binding molecule that comprises:
  (1) a domain that binds to a molecule expressed on the surface of a cell having an immune response-suppressing function; and
  (2) a T cell receptor complex-binding domain, and
inhibits the immune response-suppressing activity of the cell having an immune response-suppressing function;

[46] the combination according to [45], wherein the first antigen-binding molecule is administered simultaneously with the anticancer agent;

[47] the combination according to [45], wherein the first antigen-binding molecule is administered before or after administration of the anticancer agent;

[48] the combination according to any one of [45] to [47], wherein the first antigen-binding molecule further comprises an FcRn-binding domain;

[49] the combination according to [48] wherein the FcRn-binding domain is an antibody Fc region having decreased Fcγ receptor-binding activity;

[50] the combination according to any one of [45] to [49], wherein the first antigen-binding molecule is a multispecific antibody;

[51] the combination according to any one of [45] to [50], wherein the cell having an immune response-suppressing function is a regulatory T cell or an exhausted T cell;

[52] the combination according to any one of [45] to [51], wherein the molecule expressed on the surface of the cell having an immune response-suppressing function is any molecule selected from among CTLA4, PD1, TIM3, LAG3, CD244 (2B4), CD160, GARP, OX40, CD137 (4-1BB), CD25, VISTA, BTLA, TNFR25, CD57, KLRG1, CCR2, CCR5, CCR6, CD39, CD73, CD4, CD18, CD49b, CD1d, CD5, CD21, TIM1, CD19, CD20, CD23, CD24, CD38, CD93, IgM, B220 (CD45R), CD317, PD-L1, CD11b, Ly6G, ICAM-1, FAP, PDGFR, Podoplanin, and TIGIT;

[53] the combination according to any one of [45] to [52], wherein the T cell receptor complex-binding domain is a T cell receptor-binding domain or a CD3-binding domain;

[54] the combination according to any one of [45] to [53], wherein the anticancer agent is an alkylating agent, an antimetabolite, a plant alkaloid, an antibiotic, a platinum compound, methylhydrazine, a kinase inhibitor, an enzyme, a histone deacetylase inhibitor, a retinoid, an antibody, or an immune checkpoint inhibitor;

[55] the combination according to any one of [45] to [53], wherein the anticancer agent is a second antigen-binding molecule comprising:
  (1) a cancer-specific antigen-binding domain; and
  (2) a tumor necrosis factor (TNF) superfamily-binding domain or tumor necrosis factor (TNF) receptor superfamily-binding domain;

[56] the combination according to any one of [45] to [53], wherein the anticancer agent is a third antigen-binding molecule comprising:
  (1) a cancer-specific antigen-binding domain; and
  (2) a T cell receptor complex-binding domain;

[57] the combination according to [55] or [56], wherein the second antigen-binding molecule and/or the third antigen-binding molecule further comprises an FcRn-binding domain;

[58] the combination according to [57], wherein the FcRn-binding domain of the second antigen-binding molecule and/or the third antigen-binding molecule is an antibody Fc region having decreased Fcγ receptor-binding activity;

[59] the combination according to any one of [55] to [58], wherein the second antigen-binding molecule and/or the third antigen-binding molecule is a bispecific antibody;

[60] the combination according to any one of [55] to [59], wherein the cancer-specific antigen-binding domain of the second antigen-binding molecule and/or the third antigen-binding molecule is a GPC3-binding domain;

[61] the combination according to any one of [55] and [57] to [60], wherein the TNF superfamily-binding domain or the TNF receptor superfamily-binding domain of the second antigen-binding molecule is a CD137-binding domain or a CD40-binding domain;

[62] the combination according to any one of [56] to [61], wherein the T cell receptor complex-binding domain of the third antigen-binding molecule is a T cell receptor-binding domain or a CD3-binding domain;

[63] the combination according to any one of [45] to [62], which is for treating or preventing any cancer selected from the group consisting of ovarian cancer, gastric cancer, esophageal cancer, pancreatic cancer, renal cell carcinoma, hepatocellular carcinoma, breast cancer, malignant melanoma, non-small-cell lung cancer, cervical cancer, glioblastoma, prostate cancer, neuroblastoma, chronic lymphocytic leukemia, papillary thyroid cancer, colorectal cancer, and B-cell non-Hodgkin's lymphoma; and

[64] an agent for inducing cytotoxicity, an agent for suppressing cell proliferation, an agent for inhibiting cell proliferation, an agent for activating immune response, an agent for treating cancer, or an agent for preventing cancer, each of which comprises the combination according to any one of [45] to [63].

Furthermore, the following inventions are also provided:

[65] a method for inducing cytotoxicity, for suppressing cell proliferation, for inhibiting cell proliferation, for activating immune response, for treating cancer, or for preventing cancer in an individual, each method comprising administering an effective amount of an anticancer agent and an effective amount of a first antigen-binding molecule that comprises:
  (1) a domain that binds to a molecule expressed on the surface of a cell having an immune response-suppressing function; and
  (2) a T cell receptor complex-binding domain, and inhibits the immune response-suppressing activity of the cell having an immune response-suppressing function;

[66] a method for inducing cytotoxicity, for suppressing cell proliferation, for inhibiting cell proliferation, for activating immune response, for treating cancer, or for preventing cancer in an individual, each method comprising administering an effective amount of an anticancer agent to the individual with combined use of a first antigen-binding molecule that comprises:
  (1) a domain that binds to a molecule expressed on the surface of a cell having an immune response-suppressing function; and
  (2) a T cell receptor complex-binding domain, and inhibits the immune response-suppressing activity of the cell having an immune response-suppressing function;

[67] a method for inducing cytotoxicity, for suppressing cell proliferation, for inhibiting cell proliferation, for activating immune response, for treating cancer, or for preventing cancer in an individual, each method comprising administering to an individual, with combined use of an anticancer agent, an effective amount of a first antigen-binding molecule that comprises:
  (1) a domain that binds to a molecule expressed on the surface of a cell having an immune response-suppressing function; and
  (2) a T cell receptor complex-binding domain, and inhibits the immune response-suppressing activity of the cell having an immune response-suppressing function;

[68] a method for enhancing effects of inducing cytotoxicity, suppressing cell proliferation, inhibiting cell proliferation, activating immune response, treating cancer, or preventing cancer in an individual by a first antigen-binding molecule, each method comprising administering an effective amount of an anticancer agent to an individual, wherein the first antigen-binding molecule comprises:
  (1) a domain that binds to a molecule expressed on the surface of a cell having an immune response-suppressing function; and
  (2) a T cell receptor complex-binding domain, and inhibits the immune response-suppressing activity of the cell having an immune response-suppressing function;

[69] a method for enhancing effects of inducing cytotoxicity, suppressing cell proliferation, inhibiting cell proliferation, activating immune response, treating cancer, or preventing cancer in an individual by an anticancer agent, each method comprising administering to an individual an effective amount of a first antigen-binding molecule that comprises:
  (1) a domain that binds to a molecule expressed on the surface of a cell having an immune response-suppressing function; and
  (2) a T cell receptor complex-binding domain, and inhibits the immune response-suppressing activity of the cell having an immune response-suppressing function;

[70] the method of any one of [65] to [69], wherein the first antigen-binding molecule and the anticancer agent are administered separately;

[71] the method of any one of [65] to [69], wherein the first antigen-binding molecule and the anticancer agent are administered simultaneously or sequentially;

[72] the method of any one of [65] to [71], wherein the first antigen-binding molecule further comprises an FcRn-binding domain;

[73] the method of [72], wherein the FcRn-binding domain is an antibody Fc region having decreased Fcγ receptor-binding activity;

[74] the method of any one of [65] to [73], wherein the first antigen-binding molecule is a multispecific antibody;

[75] the method of any one of [65] to [74], wherein the cell having an immune response-suppressing function is a regulatory T cell or an exhausted T cell;

[76] the method of any one of [64] to [75], wherein the molecule expressed on the surface of the cell having an immune response-suppressing function is any molecule selected from among CTLA4, PD1, TIM3, LAG3, CD244 (2B4), CD160, GARP, OX40, CD137 (4-1BB), CD25, VISTA, BTLA, TNFR25, CD57, KLRG1, CCR2, CCR5, CCR6, CD39, CD73, CD4, CD18, CD49b, CD1d, CD5, CD21, TIM1, CD19, CD20, CD23, CD24, CD38, CD93, IgM, B220 (CD45R), CD317, PD-L1, CD11b, Ly6G, ICAM-1, FAP, PDGFR, Podoplanin, and TIGIT;

[77] the method of any one of [65] to [76], wherein the T cell receptor complex-binding domain is a T cell receptor-binding domain or a CD3-binding domain;

[78] the method of any one of [65] to [77], wherein the anticancer agent is an alkylating agent, an antimetabolite, a plant alkaloid, an antibiotic, a platinum compound, methylhydrazine, a kinase inhibitor, an enzyme, a histone deacetylase inhibitor, a retinoid, an antibody, or an immune checkpoint inhibitor;

[79] the method of any one of [65] to [77], wherein the anticancer agent is a second antigen-binding molecule comprising:
  (1) a cancer-specific antigen-binding domain; and
  (2) a tumor necrosis factor (TNF) superfamily-binding domain or a tumor necrosis factor (TNF) receptor superfamily-binding domain;

[80] the method of any one of [65] to [77], wherein the anticancer agent is a third antigen-binding molecule comprising:
  (1) a cancer-specific antigen-binding domain; and
  (2) a T cell receptor complex-binding domain;

[81] the method of [79] or [80], wherein the second antigen-binding molecule and/or the third antigen-binding molecule further comprises an FcRn-binding domain;

[82] the method of [81], wherein the FcRn-binding domain of the second antigen-binding molecule and/or the third antigen-binding molecule is an antibody Fc region having decreased Fcγ receptor-binding activity;

[83] the method of any one of [79] to [82], wherein the second antigen-binding molecule and/or the third antigen-binding molecule is a bispecific antibody;

[84] the method of any one of [79] to [83], wherein the cancer-specific antigen-binding domain of the second antigen-binding molecule and/or the third antigen-binding molecule is a GPC3-binding domain;

[85] the method of any one of [79] and [81] to [84], wherein the TNF superfamily-binding domain or the TNF receptor superfamily-binding domain of the second antigen-binding molecule is a CD137-binding domain or a CD40-binding domain;

[86] the method of any one of [80] to [85], wherein the T cell receptor complex-binding domain of the third antigen-binding molecule is a T cell receptor-binding domain or a CD3-binding domain; and

[87] the method of any one of [65] to [86], wherein the cancer is any cancer selected from the group consisting of ovarian cancer, gastric cancer, esophageal cancer, pancreatic cancer, renal cell carcinoma, hepatocellular carcinoma, breast cancer, malignant melanoma, non-small-cell lung cancer, cervical cancer, glioblastoma, prostate cancer, neuroblastoma, chronic lymphocytic leukemia, papillary thyroid cancer, colorectal cancer, and B-cell non-Hodgkin's lymphoma.

Furthermore, the following inventions are also provided:

[88] a kit comprising:
 (A) a pharmaceutical composition comprising a first antigen-binding molecule that comprises:
  (1) a domain that binds to a molecule expressed on the surface of a cell having an immune response-suppressing function; and
  (2) a T cell receptor complex-binding domain, and inhibits the immune response-suppressing activity of the cell having an immune response-suppressing function;
 (B) a container; and
 (C) an instruction or a label indicating that the first antigen-binding molecule and at least one type of anticancer agent are administered in combination to an individual for treating or preventing cancer in the individual;

[89] a kit comprising:
 (A) an anticancer agent;
 (B) a container; and
 (C) an instruction or a label indicating that the anticancer agent and a pharmaceutical composition comprising at least one type of a first antigen-binding molecule are administered in combination to an individual for treating or preventing cancer in the individual, wherein the first antigen-binding molecule comprises:
  (1) a domain that binds to a molecule expressed on the surface of a cell having an immune response-suppressing function; and
  (2) a T cell receptor complex-binding domain, and inhibits the immune response-suppressing activity of the cell having an immune response-suppressing function;

[90] a kit comprising:
 (A) a pharmaceutical composition comprising a first antigen-binding molecule that comprises:
  (1) a domain that binds to a molecule expressed on the surface of a cell having an immune response-suppressing function; and
  (2) a T cell receptor complex-binding domain, and inhibits the immune response-suppressing activity of the cell having an immune response-suppressing function;
 (B) a container; and
 (C) an anticancer agent;

[91] the kit of [88], wherein the first antigen-binding molecule and the anticancer agent are administered simultaneously;

[92] the kit of [88], wherein the first antigen-binding molecule is administered before or after administration of the anticancer agent;

[93] the kit of any one of [88] to [92], wherein the first antigen-binding molecule further comprises an FcRn-binding domain;

[94] the kit of [93], wherein the FcRn-binding domain is an antibody Fc region having decreased Fcγ receptor-binding activity;

[95] the kit of any one of [88] to [94], wherein the first antigen-binding molecule is a multispecific antibody;

[96] the kit of any one of [88] to [95], wherein the cell having an immune response-suppressing function is a regulatory T cell or an exhausted T cell;

[97] the kit of any one of [88] to [96], wherein the molecule expressed on the surface of the cell having an immune response-suppressing function is any molecule selected from among CTLA4, PD1, TIM3, LAG3, CD244 (2B4), CD160, GARP, OX40, CD137 (4-1BB), CD25, VISTA, BTLA, TNFR25, CD57, KLRG1, CCR2, CCR5, CCR6, CD39, CD73, CD4, CD18, CD49b, CD1d, CD5, CD21, TIM1, CD19, CD20, CD23, CD24, CD38, CD93, IgM, B220 (CD45R), CD317, PD-L1, CD11b, Ly6G, ICAM-1, FAP, PDGFR, Podoplanin, and TIGIT;

[98] the kit of any one of [88] to [97], wherein the T cell receptor complex-binding domain is a T cell receptor-binding domain or a CD3-binding domain;

[99] the kit of any one of [88] to [98], wherein the anticancer agent is an alkylating agent, an antimetabolite, a plant alkaloid, an antibiotic, a platinum compound, methylhydrazine, a kinase inhibitor, an enzyme, a histone deacetylase inhibitor, a retinoid, an antibody, or an immune checkpoint inhibitor;

[100] the kit of any one of [88] to [98], wherein the anticancer agent is a second antigen-binding molecule comprising:
 (1) a cancer-specific antigen-binding domain; and
 (2) a tumor necrosis factor (TNF) superfamily-binding domain or a tumor necrosis factor (TNF) receptor superfamily-binding domain;

[101] the kit of any one of [88] to [98], wherein the anticancer agent is a third antigen-binding molecule comprising:
 (1) a cancer-specific antigen-binding domain; and
 (2) a T cell receptor complex-binding domain;

[102] the kit of [100] or [101], wherein the second antigen-binding molecule and/or the third antigen-binding molecule further comprises an FcRn-binding domain;

[103] the kit of [102], wherein the FcRn-binding domain of the second antigen-binding molecule and/or the third antigen-binding molecule is an antibody Fc region having decreased Fcγ receptor-binding activity;

[104] the kit of any one of [100] to [103], wherein the second antigen-binding molecule and/or the third antigen-binding molecule is a bispecific antibody;

[105] the kit of any one of [100] to [104], wherein the cancer-specific antigen-binding domain of the second antigen-binding molecule and/or the third antigen-binding molecule is a GPC3-binding domain;

[106] the kit of any one of [100] and [102] to [105], wherein the TNF superfamily-binding domain or the TNF receptor superfamily-binding domain of the second antigen-binding molecule is a CD137-binding domain or a CD40-binding domain;

[107] the kit of any one of [101] to [106], wherein the T cell receptor complex-binding domain of the third antigen-binding molecule is a T cell receptor-binding domain or a CD3-binding domain; and

[108] the kit of any one of [101] to [107], wherein the cancer is any cancer selected from the group consisting of ovarian cancer, gastric cancer, esophageal cancer, pancreatic cancer, renal cell carcinoma, hepatocellular carcinoma, breast cancer, malignant melanoma, non-small-cell lung cancer, cervical cancer, glioblastoma, prostate cancer, neuroblastoma, chronic lymphocytic leukemia, papillary thyroid cancer, colorectal cancer, and B-cell non-Hodgkin's lymphoma.

Furthermore, the following inventions are also provided:

[109] a method for inducing damage to a cancer cell or a cancer cell-comprising tumor tissue, or a method for suppressing proliferation of a cancer cell or a cancer cell-comprising tumor tissue, by contacting a cell having an immune response-suppressing function and a cancer cell with an anticancer agent and a first antigen-binding molecule that comprises:
 (1) a domain that binds to a molecule expressed on the surface of the cell having an immune response-suppressing function; and
 (2) a T cell receptor complex-binding domain, and
inhibits the immune response-suppressing activity of the cell having an immune response-suppressing function;

[110] a method for assessing whether a first antigen-binding molecule and an anticancer agent induce damage to a cancer cell or a cancer cell-comprising tumor tissue, or suppress proliferation of a cancer cell or a cancer cell-comprising tumor tissue, by contacting a cell having an immune response-suppressing function and a cancer cell with an anticancer agent and a first antigen-binding molecule that comprises:
 (1) a domain that binds to a molecule expressed on the surface of the cell having an immune response-suppressing function; and
 (2) a T cell receptor complex-binding domain, and
inhibits the immune response-suppressing activity of the cell having an immune response-suppressing function;

[111] the method of [109] or [110], wherein the first antigen-binding molecule and the anticancer agent are simultaneously contacted with the cell having an immune response-suppressing function and the cancer cell;

[112] the method of [109] or [110], wherein the first antigen-binding molecule is contacted with the cell having an immune response-suppressing function and the cancer cell before or after the anticancer agent;

[113] the method of any one of [109] to [112], wherein the first antigen-binding molecule further comprises an FcRn-binding domain;

[114] the method of [113], wherein the FcRn-binding domain is an antibody Fc region having decreased Fcγ receptor-binding activity;

[115] the method of any one of [109] to [114], wherein the first antigen-binding molecule is a multispecific antibody;

[116] the method of any one of [109] to [115], wherein the cell having an immune response-suppressing function is a regulatory T cell or an exhausted T cell;

[117] the method of any one of [109] to [116], wherein the molecule expressed on the surface of the cell having an immune response-suppressing function is any molecule selected from among CTLA4, PD1, TIM3, LAG3, CD244 (2B4), CD160, GARP, OX40, CD137 (4-1BB), CD25, VISTA, BTLA, TNFR25, CD57, KLRG1, CCR2, CCR5, CCR6, CD39, CD73, CD4, CD18, CD49b, CD1d, CD5, CD21, TIM1, CD19, CD20, CD23, CD24, CD38, CD93, IgM, B220 (CD45R), CD317, PD-L1, CD11b, Ly6G, ICAM-1, FAP, PDGFR, Podoplanin, and TIGIT;

[118] the method of any one of [109] to [117], wherein the T cell receptor complex-binding domain is a T cell receptor-binding domain or a CD3-binding domain;

[119] the method of any one of [109] to [118], wherein the anticancer agent is an alkylating agent, an antimetabolite, a plant alkaloid, an antibiotic, a platinum compound, methylhydrazine, a kinase inhibitor, an enzyme, a histone deacetylase inhibitor, a retinoid, an antibody, or an immune checkpoint inhibitor;

[120] the method of any one of [109] to [118], wherein the anticancer agent is a second antigen-binding molecule comprising:
 (1) a cancer-specific antigen-binding domain; and
 (2) a tumor necrosis factor (TNF) superfamily-binding domain or a tumor necrosis factor (TNF) receptor superfamily-binding domain;

[121] the method of any one of [109] to [118], wherein the anticancer agent is a third antigen-binding molecule comprising:
 (1) a cancer-specific antigen-binding domain; and
 (2) a T cell receptor complex-binding domain;

[122] the method of [120] or [121], wherein the second antigen-binding molecule and/or the third antigen-binding molecule further comprises an FcRn-binding domain;

[123] the method of [122], wherein the FcRn-binding domain of the second antigen-binding molecule and/or the third antigen-binding molecule is an antibody Fc region having decreased Fcγ receptor-binding activity;

[124] the method of any one of [120] to [123], wherein the second antigen-binding molecule and/or the third antigen-binding molecule is a bispecific antibody;

[125] the method of any one of [120] to [124], wherein the cancer-specific antigen-binding domain of the second antigen-binding molecule and/or the third antigen-binding molecule is a GPC3-binding domain;

[126] the method of any one of [120] and [122] to [125], wherein the TNF superfamily-binding domain or the TNF receptor superfamily-binding domain of the second antigen-binding molecule is a CD137-binding domain or a CD40-binding domain;

[127] the method of any one of [123] to [126], wherein the T cell receptor complex-binding domain of the third antigen-binding molecule is a T cell receptor-binding domain or a CD3-binding domain; and

[128] the method of any one of [109] to [127], wherein the cancer cell is a cell of any cancer selected from the group consisting of ovarian cancer, gastric cancer, esophageal cancer, pancreatic cancer, renal cell carcinoma, hepatocellular carcinoma, breast cancer, malignant melanoma, non-small-cell lung cancer, cervical cancer, glioblastoma, prostate cancer, neuroblastoma, chronic lymphocytic leukemia, papillary thyroid cancer, colorectal cancer, and B-cell non-Hodgkin's lymphoma.

In several embodiments, the present invention relates to methods for treating or preventing cancer in an individual, the methods comprising administering to an individual effective amounts of a T cell-redirecting antigen-binding molecule and an anticancer agent.

Furthermore, the present invention relates to T cell-redirecting antigen-binding molecules, anticancer agents, or pharmaceutical compositions comprising a combination of a T cell-redirecting antigen-binding molecule and an anticancer agent, each of which is for use in combination therapy of the present invention.

Furthermore, the present invention relates to kits for use in combination therapy of the present invention, the kits comprising a T cell-redirecting antigen-binding molecule and an anticancer agent of the present invention.

Furthermore, the present invention relates to use of a T cell-redirecting antigen-binding molecule and/or an anticancer agent for the production of pharmaceutical compositions for treating or preventing cancer, the compositions comprising as active ingredients a T cell-redirecting antigen-binding molecule and/or an anticancer agent.

BRIEF DESCRIPTION OF THE DRAWINGS

FIG. 2-1 presents a schematic diagram showing crosslinking between T cells caused by crosslinking between CD3s on different T cells via an anti-CD3 antibody.

FIG. 2-2 presents a schematic diagram showing crosslinking between CD3s on the same T cell via an anti-CD3 antibody.

FIG. 7-1 presents a schematic diagram showing crosslinking between a mouse CTLA4-bound bead and a mouse CD3-bound bead by an anti-mouse CTLA4/anti-mouse CD3 bispecific antibody.

FIG. 7-2 presents a graph showing the experiment results of crosslinking between mouse CTLA4-bound beads and mouse CD3-bound beads via anti-mouse CTLA4/anti-mouse CD3 bispecific antibodies (N=3). The graph shows the mean values and standard deviations for each of the measurement results.

FIG. 7-3 presents a graph showing the experiment results of crosslinking between mouse CTLA4/mouse CD3-bound beads and mouse CD3-bound beads by anti-mouse CTLA4/anti-mouse CD3 bispecific antibodies. The graph shows the mean values and standard deviations for each of the measurement results.

FIG. 7-4 presents a schematic diagram showing crosslinking between a mouse CTLA4/mouse CD3-bound bead and a mouse CD3-bound bead by an anti-mouse CTLA4/anti-mouse CD3 bispecific antibody.

FIG. 10-1 presents graphs showing the results of analyzing CD4-positive cells based on the expression of CD25 and CD45RA, after a seven-day reaction of PBMC derived from a healthy person with a control antibody (control) and an anti-human CTLA4/anti-human CD3 bispecific antibody (TRAB).

FIG. 10-2 presents graphs showing the proportion of regulatory T cells (Treg) in CD4-positive T cells, calculated based on the expression of CD25 and CD45RA, after a seven-day reaction of PBMC derived from a healthy person with a control antibody (control) and an anti-human CTLA4/anti-human CD3 bispecific antibody (TRAB).

FIG. 10-3 presents graphs showing the ratio of effector T cells (Teff) to regulatory T cells (Treg) (Teff/Treg) calculated based on the expression of CD25 and CD45RA, after a seven-day reaction of PBMC derived from a healthy person with a control antibody (control) and an anti-human CTLA4/anti-human CD3 bispecific antibody (TRAB).

FIG. 11-1 presents graphs showing the results of analyzing CD4-positive cells based on the expression of FoxP3 and CD45RA, after a seven-day reaction of PBMC derived from a healthy person with a control antibody (control) and an anti-human CTLA4/anti-human CD3 bispecific antibody (TRAB).

FIG. 11-2 presents graphs showing the proportion of regulatory T cells (Treg) in CD4-positive T cells, calculated based on the expression of FoxP3 and CD45RA, after a seven-day reaction of PBMC derived from a healthy person with a control antibody (control) and an anti-human CTLA4/anti-human CD3 bispecific antibody (TRAB).

FIG. 11-3 presents graphs showing the ratio of effector T cells (Teff) to regulatory T cells (Treg) (Teff/Treg) calculated based on the expression of FoxP3 and CD45RA, after a seven-day reaction of PBMC derived from a healthy person with a control antibody (control) and an anti-human CTLA4/anti-human CD3 bispecific antibody (TRAB).

MODE FOR CARRYING OUT THE INVENTION

Definitions

Figure 1:
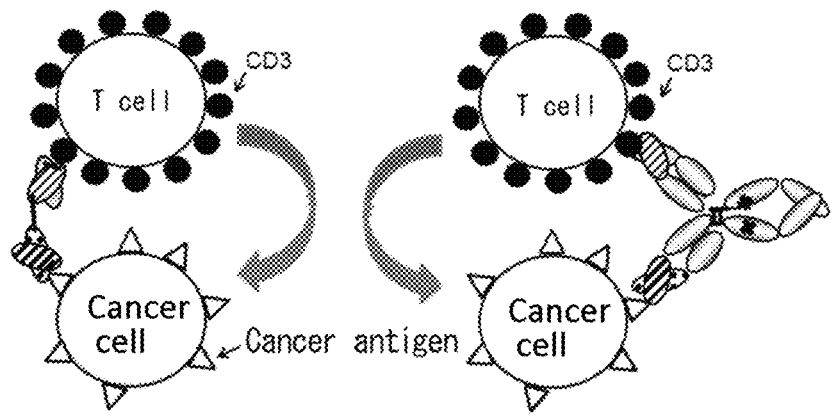
FIG. 1 presents a schematic diagram showing cytotoxic activity against cancer cells by bispecific antibodies that target a cancer antigen expressed on cancer cells and CD3 expressed on T cells.

Herein, unless otherwise defined, the chemical terms and technical terms used in relation to the present invention are regarded as having the meaning generally understood by those skilled in the art. The following definitions are provided to facilitate understanding of the invention described herein.

Indefinite Article

In the present invention, the indefinite article "a" or "an" refers to one, or two or more (i.e., at least one) grammatical object referred to by the indefinite article. For example, "a component" refers to one component or two or more components.

Amino Acids

Herein, amino acids are expressed in one- or three-letter codes or both: for example, Ala/A, Leu/L, Arg/R, Lys/K, Asn/N, Met/M, Asp/D, Phe/F, Cys/C, Pro/P, Gln/Q, Ser/S, Glu/E, Thr/T, Gly/G, Trp/W, His/H, Tyr/Y, Ile/I, or Val/V.

And/or

As used herein, the term "and/or" includes all combinations formed by appropriately combining "and" and "or". More specifically, for example, the following variations are included for the phrase "A, B, and/or C": (a) A, (b) B, (c) C, (d) A and B, (e) A and C, (f) B and C, and (g) A and B and C. That is, "A, B, and/or C" can be rephrased as "at least one of A, B, and C".

EU Numbering and Kabat Numbering

According to the method used in the present invention, the amino acid positions assigned to antibody CDRs and FRs are specified according to Kabat (Sequences of Proteins of Immunological Interest (National Institute of Health, Bethesda, Md., 1987 and 1991)). Herein, when an antigen-binding molecule is an antibody or an antigen-binding fragment, variable region amino acids are indicated according to Kabat numbering, while constant region amino acids are indicated according to EU numbering based on Kabat's amino acid positions.

Cancer

Herein, the terms "cancer", "carcinoma", "tumor", "neoplasm", and such are not differentiated from each other and are mutually interchangeable.

Antigen-Binding Molecules

In several embodiments, "antigen-binding molecules" according to the present invention are not particularly limited as long as they are molecules that comprise a "binding domain" of the present invention, and they may further comprise a peptide or protein having a length of about five amino acids or more. The peptide and protein are not limited to those derived from a living organism, and for example, they may be a polypeptide produced from an artificially designed sequence. They may also be any of a naturally-occurring polypeptide, synthetic polypeptide, recombinant polypeptide, and such.

A favorable example of an antigen-binding molecule of the present invention is an antigen-binding molecule that comprises an FcRn-binding domain contained in an antibody Fc region. As a method for extending the blood half-life of a protein administered to a living body, the method of adding an FcRn-binding domain of an antibody to the protein of interest and utilizing the function of FcRn-mediated recycling is well known.

FcRn-Binding Domains

In several embodiments, the "FcRn-binding domain" according to the present invention is not particularly limited as long as it has binding activity to FcRn, and it may be a domain that directly or indirectly binds to FcRn. Examples of the domain that directly binds to FcRn include antibody variable regions whose antigens are FcRn, Fab, antibody Fc regions, fragments thereof, albumin, albumin domain 3, human serum albumin (HSA), transferrin and such. Furthermore, an example of the domain that indirectly binds to FcRn includes a domain that has binding activity toward the aforementioned domain that directly binds to FcRn. A preferred embodiment of the present invention includes antibody Fc regions or fragments containing an FcRn-binding region of an Fc region. Herein, for example, an Fc region derived from a naturally-occurring IgG may be used as the "Fc region". A naturally-occurring IgG means a polypeptide that comprises the same amino acid sequence as an IgG found in nature, and belongs to a class of antibodies substantially encoded by immunoglobulin gamma genes. A naturally-occurring human IgG means, for example, a naturally-occurring human IgG1, a naturally-occurring human IgG2, a naturally-occurring human IgG3, or a naturally-occurring human IgG4. Naturally-occurring IgGs also include mutants and such that naturally generate therefrom. A plurality of allotype sequences that result from genetic polymorphism have been described in Sequences of Proteins of Immunological Interest, NIH Publication No. 91-3242 for the human IgG1, human IgG2, human IgG3, and human IgG4 antibody constant region, and any of the sequences may be used in the present invention. In particular, the amino acid sequence of positions 356 to 358 according to EU numbering may be DEL or EEM for the human IgG1 sequence.

Fc Regions

Existing antibody Fc regions are, for example, IgA1, IgA2, IgD, IgE, IgG1, IgG2, IgG3, IgG4, and IgM-type Fc regions. For example, an Fc region derived from a naturally-occurring human IgG antibody can be used as the antibody Fc region of the present invention. Fc regions derived from a constant region of a naturally-occurring IgG, or more specifically, a constant region derived from a naturally-occurring human IgG1 (SEQ ID NO: 1), a constant region derived from a naturally-occurring human IgG2 (SEQ ID NO: 2), a constant region derived from a naturally-occurring human IgG3 (SEQ ID NO: 3), and a constant region derived from a naturally-occurring human IgG4 (SEQ ID NO: 4), can be used as an Fc region of the present invention. Mutants and such that naturally generate therefrom are also included in the naturally-occurring IgG constant regions.

Such antibody Fc regions can be suitably obtained, for example, by partial digestion of antibodies such as monoclonal antibodies using a protease such as pepsin, then adsorption of the resulting fragments onto a protein A column or a protein G column, and subsequent elution using an appropriate elution buffer and such. The protease is not particularly limited as long as it can digest an antibody such as a monoclonal antibody by appropriately establishing the enzyme reaction conditions such as pH, and examples include pepsin and ficin.

Figure 12:
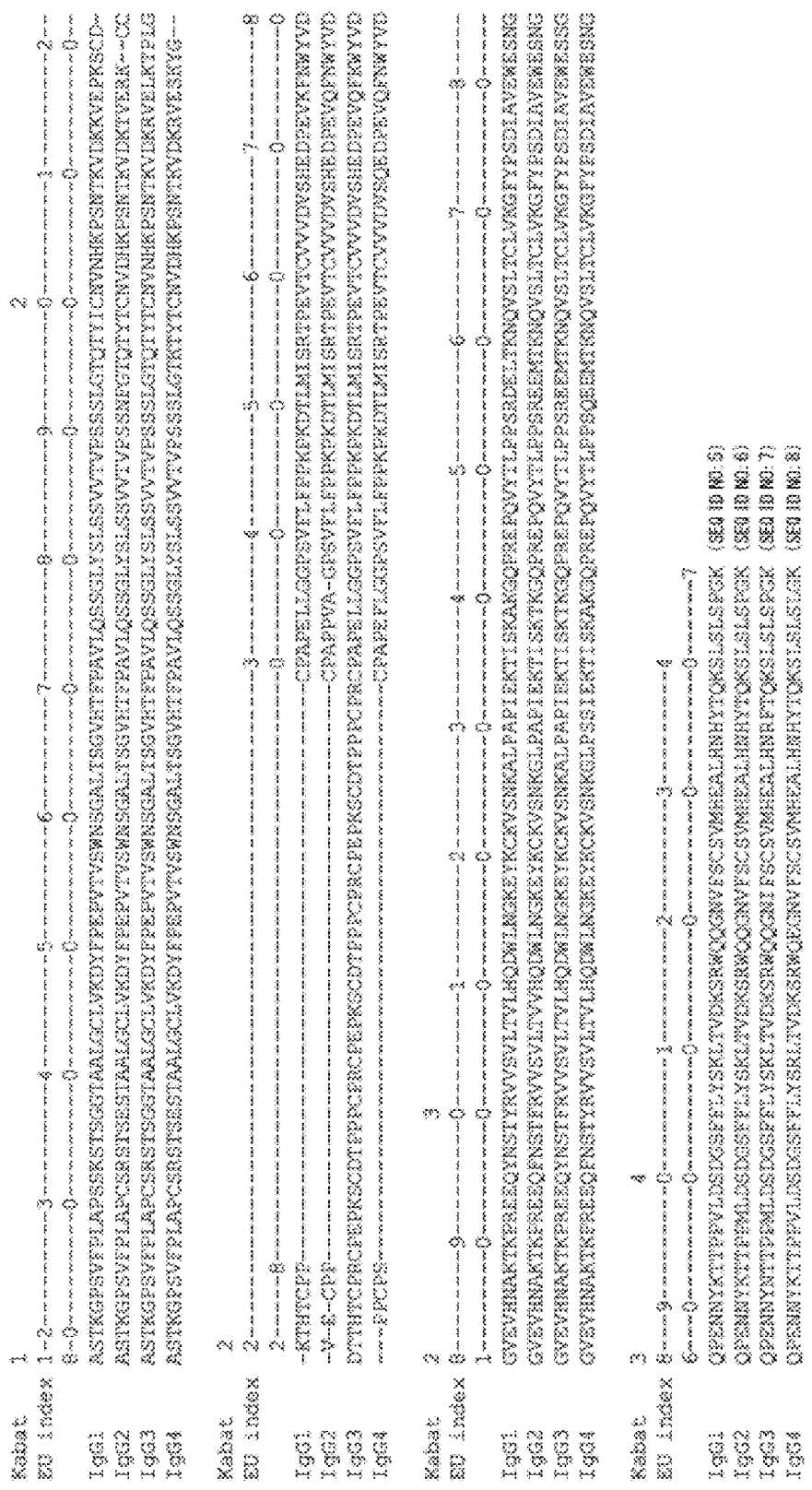
FIG. 12 presents a diagram showing the relationship between the amino acid residues constituting the Fc regions of IgG1, IgG2, IgG3, and IgG4, and Kabat's EU numbering (herein, it is also called the EU INDEX).

The isotype of an antibody is determined by the structure of the constant region. The constant region of isotypes IgG1, IgG2, IgG3, and IgG4 is called Cγ1, Cγ2, Cγ3, and Cγ4, respectively. The amino acid sequences of polypeptides constituting the Fc regions of human Cγ1, Cγ2, Cγ3, and Cγ4 are exemplified in SEQ ID NOs: 5, 6, 7, and 8. The relationship between amino acid residues constituting each of these amino acid sequences and Kabat's EU numbering (herein, also referred to as EU INDEX) is shown in FIG. 12.

An Fc region refers to a region that excludes F(ab')2 which contains two light chains and two heavy chains containing part of the constant region between the CH1 domain and the CH2 domain such that the disulfide bonds between the chains are formed between the two heavy chains. Fc regions forming the antigen-binding molecules disclosed herein can be obtained suitably by partially digesting the IgG1, IgG2, IgG3, or IgG4 monoclonal antibodies or the like using a protease such as pepsin, and then re-eluting fractions adsorbed to the protein A column. The protease is not particularly limited as long as it can digest a full-length antibody in a restrictive manner to produce F(ab')2 by appropriately establishing the enzyme reaction conditions such as pH. Such proteases include, for example, pepsin and ficin.

Fcγ Receptors

In several embodiments, a domain with decreased Fcγ receptor-binding activity is particularly preferred as the FcRn-binding domain of the present invention. Here, an Fcγ receptor (herein, also denoted as Fcγ receptor, FcγR, or FcgR) refers to a receptor that can bind to the Fc region of IgG1, IgG2, IgG3, or IgG4, and includes all members belonging to the family of proteins substantially encoded by Fcγ receptor genes. In humans, this family includes, but is not limited to, FcγRI (CD64) including isoforms FcγRIa, FcγRIb, and FcγRIc; FcγRII (CD32) including isoforms FcγRIIa (including allotypes H131 (type H) and R131 (type R), FcγRIIb (including FcγRIIb-1 and FcγRIIb-2), and FcγRIIc; and FcγRIII (CD16) including isoforms FcγRIIIa (including allotypes V158 and F158) and FcγRIIIb (including allotypes FcγRIIIb-NA1 and FcγRIIIb-NA2); as well as any undiscovered human FcγRs, and FcγR isoforms or allotypes. FcγRs include, but are not limited to, those derived from humans, mice, rats, rabbits, and monkeys, and may be derived from any organism. Mouse FcγRs include, but are not limited to, FcγRI (CD64), FcγRII (CD32), FcγRIII (CD16), and FcγRIII-2 (CD16-2), as well as any undiscovered mouse FcγRs, and FcγR isoforms or allotypes.

Suitable examples of such Fcγ receptors include human FcγRI (CD64), FcγRIIa (CD32), FcγRIIb (CD32), FcγRIIIa (CD16) and/or FcγRIIIb (CD16).

Activating receptors which carry an immunoreceptor tyrosine-based activation motif (ITAM) and inhibitory receptors which carry an immunoreceptor tyrosine-based inhibitory motif (ITIM) are present among FcγRs. FcγRs are categorized into activating FcγRs: FcγRI, FcγRIIa R, FcγRIIa H, FcγRIIIa, and FcγRIIIb, and inhibitory FcγR: FcγRIIb.

The polynucleotide sequence and amino acid sequence of FcγRI are shown in NM_000566.3 and NP_000557.1, respectively; the polynucleotide sequence and amino acid sequence of FcγRIIa are shown in BC020823.1 and AAH20823.1, respectively; the polynucleotide sequence and amino acid sequence of FcγRIIb are shown in BC146678.1 and AAI46679.1, respectively; the polynucleotide sequence and amino acid sequence of FcγRIIIa are shown in BC033678.1 and AAH33678.1, respectively; and the polynucleotide sequence and amino acid sequence of FcγRIIIb are shown in BC128562.1 and AAI28563.1, respectively (RefSeq accession number). There are two types of gene polymorphisms for FcγRIIa, where the amino acid at position 131 of FcγRIIa is substituted with histidine (type H) or arginine (type R) (J. Exp. Med, 172, 19-25, 1990). Furthermore, there are two types of gene polymorphisms for FcγRIIb, where the amino acid at position 232 of FcγRIIb is substituted with isoleucine (type I) or threonine (type T) (Arthritis. Rheum. 46: 1242-1254 (2002)). In addition, there are two types of gene polymorphisms for FcγRIIIa, where the amino acid at position 158 of FcγRIIIa is substituted with valine (type V) or phenylalanine (type F) (J. Clin. Invest. 100(5): 1059-1070 (1997)). There are also two types of gene polymorphisms for FcγRIIIb, which are type NA1 and type NA2 (J. Clin. Invest. 85: 1287-1295 (1990)).

Whether the binding activity to an Fcγ receptor is decreased can be confirmed by well-known methods such as FACS, ELISA format, screening by Amplified Luminescent Proximity Homogeneous Assay (AlphaScreen™), surface plasmon resonance (SPR)-based BIACORE™ method, and others (Proc. Natl. Acad. Sci. USA (2006) 103(11), 4005-4010).

ALPHA screening is performed with ALPHA technology which uses two beads, a donor and an acceptor bead, based on the following principle. Luminescent signals are detected only when molecules bound to donor beads interact biologically with molecules bound to the acceptor beads, and the two beads are in close proximity to each other. The laser-excited photosensitizer within the donor beads converts ambient oxygen to excited-state singlet oxygen. Singlet oxygen is dispersed around the donor beads; and when it reaches the adjacent acceptor beads, a chemiluminescent reaction is induced within the beads, and light is ultimately emitted. When molecules bound to the donor beads do not interact with molecules bound to the acceptor beads, the chemiluminescent reaction does not take place because singlet oxygen produced by the donor beads does not reach the acceptor beads.

For example, when an antigen-binding molecule contains an antibody Fc region as the FcRn-binding domain, an antigen-binding molecule having a wild-type Fc region and an antigen-binding molecule having a mutant Fc region produced by adding amino acid mutations to change the binding to an Fcγ receptor are prepared, a biotinylated antigen-binding molecule is bound to the donor beads, and an Fcγ receptor tagged with glutathione S transferase (GST) is bound to the acceptor beads. In the presence of an antigen-binding molecule having a mutant Fc region, the antigen-binding molecule having a wild-type Fc region interacts with the Fcγ receptor and produces 520-620 nm signals. When the antigen-binding molecule having a mutant Fc region is untagged, it competes with the antigen-binding molecule having a wild-type Fc region for interaction with the Fcγ receptor. The relative binding affinity can be determined by quantifying the decrease in fluorescence observed as a result of the competition. Biotinylation of antigen-binding molecules using Sulfo-NHS-biotin and such is well known. As a method for tagging an Fcγ receptor with GST, the method of expressing the Fcγ receptor and GST in a cell carrying a vector that can express a fusion gene produced by fusing a polynucleotide encoding the Fcγ receptor in frame with a GST-encoding polynucleotide, and purifying it using a glutathione column can be appropriately adopted. The obtained signals are suitably analyzed, for example, by fitting them into a one-site competition model that utilizes a non-linear regression analysis with software such as GRAPHPAD PRISM™ (GraphPad, San Diego).

One of the substances (ligand) observed for interaction is immobilized onto a gold thin film on a sensor chip, and by shining light from the reverse side of the sensor chip so that total reflection takes place at the interface between the gold thin film and glass, a portion with reduced reflection intensity is formed in part of the reflected light (SPR signal). The other substance (analyte) observed for interaction is made to flow over the sensor chip surface; and when the ligand binds to the analyte, the mass of the immobilized ligand molecule increases and the refractive index of the solvent on the sensor chip surface changes. The position of the SPR signal shifts as a result of this change in the refractive index (reversely, the signal position returns if this binding dissociates). The Biacore™ system shows the amount of shift mentioned above, or more specifically the time variable of mass, by plotting the change in mass on the sensor chip surface on the vertical axis as the measurement data (sensorgram). Kinetic parameters such as association rate constant (ka) and dissociation rate constant (kd) are determined from the curve in the sensorgram, and the affinity (KD) is determined from the ratio of these constants. In the BIACORE™ method, a method for measuring inhibition is also suitably used. An example of the method for measuring inhibition is described in Proc. Natl. Acad. Sci USA (2006) 103 (11): 4005-4010.

Herein, in several embodiments, "decreased Fcγ receptor-binding activity" means that, for example, based on the above-described analytical method, the binding activity of the test antigen-binding molecule is 50% or less, preferably 45% or less, 40% or less, 35% or less, 30% or less, 20% or less, 15% or less, or particularly preferably 10% or less, 9% or less, 8% or less, 7% or less, 6% or less, 5% or less, 4% or less, 3% or less, 2% or less, or 1% or less as compared to the binding activity of the control antigen-binding molecule containing an Fc region.

For the control antigen-binding molecule, antigen-binding molecules having, for example, a domain comprising an Fc region of a monoclonal IgG1, IgG2, IgG3, or IgG4 antibody may be suitably used. The structures of the Fc regions are shown in SEQ ID NO: 1 (A is added to the N terminus of RefSeq Accession No. AAC82527.1), SEQ ID NO: 2 (A is added to the N terminus of RefSeq Accession No. AAB59393.1), SEQ ID NO: 3 (A is added to the N terminus of RefSeq Accession No. CAA27268.1), and SEQ ID NO: 4 (A is added to the N terminus of RefSeq Accession No. AAB59394.1). Further, when an antigen-binding molecule containing a mutant of an Fc region of a particular antibody isotype is used as the test substance, the effect of a mutation possessed by the mutant on the Fcγ receptor-binding activity is tested by using as a control an antigen-binding molecule having an Fc region of an antibody of that particular isotype. In this way, antigen-binding molecules containing an Fc region mutant whose binding activity toward the Fcγ receptor verified to be decreased are suitably produced.

Examples of such mutants include mutants with a 231A-238S deletion (WO 2009/011941), or C226S, C229S, P238S, (C220S) (J. Rheumatol (2007) 34, 11), C226S, C229S (Hum. Antibod. Hybridomas (1990) 1(1), 47-54), C226S, C229S, E233P, L234V, or L235A (Blood (2007) 109, 1185-1192) mutants, where the amino acids are specified by EU numbering.

That is, suitable examples include antigen-binding molecules having an Fc region in which any of the amino acids at positions 220, 226, 229, 231, 232, 233, 234, 235, 236, 237, 238, 239, 240, 264, 265, 266, 267, 269, 270, 295, 296, 297, 298, 299, 300, 325, 327, 328, 329, 330, 331, and 332 specified according to EU numbering has been substituted in the amino acids constituting the Fc region of an antibody of a specific isotype. The isotype of the antibody from which the Fc region originates is not particularly limited, and the Fc region derived from an IgG1, IgG2, IgG3, or IgG4 monoclonal antibody can be used appropriately, and the Fc region derived from a naturally-occurring human IgG1 antibody is suitably used.

For example, an antigen-binding molecule having an Fc region that comprises any substitution specified below based on EU numbering from among amino acids constituting the IgG1 antibody Fc region (wherein the number indicates the position of the amino acid residue specified according to EU numbering, the one-letter amino acid code positioned before the number indicates the amino acid residue before the substitution, and the one-letter amino acid code positioned after the number indicates the amino acid residue after the substitution):

(a) L234F, L235E, P331S
(b) C226S, C229S, P238S
(c) C226S, C229S
(d) C226S, C229S, E233P, L234V, L235A;

or an Fc region lacking the amino acid sequence of positions 231 to 238 from among amino acids constituting the IgG1 antibody Fc region may be appropriately used.

Furthermore, antigen-binding molecules having an Fc region that comprises any substitution specified below based on EU numbering from among amino acids constituting the IgG2 antibody Fc region (wherein the number indicates the position of the amino acid residue specified according to EU numbering, the one-letter amino acid code positioned before the number indicates the amino acid residue before the substitution, and the one-letter amino acid code positioned after the number indicates the amino acid residue after the substitution):

(e) H268Q, V309L, A330S, P331S
(f) V234A
(g) G237A
(h) V234A, G237A
(i) A235E, G237A
(j) V234A, A235E, G237A may be appropriately used.

Furthermore, antigen-binding molecules having an Fc region that comprises any substitution specified below based on EU numbering from among amino acids constituting the IgG3 antibody Fc region (wherein the number indicates the position of the amino acid residue specified according to EU numbering, the one-letter amino acid code positioned before the number indicates the amino acid residue before the substitution, and the one-letter amino acid code positioned after the number indicates the amino acid residue after the substitution):

(k) F241A
(l) D265A
(m) V264A may be appropriately used.

Furthermore, antigen-binding molecules having an Fc region that comprises any substitution specified below based on EU numbering from among amino acids constituting the IgG4 antibody Fc region (wherein the number indicates the position of the amino acid residue specified according to EU numbering, the one-letter amino acid code positioned before the number indicates the amino acid residue before the substitution, and the one-letter amino acid code positioned after the number indicates the amino acid residue after the substitution):

(n) L235A, G237A, E318A
(o) L235E
(p) F234A, L235A may be appropriately used.

Other preferred examples include antigen-binding molecules having an Fc region in which any of the amino acids at positions 233, 234, 235, 236, 237, 327, 330, and 331 specified according to EU numbering in the amino acids constituting the Fc region of a naturally-occurring human IgG1 antibody is substituted with amino acids of corresponding EU numbering in the corresponding IgG2 or IgG4.

Other preferred examples suitably include antigen-binding molecules having an Fc region in which any one or more of the amino acids at positions 234, 235, and 297 specified according to EU numbering in the amino acids constituting the Fc region of a naturally-occurring human IgG1 antibody are substituted by other amino acids. The type of amino acid present after substitution is not particularly limited, and an antigen-binding molecule having an Fc region in which any one or more of the amino acids at positions 234, 235, and 297 are substituted with alanine is particularly preferred.

Other preferred examples suitably include antigen-binding molecules having an Fc region in which the amino acid at position 265 specified according to EU numbering in the amino acids constituting an IgG1 antibody Fc region is substituted by another amino acid. The type of amino acid present after substitution is not particularly limited, and an antigen-binding molecule having an Fc region in which the amino acid at position 265 is substituted with alanine is particularly preferred.

Antigen-Binding Domains

"A domain that binds to a molecule expressed on the surface of a cell having immune response-suppressing function", "a T cell receptor complex-binding domain", "a cancer-specific antigen-binding domain", "a tumor necrosis factor (TNF) superfamily-binding domain", and "a tumor necrosis factor (TNF) receptor superfamily-binding domain" (hereinafter, these binding domains are collectively referred to as "antigen-binding domains") which are included in antigen-binding molecules of the present invention mean regions that specifically bind to all or a portion of their respective antigens. An example of such binding domain is a region comprising the antigen-binding region of an antibody. When the molecular weight of the antigen is large, the antigen-binding region of the antibody can bind only to a specific portion of the antigen. This specific portion is called an epitope. One or more of antibody variable domains may provide an antigen-binding domain. Preferably, antigen-binding domains comprise an antibody light chain variable region (VL) and an antibody heavy chain variable region (VH). Suitable examples of such antigen-binding domains include "single chain Fv (scFv)", "single chain antibody", "Fv", "single chain Fv2 (scFv2)", "Fab", "F(ab')2", or such.

In several embodiments, "a cell having immune response-suppressing function" is not particularly limited as long as it has a function of suppressing an immune response, and examples include regulatory T cells (Treg), exhausted T cells, myeloma-derived stromal cells (MDSC), tumor-associated macrophages (TAM), induced regulatory T cells (Trl), tumor-associated dendritic cells (TADC), tumor-associated neutrophils (TAN), cancer-associated fibroblasts (CAF), regulatory B cells (Breg), and such. In particular, regulatory T cells and exhausted T cells are preferable as the cells of interest. Specific examples of the molecules expressed on the surface of such cells having immune response-suppressing functions include CTLA4, PD1, TIM3, LAG-3, CD244 (2B4), CD160, GARP, OX40, CD137 (4-1BB), CD25, VISTA, VISATA, BTLA, TNFR25, CD57, KLRG1, CCR2, CCR5, CCR6, CD39, CD73, CD4, CD18, CD49b, CD1d, CD5, CD21, TIM1, CD19, CD20, CD23, CD24, CD38, CD93, IgM, B220(CD45R), CD317, PD-L1, CD11b, Ly6G, ICAM-1, FAP, PDGFR, Podoplanin, TIGIT, and such. Among these molecules, examples of favorable molecules for binding targets of the binding domains of the present invention include CTLA4, TIM3, LAG3, CD137 (4-1BB), CD25, CCR5, CCR6, CD38, and TIGIT, which are cell surface molecules specifically expressed in cell fractions (CD4+, $CD25^{high}$, and CD45RA−) that have been reported to have high immune response-suppressing functions. Examples of favorable molecules for binding targets of the binding domains of the present invention include CTLA4, LAG3, and OX40 in particular.

In several embodiments, "regulatory T cell" according to the present invention means a type of T cell in charge of inhibitory regulation of an immune response. This cell plays an important role in the negative regulation mechanism for suppressing excessive immune responses and in homeostasis of immunity, and is classified into two types of regulatory T cells (Tregs) which express CD4 or CD8. CD4 Tregs are classified into endogenous Treg cells (natural Tregs or nTregs) which constitutively express CD25 and FoxP3, and adaptive or inducible Tregs (iTregs) which have low self-recognition ability and which are differentiated from naive CD4-positive T cells. Existing iTregs include Foxp3+ Treg and Fop3− Treg, and Fop3− Treg is called a Type I Treg (Trl). CD4+CD25+LAG3+ Treg has been identified as a Treg having properties very similar to Trl (Proc Natl Acad Sci USA.2009). Furthermore, CD127 expression is known to be decreased in Treg cells, and the fraction containing CD127loCD25hi-int (population showing low CD127 expression and high to intermediate CD25 expression) includes all of the Foxp3-positive Treg population. CD8 Tregs can also be separated into endogenous Tregs and inducible Tregs. The former are classified as CD8+CD122+ Treg, and the latter are classified as Qa-1a-restricted CD8+ Treg. Tregs are known to express regulatory molecules, and have increased expression levels of CTLA4, PD1, TIM3, LAG3, and the like, and such molecules are favorable as the molecules to which the binding domains of the antigen-binding molecules of the present invention bind.

Furthermore, in several embodiments, "exhausted T cell" according to the present invention means a T cell whose cytokine production function and effector function have been markedly weakened by continuous stimulation by antigens, and proliferation ability and long-term survival ability have become low. These exhausted T cells produce regulatory receptors such as PD1 and regulatory cytokines; therefore, they not only become dysfunctional, but also act suppressive towards immune responses. In exhausted T cells, expression of PD1 is mainly increased (Nature 439, 682-687 (2006)). In addition to PD1, expression of molecules such as LAG-3, CD244 (2B4), CD160, TIM-3, and CTLA-4 are also increased (Nature Immunology Volume: 12, Pages: 492-499 Year published: (2011)). These molecules are favorable as the molecules to which the binding domains of the antigen-binding molecules of the present invention bind.

A "T cell-receptor complex" may be a T cell receptor itself, or an adaptor molecule constituting a T cell-receptor complex together with a T cell receptor. CD3 is suitable as an adaptor molecule.

For the T cell receptor, an epitope to which the T cell receptor binding domain binds may be a variable region or a constant region, but an epitope present in the constant region is preferred. Examples of the constant region sequence include the T cell receptor α chain of RefSeq Accession No. CAA26636.1 (SEQ ID NO: 9), the T cell receptor β chain of RefSeq Accession No. C25777 (SEQ ID NO: 10), the T cell receptor γ1 chain of RefSeq Accession No. A26659 (SEQ ID NO: 11), the T cell receptor γ2 chain of RefSeq Accession No. AAB63312.1 (SEQ ID NO: 12), and the T cell receptor δ chain of RefSeq Accession No. AAA61033.1 (SEQ ID NO: 13).

In several embodiments, when the "CD3-binding domain" is used as the T cell receptor complex-binding domain in the present invention, the CD3-binding domain may be provided by one or more antibody variable domains. Preferably, the CD3-binding domain includes a light chain variable region (VL) and a heavy chain variable region (VH) of a CD3 antibody. Suitable examples of such CD3-binding domains include "single chain Fv (scFv)", "single chain antibody", "Fv", "single chain Fv 2 (scFv2)", "Fab", "F(ab')$_2$", and such.

In several embodiments, the CD3-binding domain of the present invention may be those that bind to any epitope as long as the epitope exists in the γ-chain, δ-chain, or ε-chain sequence constituting human CD3. In the present invention, preferably, a CD3-binding domain that comprises a light chain variable region (VL) of a CD3 antibody and a heavy chain variable region (VH) of a CD3 antibody, and which binds to an epitope present in the extracellular region of the ε chain of the human CD3 complex, is suitably used. For such CD3-binding domain, a CD3-binding domain comprising the light chain variable region (VL) and heavy chain variable region (VH) of the OKT3 antibody (Proc. Natl. Acad. Sci. USA (1980) 77, 4914-4917) or various known CD3 antibodies is suitably used. A CD3-binding domain derived from a CD3 antibody that has the desired properties and is obtained by immunizing a desired animal with the γ-chain, δ-chain, or ε-chain constituting the human CD3 by the above-mentioned method may be appropriately used. Human antibodies and appropriately humanized antibodies as described below may be suitably used as the CD3 antibody that serves as the origin for the CD3-binding domain. For the structure of the CD3-constituting γ-chain, δ-chain, or ε-chain, their polynucleotide sequences are shown in SEQ ID NOs: 14 (NM_000073.2), 16 (NM_000732.4), and 18 (NM_000733.3), and their polypeptide sequences are shown in SEQ ID NOs: 15

(NP_000064.1), 17 (NP_000723.1), and 19 (NP_000724.1) (the RefSeq accession number is shown in parentheses).

In several embodiments, a "cancer-specific antigen" refers to an antigen expressed by cancer cells, which enables discrimination between cancer cells and healthy cells; and for example, it includes antigens that are expressed as cells become malignant, or abnormal sugar chains that appear on protein molecules or cell surface when cells become cancerous. Specific examples include GPC3 which belongs to the GPI anchor-type receptor family and is expressed in several cancers including liver cancer (Int. J. Cancer. (2003) 103 (4): 455-65); ALK receptor (pleiotrophin receptor); pleiotrophin; KS 1/4 pancreatic cancer antigen; ovarian cancer antigen (CA125); prostatic acid phosphate; prostate-specific antigen (PSA); melanoma-associated antigen p97; melanoma antigen gp75; high molecular weight melanoma antigen (HMW-MAA); prostate-specific membrane antigen; carcinoembryonic antigen (CEA); polymorphic epithelial mucin antigen; human milk fat globule antigen; colorectal tumor-associated antigens such as CEA, TAG-72, C017-1A, GICA 19-9, CTA-1, and LEA; Burkitt's lymphoma antigen-38.13; CD19; human B-lymphoma antigen-CD20; CD33; melanoma-specific antigens such as ganglioside GD2, ganglioside GD3, ganglioside GM2, and ganglioside GM3; tumor-specific transplantation type cell-surface antigen (TSTA); virus-induced tumor antigens including T antigen and envelope antigens of DNA tumor viruses and RNA tumor viruses; CEA of colon; oncofetal antigens such as 5T4 oncofetal trophoblast glycoprotein and bladder tumor oncofetal antigen; α-fetoprotein; differentiation antigens such as human lung cancer antigens L6 and L20; antigens of fibrosarcoma; human leukemia T cell antigen-Gp37; breast cancer antigens such as neoglycoprotein, sphingolipids, and EGFR (epidermal growth factor receptor); NY-BR-16; NY-BR-16 and HER2 antigen (p185HER2); polymorphic epithelial mucin (PEM); malignant human lymphocyte antigen-APO-1; differentiation antigens such as I antigen found in fetal erythrocytes; primary endoderm I antigen found in adult erythrocytes; I(Ma) found in preimplantation embryos and gastric cancer; M18 and M39 found in mammary epithelium; SSEA-1, VEP8, VEP9, Myl, and VIM-D5 found in myeloid cells; D156-22 found in colorectal cancer; TRA-1-85 (blood group H); SCP-1 found in testis and ovarian cancer; C14 found in rectal cancer; F3 found in lung cancer; AH6 found in gastric cancer; Y hapten; Ley found in embryonal carcinoma cells; TL5 (blood group A); EGF receptor found in A431 cells; E1 series (blood group B) found in pancreatic cancer; FC10.2 found in embryonal carcinoma cells; gastric cancer antigen; CO-514 (blood group Lea) found in adenocarcinomas; NS-10 found in adenocarcinomas; CO-43 (blood group Leb); G49 found in EGF receptor of A431 cells; MH2 (blood group ALeb/Ley) found in colon cancer; 19.9 found in colon cancer; gastric cancer mucins; T5A7 found in myeloid cells; R24 found in melanoma; 4.2, GD3, D1.1, OFA-1, GM2, OFA-2, GD2, and M1:22:25:8 found in embryonal carcinoma cells; SSEA-3 and SSEA-4 found in 4 to 8-cell stage embryos; subcutaneous T cell lymphoma antigen; MART-1 antigen; sialyl Tn (STn) antigen; colon cancer antigen NY-CO-45; lung cancer antigen NY-LU-12 variant A; adenocarcinoma antigen ART1; paraneoplastic associated brain-testis-cancer antigen (onconeuronal antigen MA2; paraneoplastic neuronal antigen); neuro-oncological ventral antigen 2 (NOVA2); hemocyte carcinoma antigen gene 520; tumor-associated antigen CO-029; tumor-associated antigens MAGE-C1 (cancer/testis antigen CT7), MAGE-B1 (MAGE-XP antigen), MAGE-B2 (DAM6), MAGE-2, MAGE-4a, MAGE-4b and MAGE-X2; Cancer-Testis Antigen (NY-EOS-1); YKL-40, fragments of any of the aforementioned polypeptides, or structures produced by modification thereof (for example, the above-mentioned modified phosphate group or sugar chain); EpCAM; EREG; CA19-9; CA15-3; sialyl SSEA-1 (SLX); HER2; PSMA; CEA; and CLEC12A. Cancer-specific antigens which are binding targets of the cancer-specific antigen-binding domains of the present invention are, in particular, preferably those expressed on cell surface, and examples of such cancer-specific antigens include GPC3, CD 19, CD20, EGFR, HER2, EpCAM, and EREG.

In several embodiments, as factors belonging to the "TNF superfamily" or the "TNF receptor superfamily", ligands having a trimeric structure and receptors with a trimeric structure to which the ligands bind, which contribute to activation of various immune cells, are known (Nat. Rev. Immunol., 2012, 12, 339-51). Examples of factors belonging to the TNF superfamily or the TNF receptor superfamily include CD137, CD137L, CD40, CD40L, OX40, OX40L, CD27, CD70, HVEM, LIGHT, RANK, RANKL, CD30, CD153, GITR, and GITRL. Preferred factors include, for example, CD137 and CD40. A more preferred factor is, for example, CD137.

Antibodies

In several embodiments, an "antigen-binding molecule" of the present invention includes an antibody. Furthermore, a part of a preferred embodiment of the present invention includes an antibody comprising an antibody variable region described herein.

Herein, in several embodiments, an "antibody" refers to a naturally occurring immunoglobulin or an immunoglobulin produced by partial or complete synthesis. Antibodies can be isolated from natural sources such as naturally-occurring plasma and serum, or culture supernatants of antibody-producing hybridoma cells. Alternatively, antibodies can be partially or completely synthesized using techniques such as genetic recombination. Suitable examples of the antibodies include antibodies of an immunoglobulin isotype or subclass of such isotype. Known human immunoglobulins include those of the following nine classes (isotypes): IgG1, IgG2, IgG3, IgG4, IgA1, IgA2, IgD, IgE, and IgM. Of these isotypes, antibodies of the present invention include IgG1, IgG2, IgG3, and IgG4.

Methods for producing antibodies having the desired binding activity are known to those skilled in the art, and the antibodies may be obtained as polyclonal or monoclonal antibodies. Monoclonal antibodies derived from mammals may be suitably produced as the antibodies of the present invention. Such mammalian-derived monoclonal antibodies include antibodies produced by hybridomas and antibodies produced by host cells transformed with an expression vector carrying an antibody gene by genetic engineering techniques.

There is no particular limitation on the mammals to be immunized for obtaining antibodies. It is preferable to select the mammals by considering its compatibility with the parent cells to be used in cell fusion for hybridoma production. In general, rabbits, monkeys, and rodents such as mice, rats, and hamsters are suitably used.

The above animals are immunized with a sensitizing antigen by known methods. Generally performed immunization methods include, for example, intraperitoneal or subcutaneous injection of a sensitizing antigen into mammals. Specifically, a sensitizing antigen is appropriately diluted with Phosphate-Buffered Saline (PBS), physiological saline, or the like. If desired, a conventional adjuvant such as Freund's complete adjuvant is mixed with the antigen, and the mixture is emulsified. Then, the sensitizing antigen is administered to mammals several times at 4- to 21-day intervals. Appropriate carriers may be used in immunization with the sensitizing antigen. In particular, when a low-molecular-weight partial peptide is used as the sensitizing antigen, it is sometimes desirable to couple the sensitizing antigen peptide to a carrier protein such as albumin or keyhole limpet hemocyanin for immunization.

Alternatively, hybridomas producing a desired antibody can be prepared using DNA immunization as mentioned below. DNA immunization is an immunization method that confers immunostimulation by expressing a sensitizing antigen in an animal immunized as a result of administering a vector DNA constructed to allow expression of an antigen protein-encoding gene in the animal. As compared to conventional immunization methods in which a protein antigen is administered to animals to be immunized, DNA immunization is expected to be superior in that:

immunostimulation can be provided while retaining the structure of a membrane protein; and there is no need to purify the antigen for immunization.

In order to prepare a monoclonal antibody of the present invention using DNA immunization, first, a DNA expressing an antigen protein is administered to animals to be immunized. The antigen protein-encoding DNA can be synthesized by known methods such as PCR. The obtained DNA is inserted into an appropriate expression vector, and then this is administered to animals to be immunized. Preferably used expression vectors include, for example, commercially-available expression vectors such as pcDNA3.1. Vectors can be administered to an organism using conventional methods. For example, DNA immunization is performed by using a gene gun to introduce expression vector-coated gold particles into cells in the body of animals to be immunized.

After immunizing mammals as described above, an increase in the titer of an antigen-binding antibody is confirmed in the serum. Then, immune cells are collected from the mammals, and then subjected to cell fusion. In particular, splenocytes are preferably used as immune cells.

A mammalian myeloma cell is used as a cell to be fused with the above-mentioned immune cells. The myeloma cells preferably comprise a suitable selection marker for screening. A selection marker confers characteristics to cells for their survival (or death) under a specific culture condition. Hypoxanthine-guanine phosphoribosyltransferase deficiency (hereinafter abbreviated as HGPRT deficiency) and thymidine kinase deficiency (hereinafter abbreviated as TK deficiency) are known as selection markers. Cells with HGPRT or TK deficiency have hypoxanthine-aminopterin-thymidine sensitivity (hereinafter abbreviated as HAT sensitivity). HAT-sensitive cells cannot synthesize DNA in a HAT selection medium, and are thus killed. However, when the cells are fused with normal cells, they can continue DNA synthesis using the salvage pathway of the normal cells, and therefore they can grow even in the HAT selection medium.

HGPRT-deficient and TK-deficient cells can be selected in a medium containing 6-thioguanine, 8-azaguanine (hereinafter abbreviated as 8AG), or 5'-bromodeoxyuridine. Normal cells are killed because they incorporate these pyrimidine analogs into their DNA. Meanwhile, cells that are deficient in these enzymes can survive in the selection medium, since they cannot incorporate these pyrimidine analogs. In addition, a selection marker referred to as G418 resistance provided by the neomycin-resistant gene confers resistance to 2-deoxystreptamine antibiotics (gentamycin analogs). Various types of myeloma cells that are suitable for cell fusion are known.

For example, myeloma cells including the following cells can be preferably used:

P3(P3×63Ag8.653) (J. Immunol. (1979) 123 (4), 1548-1550);

P3×63Ag8U.1 (Current Topics in Microbiology and Immunology (1978)81, 1-7);

NS-1 (C. Eur. J. Immunol. (1976)6 (7), 511-519);

MPC-11 (Cell (1976) 8 (3), 405-415);

SP2/0 (Nature (1978) 276 (5685), 269-270);

FO (J. Immunol. Methods (1980) 35 (1-2), 1-21);

S194/5.XX0.BU.1 (J. Exp. Med. (1978) 148 (1), 313-323);

R210 (Nature (1979) 277 (5692), 131-133), etc.

Cell fusions between the immunocytes and myeloma cells are essentially carried out using known methods, for example, a method by Kohler and Milstein et al. (Methods Enzymol. (1981) 73: 3-46).

More specifically, cell fusion can be carried out, for example, in a conventional culture medium in the presence of a cell fusion-promoting agent. The fusion-promoting agents include, for example, polyethylene glycol (PEG) and Sendai virus (HVJ). If required, an auxiliary substance such as dimethyl sulfoxide is also added to improve fusion efficiency.

The ratio of immunocytes to myeloma cells may be arbitrarily set, preferably, for example, one myeloma cell for every one to ten immunocytes. Culture media to be used for cell fusions include, for example, media that are suitable for the growth of myeloma cell lines, such as RPMI1640 medium and MEM medium, and other conventional culture medium used for this type of cell culture. In addition, serum supplements such as fetal calf serum (FCS) may be preferably added to the culture medium.

For cell fusion, predetermined amounts of the above immune cells and myeloma cells are mixed well in the above culture medium. Then, a PEG solution (for example, the average molecular weight is about 1,000 to 6,000) pre-warmed to about 37° C. is added thereto at a concentration of generally 30% to 60% (w/v). The mixed solution is gently mixed to produce desired fusion cells (hybridomas). Then, an appropriate culture medium mentioned above is gradually added to the cells, and this is repeatedly centrifuged to remove the supernatant. Thus, cell fusion agents and such which are unfavorable to hybridoma growth can be removed.

The hybridomas thus obtained can be selected by culture using a conventional selective medium, for example, HAT medium (a culture medium containing hypoxanthine, aminopterin, and thymidine). Culture is continued in the above medium using the HAT medium for a period of time sufficient to kill cells other than the desired hybridomas (non-fused cells). Typically, the period is several days to several weeks. Then, hybridomas producing the desired antibody are screened and singly cloned by conventional limiting dilution methods.

The hybridomas thus obtained can be selected using a selection medium based on the selection marker possessed by the myeloma used for cell fusion. For example, HGPRT- or TK-deficient cells can be selected by culture using the HAT medium (a culture medium containing hypoxanthine, aminopterin, and thymidine). Specifically, when HAT-sensitive myeloma cells are used for cell fusion, cells successfully fused with normal cells can selectively proliferate in the HAT medium. Culture is continued in the above medium using the HAT medium for a period of time sufficient to kill cells other than the desired hybridomas (non-fused cells). Specifically, desired hybridomas can be selected by culture for generally several days to several weeks. Then, hybridomas producing the desired antibody are screened and singly cloned by conventional limiting dilution methods.

Screening and single cloning of desired antibodies can be suitably performed by screening methods based on known antigen-antibody reaction. For example, a desired antibody can be selected by screening using fluorescence activated cell sorting (FACS). FACS is a system that enables measurement of the binding of an antibody to cell surface by analyzing cells contacted with a fluorescent antibody using laser beam, and measuring the fluorescence emitted from individual cells.

To screen for hybridomas that produce a monoclonal antibody of the present invention by FACS, cells that express the antigen bound by the produced antibody are first prepared. Preferred cells used for screening are mammalian cells that are forced to express the antigen. By using mammalian cells that are used as the host cell but have not been transformed as a control, the activity of an antibody to bind to the cell-surface antigen can be selectively detected. Specifically, hybridomas producing a desired monoclonal antibody can be obtained by selecting hybridomas that produce an antibody which binds to cells forced to express the antigen but not to the host cell.

Alternatively, cells expressing the antigen of interest are immobilized and the activity of an antibody to bind to the antigen-expressing cells can be assessed based on the principle of ELISA. For example, antigen-expressing cells are immobilized to the wells of an ELISA plate. Culture supernatants of hybridomas are contacted with the immobilized cells in the wells, and antibodies that bind to the immobilized cells are detected. When the monoclonal antibodies are derived from mouse, antibodies bound to the cells can be detected using an anti-mouse immunoglobulin antibody. Hybridomas producing a desired antibody having the antigen-binding ability are selected by the above screening, and they can be cloned by a limiting dilution method or the like.

Monoclonal antibody-producing hybridomas thus prepared can be passaged in a conventional culture medium. The hybridomas can be stored in liquid nitrogen for a long period.

The above hybridomas are cultured by a conventional method, and desired monoclonal antibodies can be obtained from the culture supernatants. Alternatively, the hybridomas are administered to and grown in compatible mammals, and monoclonal antibodies can be obtained from the ascites. The former method is suitable for obtaining antibodies with high purity.

Antibodies that are encoded by antibody genes cloned from antibody-producing cells such as the above hybridomas can also be preferably used. A cloned antibody gene is inserted into an appropriate vector, and this is introduced into a host to express the antibody encoded by the gene. Methods for isolating antibody genes, inserting the genes into vectors, and transforming host cells have already been established, for example, by Vandamme et al. (Eur. J. Biochem. (1990) 192(3), 767-775). Methods for producing recombinant antibodies are also known as described below.

Generally, to obtain a cDNA encoding the antibody variable region (V region), total RNA is first extracted from hybridomas. For example, the following methods can be used as methods for extracting mRNAs from cells:
the guanidine ultracentrifugation method (Biochemistry (1979) 18(24), 5294-5299), and
the AGPC method (Anal. Biochem. (1987) 162(1), 156-159).

Extracted mRNAs can be purified using the mRNA Purification Kit (GE Healthcare Bioscience) or such. Alternatively, kits for extracting total mRNA directly from cells, such as the QuickPrep™ mRNA Purification Kit (GE Healthcare Bioscience), are also commercially available. mRNAs can be prepared from hybridomas using such kits. cDNAs encoding the antibody V region can be synthesized from the prepared mRNAs using a reverse transcriptase. cDNAs can be synthesized using the AMV Reverse Transcriptase First-strand cDNA Synthesis Kit (Seikagaku Corporation) or such. Furthermore, the SMART™ RACE cDNA amplification kit (Clontech) and the PCR-based 5'-RACE method (Proc. Natl. Acad. Sci. USA (1988) 85(23), 8998-9002; Nucleic Acids Res. (1989) 17(8), 2919-2932) can be appropriately used to synthesize and amplify cDNAs. In such a cDNA synthesis process, appropriate restriction enzyme sites described below may be introduced into both ends of a cDNA.

The cDNA fragment of interest is purified from the resulting PCR product, and then this is ligated to a vector DNA. A recombinant vector is thus constructed, and introduced into E. coli or such. After colony selection, the desired recombinant vector can be prepared from the colony-forming E. coli. Then, whether the recombinant vector has the cDNA nucleotide sequence of interest is tested by a known method such as the dideoxy nucleotide chain termination method.

The 5'-RACE method which uses primers to amplify the variable region gene is conveniently used for isolating the gene encoding the variable region. First, a 5'-RACE cDNA library is constructed by cDNA synthesis using RNAs extracted from hybridoma cells as a template. A commercially available kit such as the SMART™ RACE cDNA amplification kit is appropriately used to synthesize the 5'-RACE cDNA library.

The antibody gene is amplified by PCR using the prepared 5'-RACE cDNA library as a template. Primers for amplifying the mouse antibody gene can be designed based on known antibody gene sequences. The nucleotide sequences of the primers vary depending on the immunoglobulin subclass. Therefore, it is preferable that the subclass is determined in advance using a commercially available kit such as the Iso Strip mouse monoclonal antibody isotyping kit (Roche Diagnostics).

Specifically, for example, primers that allow amplification of genes encoding γ1, γ2a, γ 2b, and γ3 heavy chains and κ and λ light chains are used to isolate mouse IgG-encoding genes. In general, a primer that anneals to a constant region site close to the variable region is used as a 3'-side primer to amplify an IgG variable region gene. Meanwhile, a primer attached to a 5' RACE cDNA library construction kit is used as a 5'-side primer.

Immunoglobulins composed of a combination of heavy and light chains may be reshaped using the thus amplified PCR products. A desired antibody can be selected by screening using the antigen-binding activity of a reshaped immunoglobulin as an indicator.

The screening can be carried out, for example, by the following steps:
(1) contacting a desired antigen-expressing cell with an antibody comprising the V region encoded by a cDNA obtained from a hybridoma;
(2) detecting the binding of the antibody to the antigen-expressing cell; and
(3) selecting an antibody that binds to the antigen-expressing cell.

Methods for detecting the binding of an antibody to the antigen-expressing cells are known. Specifically, the binding of an antibody to the antigen-expressing cells can be detected by the above-described techniques such as FACS. Fixed samples of the antigen-expressing cells may be appropriately used to assess the binding activity of an antibody.

For antibody screening methods that use the binding activity as an indicator, panning methods that use phage vectors can also be used suitably. Screening methods using phage vectors are advantageous when the antibody genes are obtained from a polyclonal antibody-expressing cell population as heavy-chain and light-chain subclass libraries. Genes encoding the heavy-chain and light-chain variable regions can be linked by an appropriate linker sequence to form a single-chain Fv (scFv). Phages expressing scFv on their surface can be produced by inserting an scFv-encoding gene into a phage vector. The phages are contacted with an antigen of interest. Then, a DNA encoding scFv having the binding activity of interest can be isolated by collecting phages bound to the antigen. This process can be repeated as necessary to enrich scFv having the binding activity of interest.

After isolation of the cDNA encoding the V region of the antibody of interest, the cDNA is digested with restriction enzymes that recognize the restriction sites introduced into both ends of the cDNA. Preferred restriction enzymes recognize and cleave a nucleotide sequence that occurs in the nucleotide sequence of the antibody gene at a low frequency. Furthermore, a restriction site for an enzyme that produces a sticky end is preferably introduced into a vector to insert a single-copy digested fragment in the correct orientation. The cDNA encoding the V region of the antibody is digested as described above, and this is inserted into an appropriate expression vector to construct an antibody expression vector. In this case, if a gene encoding the antibody constant region (C region) and a gene encoding the above V region are fused in-frame, a chimeric antibody is obtained. Herein, a "chimeric antibody" means that the origin of the constant region is different from that of the variable region. Thus, in addition to mouse/human heterochimeric antibodies, human/human allochimeric antibodies are included in the chimeric antibodies of the present invention. A chimeric antibody expression vector can be constructed by inserting the above V region gene into an expression vector that already has the constant region. Specifically, for example, a recognition sequence for a restriction enzyme that excises the above V region gene can be appropriately placed on the 5' side of an expression vector carrying a DNA that encodes a desired antibody constant region (C region). A chimeric antibody expression vector is constructed by fusing in-frame two genes digested with the same combination of restriction enzymes.

To produce a monoclonal antibody, antibody genes are inserted into an expression vector so that the genes are expressed under the control of an expression regulatory region. The expression regulatory region for antibody expression includes, for example, enhancers and promoters. Furthermore, an appropriate signal sequence may be attached to the amino terminus so that the expressed antibody is secreted to the outside of cells. The signal sequence is cleaved from the carboxyl terminus of the expressed polypeptide, and the resulting antibody can be secreted to the outside of cells. Then, appropriate host cells are transformed with the expression vector, and recombinant cells expressing the antibody-encoding DNA can be obtained.

DNAs encoding the antibody heavy chain (H chain) and light chain (L chain) are separately inserted into different expression vectors to express the antibody gene. An antibody molecule having the H and L chains can be expressed by co-transfecting the same host cell with vectors inserted with the H chain and L chain. Alternatively, host cells can be transformed with a single expression vector into which DNAs encoding the H and L chains are inserted (see WO 94/11523).

There are many known combinations of host cells and expression vectors for antibody preparation by introducing isolated antibody genes into appropriate hosts. All these expression systems are applicable to isolation of domains that bind to a molecule expressed on the surface of a cell having immune response-suppressing function, T cell receptor complex-binding domains, cancer-specific antigen-binding domains, tumor necrosis factor (TNF) superfamily-binding domains, and tumor necrosis factor (TNF) receptor superfamily-binding domains of the present invention.

Appropriate eukaryotic cells used as host cells include animal cells, plant cells, and fungal cells. Specifically, the animal cells include, for example, the following cells.

(1) mammalian cells: CHO, COS, myeloma, baby hamster kidney (BHK), HeLa, Vero, or such;
(2) amphibian cells: *Xenopus* oocytes, or such; and
(3) insect cells: sf9, sf21, Tn5, or such.

In addition, as a plant cell, an antibody gene expression system using cells derived from the *Nicotiana* genus such as *Nicotiana tabacum* is known. Callus cultured cells can be appropriately used to transform plant cells.

Furthermore, the following cells can be used as fungal cells:

yeasts: the *Saccharomyces* genus such as *Saccharomyces cerevisiae*, and the *Pichia* genus such as *Pichia pastoris*; and filamentous fungi: the *Aspergillus* genus such as *Aspergillus niger*.

Furthermore, antibody gene expression systems that utilize prokaryotic cells are also known. For example, when using bacterial cells, *E. coli* cells, *Bacillus subtilis* cells, and such can suitably be utilized in the present invention. Expression vectors carrying the antibody genes of interest are introduced into these cells by transfection. The transfected cells are cultured in vitro, and the desired antibody can be prepared from the culture of transformed cells.

In addition to the above-described host cells, transgenic animals can also be used to produce a recombinant antibody. That is, the antibody can be obtained from an animal into which the gene encoding the antibody of interest is introduced. For example, the antibody gene can be constructed as a fusion gene by inserting in frame into a gene that encodes a protein produced specifically in milk. Goat β-casein or such can be used, for example, as the protein secreted in milk. DNA fragments containing the fused gene inserted with the antibody gene is injected into a goat embryo, and then this embryo is introduced into a female goat. Desired antibodies can be obtained as a protein fused with the milk protein from milk produced by the transgenic goat born from the embryo-recipient goat (or progeny thereof). In addition, to increase the volume of milk containing the desired antibody produced by the transgenic goat, hormones can be administered to the transgenic goat as necessary (Bio/Technology (1994) 12 (7), 699-702).

In several embodiments, when an antigen-binding molecule described herein is administered to human, an antigen-binding domain derived from a genetically recombinant antibody that has been artificially modified to reduce the heterologous antigenicity against human and such, can be appropriately used as the various binding domains in the molecule when domains comprising an antibody variable region are used. Such genetically recombinant antibodies include, for example, humanized antibodies. These modified antibodies are appropriately produced by known methods.

In several embodiments, an antibody variable region used to produce the various binding domains of antigen-binding molecules described herein is generally formed by three complementarity-determining regions (CDRs) that are separated by four framework regions (FRs). CDR is a region that substantially determines the binding specificity of an antibody. The amino acid sequences of CDRs are highly diverse. On the other hand, the FR-forming amino acid sequences often have high identity even among antibodies with different binding specificities. Therefore, generally, the binding specificity of a certain antibody can be introduced into another antibody by CDR grafting.

A humanized antibody is also called a reshaped human antibody. Specifically, humanized antibodies prepared by grafting the CDR of a non-human animal antibody such as a mouse antibody to a human antibody and such are known. Common genetic engineering techniques for obtaining humanized antibodies are also known. Specifically, for example, overlap extension PCR is known as a method for grafting a mouse antibody CDR to a human FR. In overlap extension PCR, a nucleotide sequence encoding a mouse antibody CDR to be grafted is added to primers for synthesizing a human antibody FR. Primers are prepared for each of the four FRs. It is generally considered that when grafting a mouse CDR to a human FR, selecting a human FR that has high identity to a mouse FR is advantageous for maintaining the CDR function. That is, it is generally preferable to use a human FR comprising an amino acid sequence which has high identity to the amino acid sequence of the FR adjacent to the mouse CDR to be grafted.

Nucleotide sequences to be ligated are designed so that they will be connected to each other in frame. Human FRs are individually synthesized using the respective primers. As a result, products in which the mouse CDR-encoding DNA is attached to the individual FR-encoding DNAs are obtained. Nucleotide sequences encoding the mouse CDR of each product are designed so that they overlap with each other. Then, complementary strand synthesis reaction is conducted to anneal the overlapping CDR regions of the products synthesized using a human antibody gene as template. Human FRs are ligated via the mouse CDR sequences by this reaction.

The full length V region gene, in which three CDRs and four FRs are ultimately ligated, is amplified using primers that anneal to its 5'- or 3'-end, which are added with suitable restriction enzyme recognition sequences. An expression vector for humanized antibody can be produced by inserting the DNA obtained as described above and a DNA that encodes a human antibody C region into an expression vector so that they will ligate in frame. After the recombinant vector is transfected into a host to establish recombinant cells, the recombinant cells are cultured, and the DNA encoding the humanized antibody is expressed to produce the humanized antibody in the cell culture (see, European Patent Publication No. EP 239400 and International Patent Publication No. WO 1996/002576).

By qualitatively or quantitatively measuring and evaluating the antigen-binding activity of the humanized antibody produced as described above, one can suitably select human antibody FRs that allow CDRs to form a favorable antigen-binding site when ligated through the CDRs. Amino acid residues in FRs may be substituted as necessary, so that the CDRs of a reshaped human antibody form an appropriate antigen-binding site. For example, amino acid sequence mutations can be introduced into FRs by applying the PCR method used for grafting a mouse CDR into a human FR. More specifically, partial nucleotide sequence mutations can be introduced into primers that anneal to the FR. Nucleotide sequence mutations are introduced into the FRs synthesized by using such primers. Mutant FR sequences having the desired characteristics can be selected by measuring and evaluating the activity of the amino acid-substituted mutant antibody to bind to the antigen by the above-mentioned method (Sato, K. et al., Cancer Res. (1993) 53: 851-856).

Alternatively, desired human antibodies can be obtained by immunizing transgenic animals having the entire repertoire of human antibody genes (see WO 1993/012227; WO 1992/003918; WO 1994/002602; WO 1994/025585; WO 1996/034096; WO 1996/033735) by DNA immunization.

Furthermore, techniques for preparing human antibodies by panning using human antibody libraries are also known. For example, the V region of a human antibody is expressed as a single-chain antibody (scFv) on phage surface by the phage display method. Phages expressing an scFv that binds to the antigen can be selected. The DNA sequence encoding the human antibody V region that binds to the antigen can be determined by analyzing the genes of selected phages. The DNA sequence of the scFv that binds to the antigen is determined. An expression vector is prepared by fusing the V region sequence in frame with the C region sequence of a desired human antibody, and inserting this into an appropriate expression vector. The expression vector is introduced into cells appropriate for expression such as those described above. The human antibody can be produced by expressing the human antibody-encoding gene in the cells. These methods are already known (see WO 1992/001047; WO 1992/020791; WO 1993/006213; WO 1993/011236; WO 1993/019172; WO 1995/001438; WO 1995/015388).

In addition to the phage display method, techniques that use a cell-free translation system, techniques for displaying antigen-binding molecules on the surface of viruses or cells, and techniques that use emulsions are also known as techniques for obtaining human antibodies by panning using human antibody libraries. For example, the ribosome display method where a complex is formed between the translated protein and mRNA via the ribosome by removing the stop codon and such, the cDNA display method or the mRNA display method where a genetic sequence and the translated protein are covalently linked using a compound such as puromycin, the CIS display method where a complex is formed between the gene and the translated protein using a nucleic acid-binding protein, or such may be used as techniques of using a cell-free translation system. For the technique of presenting antigen-binding molecules on the surface of cells or viruses, besides the phage display method, the *E. coli* display method, Gram-positive bacteria display method, yeast display method, mammalian cell display method, virus display method, and such may be used. As a technique that uses emulsions, the in vitro virus display method which involves incorporating genes and translation-related molecules into an emulsion, and such may be used. These methods are already publicly known (Nat Biotechnol. 2000 December; 18(12):1287-92; Nucleic Acids Res. 2006; 34(19): e127; Proc Natl Acad Sci USA. 2004 Mar. 2; 101(9):2806-10; Proc Natl Acad Sci USA. 2004 Jun. 22; 101(25):9193-8; Protein Eng Des Sel. 2008 April; 21(4): 247-55; Proc Natl Acad Sci USA. 2000 Sep. 26; 97(20): 10701-5; MAbs. 2010 September-October; 2(5):508-18; and Methods Mol Biol. 2012, 911:183-98).

Specific

In several embodiments, "specific" according to the present invention means a condition where one of the molecules involved in specific binding does not show any significant binding to molecules other than a single or a number of binding partner molecules. Furthermore, "specific" is also used when an antigen-binding domain is specific to a particular epitope among multiple epitopes contained in an antigen. When an epitope bound by an antigen-binding domain is contained in multiple different antigens, antigen-binding molecules containing the antigen-binding domain can bind to various antigens that have the epitope.

Epitopes

In several embodiments, an "epitope" means an antigenic determinant in an antigen, and refers to an antigen site to which various binding domains in antigen-binding molecules disclosed herein bind. Thus, for example, an epitope can be defined according to its structure. Alternatively, the epitope may be defined according to the antigen-binding activity of an antigen-binding molecule that recognizes the epitope. When the antigen is a peptide or polypeptide, the epitope can be specified by the amino acid residues that form the epitope. Alternatively, when the epitope is a sugar chain, the epitope can be specified by its specific sugar chain structure.

A linear epitope is an epitope that contains an epitope whose primary amino acid sequence is recognized. Such a linear epitope typically contains at least three and most commonly at least five, for example, about 8 to 10 or 6 to 20 amino acids in its specific sequence.

In contrast to the linear epitope, "conformational epitope" is an epitope in which the primary amino acid sequence containing the epitope is not the only determinant of the recognized epitope (for example, the primary amino acid sequence of a conformational epitope is not necessarily recognized by an epitope-defining antibody). Conformational epitopes may contain a greater number of amino acids compared to linear epitopes. A conformational epitope-recognizing antibody recognizes the three-dimensional structure of a peptide or protein. For example, when a protein molecule folds and forms a three-dimensional structure, amino acids and/or polypeptide main chains that form a conformational epitope become aligned, and the epitope is made recognizable by the antibody. Methods for determining epitope conformations include, for example, X ray crystallography, two-dimensional nuclear magnetic resonance spectroscopy, site-specific spin labeling, and electron paramagnetic resonance spectroscopy, but are not limited thereto. See, for example, Epitope Mapping Protocols in Methods in Molecular Biology (1996), Vol. 66, Morris (ed.).

Examples of a method for assessing the binding of an epitope in a molecule expressed on the surface of a cell having immune response-suppressing function by a test antigen-binding molecule are shown below. According to the examples below, methods for assessing the binding of an epitope in a target antigen by another binding domain, for example, a T cell receptor complex-binding domain, a cancer-specific antigen-binding domain, a tumor necrosis factor (TNF) superfamily-binding domain, or a tumor necrosis factor (TNF) receptor superfamily-binding domain, can also be appropriately conducted.

For example, when CTLA4 is selected as the molecule expressed on the surface of a cell having immune response-suppressing function, whether a test antigen-binding molecule that comprises an antigen-binding domain for the molecule recognizes a linear epitope in the antigen molecule can be confirmed for example as mentioned below. For example, a linear peptide comprising an amino acid sequence forming the extracellular domain of CTLA4 is synthesized for the above purpose. The peptide can be synthesized chemically, or obtained by genetic engineering techniques using a region in a cDNA of CTLA4 encoding the amino acid sequence that corresponds to the extracellular domain. Then, a test antigen-binding molecule containing an antigen-binding domain for CTLA4 is assessed for its binding activity towards a linear peptide comprising the extracellular domain-constituting amino acid sequence. For example, an immobilized linear peptide can be used as an antigen to evaluate the binding activity of the antigen-binding molecule towards the peptide by ELISA. Alternatively, the binding activity towards a linear peptide can be assessed based on the level at which the linear peptide inhibits binding of the antigen-binding molecule to CTLA4-expressing cells. The binding activity of the antigen-binding molecule towards the linear peptide can be demonstrated by these tests.

Whether the above-mentioned test antigen-binding molecule containing an antigen-binding domain towards an antigen recognizes a conformational epitope can be confirmed as below. For example, the above-mentioned antigen-binding molecule that comprises an antigen-binding domain for CTLA4 strongly binds to CTLA4-expressing cells upon contact, but does not substantially bind to an immobilized linear peptide comprising an amino acid sequence forming the extracellular domain of CTLA4. Herein, "does not substantially bind" means that the binding activity is 80% or less, generally 50% or less, preferably 30% or less, and particularly preferably 15% or less compared to the binding activity to antigen-expressing cells.

Methods for assaying the binding activity of a test antigen-binding molecule comprising an antigen-binding domain to antigen-expressing cells include, for example, the methods described in Antibodies A Laboratory Manual (Ed Harlow, David Lane, Cold Spring Harbor Laboratory (1988) 359-420). Specifically, the assessment can be performed based on the principle of ELISA or fluorescence activated cell sorting (FACS) using antigen-expressing cells as antigen.

In the ELISA format, the binding activity of a test antigen-binding molecule comprising an antigen-binding domain towards antigen-expressing cells can be assessed quantitatively by comparing the levels of signals generated by enzymatic reaction. Specifically, a test antigen-binding molecule is added to an ELISA plate onto which antigen-expressing cells are immobilized. Then, the test antigen-binding molecule bound to the cells is detected using an enzyme-labeled antibody that recognizes the test antigen-binding molecule. Alternatively, when FACS is used, a dilution series of a test antigen-binding molecule is prepared, and the antibody-binding titer for antigen-expressing cells can be determined to compare the binding activity of the test antigen-binding molecule towards antigen-expressing cells.

The binding of a test antigen-binding molecule to an antigen expressed on the surface of cells suspended in buffer or the like can be detected using a flow cytometer. Known flow cytometers include, for example, the following devices:

FACSCanto™ II
FACSAria™
FACSArray™
FACSVantage™ SE

FACSCalibur™ (all are trade names of BD Biosciences)
EPICS® ALTRA HyPerSort
Cytomics FC 500
EPICS® XL-MCL ADC EPICS® XL ADC
Cell Lab Quanta™/Cell Lab Quanta™ SC (all are trade names of Beckman Coulter).

Suitable methods for assaying the binding activity of the above-mentioned test antigen-binding molecule comprising an antigen-binding domain towards an antigen include, for example, the method below. First, antigen-expressing cells are reacted with a test antigen-binding molecule, and then this is stained with an FITC-labeled secondary antibody that recognizes the antigen-binding molecule. The test antigen-binding molecule is appropriately diluted with a suitable buffer to prepare and use it at a desired concentration. For example, the molecule can be used at a concentration within the range of 10 μg/ml to 10 ng/ml. Then, the fluorescence intensity and cell count are determined using FACSCalibur™ (BD). The fluorescence intensity obtained by analysis using the CELLQUEST™ Software (BD), i.e., the Geometric Mean value, reflects the quantity of antibody bound to the cells. That is, the binding activity of a test antigen-binding molecule, which is represented by the quantity of the test antigen-binding molecule bound, can be measured by determining the Geometric Mean value.

In several embodiments, whether a test antigen-binding molecule comprising an antigen-binding domain of the present invention shares a common epitope with another antigen-binding molecule can be assessed based on competition between the two molecules for the same epitope. The competition between antigen-binding molecules can be detected by a cross-blocking assay or the like. For example, the competitive ELISA assay is a preferred cross-blocking assay.

Specifically, in a cross-blocking assay, the antigen coating the wells of a microtiter plate is pre-incubated in the presence or absence of a candidate competitor antigen-binding molecule, and then a test antigen-binding molecule is added thereto. The quantity of test antigen-binding molecule bound to the antigen in the wells indirectly correlates with the binding ability of a candidate competitor antigen-binding molecule that competes for the binding to the same epitope. That is, the greater the affinity of the competitor antigen-binding molecule for the same epitope, the lower the binding activity of the test antigen-binding molecule towards the antigen-coated wells.

The quantity of the test antigen-binding molecule bound to the wells via the antigen can be readily determined by labeling the antigen-binding molecule in advance. For example, a biotin-labeled antigen-binding molecule can be measured using an avidin/peroxidase conjugate and appropriate substrate. In particular, a cross-blocking assay that uses enzyme labels such as peroxidase is called "competitive ELISA assay". The antigen-binding molecule can also be labeled with other labeling substances that enable detection or measurement. Specifically, radiolabels, fluorescent labels, and such are known.

When the candidate competitor antigen-binding molecule can block the binding of a test antigen-binding molecule comprising an antigen-binding domain by at least 20%, preferably at least 20 to 50%, and more preferably at least 50% compared to the binding activity in a control experiment conducted in the absence of the competitor antigen-binding molecule, the test antigen-binding molecule is determined to substantially bind to the same epitope bound by the competitor antigen-binding molecule, or to compete for binding to the same epitope.

In several embodiments, when the structure of an epitope bound by a test antigen-binding molecule comprising an antigen-binding domain of the present invention is already identified, whether the test and control antigen-binding molecules share a common epitope can be assessed by comparing the binding activities of the two antigen-binding molecules towards a peptide prepared by introducing amino acid mutations into the peptide forming the epitope.

As a method for measuring such binding activities, for example, the binding activities of test and control antigen-binding molecules towards a linear peptide into which a mutation is introduced are measured by comparison in the above ELISA format. Besides the ELISA methods, the binding activity towards the mutant peptide bound to a column can be determined by passing the test and control antigen-binding molecules through the column, and then quantifying the antigen-binding molecule eluted in the eluate. Methods for adsorbing a mutant peptide to a column, for example, in the form of a GST fusion peptide, are known.

Alternatively, when the identified epitope is a conformational epitope, whether test and control antigen-binding molecules share a common epitope can be assessed by the following method. First, cells expressing an antigen which is a binding target of an antigen-binding domain and cells expressing an antigen having an epitope introduced with a mutation are prepared. The test and control antigen-binding molecules are added to a cell suspension prepared by suspending these cells in an appropriate buffer such as PBS. Then, the cell suspension is appropriately washed with a buffer, and an FITC-labeled antibody that can recognize the test and control antigen-binding molecules is added thereto. The fluorescence intensity and number of cells stained with the labeled antibody are determined using FACSCalibur™ (BD). The test and control antigen-binding molecules are appropriately diluted using a suitable buffer, and used at desired concentrations. For example, they may be used at a concentration within the range of 10 μg/ml to 10 ng/ml. The fluorescence intensity determined by analysis using the CELLQUEST™ Software (BD), i.e., the Geometric Mean value, reflects the quantity of the labeled antibody bound to the cells. That is, the binding activities of the test and control antigen-binding molecules, which are represented by the quantity of the labeled antibody bound, can be measured by determining the Geometric Mean value.

In several embodiments, an "antigen-binding molecule" of the present invention comprises both heavy and light chains which form an "antibody variable region" of this invention within a single polypeptide chain; however, it may be an antibody fragment lacking a constant region. Examples of such antibody fragments include a diabody (Db), an scFv, a single-chain antibody, an sc(Fv)2, an sc(Fab')2, Fab, F(ab')2, and Fab'.

Db is a dimer composed of two polypeptide chains (Holliger P et al., Proc. Natl. Acad. Sci. USA 90: 6444-6448 (1993); EP404,097; WO93/11161). In each polypeptide chain, an L-chain variable region (VL) and an H-chain variable region (VH) are linked by a linker short enough so that these two regions on the same chain cannot associate with each other, for example, a linker of about five residues.

Because the linker between VL and VH is too short for formation of a single chain variable region fragment, VL and VH encoded on the same polypeptide chain dimerize to form two antigen-binding sites.

scFv, Single-Chain Antibody, and Sc(Fv)2

Furthermore, in several embodiments, the terms "scFv", "single-chain antibody", and "sc(Fv)2" described herein all refer to an antibody fragment of a single polypeptide chain that contains variable regions derived from the heavy and light chains, but not the constant region. In general, a single-chain antibody also contains a polypeptide linker between the VH and VL domains, which enables formation of a desired structure that is thought to allow antigen binding. The single-chain antibody is discussed in detail by Pluckthun in "The Pharmacology of Monoclonal Antibodies, Vol. 113, Rosenburg and Moore, eds., Springer-Verlag, New York, 269-315 (1994)". See also International Patent Publication WO 1988/001649; U.S. Pat. Nos. 4,946,778 and 5,260,203. In a particular embodiment, the single-chain antibody can be bispecific and/or humanized.

scFv is an antigen-binding domain in which VH and VL forming Fv are linked together by a peptide linker (Proc. Natl. Acad. Sci. U.S.A. (1988) 85(16), 5879-5883). VH and VL can be retained in close proximity by the peptide linker.

sc(Fv)2 is a single-chain antibody in which four variable regions of two VL and two VH are linked by linkers such as peptide linkers to form a single chain (J Immunol. Methods (1999) 231(1-2), 177-189). The two VH and two VL may be derived from different monoclonal antibodies. Such sc(Fv)2 preferably includes, for example, a bispecific sc(Fv)2 that recognizes two types of epitopes present in a single antigen as disclosed in the Journal of Immunology (1994) 152(11), 5368-5374. sc(Fv)2 can be produced by methods known to those skilled in the art. For example, sc(Fv)2 can be produced by linking scFv by a linker such as a peptide linker.

In several embodiments, the form of an antigen-binding domain forming an sc(Fv)2 described herein include an antibody in which the two VH units and two VL units are arranged in the order of VH, VL, VH, and VL ([VH]-linker-[VL]-linker-[VH]-linker-[VL]) beginning from the N terminus of a single-chain polypeptide. The order of the two VH units and two VL units is not limited to the above form, and they may be arranged in any order. Example order of the form is listed below.

[VL]-linker-[VH]-linker-[VH]-linker-[VL]
[VH]-linker-[VL]-linker-[VL]-linker-[VH]
[VH]-linker-[VH]-linker-[VL]-linker-[VL]
[VL]-linker-[VL]-linker-[VH]-linker-[VH]
[VL]-linker-[VH]-linker-[VL]-linker-[VH]

The molecular form of sc(Fv)$_2$ is also described in detail in WO2006/132352. According to these descriptions, those skilled in the art can appropriately prepare desired sc(Fv)2 to produce the antigen-binding molecules disclosed herein.

Herein, the term "variable fragment (Fv)" refers to the minimum unit of an antibody-derived antigen-binding domain composed of a pair of the antibody light chain variable region (VL) and antibody heavy chain variable region (VH). In 1988, Skerra and Pluckthun found that homogeneous and active antibodies can be prepared from the E. coli periplasm fraction by inserting an antibody gene downstream of a bacterial signal sequence and inducing expression of the gene in E. coli (Science (1988) 240(4855), 1038-1041). In the Fv prepared from the periplasm fraction, VH associates with VL in a manner so as to bind to an antigen.

Furthermore, in several embodiments, the antigen-binding molecule of the present invention may be conjugated with a carrier polymer such as PEG or an organic compound such as an anticancer agent. Alternatively, a glycosylation sequence can be inserted to suitably add a sugar chain for the purpose of producing a desired effect.

The linkers to be used for linking the variable regions of an antibody comprise arbitrary peptide linkers that can be introduced by genetic engineering, or synthetic linkers (for example, linkers disclosed in Protein Engineering, 9(3), 299-305, 1996). However, peptide linkers are preferred in the present invention. The length of the peptide linkers is not particularly limited, and can be suitably selected by those skilled in the art according to the purpose. The length is preferably five amino acids or more (without particular limitation, the upper limit is generally 30 amino acids or less, preferably 20 amino acids or less), and particularly preferably 15 amino acids. When sc(Fv)2 contains three peptide linkers, their length may be all the same or different.

For example, such peptide linkers include:
Ser
Gly•Ser
Gly•Gly•Ser
Ser•Gly•Gly
Gly•Gly•Gly•Ser (SEQ ID NO: 20)
Ser•Gly•Gly•Gly (SEQ ID NO: 21)
Gly•Gly•Gly•Gly•Ser (SEQ ID NO: 22)
Ser•Gly•Gly•Gly•Gly (SEQ ID NO: 23)
Gly•Gly•Gly•Gly•Gly•Ser (SEQ ID NO: 24)
Ser•Gly•Gly•Gly•Gly•Gly (SEQ ID NO: 25)
Gly•Gly•Gly•Gly•Gly•Gly•Ser (SEQ ID NO: 26)
Ser•Gly•Gly•Gly•Gly•Gly•Gly (SEQ ID NO: 27)
(Gly•Gly•Gly•Gly•Ser (SEQ ID NO: 22))n
(Ser•Gly•Gly•Gly•Gly (SEQ ID NO: 23))n
where n is an integer of 1 or larger. The length or sequences of peptide linkers can be selected accordingly by those skilled in the art depending on the purpose.

Synthetic linkers (chemical crosslinking agents) is routinely used to crosslink peptides, and for example:
N-hydroxy succinimide (NHS),
disuccinimidyl suberate (DSS),
bis(sulfosuccinimidyl) suberate (BS3),
dithiobis(succinimidyl propionate) (DSP),
dithiobis(sulfosuccinimidyl propionate) (DTSSP),
ethylene glycol bis(succinimidyl succinate) (EGS),
ethylene glycol bis(sulfosuccinimidyl succinate) (sulfo-EGS),
disuccinimidyl tartrate (DST), disulfosuccinimidyl tartrate (sulfo-DST),
bis[2-(succinimidoxycarbonyloxy)ethyl] sulfone (BSOCOES),
and bis[2-(sulfosuccinimidoxycarbonyloxy)ethyl] sulfone (sulfo-BSOCOES).
These crosslinking agents are commercially available.

In general, three linkers are required to link four antibody variable regions together. The linkers to be used may be of the same type or different types.

Fab, F(ab')2, and Fab'

Furthermore, "Fab" is composed of a single light chain, and a CH1 domain and variable region from a single heavy chain. The heavy chain of Fab molecule cannot form disulfide bonds with another heavy chain molecule.

"F(ab')2" or "Fab'" is produced by treating an immunoglobulin (monoclonal antibody) with a protease such as pepsin and papain, and refers to an antibody fragment generated by digesting an immunoglobulin (monoclonal antibody) at near the disulfide bonds present between the hinge regions in each of the two H chains. For example, papain cleaves IgG upstream of the disulfide bonds present between the hinge regions in each of the two H chains to generate two homologous antibody fragments, in which an L chain comprising VL (L-chain variable region) and CL (L-chain constant region) is linked to an H-chain fragment comprising VH (H-chain variable region) and CHγ1 (γ1 region in an H-chain constant region) via a disulfide bond at their C-terminal regions. Each of these two homologous antibody fragments is called Fab'.

"F(ab')2" contains two light chains and two heavy chains comprising the constant region of a CH1 domain and a portion of a CH2 domain so that disulfide bonds are formed between the two heavy chains. In several embodiments, the F(ab')2 constituting an antigen-binding molecule disclosed herein can be preferably obtained as below. A full-length monoclonal antibody or such comprising a desired antigen-binding domain is partially digested with a protease such as pepsin, and then Fc fragments are removed by adsorption onto a Protein A column. The protease is not particularly limited, as long as it can digest the full-length antibody in a restrictive manner to produce F(ab')2 under an appropriately established enzyme reaction condition such as pH. Such proteases include, for example, pepsin and ficin.

Multispecific Antibodies

A preferred embodiment of the "antigen-binding molecule" or "antibody" of the present invention includes a multispecific antibody. When using an Fc region with decreased Fcγ receptor-binding activity as the Fc region of a multispecific antibody, an Fc region derived from a multispecific antibody may also be used appropriately. For the multispecific antibodies of the present invention, in particular, bispecific antibodies are preferred.

For association of multispecific antibodies, one can apply the technique of introducing charge repulsion at the interface of the second constant region of the antibody H chain (CH2) or the third constant region of the H chain (CH3) to suppress undesired associations between H chains (WO2006/106905).

In the technique of suppressing unintended association between H chains by introducing charge repulsion at the interface of CH2 or CH3, examples of the amino acid residues that are contacted at the interface of other constant regions of the H chain include the region facing the residue at position 356 (EU numbering), the residue at position 439 (EU numbering), the residue at position 357 (EU numbering), the residue at position 370 (EU numbering), the residue at position 399 (EU numbering), and the residue at position 409 (EU numbering) in the CH3 region.

More specifically, for example, for an antibody comprising two types of H chain CH3 regions, the antibody can be made so that one to three pairs of amino acid residues selected from the amino acid residue pairs shown below in (1) to (3) in the first H chain CH3 region have the same charge: (1) amino acid residues at positions 356 and 439 (EU numbering) which are amino acid residues contained in the H chain CH3 region; (2) amino acid residues at positions 357 and 370 (EU numbering) which are amino acid residues contained in the H chain CH3 region; and (3) amino acid residues at positions 399 and 409 (EU numbering) which are amino acid residues contained in the H chain CH3 region.

Furthermore, the antibody can be made so that one to three pairs of amino acid residues corresponding to the amino acid residue pairs shown above in (1) to (3) having the same type of charge in the first H chain CH3 region, which are amino acid residue pairs selected from the amino acid residue pairs shown above in (1) to (3) in the second H chain CH3 region which differs from the first H chain CH3 region, have a charge opposite to the corresponding amino acid residues in the aforementioned first H chain CH3 region.

The respective amino acid residues of (1) to (3) mentioned above are positioned close to each other when associated. For the desired H chain CH3 region or H chain constant region, those skilled in the art can find sites corresponding to the above-mentioned amino acid residues of (1) to (3) by homology modeling and such using commercially available software, and amino acid residues of these sites can be subjected to modifications as appropriate.

In the above-mentioned antibodies, "amino acid residues having a charge" are preferably selected, for example, from amino acid residues contained in either one of groups (a) and (b) below:

(a) glutamic acid (E) and aspartic acid (D); and
(b) lysine (K), arginine (R), and histidine (H).

Regarding the above-mentioned antibodies, "having the same type of charge" means, for example, that two or more amino acid residues all have amino acid residues included in either one of the above-mentioned groups (a) and (b). The phrase "having the opposite charge" means that, for example, when at least one of the two or more amino acid residues has an amino acid residue included in either one of the above-mentioned groups (a) and (b), the remaining amino acid residue(s) will have an amino acid residue included in the other group.

In a preferred embodiment of the above-mentioned antibody, the first H chain CH3 region and the second H chain CH3 region may be cross-linked by a disulfide bond.

In the present invention, the amino acid residue to be subjected to alteration is not limited to an amino acid residue of the constant region or variable region of the antibody described above. With regard to polypeptide mutants or heteromultimers, those skilled in the art can find amino acid residues that form the interface through homology modeling and such using commercially available software, and can subject the amino acid residues at those sites to alterations so that association is regulated.

In several embodiments, other known techniques can also be used for the association of multispecific antibodies of the present invention. Polypeptides with different amino acids having an Fc region can be efficiently associated with each other by substituting an amino acid side chain present in one of the H chain variable regions of the antibody with a larger side chain (knob), and substituting an amino acid side chain present in the corresponding variable region of the other H chain with a smaller side chain (hole), to allow placement of the knob within the hole (WO1996/027011; Ridgway J B et al., Protein Engineering (1996) 9, 617-621; Merchant A M et al. Nature Biotechnology (1998) 16, 677-681; and US20130336973).

In addition, other known techniques can also be used to form multispecific antibodies of the present invention. Association of polypeptides having different sequences can be induced efficiently by complementary association of CH3s, using a strand-exchange engineered CH3 domain produced by changing part of CH3 in one of the H chains of an antibody into its corresponding IgA-derived sequence, and introducing into the complementary portion of the CH3 in the other H chain its corresponding IgA-derived sequence (Protein Engineering Design & Selection, 23; 195-202, 2010). This known technique can also be used to efficiently form multispecific antibodies of interest.

In addition, the following techniques and such may be used for the formation of multispecific antibodies: techniques for antibody production using association of antibody CH1 and CL, and association of VH and VL as described in WO 2011/028952, WO2014/018572, and Nat Biotechnol. 2014 February; 32(2):191-8; techniques for producing bispecific antibodies using separately prepared monoclonal antibodies in combination (Fab Arm Exchange) as described in WO2008/119353 and WO2011/131746; techniques for regulating association between antibody heavy chain CH3s as described in WO2012/058768 and WO2013/063702; techniques for producing bispecific antibodies composed of two types of light chains and one type of heavy chain as described in WO2012/023053; techniques for producing bispecific antibodies using two bacterial cell strains that individually express one of the chains of an antibody comprising a single H chain and a single L chain as described by Christoph et al. (Nature Biotechnology Vol. 31, p 753-758 (2013)).

An embodiment of multispecific antibody formation includes methods for obtaining bispecific antibodies by mixing two types of monoclonal antibodies in the presence of a reducing agent to cleave the disulfide bonds in the core hinge region, followed by re-association for heterodimerization (FAE) as described above. Meanwhile, introduction of electrostatic interactions at the interacting interface of the CH3 region (WO2006/106905) can induce even more efficient heterodimerization during the re-association (WO2015/046467). In FAE using naturally-occurring IgG, re-association takes place randomly; and thus theoretically, bispecific antibodies can only be obtained at 50% efficiency; however, in this method, bispecific antibodies can be produced in high yield.

Alternatively, even when a multispecific antibody of interest cannot be formed efficiently, a multispecific antibody of the present invention can be obtained by separating and purifying the multispecific antibody of interest from the produced antibodies. For example, a method has been reported that enables purification of two types of homologous forms and the heterologous antibody of interest by ion exchange chromatography, by conferring a difference in the isoelectric points by introducing amino acid substitutions into the variable regions of the two types of H chains (WO2007114325). To date, as a method for purifying heterologous forms, a method using Protein A to purify a heterodimerized antibody comprising a mouse IgG2a H chain that binds to Protein A and a rat IgG2b H chain that does not bind to Protein A has been reported (WO98050431 and WO95033844). Furthermore, the heterodimerized antibody per se can be purified efficiently using a Protein A column by changing the interaction between each of the H chains and Protein A, by using H chains in which amino acid residues at the IgG-Protein A binding site, positions 435 and 436 (EU numbering), are substituted with amino acids that yield a different binding strength to Protein A such as Tyr, His, or such.

Alternatively, a common L chain that can confer binding ability to a plurality of different H chains can be obtained and used as the common L chain of a multispecific antibody. Efficient expression of a multispecific IgG can be achieved by introducing the genes of such a common L chain and a plurality of different H chains into cells and expressing the IgG (Nature Biotechnology (1998) 16, 677-681). A method for selecting a common L chain that shows strong binding ability to any different H chains can also be used when selecting a common H chain (WO 2004/065611).

Furthermore, an Fc region whose C-terminal heterogeneity has been improved can be appropriately used as an Fc region of the present invention. More specifically, Fc regions lacking glycine at position 446 and lysine at position 447, as specified by EU numbering, in the amino acid sequences of two polypeptides constituting an Fc region derived from IgG1, IgG2, IgG3, or IgG4, are provided.

A plurality, such as two or more, of these techniques can be used in combination. Furthermore, these techniques can be appropriately and separately applied to the two H chains to be associated. Furthermore, these techniques can be used in combination with the above-mentioned Fc region of which Fcγ receptor-binding activity has been decreased.

Furthermore, an antigen-binding molecule of the present invention may be a molecule produced separately based on an antigen-binding molecule subjected to the above-described modifications so as to have the same amino acid sequence.

T Cell-Redirecting Antigen-Binding Molecules Towards Cells Having Immunosuppressive Functions In several embodiments, an antigen-binding molecule of the present invention is a T cell-redirecting antigen-binding molecule towards cells having immunosuppressive functions (T cell-redirecting antigen-binding molecule).

In several embodiments, a T cell-redirecting antigen-binding molecule of the present invention can be any molecule as long as it comprises:
(1) a domain that binds to a molecule expressed on the surface of a cell having an immune response-suppressing function; and
(2) a T cell receptor complex-binding domain, and its structure is not limited. By comprising these two binding domains, the T cell-redirecting antigen-binding molecule can activate immune responses through inhibition of the immune response-suppressing effects of the cell expressing the molecule described in (1), and induce excellent cytotoxicity on cancer cells or cancer cell-comprising tumor tissues.
The binding domains described in (1) and (2) of the present invention can be appropriately selected for the above-described molecules expressed on the surface of the cells having an immune response-suppressing function, or antigens belonging to the T cell receptor complex, respectively. These binding domains can be linked directly by a peptide bond or connected via a linker.

In several embodiments, the T cell-redirecting antigen-binding molecules of the present invention may further comprise an FcRn-binding domain. When using the Fc region of the above-described antibody as the FcRn-binding domain, an Fc region with decreased Fcγ receptor-binding activity is preferred. Reducing the Fcγ receptor-binding activity enables suppression of side effects produced by systemic immune activation, such as cytokine release, caused by crosslinking between Fcγ receptor-expressing cells and T cell receptor complex-expressing cells.

In several embodiments, T cell-redirecting antigen-binding molecules of the present invention can be produced using the known methods described above.

For example, when (i) F(ab')2 is used as the domain that binds to a molecule expressed on the surface of a cell having immune response-suppressing functions, (ii) F(ab')2 is used as a T cell receptor complex-binding domain, and (iii) a domain comprising an Fc region with decreased Fcγ receptor-binding activity is used as the FcRn-binding domain, and when the antigen-binding domains described in (i) and (ii) and the Fc region-comprising domain described in (iii) are directly linked by peptide bonds, the linked polypeptides form an antibody structure. Such antibodies can be produced by purification from the above-described hybridoma culture medium, and also by purifying antibodies from the culture medium of desired host cells that stably carry polynucleotides encoding polypeptides constituting the antibody.

In addition to the linkers exemplified above, linkers with peptide tags such as His tag, HA tag, myc tag, and FLAG tag may also be suitably used as the linkers to be employed when connecting each of the domains via linkers. Furthermore, hydrogen bonding, disulfide bonding, covalent bonding, ionic interaction, or the property of mutual binding as a result of combination thereof may be suitably used. For example, the affinity between antibody CH1 and CL may be used, and Fc regions derived from the above-described multispecific antibodies may also be used for heterologous Fc region association.

In several embodiments, the present invention also relates to polynucleotides encoding the T cell-redirecting antigen-binding molecules of the present invention, and the polynucleotides can be incorporated into arbitrary expression vectors. Suitable hosts can be transformed with the expression vectors to produce cells that express the T cell-redirecting antigen-binding molecules. T cell-redirecting antigen-binding molecules encoded by the polynucleotides can be obtained by culturing cells that express the T cell-redirecting antigen-binding molecules, and collecting expression products from the culture supernatant. That is, the present invention relates to vectors comprising a polynucleotide that encodes a T cell-redirecting antigen-binding molecule of the present invention, cells carrying such a vector, and methods for producing T cell-redirecting antigen-binding molecules, which comprise culturing the cells and collecting T cell-redirecting antigen-binding molecules from the culture supernatant. These can be obtained by techniques similar to those for recombinant antibodies mentioned above.

Pharmaceutical Compositions Comprising T Cell-Redirecting Antigen-Binding Molecules Towards Cells Having Immunosuppressive Functions From another perspective, the present invention provides pharmaceutical compositions comprising the above-described T cell-redirecting antigen-binding molecule as an active ingredient. Furthermore, the present invention relates to pharmaceutical compositions for inhibiting immune response-suppressing activity (agents for inhibiting immune response-suppressing activity), agents for activating immune response, agents for inducing cytotoxicity, agents for suppressing cell proliferation (agents for inhibiting cell proliferation), and anticancer agents, each comprising the T cell-redirecting antigen-binding molecule as an active ingredient (hereinafter, pharmaceutical compositions and such). The pharmaceutical compositions can be used as agents for treating cancer or agents for preventing cancer. The agents for inhibiting immune response-suppressing activity, agents for activating immune response, therapeutic agents for inducing cytotoxicity, agents for suppressing cell proliferation, and anticancer agents of the present invention are preferably administered to individuals suffering from cancer, or individuals who may relapse.

Furthermore, in the present invention, agents for inhibiting immune response-suppressing activity, agents for activating immune response, therapeutic agents for inducing cytotoxicity, agents for suppressing cell proliferation, and anticancer agents, the agents comprising the above-described T cell-redirecting antigen-binding molecule as an active ingredient can be presented as methods for inhibiting immune response-suppressing activity, methods for activating immune response, methods for inducing cytotoxicity, methods for suppressing cell proliferation, methods for activating immunity against cancer cells or cancer cell-comprising tumor tissues, or as methods for preventing or treating cancer, the methods comprising the step of administering the T cell-redirecting antigen-binding molecule to an individual; or presented as use of the T cell-redirecting antigen-binding molecules in the production of pharmaceutical compositions for inhibiting immune response-suppressing activity, pharmaceutical compositions for activating immune response, pharmaceutical compositions for inducing cytotoxicity, agents for suppressing cell proliferation, and anticancer agents; or alternatively, presented as T cell-redirecting antigen-binding molecules for use in inhibiting immune response-suppressing activity, activating immune response, inducing cytotoxicity, suppressing cell proliferation, activating immunity against cancer cells or cancer cell-comprising tumor tissues, or treating or preventing cancer.

In the present invention, "comprising a T cell-redirecting antigen-binding molecule as an active ingredient" means containing a T cell-redirecting antigen-binding molecule as a major active component, and does not limit the content of the T cell-redirecting antigen-binding molecule.

Furthermore, pharmaceutical compositions or such comprising a T cell-redirecting antigen-binding molecule of the present invention can be used by combining multiple types of T cell-redirecting antigen-binding molecules as necessary. For example, by using a cocktail of a plurality of T cell-redirecting antigen-binding molecules of the present invention that bind to the same antigen, one can enhance the effect on cells expressing the antigen.

If necessary, the T cell-redirecting antigen-binding molecules of the present invention may be encapsulated in microcapsules (microcapsules made from hydroxymethylcellulose, gelatin, poly[methylmethacrylate], and the like), and made into components of colloidal drug delivery systems (liposomes, albumin microspheres, microemulsions, nano-particles, and nano-capsules) (for example, see "Remington's Pharmaceutical Science 16th edition", Oslo Ed. (1980)). Moreover, methods for preparing agents as sustained-release agents are known, and these can be applied to the T cell-redirecting antigen-binding molecules of the present invention (J. Biomed. Mater. Res. (1981) 15, 267-277; Chemtech. (1982) 12, 98-105; U.S. Pat. No. 3,773,719; European Patent Application (EP) Nos. EP58481 and EP133988; Biopolymers (1983) 22, 547-556).

The pharmaceutical compositions, immune response activating agents, cytotoxicity inducing agents, cell proliferation-suppressing agents (cell proliferation inhibiting agents), or anticancer agents, each comprising the T cell-redirecting antigen-binding molecules of the present invention may be administered either orally or parenterally to patients. Parental administration is preferred. Specifically, such administration methods include injection, nasal administration, transpulmonary administration, and percutaneous administration. Injections include, for example, intravenous injections, intramuscular injections, intraperitoneal injections, and subcutaneous injections. For example, pharmaceutical compositions, immune response activating agents, therapeutic agents for inducing cellular cytotoxicity, cell proliferation-suppressing agents (cell proliferation-inhibiting agents), or anticancer agents, each comprising the T cell-redirecting antigen-binding molecules of the present invention can be administered locally or systemically by injection. Furthermore, appropriate administration methods can be selected according to the patient's age and symptoms. The administered dose can be selected, for example, from the range of 0.0001 mg to 1,000 mg per kg of body weight for each administration. Alternatively, the dose can be selected, for example, from the range of 0.001 mg/body to 100,000 mg/body per patient. However, the dose of a pharmaceutical composition or such comprising a T cell-redirecting antigen-binding molecule of the present invention is not limited to these doses.

The pharmaceutical compositions or such comprising the T cell-redirecting antigen-binding molecules of the present invention can be formulated according to conventional methods (for example, Remington's Pharmaceutical Science, latest edition, Mark Publishing Company, Easton, U.S.A.), and may also contain pharmaceutically acceptable carriers and additives. Examples include, but are not limited to, surfactants, excipients, coloring agents, flavoring agents, preservatives, stabilizers, buffers, suspension agents, isotonic agents, binders, disintegrants, lubricants, fluidity promoting agents, and corrigents, and other commonly used carriers can be suitably used. Specific examples of the carriers include light anhydrous silicic acid, lactose, crystalline cellulose, mannitol, starch, carmellose calcium, carmellose sodium, hydroxypropyl cellulose, hydroxypropyl methylcellulose, polyvinylacetal diethylaminoacetate, polyvinylpyrrolidone, gelatin, medium-chain triglyceride, polyoxyethylene hardened castor oil 60, saccharose, carboxymethyl cellulose, corn starch, inorganic salt, and such.

Anticancer Agents

In several embodiments, anticancer agents of the present invention are not particularly limited and any anticancer agent can be used as long as, when used in combination with a T cell-redirecting antigen-binding molecule, the therapeutic effect or prophylactic effect of an anticancer agent is enhanced or the therapeutic effect or the prophylactic effect of the T cell-redirecting antigen-binding molecule is enhanced.

In several embodiments, the anticancer agents include, but is not limited to, nitrogen mustard analogues, alkyl sulfonates, ethylene imines, nitrosoureas, epoxides, other alkylating agents, folic acid analogues, purine analogues, pyrimidine analogues, other antimetabolic agents, *vinca* alkaloids or analogues thereof, podophyllotoxin derivatives, camptothecan analogs, colchicine derivatives, taxanes, other plant alkaloids or natural products, actinomycines, anthracyclines or related substances, other cytotoxic antibiotics, platinum compounds, methylhydrazines, kinase inhibitors, enzymes, histone deacetylase inhibitors, retinoids, immune checkpoint inhibitors, monoclonal antibodies and other molecular-targeted drugs, or other anticancer agents.

In several embodiments, an "immune checkpoint" according to the present invention refers to a molecule that is expressed on cytotoxic T cells and binds to a ligand to thereby transduce to the T cells signals inhibiting the immune response. Examples of the immune checkpoints include but are not limited to molecules such as PD-1, CTLA-4, TIM3, LAG3, and VISTA. In several embodiments, an "immune checkpoint inhibitor" according to the present invention refers to a pharmaceutical agent that inhibits binding between an immune checkpoint and its ligand, and thereby inhibits signal transduction mediated by the immune checkpoint, and examples include PD-1 inhibitors, CTLA-4 inhibitors, TIM3 inhibitors, LAG3 inhibitors, and VISTA inhibitors. An immune checkpoint inhibitor may be a pharmaceutical agent that binds to the immune checkpoint, or a pharmaceutical agent that binds to its binding partner ligand. For example, a PD-1 inhibitor may be a pharmaceutical agent that binds to PD-1, or it may be a pharmaceutical agent that binds to PD-L1 and/or PD-L2, which is PD-1 binding partner ligand(s).

In several embodiments, a PD-1 inhibitor is selected from the group consisting of PD-1-binding antagonists, PD-L1-binding antagonists, and PD-L2-binding antagonists.

In several embodiments, a PD-1 inhibitor is a PD-1-binding antagonist. In several embodiments, a PD-1-binding antagonist inhibits binding of PD-1 to its binding partner ligand. In several embodiments, a PD-1-binding antagonist inhibits binding of PD-1 to PD-L1. In several embodiments, a PD-1-binding antagonist inhibits binding of PD-1 to PD-L2. In several embodiments, a PD-1-binding antagonist inhibits binding of PD-1 to both PD-L1 and PD-L2. In several embodiments, a PD-1-binding antagonist is an antibody. In several embodiments, a PD-1-binding antagonist is MDX-1106 (nivolumab). In several embodiments, a PD-1-binding antagonist is MK-3475 (lambrolizumab). In several embodiments, a PD-1-binding antagonist is CT-011 (pidilizumab). In several embodiments, a PD-1-binding antagonist is AMP-224.

In several embodiments, a PD-1 inhibitor is a PD-L1-binding antagonist. In several embodiments, a PD-L1-binding antagonist inhibits binding of PD-L1 to PD-1. In several embodiments, a PD-L1-binding antagonist inhibits binding of PD-L1 to B7-1. In several embodiments, a PD-L1-binding antagonist inhibits binding of PD-L1 to both PD-1 and B7-1. In several embodiments, a PD-L1-binding antagonist is an antibody. In several embodiments, a PD-L1-binding antagonist is selected from the group consisting of YW243.55.S70, MPDL3280A, MDX-1105, and MEDI4736. In several embodiments, a PD-L1-binding antagonist is MPDL3280A (atezolizumab). In several embodiments, a PD-L1-binding antagonist is MEDI4736 (durvalumab).

In several embodiments, a PD-1 inhibitor is a PD-L2-binding antagonist. In several embodiments, a PD-L2-binding antagonist is an antibody. In several embodiments, a PD-L2-binding antagonist is immunoadhesin.

Immunoactivating Antigen-Binding Molecules

In several embodiments, an example of anticancer agents of the present invention includes an immunoactivating antigen-binding molecule (a first immunoactivating antigen-binding molecule). In several embodiments, the first immunoactivating antigen-binding molecules can be any molecule as long as they comprise:

(1) a cancer-specific antigen-binding domain; and
(2) a tumor necrosis factor (TNF) superfamily-binding domain or a tumor necrosis factor (TNF) receptor superfamily-binding domain; and their structure is not limited.

By comprising these two binding domains, the immunoactivating antigen-binding molecules specifically activate cells that express a molecule belonging to the TNF superfamily or the TNF receptor superfamily and that express a cancer-specific antigen, or cells contained in tumor tissues comprising these cells, to thereby enable induction of excellent (specific) cytotoxicity against these cancer-specific antigen-expressing cells or tumor tissues containing these cells. A cancer-specific antigen-binding domain, TNF superfamily-binding domain, and TNF receptor superfamily-binding domain of the present invention can be appropriately selected for the above-described cancer-specific antigens or antigens belonging to the TNF superfamily or the TNF receptor superfamily, respectively. These binding domains can be linked directly by peptide bonds or connected via linkers.

In several embodiments, the first immunoactivating antigen-binding molecules of the present invention may further comprise an FcRn-binding domain. When using an antibody Fc region described above as the FcRn-binding domain, Fc regions having decreased Fcγ receptor-binding activity are preferred. Reducing the Fcγ receptor-binding activity enables suppression of side effects produced by immune activation such as cytokine release caused by crosslinking between Fcγ receptor-expressing cells and cells that express factors belonging to the TNF superfamily or the TNF receptor superfamily.

The first immunoactivating antigen-binding molecules of the present invention can be produced using known methods described above. For example, when (1) using F(ab')2 as the cancer-specific antigen-binding domain, (2) using F(ab')2 as the TNF superfamily-binding domain or the TNF receptor superfamily-binding domain, and (3) using a domain comprising an Fc region with decreased Fcγ receptor-binding activity as the FcRn-binding domain, and when the antigen-binding domains described in (1) and (2) and the Fc region-containing domain described in (3) are directly linked by peptide bonds, the linked polypeptides will form an antibody structure. To produce such antibodies, antibodies can be purified from the afore-mentioned hybridoma culture medium, and also purified from the culture medium of desired host cells that stably carry polynucleotides encoding polypeptides constituting the antibodies.

In addition to the linkers exemplified above, linkers with peptide tags such as His tag, HA tag, myc tag, and FLAG tag may also be suitably used as the linkers to be employed when connecting each of the domains via linkers. Furthermore, the property of mutual binding by hydrogen bonding, disulfide bonding, covalent bonding, ionic interaction, or combination thereof may be suitably used. For example, the affinity between antibody CH1 and CL may be used, and Fc regions derived from the above-described multispecific antibodies may also be used for heterologous Fc region association.

In several embodiments, for example, the "first antigen-binding molecules" disclosed in WO2015/156268 may be used favorably as the first immunoactivating antigen-binding molecules described above.

In several embodiments, an example of anticancer agents of the present invention includes an immunoactivating antigen-binding molecule different from that described above (a second immunoactivating antigen-binding molecule). In several embodiments, as in the case with the first immunoactivating antigen-binding molecules, the structure of the second immunoactivating antigen-binding molecules is not limited and they may be any molecule as long as they comprise:

(1) a cancer-specific antigen-binding domain, and
(2) a T cell receptor complex-binding domain;

and they can be obtained by methods similar to those for the first immunoactivating antigen-binding molecules. Furthermore, as long as the second immunoactivating antigen-binding molecules contain a cancer-specific antigen-binding domain and a T cell receptor complex-binding domain, their structure does not have to be the same as that of the first immunoactivating antigen-binding molecules. A cancer-specific antigen bound by the cancer-specific antigen-binding domain of the first immunoactivating antigen-binding molecules may be the same as or different from a cancer-specific antigen bound by the cancer-specific antigen-binding domain of the second immunoactivating antigen-binding molecules.

Similarly to the first antigen-binding molecules, the second antigen-binding molecules of the present invention may further comprise an FcRn-binding domain. When an antibody Fc region described above is used as the FcRn-binding domain, Fc regions having decreased Fcγ receptor-binding activity are preferred, as in the case of the first antigen-binding molecules. Reducing the Fcγ receptor-binding activity enables suppression of side effects produced by immune activation such as cytokine release caused by crosslinking between Fcγ receptor-expressing cells and T cell receptor complex-expressing cells.

In several embodiments, for example, the "second antigen-binding molecules" disclosed in WO2015/156268 may be used favorably as the second immunoactivating antigen-binding molecules described above.

Furthermore, in other embodiments, the second immunoactivating antigen-binding molecules may be a molecule that comprises:

(1) an antigen-binding domain towards an antigen other than a cancer-specific antigen; and
(2) a T cell receptor complex-binding domain.

For example, the "polypeptide complexes" disclosed in WO2012/073985 may be used favorably as the second immunoactivating antigen-binding molecules comprising the "antigen-binding domain towards an antigen other than a cancer-specific antigen" mentioned above.

In several embodiments, an antigen of the above-mentioned "antigen-binding domain towards an antigen other than a cancer-specific antigen" is not particularly limited, and may be any antigen excluding CD3. Examples of the antigens favorably include receptors, MHC antigens, and differentiation antigens. For example, the receptors, MHC antigens, differentiation antigens, and such disclosed in WO2012/073985 may be favorably used.

Combination Therapies

In several embodiments, a combination therapy of the present invention provides methods for damaging cells, for suppressing cell proliferation, for activating immunity towards cancer cells or cancer cell-comprising tumor tissues, for treating cancer, or for preventing cancer, each of the methods comprising administering effective amounts of an anticancer agent and a T cell-redirecting antigen-binding molecule. In several embodiments, a combination therapy of the present invention is highly effective for damaging cells, suppressing cell proliferation, activating immunity towards cancer cells or cancer cell-comprising tumor tissues, treating cancer, or preventing cancer, as compared to monotherapy using an anticancer agent or a T cell-redirecting antigen-binding molecule. In another embodiment, a combination therapy of the present invention has synergistic effects or additive effects on damaging cells, suppressing cell proliferation, activating immunity towards cancer cells or cancer cell-comprising tumor tissues, treating cancer, or preventing cancer.

In several embodiments, the term "effective amount" according to the present invention refers to a dose of a T cell-redirecting antigen-binding molecule and/or an anticancer agent effective for treating or preventing a disease in individuals. The disease is not particularly limited but is preferably cancer.

In several embodiments, "treatment/treating/therapeutic" according to the present invention means that a combination therapy of the present invention decreases the number of cancer cells in individuals, suppresses cancer cell proliferation, decreases tumor size, suppresses infiltration of cancer cells into peripheral organs, suppresses cancer cell metastasis, or ameliorates various symptoms caused by cancer. Furthermore, in several embodiments, "prevention/preventing/prophylactic" according to the present invention refers to inhibiting increase in the number of cancer cells due to repopulation of cancer cells that have decreased, inhibiting repopulation of cancer cells whose proliferation have been suppressed, and inhibiting the decreased tumor size to become large again.

In several embodiments, a combination therapy of the present invention provides a method for enhancing therapeutic or prophylactic effects of an anticancer agent by using a T cell-redirecting antigen-binding molecule in cancer treatment or prevention with the anticancer agent. In another embodiment, a combination therapy of the present invention provides a method for enhancing therapeutic or prophylactic effects of a T cell-redirecting antigen-binding molecule by using an anticancer agent in cancer treatment with the T cell-redirecting antigen-binding molecule. Herein, enhancement of therapeutic or prophylactic effects refers to, for example, increase in efficacy rate of the treatment, decrease in the amount of an anticancer agent that is administered for the treatment, and/or shortening of the period of the treatment with an anticancer agent, but is not limited thereto. In another embodiment, a combination therapy of the present invention provides a method for extending the progression-free survival in individuals, the method comprising administering an effective amount of a T cell-redirecting antigen-binding molecule and an anticancer agent.

In several embodiments, an "individual" to which an antigen-binding molecule and an anticancer agent are administered refers to a human or a non-human mammal such as a mammal including cattle, horse, dog, sheep, or cat. Preferably, the individuals are humans. Individuals include patients (including humans and non-human mammals). In several embodiments, the individuals are patients who have cancer cells or cancer cell-comprising tumor tissues. Such tumor cells are not particularly limited, but they are preferably cancer types in which cells having immune response-suppressing activity are involved in cancer progression, or cancer types in which the number of regulatory T cells or exhausted T cells in the tumor correlates with the prognosis. Reported examples of such cancer types include ovarian cancer (Non-patent Documents 15 and 16), gastric cancer (Non-patent Documents 17 and 18), esophageal cancer (Non-patent Document 18), pancreatic cancer (Non-patent Document 19), renal cell carcinoma (Non-patent Document 20), hepatocellular carcinoma (Non-patent Document 21), breast cancer (Non-patent Documents 22 and 23), malignant melanoma (Non-patent Document 24), non-small-cell lung cancer (Non-patent Document 25), cervical cancer (Non-patent Document 26), glioblastoma (Non-patent Document 27), prostate cancer (Non-patent Document 28), neuroblastoma (Non-patent Document 29), chronic lymphocytic leukemia (Non-patent Document 30), papillary thyroid cancer (Non-patent Document 31), colorectal cancer (Non-patent Document 32), and B-cell non-Hodgkin's lymphoma (Non-patent Documents 33 and 34), and they are suitable examples of cancer types for the present invention. In several embodiments, the patients are those who have been treated with a T cell-redirecting antigen-binding molecule and/or some kind of an anticancer agent prior to combination therapy using a T cell-redirecting antigen-binding molecule and an anticancer agent. In several embodiments, the patients have early-stage or end-stage cancer.

In several embodiments, a combination therapy of the present invention comprises administering a T cell-redirecting antigen-binding molecule and an anticancer agent. The T cell-redirecting antigen-binding molecule and the anticancer agent can be administered by any appropriate method known in the art. For example, the T cell-redirecting antigen-binding molecule and the anticancer agent can be administered in parallel (i.e., simultaneously), or successively (i.e., at different time points). In several embodiments, when administering the T cell-redirecting antigen-binding molecule and the anticancer agent successively (i.e., at different time points), the interval between administration of the T cell-redirecting antigen-binding molecule and the anticancer agent is not particularly limited, and the interval can be determined by taking account of factors such as the administration route and dosage form. For example, the interval is 0 to 168 hours, preferably 0 to 72 hours, more preferably 0 to 24 hours, and even more preferably 0 to 12 hours, but is not limited thereto.

In several embodiments, the T cell-redirecting antigen-binding molecule and the anticancer agent are administered simultaneously. In several embodiments, the T cell-redirecting antigen-binding molecule is administered at intervals (i.e., intermittently). In some embodiments, the T cell-redirecting antigen-binding molecule is administered before administration of the anticancer agent. In several embodiments, the T cell-redirecting antigen-binding molecule is administered after administration of the anticancer agent.

In several embodiments, the anticancer agent is administered at intervals (i.e., intermittently). In some embodiments, the anticancer agent is administered before administration of the T cell-redirecting antigen-binding molecule. In several embodiments, the anticancer agent is administered after administration of the T cell-redirecting antigen-binding molecule.

In several embodiments, the T cell-redirecting antigen-binding molecule and the anticancer agent can be administered through the same administration route or different administration routes. In several embodiments, the T cell-redirecting antigen-binding molecule and/or the anticancer agent can be administered to patients by either oral or parenteral administration. Specific examples of methods for parenteral administration include administration by injection, transnasal administration, transpulmonary administration, and transdermal administration. Examples of administration by injection include intravenous injection, intramuscular injection, intraperitoneal injection, and subcutaneous injection. The T cell-redirecting antigen-binding molecule and/or the anticancer agent can be administered systemically or locally, for example, through administration by injection. The dose can be selected, for example, from the range of 0.0001 mg to 1000 mg per kilogram body weight for a single administration. Alternatively, for example, the dose may be selected from the range of 0.001 mg/body to 100000 mg/body per patient. However, the method of administration and dose of the T cell-redirecting antigen-binding molecule and/or the anticancer agent in combination therapy are not limited to the above, and a suitable method for administration and dose can be selected according to the patient's age and symptoms. Furthermore, when the T cell-redirecting antigen-binding molecule and the anticancer agent are used in combination according to the present invention, the respective doses may be reduced, if desired, as compared to when either one of them is used alone.

In several embodiments, T cell-redirecting antigen-binding molecules described herein and anticancer agents which are known or described herein may be used in the above-mentioned combination therapy using a T cell-redirecting antigen-binding molecule and an anticancer agent.

Additional Combination Therapies

In several embodiments, in addition to the combination therapy using a T cell-redirecting antigen-binding molecule and an anticancer agent, additional therapy can be carried out. In several embodiments, a therapy to be added to the combination therapy of the present invention may comprise additional administration of a T cell-redirecting antigen-binding molecule and/or an anticancer agent. For example, in addition to a combination therapy using a T cell-redirecting antigen-binding molecule and a first immunoactivating antigen-binding molecule, a second immunoactivating antigen-binding molecule may be suitably used.

Pharmaceutical Compositions

In several embodiments, the present invention provides agents for inducing cytotoxicity, agents for suppressing cell proliferation (agents for inhibiting cell proliferation), agents for activating immune response towards cancer cells or cancer cell-comprising tumor tissues, and agents for treating or preventing cancer (hereinafter, pharmaceutical compositions, and such), each comprising a T cell-redirecting antigen-binding molecule, an anticancer agent, or a combination of a T cell-redirecting antigen-binding molecule and an anticancer agent. In several embodiments, pharmaceutical compositions and such of the present invention may be used in a combination therapy of the present invention. In several embodiments, pharmaceutical compositions and such of the present invention are highly effective for damaging cells, suppressing cell proliferation, activating immunity towards cancer cells or cancer cell-comprising tumor tissues, treating cancer, or preventing cancer through combined use of a T cell-redirecting antigen-binding molecule and an anticancer agent, as compared to monotherapy using the T cell-redirecting antigen-binding molecule or the anticancer agent. In another embodiment, pharmaceutical compositions of the present invention have synergistic effects or additive effects on damaging cells, suppressing cell proliferation, activating immunity towards cancer cells or cancer cell-comprising tumor tissues, treating cancer, or preventing cancer through combined use of a T cell-redirecting antigen-binding molecule and an anticancer agent.

In several embodiments, pharmaceutical compositions and such according to the present invention "comprising a combination of a T cell-redirecting antigen-binding molecule and an anticancer agent" refer to pharmaceutical compositions and such in which the T cell-redirecting antigen-binding molecule and the anticancer agent are combined for use in simultaneous, separate, or sequential administration in treatment or prevention of a disease. For example, pharmaceutical compositions and such of the present invention can be provided in the form of a combination preparation comprising both a T cell-redirecting antigen-binding molecule and an anticancer agent. Alternatively, for example, as the pharmaceutical compositions and such of the present invention a pharmaceutical agent containing a T cell-redirecting antigen-binding molecule and a pharmaceutical agent containing an anticancer agent can be separately provided, and these pharmaceutical agents can be used simultaneously or sequentially. The disease mentioned above is not particularly limited, but is preferably cancer.

In several embodiments, the present invention provides pharmaceutical compositions and such for use in combination with an anticancer agent, the compositions comprising a T cell-redirecting antigen-binding molecule as an active ingredient.

In several embodiments, the present invention provides pharmaceutical compositions and such for use in combination with a T cell-redirecting antigen-binding molecule, the compositions comprising an anticancer agent as an active ingredient.

In several embodiments, the present invention provides pharmaceutical compositions and such for enhancing therapeutic effects of an anticancer agent in cancer treatment with the anticancer agent, by using a T cell-redirecting antigen-binding molecule in combination with the anticancer agent.

In several embodiments, the present invention provides pharmaceutical compositions and such for enhancing therapeutic effects of a T cell-redirecting antigen-binding molecule in cancer treatment with the T cell-redirecting antigen-binding molecule, by using an anticancer agent in combination with the T cell-redirecting antigen-binding molecule.

In several embodiments, the present invention provides use of a T cell-redirecting antigen-binding molecule and/or an anticancer agent for the production of pharmaceutical compositions and such comprising as active ingredients a T cell-redirecting antigen-binding molecule and/or an anticancer agent.

In the present invention, "comprising as active ingredients a T cell-redirecting antigen-binding molecule and/or an anticancer agent" means containing a T cell-redirecting antigen-binding molecule and/or an anticancer agent as major active component(s), and does not limit the content of the T cell-redirecting antigen-binding molecule and/or the anticancer agent.

In several embodiments, T cell-redirecting antigen-binding molecules described herein and anticancer agents which are known or described herein may be used in the pharmaceutical compositions and such described above.

Methods for Contacting a T Cell-Redirecting Antigen-Binding Molecule and an Anticancer Agent with Cancer Cells.

In several embodiments, the present invention provides methods for inducing damage to cancer cells or cancer cell-comprising tumor tissues, or methods for suppressing proliferation of cancer cells or cancer cell-comprising tumor tissues, by contacting the cancer cells and the cells having an immune response-suppressing function with anticancer agents and T cell-redirecting antigen-binding molecules that bind to molecules expressed on the surface of the cells having an immune response-suppressing function. In another embodiment, the present invention provides methods for assessing whether T cell-redirecting antigen-binding molecules and anticancer agents induce damage to cancer cells or cancer cell-comprising tumor tissues or suppress proliferation of cancer cells or cancer cell-comprising tumor tissues, by contacting the cancer cells and the cells having an immune response-suppressing function with the anticancer agents and the T cell-redirecting antigen-binding molecules that bind to molecules expressed on the surface of the cells having an immune response-suppressing function. The cancer cells to be contacted with T cell-redirecting antigen-binding molecules and anticancer agents are not particularly limited, but for example, cancer types which become targets of combination therapy of the present invention may be used favorably.

In several embodiments, "contact" according to the present invention is carried out, for example, by adding an anticancer agent and a T cell-redirecting antigen-binding molecule that binds to an antigen to a culture medium of in vitro cultured cancer cells or cancer cell-comprising tumor tissues, and/or cells expressing an antigen which is the binding target of the T cell-redirecting antigen-binding molecules. In this case, the T cell-redirecting antigen-binding molecule and the anticancer agent to be added may be mixed, or they may be separate. Furthermore, the T cell-redirecting antigen-binding molecules or the anticancer agents to be added may be individually used in a suitable form such as a solution, or a solid obtained by freeze-drying and the like. When added as an aqueous solution, an aqueous solution containing purely the T cell-redirecting antigen-binding molecule or the anticancer agent alone may be used, or a solution containing surfactants, excipients, coloring agents, perfumes, preservatives, stabilizers, buffers, suspending agents, isotonization agents, binders, disintegrants, lubricants, fluidity promoting agents, flavoring agents, and such described above may be used. The concentration of the T cell-redirecting antigen-binding molecule or the anticancer agent to be added is not particularly limited, but a suitable final concentration in the culture solution may be preferably in the range of 1 pg/ml to 1 g/ml, more preferably 1 ng/ml to 1 mg/ml, and even more preferably 1 µg/ml to 1 mg/ml, individually.

In several embodiments, "contact" according to the present invention is carried out, for example, by administering to a non-human animal into which a cancer cell line of interest has been transplanted, an anticancer agent and a T cell-redirecting antigen-binding molecule that binds to a molecule expressed on the surface of a cell having the function of suppressing the immune response in the non-human animal; or by transplanting a cancer cell line of interest into a non-human animal expressing human-derived cells having an immune response-suppressing function, and then administering to the animal an anticancer agent and a T cell-redirecting antigen-binding molecule that binds to a molecule expressed on the surface of the human-derived cells. The method of administration and the dose are not particularly limited, but administration methods and doses used in combination therapies of the present invention may be suitably used.

In several embodiments, examples of in vitro methods for evaluating or measuring the effects of damaging cancer cells or cancer cell-comprising tumor tissues, or the effects of suppressing proliferation of cancer cells or cancer cell-comprising tumor tissues include methods for measuring cytotoxic T cell activity, and such. Whether an antigen-binding molecule of the present invention has cytotoxic T cell activity can be measured by known methods (for example, Current protocols in Immunology, Chapter 7. Immunologic studies in humans, Editor, John E. Coligan et al., John Wiley & Sons, Inc., (1993)). As a result of the measurements, for example, when the cytotoxic T cell activity in the group of combined use of a T cell-redirecting antigen-binding molecule and an anticancer agent is stronger than the cytotoxic T cell activity in the control group, the group to which the T cell-redirecting antigen-binding molecule is administered alone, or the group to which the antitumor agent is administered alone, combined administration of the T cell-redirecting antigen-binding molecule and the anticancer agent can be determined as being highly effective for or having synergistic effects or additive effects on damaging cancer cells or cancer cell-comprising tumor tissues or suppressing proliferation of cancer cells or cancer cell-comprising tumor tissues.

In several embodiments, for in vivo evaluation or measurement of the effects of damaging cancer cells or cancer cell-comprising tumor tissues, or the effects of suppressing proliferation of cancer cells or cancer cell-comprising tumor tissues, for example, cancer cells or cancer cell-comprising tumor tissues are intradermally or subcutaneously transplanted to a non-human test animal, and then a T cell-redirecting antigen-binding molecule and/or an anticancer agent are intravenously or intraperitoneally administered daily or at intervals of a few days, starting from the day of transplantation or the following day. Tumor size is measured daily and the differences in the change of tumor size can be defined as the effects of damaging cancer cells or cancer cell-comprising tumor tissues, or the effects of suppressing proliferation of cancer cells or cancer cell-comprising tumor tissues. For determination of the above-mentioned effects, for example, a control antigen-binding molecule, a T cell-redirecting antigen-binding molecule and/or an anticancer agent are administered, and the tumor size in each of the administered groups can be measured. As a result of the measurements, for example, when the tumor size in the group of combined use of a T cell-redirecting antigen-binding molecule and an anticancer agent is smaller than the tumor size in the control group, the group to which the T cell-redirecting antigen-binding molecule is administered alone, or the group to which the anticancer agent is administered alone, the combined administration of the T cell-redirecting antigen-binding molecule and the anticancer agent can be determined as being highly effective for or having synergistic effects or additive effects on damaging cancer cells or cancer cell-comprising tumor tissues or suppressing proliferation of cancer cells or cancer cell-comprising tumor tissues.

Kits

In several embodiments, the present invention provides a kit comprising (1) a T cell-redirecting antigen-binding molecule, (2) a container, and (3) an instruction or a label indicating that the T cell-redirecting antigen-binding molecule and at least one type of anticancer agent are administered in combination to a subject individual for treating cancer in the individual. In another embodiment, the present invention provides a kit comprising (1) an anticancer agent, (2) a container, and (3) an instruction or a label indicating that the anticancer agent and at least one type of T cell-redirecting antigen-binding molecule are administered in combination to an individual for treating cancer in the individual.

In another embodiment, the present invention provides a kit comprising (1) a T cell-redirecting antigen-binding molecule, (2) an anticancer agent, (3) a container, and (4) an instruction or a label indicating that the T cell-redirecting antigen-binding molecule and the anticancer agent are administered in combination to an individual for treating cancer in the individual.

In several embodiments, the kit further comprises a pharmaceutically acceptable carrier. Additionally, the kit may further comprise a sterilized diluent preferably stored in a separate additional container. The kit may also comprise an instruction relating to combination therapy for treating or preventing cancer.

In several embodiments, an "instruction" refers to the written instruction usually contained in the commercially available box carrying a pharmaceutical, and may contain information on indications, usage, dosage, administration, contraindications and/or warnings regarding the use of the pharmaceutical.

Those skilled in the art will naturally understand that optional combinations of one or more of the embodiments described herein are included in the present invention, as long as they are not technically inconsistent based on common technical knowledge of those skilled in the art.

All prior art references cited herein are incorporated by reference into this description.

EXAMPLES

[Reference Example 1] Concept of T Cell-Redirecting Antibody Targeting a Cell Surface Marker of a Regulatory T Cell (1-1) Antitumor Effects of Anti-CTLA4 Antibodies Through Elimination of Regulatory T Cells As described above in Background Art, Ipilimumab had been considered to inhibit CTLA4 expressed on the surface of effector T cells from suppressing effector T-cell activation, and thereby exhibit antitumor effects However, recently, antibody-dependent cellular cytotoxic activity (ADCC activity) against CTLA4-expressing T cells was also reported to be important, and elimination of regulatory T cells in tumors and ADCC activity have been found to be important mechanisms of action for the antitumor effects of anti-CTLA4 antibodies.

On the other hand, ADCC activity by an IgG1 antibody induces cytotoxic activity through binding of the antibody constant region to FcγR of NK cells or macrophages, and antibodies having a constant region that have been modified so as to enhance such binding are known to induce stronger cytotoxic activities and demonstrate antitumor effects.

As mentioned above, binding to regulatory T cells or exhausted T cells in a cancer microenvironment, and elimination of regulatory T cells or exhausted T cells by cytotoxic activity were found to exert strong antitumor effects. Therefore, if regulatory T cells or exhausted T cells can be eliminated more powerfully, or more specifically, if stronger cytotoxic activity can be exhibited, stronger antitumor effects can be expected to be exerted.

(1-2) T Cell-Redirecting Antibody

Enhancement of the aforementioned ADCC activity, increase of retention in blood, improvement of antigen-binding activity, and reduction of immunogenicity risk have been performed as techniques for improving antibodies. Generally, antibodies recognize and bind a single epitope of an antigen, therefore even when such techniques for improvement are applied to the antibodies, only one type of antigen becomes the target. As molecules that inhibit multiple targets, antibodies that bind to two or more types of antigens by one molecule (referred to as bispecific antibodies) have been studied. Since bispecific antibodies interact with two or more types of antigens, they have not only the effect of neutralizing two or more types of antigens with one molecule, but also the effect of enhancing antitumor activities by crosslinking cells having cytotoxic activity with cancer cells.

Blinatumomab, which is a BiTE molecule, and Catumaxomab are known as bispecific antibodies that recognize a protein expressed on T cells (CD3E or TCR) and a protein expressed on cancer cells (a cancer antigen). These molecules can bind to a cancer antigen and the CD3E chain expressed on a T cell with each of their two antigen-binding domains (scFv or Fab), and form intercellular crosslinks between the T cells and the cancer antigen-expressing cells (FIG. 1). This way, such T cell-redirecting antibodies can use T cells as effector cells to induce strong cytotoxic activity against cancer antigen-expressing cells.

Figures 1, 2:
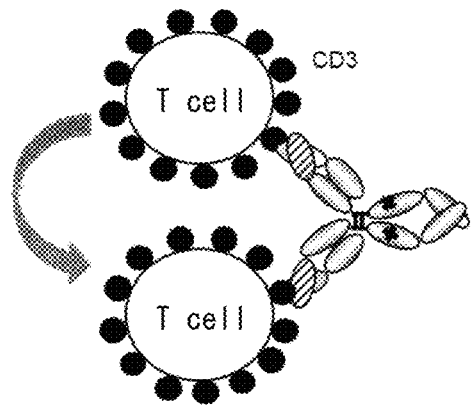
Figure 2:
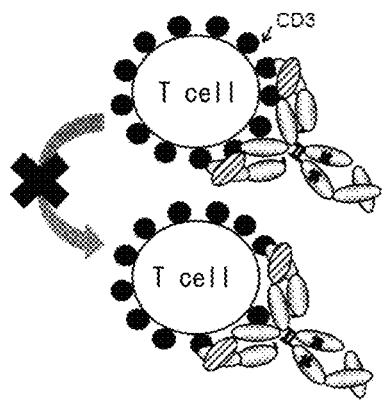

Meanwhile, antibodies that use T cells as effector cells and induce strong cytotoxic activity against T cells have not been reported so far. For example, since CD3ε is a standard T cell marker, an IgG antibody (not having FcgR-binding activity) which binds to CD3εs using both arms (two Fabs) may be able to cause T cells to induce strong cytotoxic activity against T cells by forming intercellular crosslink between a CD3ε-expressing T cell which will become an effector cell and a CD3ε-expressing T cell, as shown in FIG. 2-1, but this hardly occurs in reality. That is because an IgG antibody that binds to CD3εs using both arms (two Fabs) strongly binds to CD3εs expressed on the same cell due to avidity via bivalent binding, intercellular crosslink is not formed between CDR-expressing T cells (FIG. 2-2).

Figure 3:
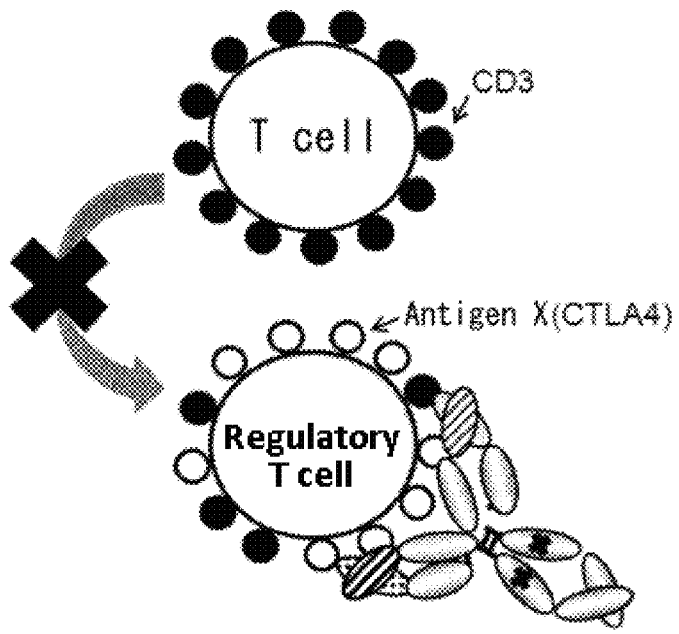
FIG. 3 presents a schematic diagram showing that an anti-CTLA4/CD3 bispecific antibody causes crosslinking between CTLA4 and CD3 on the same regulatory T cell, and therefore, does not cause intercellular crosslinking between an effector T cell and a regulatory T cell. This schematic diagram shows a regulatory T cell as the target cell and CTLA4 as the antigen, but the target cell and antigen are not limited thereto.

Since CD3 is a standard T cell marker and it is expressed in both T cells which will become the effector cells and T cells which will become the target (for example, regulatory T cells and exhausted T cells), T cell-redirecting antibodies had been considered to be not able to exert cytotoxic activity against target T cells. More specifically, a T cell-redirecting antibody against a T cell expressing antigen X, a surface marker of a specific T cell population (bispecific antibody against CD3ε and antigen X) strongly binds to the target T cell (for example, a regulatory T cell and an exhausted T cell) with avidity via bivalent binding, since CD3ε and antigen X are expressed on the target T cell. Therefore, intercellular crosslinking was considered not to take place with T cells which will become effector cells (FIG. 3). In fact, there have been no reports of T cell-redirecting antibodies against T cell antigens.

Figure 4:
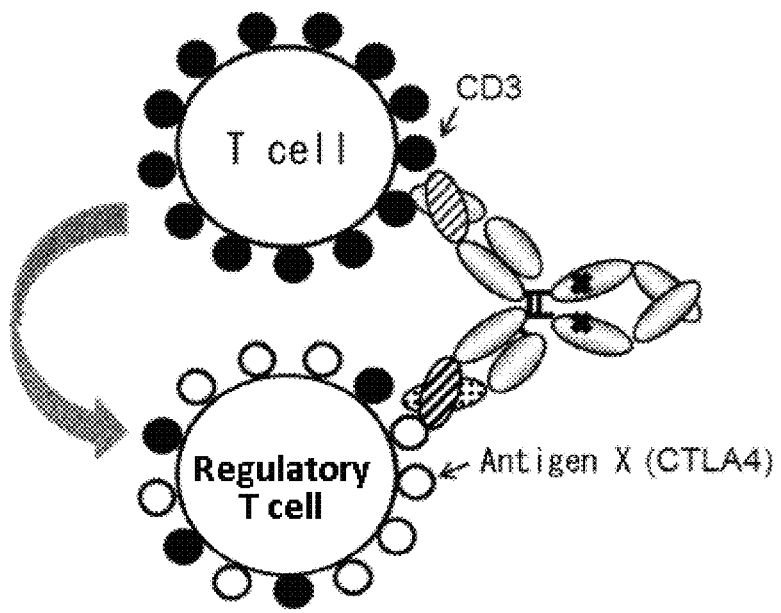
FIG. 4 presents a schematic diagram showing intercellular crosslinking caused by crosslinking between CD3 on an effector T cell and CTLA4 on a regulatory T cell via an anti-CTLA4/CD3 bispecific antibody. This schematic diagram shows a regulatory T cell as the target cell and CTLA4 as the antigen, but the target cell and antigen are not limited thereto.

Therefore, T cell-redirecting antibodies against CTLA4 expressed on regulatory T cells and exhausted T cells (bispecific antibodies against CD3ε and CTLA4), as shown in FIG. 4, are considered not to be able to induce strong cytotoxic activity against regulatory T cells and exhausted T cells because both CD3ε and CTLA4 are expressed on regulatory T cells and exhausted T cells, which are target cells, and the T cells which will become effector cells are not crosslinked with regulatory T cells and exhausted T cells. So far, there have been no reports on T cell-redirecting antibodies against regulatory T cells or exhausted T cells.

More specifically, it was unknown whether T cell-redirecting antibodies against CTLA4 (anti-CTLA4/anti-CD3ε bispecific antibodies) can actually damage regulatory T cells by inducing intercellular crosslinking and demonstrate antitumor effects in vivo. Therefore, we actually produced bispecific antibodies against CTLA4 and CD3 and tested whether they can achieve effects in vivo in mice and in vitro in humans.

Against standard cancer antigens, T cell-redirecting antibodies have been known to have stronger antitumor effects than antibodies having NK cell-utilizing ADCC activity; however, it had been unknown whether T cell-redirecting antibodies against CTLA4 show stronger antitumor effects than anti-CTLA4 antibodies with enhanced ADCC activity.

[Reference Example 2] Preparation and Assessment of ADCC Activity-Enhanced Antibodies Targeting Regulatory T Cells (2-1) Expression and Purification of an ADCC Activity-Enhanced Antibody that Binds Specifically to Mouse CTLA4 (hUH02hUL01-mFa55)

Genes encoding the variable regions of the anti-mouse CTLA4 antibody hUH02hUL01 (the heavy chain variable region UH02 is SEQ ID NO: 28, and the light chain variable region UL01 is SEQ ID NO: 29) were each inserted into mouse IgG2a/kappa plasmids for expression in animals. Here, constant regions that have been modified so as to enhance binding to mouse FcγR were used (the heavy chain constant region mFa55 is SEQ ID NO: 30, and the light chain constant region mk1 is SEQ ID NO: 31).

Antibodies were expressed by the method described below. Cells of human embryonic kidney cell-derived FreeStyle™ 293-F strain (Invitrogen) were suspended in FreeStyle™ 293 Expression Medium (Invitrogen) at a cell density of $1.33 \times 10^6$ cells/mL, and seeded into each well of a 6-well plate at 3 mL/well. The prepared plasmids were introduced into the cells by a lipofection method. The cells were cultured for four days in a $CO_2$ incubator (37° C., 8% $CO_2$, 90 rpm). From the culture supernatants, antibodies were purified using rProtein A Sepharose™ Fast Flow (Amersham Biosciences) by a method known to those skilled in the art. Absorbance at 280 nm of the purified antibody solutions was measured using a spectrophotometer. Concentrations of the purified antibodies were calculated from the determined values using an extinction coefficient calculated by the PACE method (Protein Science (1995) 4: 2411-2423).

(2-2) Assessment of Binding of the Anti-Mouse CTLA4 Antibody (hUH02UL01-mFa55) to Various Mouse FcgRs Anti-mouse CTLA4 antibody hUH02hUL01-mFa55 and control antibody hUH02hUL01-mIgG2a (the heavy chain variable region UH02 is SEQ ID NO: 28, the light chain variable region UL01 is SEQ ID NO: 29, the heavy chain constant region mIgG2a is SEQ ID NO: 32, and the light chain constant region mk1 is SEQ ID NO: 31) purified and prepared by the method of Reference Example 2-1 were analyzed for their antigen-antibody reactions with various mouse FcgRs (mFcgRI, II, III, and IV) using Biacore™ T200 (GE Healthcare). The running buffer used was 20 mmol/L ACES, 150 mmol/L NaCl, 0.05% (w/v) Tween®20 at pH7.4, and measurements were taken at 25° C. Protein A/G was immobilized onto a Sensor Chip CM7 by amine coupling. hUH02hUL01-mFa55 was captured onto the sensorchip, and then FcgR was allowed to interact as an analyte for 120 seconds, and change in the bound amount was observed. The running buffer was used for dilution of hUH02hUL01-mFa55. The measurement results were analyzed by curve fitting using the Biacore™ T200 Evaluation Software (GE Healthcare) to calculate the association rate constants ka (1/Ms) and the dissociation rate constants kd (1/s). From those values, the dissociation constants $K_D$ (M) were determined. The measurement results are shown in Table 1.

region UL01 is SEQ ID NO: 29) were each inserted into human IgG1/kappa plasmids for expression in animals. Here, constant regions that have been modified so as to reduce binding to Fcγ receptors and to produce heterologous association of two heavy chains were used (the heavy chain constant region F760nN17 is SEQ ID NO: 33, and the light chain constant region k0 is SEQ ID NO: 34).

Genes encoding the variable regions of the anti-mouse CD3 antibody 2C11 (the heavy chain variable region is SEQ ID NO: 35, and the light chain variable region is SEQ ID NO: 36) were each inserted into human IgG1/kappa plasmids for expression in animals. Here, constant regions that have been modified so as to reduce binding to Fcγ receptors and to produce heterologous association of two heavy chains were used (the heavy chain constant region F760nP17 is SEQ ID NO: 37, and the light chain constant region k0 is SEQ ID NO: 34).

Each of hUH02hUL01-F760nN17 and 2C11-F760nP17 was expressed and purified by the method shown in Reference Example 2. Each of the purified homologous forms was mixed by a method known to those skilled in the art that uses differences in the charges of the constant regions (Proc. Natl. Acad. Sci., 110, 5145-5150, 2013) to produce the bispecific antibody of interest (hUH02UL01/2C11-F760).

TABLE 1

| No. | Name of Fc | mFcgRI 1:1 binding RI = 0 | | | mFcgRII 1:1 binding RI = 0 | | |
|---|---|---|---|---|---|---|---|
| | | ka (1/Ms) | kd (1/s) | KD (M) | ka (1/Ms) | kd (1/s) | KD (M) |
| 1 | mIgG2a | 7.8E+05 | 4.7E−03 | 6.1E−09 | 1.3E+06 | 1.1E+00 | 7.8E−07 |
| 2 | mFa55 | 1.2E+06 | 3.1E−03 | 2.5E−09 | 2.1E+06 | 7.6E−01 | 3.7E−07 |

| No. | Name of Fc | mFcgRIII 1.1 binding RI = 0 | | | mFcgRIV 1:1 binding RI = 0 | | |
|---|---|---|---|---|---|---|---|
| | | ka (1/Ms) | kd (1/s) | KD (M) | ka (1/Ms) | kd (1/s) | KD (M) |
| 1 | mIgG2a | 2.0E+06 | 5.1E−01 | 2.5E−07 | 1.2E+06 | 1.6E−02 | 1.3E−08 |
| 2 | mFa55 | 2.4E+06 | 6.2E−01 | 2.6E−07 | 1.5E+06 | 2.8E−03 | 1.9E−09 |

Figure 5:
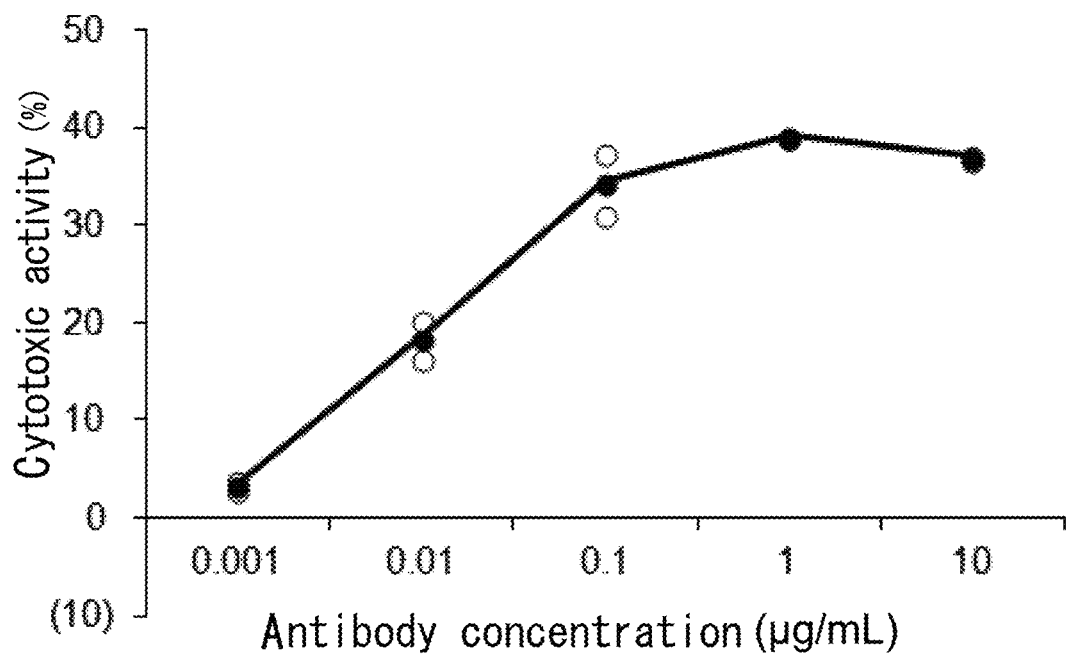
FIG. 5 presents a graph showing the ADCC activity of the anti-mouse CTLA4 antibody hUH02hUL01-mFa55 on mouse CTLA4-expressing cells.

(2-3) Evaluation of an Anti-Mouse CTLA4 Antibody (hUH02UL01-mFa55) as an ADCC Activity-Enhanced Antibody Whether anti-mouse CTLA4 antibody hUH02hUL01-mFa55 purified and prepared by the method of Reference Example 2-1 exerts ADCC activity on mouse CTLA4-expressing cells (mouse CTLA4-expressing cells were produced by a method known to those skilled in the art by introducing the full length mouse CTLA4 gene into CHO cells) was examined according to the method of Reference Example 11. The measurement results show ADCC activity in an antibody concentration-dependent manner (FIG. 5).

[Reference Example 3] Preparation and Assessment of Bispecificity which Recognizes Surface Antigens of Regulatory T Cells and Effector T Cells (3-1) Expression and Purification of Bispecific Antibodies that Specifically Bind to Mouse CTLA4 and Mouse CD3

Genes encoding the variable regions of the anti-mouse CTLA4 antibody hUH02hUL01 (the heavy chain variable region UH02 is SEQ ID NO: 28, and the light chain variable (3-2) Evaluation of a Bispecific Antibody that Specifically Binds to Mouse CTLA4 and Mouse CD3 for the Antigen (mCTLA4 and mCD3)-Binding Properties Anti-mouse CTLA4/anti-mouse CD3 bispecific antibodies (hUH02UL01/2C11-F760) purified and prepared by the method of Reference Example 3-1 were analyzed for their antigen-antibody reactions with each antigen (mCTLA4 and mCD3) using Biacore™ T200 (GE Healthcare). The running buffer used was HBS-EP+ at pH7.4, and measurements were taken at 37° C. Protein A/G was immobilized onto a Sensor Chip CM4 by amine coupling. hUH02UL01/2C11-F760 was captured onto the sensor chip, and then the antigen (mouse CTLA4 or mouse CD3) was allowed to interact as an analyte (for 120 seconds for mouse CTLA4 and for 90 seconds for mouse CD3), and changes in the bound amount were observed. The running buffer was used for dilution of hUH02UL01/2C11-F760. The measurement results were analyzed by curve fitting using the Biacore™ T200 Evaluation Software (GE Healthcare) to calculate the association rate constants ka (1/Ms) and the dissociation rate constants kd (1/s). From those values, the dissociation constants KD (M) were determined. The results are shown in Table 2.

TABLE 2

| No | Analyte | ka (1/Ms) | kd (1/s) | KD (M) |
| --- | --- | --- | --- | --- |
| 1 | MouseCTLA4 | 4.30E+05 | 5.30E−04 | 1.23E−09 |
| 2 | Mouse CD3 | 6.16E+04 | 7.12E−02 | 1.16E−06 |

(3-2) Evaluation of Cytotoxic Activity by an Anti-Mouse CTLA4/Anti-Mouse CD3 Bispecific Antibody (hUH02UL01/2C11-F760)

Figure 6:
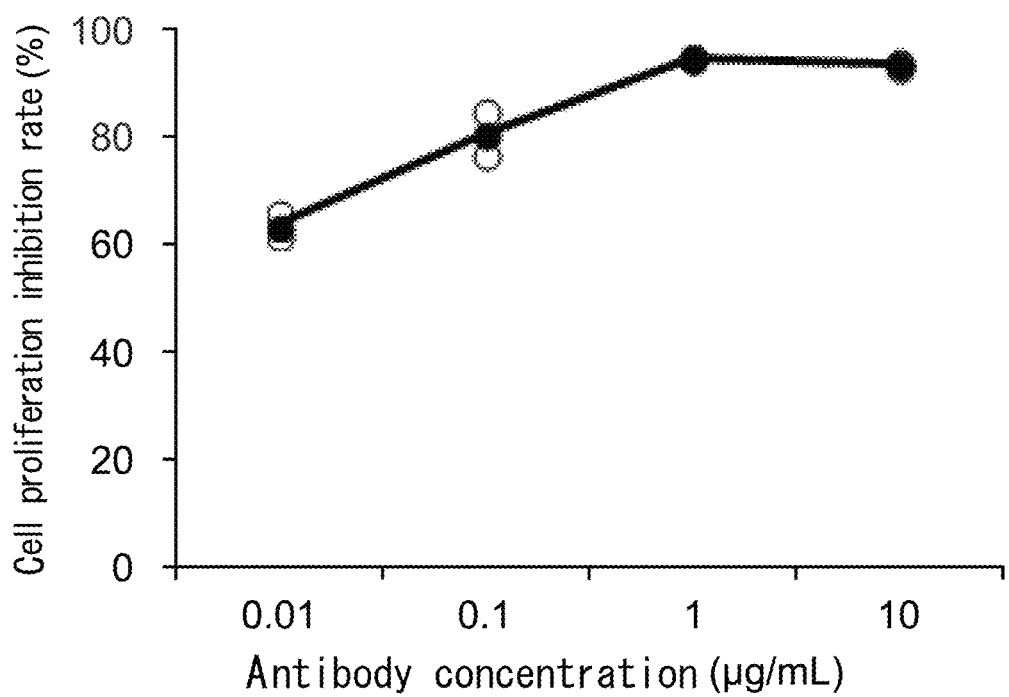
FIG. 6 presents a graph showing the cytotoxic activity of the anti-mouse CTLA4/anti-mouse CD3 bispecific antibody (hUH02UL01/2C11-F760) on mouse CTLA4-expressing cells.

Whether anti-mouse CTLA4/anti-mouse CD3 bispecific antibody (hUH02UL01/2C11-F760) purified and prepared by the method of Reference Example 3-1 exerts cytotoxic activity on mouse CTLA4-expressing cell lines was examined according to the method of Reference Example 12. The measurement results show cytotoxic activity in an antibody concentration-dependent manner (FIG. 6).

[Reference Example 4] Assessment of Crosslinking Between Beads to which CD3 and CTLA4 have been Immobilized and CD3-Bound Beads by an Anti-Mouse CTLA4/Anti-Mouse CD3 Bispecific Antibody (hUH02UL01/2C11-F760)

Whether an anti-CTLA4/anti-CD3 bispecific antibody recognizes surface antigens of a regulatory T cell (expressing CTLA4 and CD3) and an effector T cell (expressing CD3) and forms a crosslink between the two cells was verified by a physicochemical experiment.

Figures 1, 7:
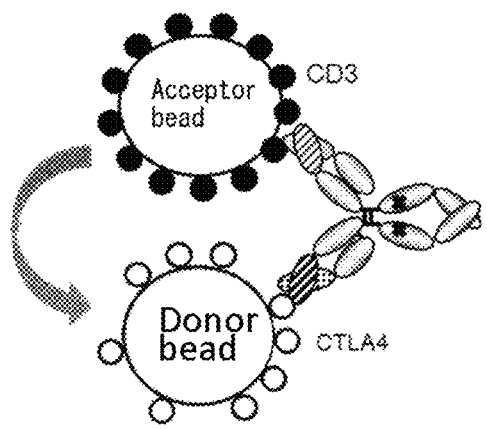
Figures 2, 7:
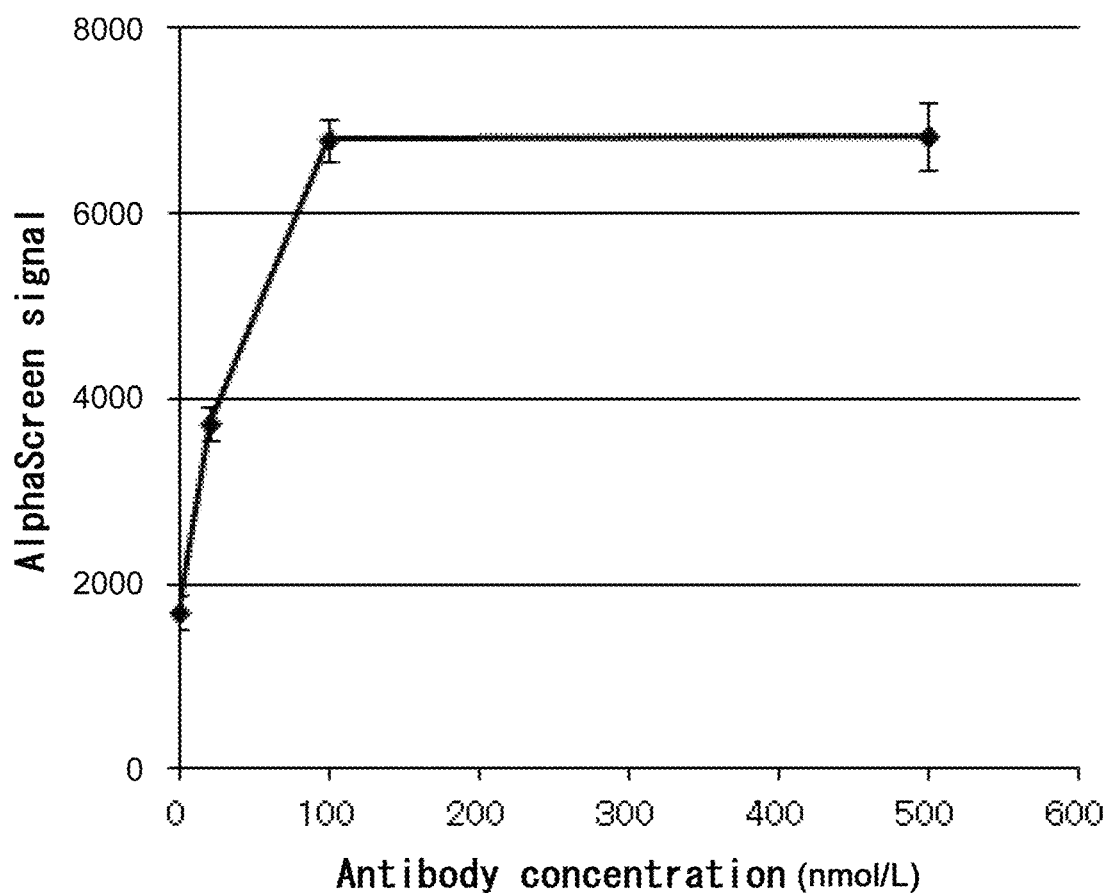
Figures 3, 7:
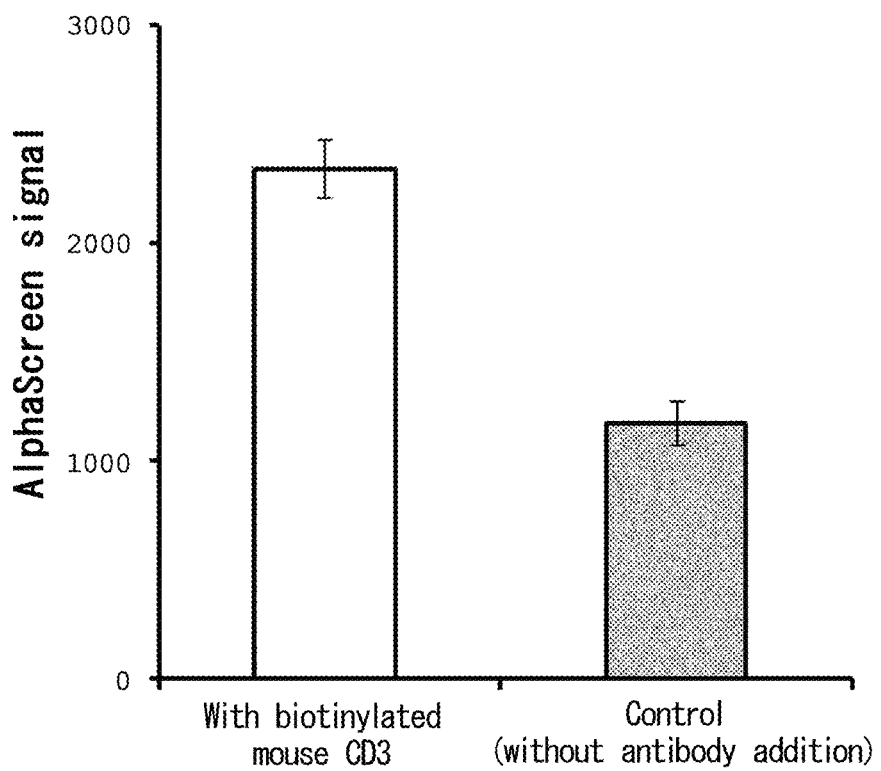
Figures 4, 7:
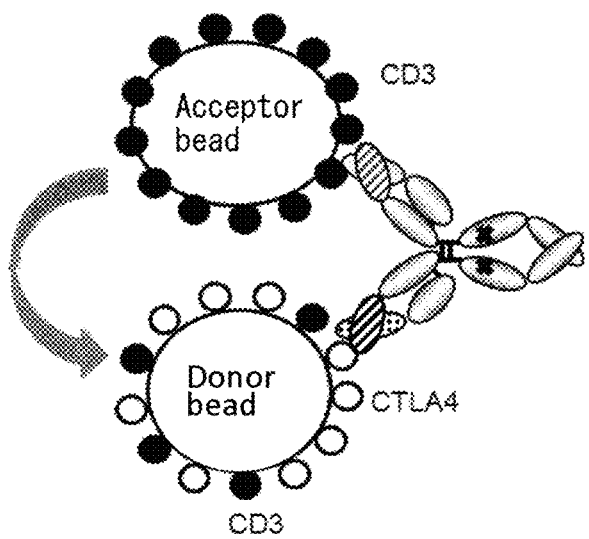

First, the present inventors investigated, using Alpha technology from Perkin Elmer Inc., construction of a system that can evaluate crosslinking between mouse CD3-immobilized beads and mouse CTLA4-immobilized beads using the anti-mouse CTLA4/anti-mouse CD3 bispecific antibody (hUH02UL01/2C11-F760) purified and prepared by the method of Reference Example 3-1. More specifically, 100 nmol/L of biotinylated mouse CTLA4; 0, 20, 100, or 500 nmol/L of hUH02UL01/2C11-F760; 50 µg/mL of AlphaScreen™ Streptavidin-coated Donor Beads (PerkinElmer); and mouse CD3-acceptor beads prepared by conjugating 50 µg/mL of mouse CD3 to AlphaScreen™ Unconjugated Acceptor Beads (PerkinElmer) were used. Under this condition, it was thought that biotinylated mouse CTLA4 bound to AlphaScreen™ Streptavidin-coated Donor Beads and mouse CD3-acceptor beads may be crosslinked by hUH02UL01/2C11-F760 as shown in FIG. 7-1, and chemiluminescence may be emitted. Alpha 384 (PerkinElmer) was used as the plate, and the measurements were taken using Envision. All experiments were performed three times. As a result, hUH02UL01/2C11-F760 concentration-dependent crosslinking between beads was observed as shown in FIG. 7-2.

Next, 100 nmol/L of biotinylated mouse CTLA4 and 10 nmol/L of biotinylated mouse CD3 were added to AlphaScreen™ Streptavidin-coated Donor Beads (PerkinElmer) to produce donor beads that mimic regulatory T cells expressing CTLA4 and CD3. Whether addition of 100 nmol/L of hUH02UL01/2C11-F760 can cause crosslinking between donor beads and acceptor beads in the presence of 50 µg/mL mouse CD3-acceptor beads (acceptor beads mimicking effector T cells) was examined. The condition in which hUH02UL01/2C11-F760 is not added to 100 nmol/L of biotinylated mouse CTLA4; 50 µg/mL of AlphaScreen™ Streptavidin-coated Donor Beads (PerkinElmer); and 50 µg/mL of mouse CD3-acceptor beads was used as the control in which crosslinking between each of the beads are not caused. All experiments were performed three times.

The results shown in FIG. 7-3 were obtained from the experiments, and it was confirmed that even under the condition where biotinylated mouse CD3 and mouse CTLA4 may be present on the same bead, the anti-mouse CTLA4/anti-mouse CD3 bispecific antibody crosslinks the donor bead and acceptor bead as shown in FIG. 7-4.

The condition where biotinylated mouse CD3 and mouse CTLA4 are bound on the donor beads was considered to be mimicking regulatory T cells (expressing CTLA4 and CD3), and mouse CD3-conjugated acceptor beads was considered to be mimicking effector T cells (expressing CD3). It was confirmed that the anti-mouse CTLA4/anti-mouse CD3 bispecific antibody crosslinks donor beads with acceptor beads under this condition as well, which suggests that even for regulatory T cells and effector T cells, an anti-CTLA4/anti-CD3 bispecific antibody may be able to form crosslinking between the two cells in a similar manner.

[Reference Example 5] In Vivo Drug Efficacy Evaluation Using an Anti-Mouse CTLA4/Anti-Mouse CD3 Bispecific Antibody (hUH02UL01/2C11-F760) (Intratumoral Administration)

Figure 8:
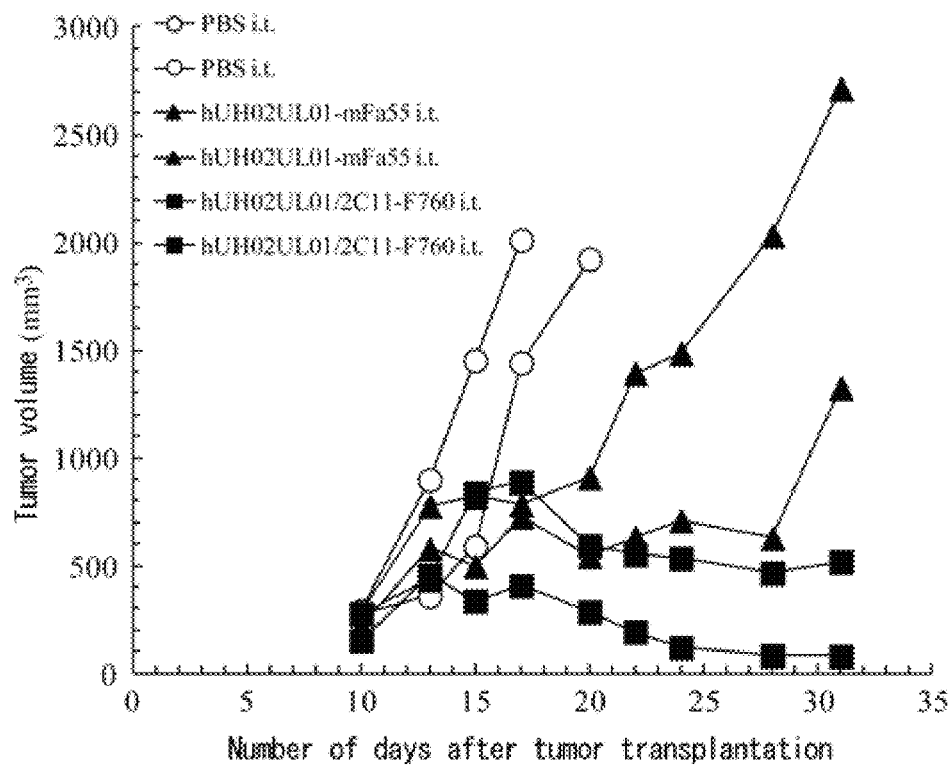
FIG. 8 presents a graph showing the in vivo antitumor effects obtained by intratumoral (i.t.) administration of an anti-mouse CTLA4 antibody (hUH02hUL01-mFa55, ADCC-enhanced antibody) and an anti-mouse CTLA4/anti-mouse CD3 bispecific antibody (hUH02UL01/2C11-F760, a T cell-redirecting antibody) on mouse colorectal cancer cell line CT26.WT (n=2 for each group; the plot shows the tumor volume of each individual).

Whether the anti-mouse CTLA4 antibody hUH02hUL01-mFa55 purified and prepared by the method of Reference Example 2-1 and the anti-mouse CTLA4/anti-mouse CD3 bispecific antibody (hUH02UL01/2C11-F760) purified and prepared by the method of Reference Example 3-1 shows in vivo drug efficacy against a mouse colorectal cancer cell line was verified. $1\times10^6$ mouse colorectal cancer cell line CT26.WT cells (ATCC) were subcutaneously transplanted into the right abdomen of BALB/c mice (Japan Charles River) to establish solid tumor. Ten days after the transplantation, hUH02hUL01-mFa55 was administered at a dose of 200 µg/mouse and hUH02UL01/2C11-F760 was administered at a dose of 100 µg/mouse, intratumorally (i.t.) (n=2 for each group). The results elucidated that hUH02UL01/2C11-F760 shows stronger antitumor effects in comparison to hUH02hUL01-mFa55, and shows remarkable antitumor effects in vivo (FIG. 8). More specifically, the results suggested that hUH02UL01/2C11-F760 recognizes the surface antigens of regulatory T cells (expressing CTLA4 and CD3) and effector T cells (expressing CD3), and causes crosslinking between the two cells in vivo.

[Reference Example 6] In Vivo Drug Efficacy Evaluation of an Anti-Mouse CTLA4/Anti-Mouse CD3 Bispecific Antibody (hUH02UL01/2C11-F760) (Comparison Between Intratumoral Administration and Intravenous Administration)

Figure 9:
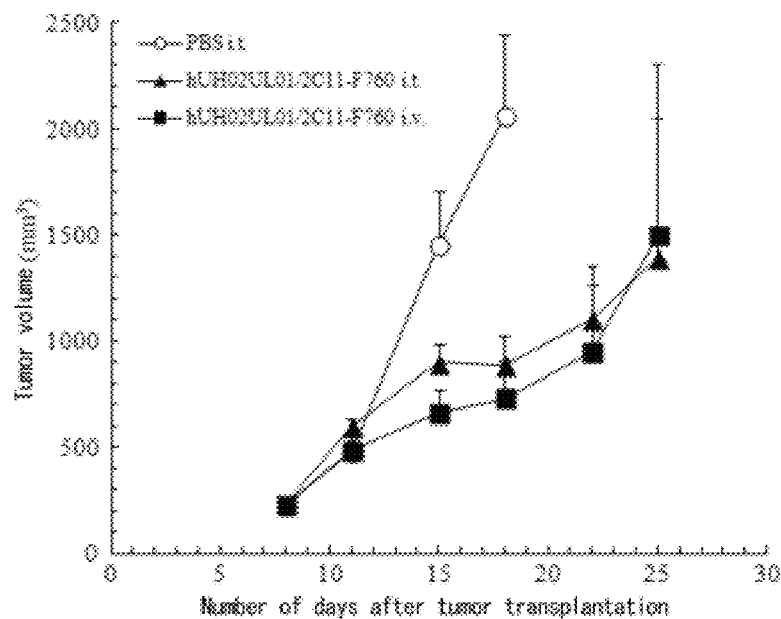
FIG. 9 presents a graph showing the in vivo antitumor effects obtained by intratumoral (i.t.) administration and intravenous (i.v.) administration of an anti-mouse CTLA4/anti-mouse CD3 bispecific antibody (hUH02UL01/2C11-F760, a T cell-redirecting antibody) on mouse colorectal cancer cell line CT26.WT (n=5 for each group; the plot shows the mean tumor volume+standard deviation of each group).

The anti-mouse CTLA4/anti-mouse CD3 bispecific antibody (hUH02UL01/2C11-F760) purified and prepared by the method of Reference Example 3-1 was assessed on whether it shows drug efficacy on the mouse colorectal cancer cell line CT26.WT-transplanted model described in Reference Example 5 even when administered intravenously (i.v.). $1\times10^6$ CT26.WT cells (ATCC) were subcutaneously transplanted into the right abdomen of BALB/c mice (Japan Charles River) to establish solid tumor. Eight days after the transplantation, hUH02UL01/2C11-F760 was administered at a dose of 100 µg/mouse intratumorally (i.t.) or intravenously (i.v.) (n=5 for each group). The results elucidated that hUH02UL01/2C11-F760 shows equivalent antitumor effects in both intratumoral and intravenous administration, and shows antitumor effects in vivo regardless of whether it is administered locally or systemically (FIG. 9).

[Reference Example 7] In Vitro Drug Efficacy Evaluation of an Anti-Human CTLA4/Anti-Human CD3 Bispecific Antibody (7-1) Expression and Purification of a Bispecific Antibody that Specifically Binds to Human CTLA4 and Human CD3

Genes encoding the variable regions of the anti-human CTLA4 antibody MDX10-F760nN17 (the heavy chain variable region MDX10H is SEQ ID NO: 38, and the light chain variable region MDX10L is SEQ ID NO: 39) were each inserted into human IgG1/kappa plasmids for expression in animals. Here, constant regions that have been modified so as to reduce binding to Fcγ receptors and to produce heterologous association of two heavy chains were used (the heavy chain constant region F760nN17 is SEQ ID NO: 33, and the light chain constant region k0 is SEQ ID NO: 34).

Genes encoding the variable regions of the anti-human CD3 antibody TR01H113-F760nG3P17 (the heavy chain variable region TR01H113 is SEQ ID NO: 40, and the light chain variable region L0011 is SEQ ID NO: 41) were each inserted into human IgG1/kappa plasmids for expression in animals. Here, constant regions that have been modified so as to reduce binding to Fcγ receptors and to produce heterologous association of two heavy chains were used (the heavy chain constant region F760nG3P17 is SEQ ID NO: 42, and the light chain constant region k0 is SEQ ID NO: 34).

Each of MDX10-F760nN17 and TR01H113-F760nG3P17 was expressed and purified by the method shown in Reference Example 2. Each of the purified homologous forms was mixed in the combination shown in Table 3, and the bispecific antibody of interest was produced by a method known to those skilled in the art (WO2015/046467).

TABLE 3

| No | Name of clone | Antibody 1 | Antibody 2 |
|---|---|---|---|
| 1 | MDX10//TR01H113 | MDX10-F760nN17 | TR01H113-F760nG3P17 |

In addition, there are other techniques for forming bispecific antibodies. Examples include methods for antibody production using association of antibody CH1 and CL, and association of VH and VL as described in WO 2011/028952, WO2014/018572, and Nat Biotechnol. 2014 February; 32(2):191-8; methods using association of CH1 and CL or VH and VL, which are described in Proc Natl Acad Sci USA. 2011 Jul. 5; 108(27):11187-92, WO2009/080251, WO2009/080252, and WO2009/080253; methods for regulating association between antibody heavy chain CH3s, which are described in WO2012/058768 and WO2013/063702; methods that utilize charge regulation of CH1 and CL, which are described in WO2006/106905; and methods that utilize charge regulation of VH and VL, which are described in WO2013/065708. The bispecific antibody of interest can be produced by applying the above-mentioned technologies to an anti-human CTLA4 antibody (the heavy chain variable region MDX10H is SEQ ID NO: 38, and the light chain variable region MDX10L is SEQ ID NO: 39) and an anti-human CD3 antibody (the heavy chain variable region TR01H113 is SEQ ID NO: 40, and the light chain variable region L0011 is SEQ ID NO: 41).

(7-2) In Vitro Cytotoxic Activity of an Anti-Human CTLA4/Anti-Human CD3 Bispecific Antibody on Regulatory T Cells Blood was collected using heparin from two healthy donors. Each blood sample was diluted with HBSS (GIBCO) containing 5% FBS (Moregate BioTech), and then layered onto Ficoll-Paque Plus (GE healthcare). This was centrifuged at 400×g for 30 minutes to separate the peripheral blood monocyte (PBMC) fraction. The obtained PBMCs were seeded into a 96-well round-bottom plate (Corning) at $5 \times 10^5$ cells/well using RPMI 1640 (Nacalai Tesque) medium containing 10% FBS, and 100 Units/mL penicillin-100 μg/mL Streptomycin (GIBCO).

The control antibody (the anti-KLH human IgG1 heavy chain variable region IC17H is SEQ ID NO: 43, the light chain variable region IC17L is SEQ ID NO: 44, the heavy chain constant region hIgGld is SEQ ID NO: 45, and the light chain constant region k0 is SEQ ID NO: 34) or MDX10/TR01H113 was diluted with the medium to each produce a final concentration of 0.1 μg/mL, 1 μg/mL, or 10 μg/mL, and added to the wells. The cells were cultured for seven days in a $CO_2$ incubator set at 37° C. and 5% $CO_2$.

Seven days later, the cells were transferred to a V-bottom plate (Corning), and centrifuged at 400×g for five minutes to remove the supernatant. The cells were resuspended in 100 μL of FcR blocking reagent (Miltenyi Biotec) diluted ten times with PBS containing 1% FBS and 2 mM EDTA (Sigma) (FACS buffer). After incubating at room temperature for ten minutes, 2.5 μL of PerCP-Cγ5.5 Mouse Anti-Human CD4 (BD Pharmingen), 5 μL of PE Mouse Anti-Human CD25 (BD Pharmingen), and 2.5 μL of PE-Cγ7 Mouse Anti-Human CD45RA (BD Pharmingen) were added to each well. After incubating at 4° C. for one hour, 100 μL of FACS buffer was added. Centrifugation was performed at 400×g for five minutes to remove the supernatant.

Based on the protocol of Intracellular Fixation and Permeabilization buffer set (eBioscience), Human FoxP3 buffer A was added 100 μL at a time, this was incubated at room temperature for ten minutes in the dark. Subsequently, centrifugation was performed at 400×g for five minutes to remove the supernatant. Permeabilization buffer was added 100 μL at a time, this was incubated at room temperature for 30 minutes in the dark. Next, 100 μL of FACS buffer was added, centrifugation was performed at 400×g for five minutes to remove the supernatant. This washing procedure was performed one more time.

The cells were resuspended in 100 μL of FACS buffer, Alexa Fluor488 Anti-Human FoxP3 (BioLegend) was added 5 μL at a time, this was incubated at room temperature for 30 minutes in the dark. 100 μL of FACS buffer was added, and centrifugation was performed at 400×g for five minutes to remove the supernatant. This washing procedure was performed one more time. The cells were resuspended in 200 μL of FACS buffer, and analyzed on a FACSCanto™ II flow cytometer (BD).

Expression analyses were performed using the FACSDiva™ Software (BD). CD4-positive cells were gated from the cell population subjected to analysis and the expression of CD25 and CD45RA was analyzed. The $CD25^{high}$ CD45RA− fraction and the CD25− CD45RA+ fraction were regarded as the regulatory T cells (Treg) and effector T cells (Teff), respectively. Furthermore, the FoxP3highCD45RA− fraction and the FoxP3−CD45RA+ fraction were regarded as Treg and Teff, respectively. The Teff/Treg ratio was calculated from the proportion of Treg and Teff present in CD4-positive cells.

Figures 1, 10:
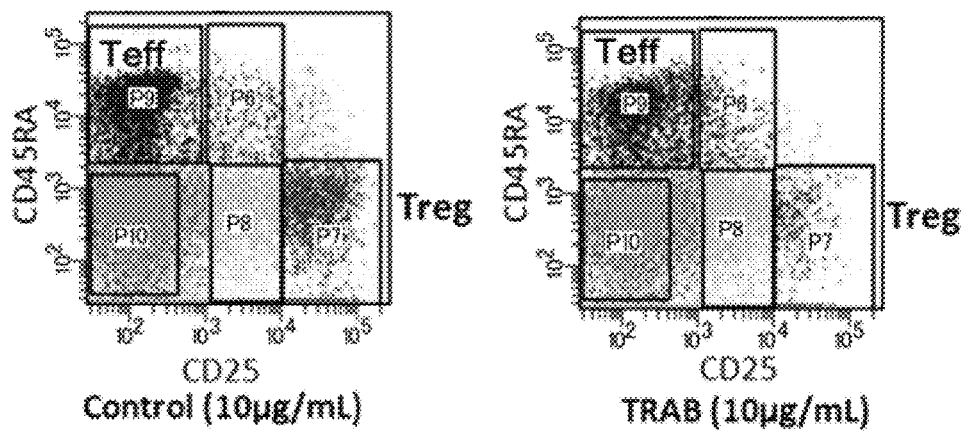
Figures 2, 10:
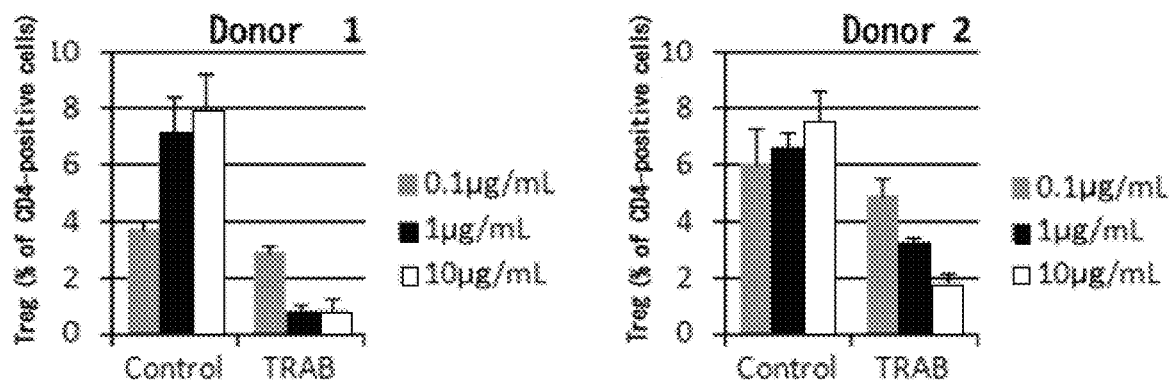
Figures 3, 10:
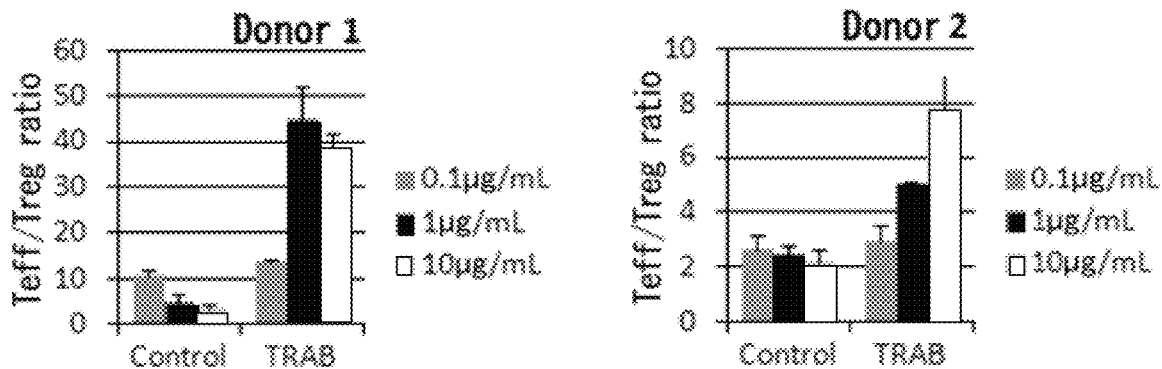

The results of analyzing CD4-positive cells based on the expression of CD25 and CD45RA are shown (FIG. 10-1). In Donor 1, treatment with MDX10/TR01H113 at 1 μg/mL and 10 μg/mL showed decrease in Treg. In Donor 2, treatment at 1 μg/mL showed a decreasing trend in Treg, and treatment at 10 μg/mL showed marked decrease in Treg (FIG. 10-2). In both donors, treatment with MDX10/TR01H113 at 1 μg/mL and 10 μg/mL increased the Teff/Treg ratios (FIG. 10-3).

Figures 1, 11:
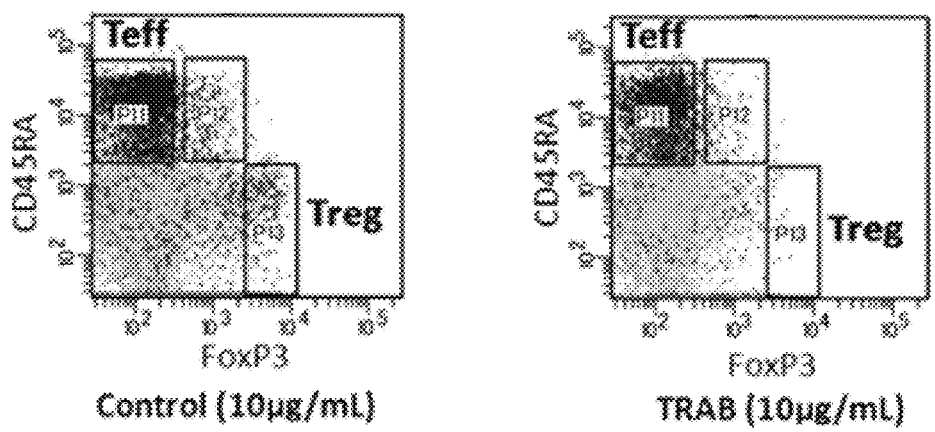
Figures 2, 11:
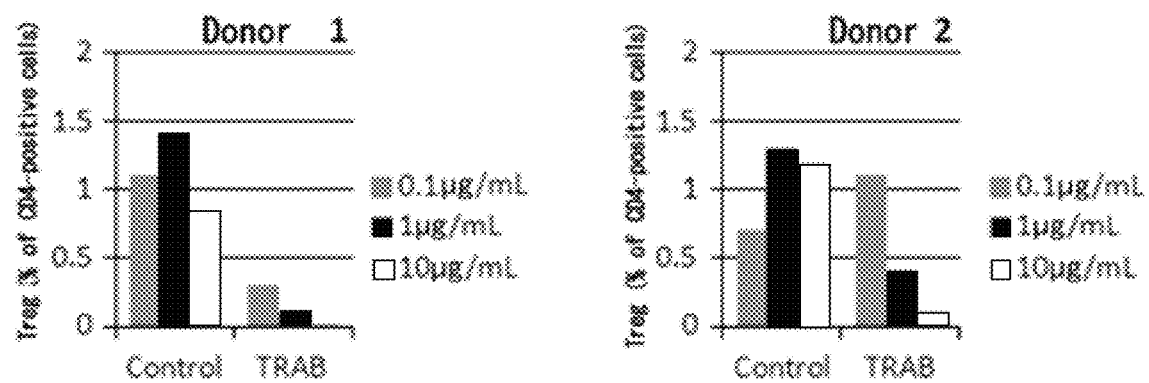
Figures 3, 11:
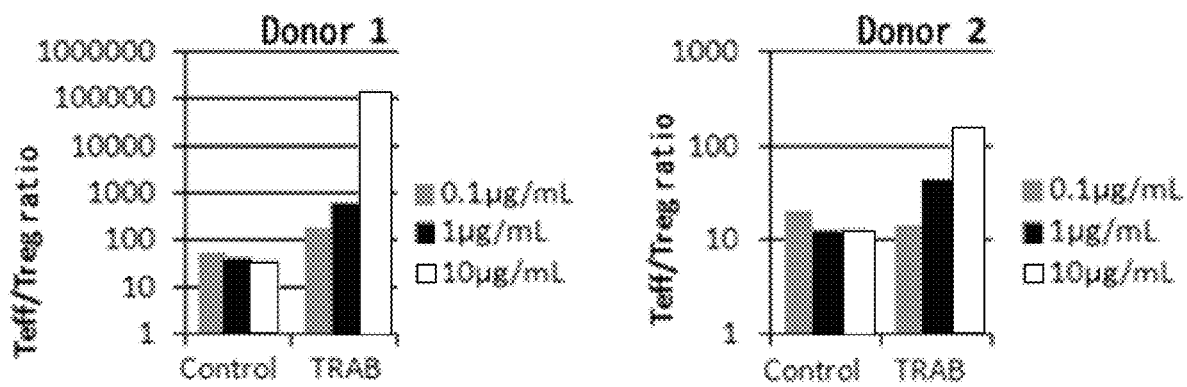

Furthermore, results of analyzing Treg based on the expression of FoxP3 and CD45RA are shown in FIG. 11-1. Similarly to the analyses using CD25 and CD45RA, treatment with MDX10/TR01H113 decreased Treg and increased the Teff/Treg ratios (FIGS. 11-2 and 11-3).

According to these examinations, TRAB (a bispecific antibody against CTLA4 and CD3) which showed stronger antitumor effects with regard to cytotoxic activity against regulatory T cells expressing CTLA4 in vivo in mice, also showed strong cytotoxic activity against regulatory T cells in vitro in humans; therefore, TRAB is expected to demonstrate strong antitumor effects towards cancer patients.

[Reference Example 8] Analysis of Surface Molecules Expressed in Cell Fractions (CD4+, CD25$^{high}$, CD45RA−) that have been Reported to have High Immune Response-Suppressing Function Among the cells having immune response-suppressing functions, regulatory T cells (Treg) in CD4-positive T cells calculated based on CD25 and CD45RA expression, that is the CD4+ CD25$^{high}$ CD45RA− cell fraction, have been reported to have high immune response-suppressing functions (Immunity, 2009, 30 (6), 899-911). Based on this information, a gene which encodes a cell surface molecule showing significantly high expression in the CD25$^{high}$ CD45RA− cell fraction among the CD4-positive cells was identified using RNA-seq. As a result, among CTLA4, PD1, TIM3, LAG3, CD244 (2B4), CD160, GARP, OX40, CD137 (4-1BB), CD25, VISTA, BTLA, TNFR25, CD57, KLRG1, CCR2, CCR5, CCR6, CD39, CD73, CD4, CD18, CD49b, CD1d, CD5, CD21, TIM1, CD19, CD20, CD23, CD24, CD38, CD93, IgM, B220(CD45R), CD317, PD-L1, CD11b, Ly6G, ICAM-1, FAP, PDGFR, Podoplanin, and TIGIT, which are molecules expressed on the surface of cells having immune response-suppressing function, nine molecules which are CTLA4, TIM3, LAG3, CD137 (4-1BB), CD25, CCR5, CCR6, CD38, and TIGIT were found to be cell surface molecules highly expressed specifically in the cell fractions (CD4+, CD25$^{high}$ CD45RA−) that have been reported to have high immune response-suppressing functions.

[Reference Example 9] In Vitro Drug Efficacy Evaluation of an Anti-Human LAG3/Anti-Human CD3 Bispecific Antibody (9-1) Expression and Purification of a Bispecific Antibody that Specifically Binds to Human LAG3 and Human CD3

Genes encoding the variable regions of the anti-human LAG3 antibody 25F7-F760nN17 (the heavy chain variable region 25F7H is SEQ ID NO: 46, and the light chain variable region 25F7L is SEQ ID NO: 47) were each inserted into human IgG1/kappa plasmids for expression in animals. Here, constant regions that have been modified so as to reduce binding to Fcγ receptors and to produce heterologous association of two heavy chains were used (the heavy chain constant region F760nN17 is SEQ ID NO: 33, and the light chain constant region k0 is SEQ ID NO: 34).

Genes encoding the variable regions of the anti-human CD3 antibody TR01H113-F760nG3P17 (the heavy chain variable region TR01H113 is SEQ ID NO: 40, and the light chain variable region L0011 is SEQ ID NO: 41) were each inserted into human IgG1/kappa plasmids for expression in animals. Here, constant regions that have been modified so as to reduce binding to Fcγ receptors and to produce heterologous association of two heavy chains were used (the heavy chain constant region F760nG3P17 is SEQ ID NO: 42, and the light chain constant region k0 is SEQ ID NO: 34).

Each of 25F7-F760nN17 and TR01H113-F760nG3P17 was expressed and purified by the method shown in Reference Example 2. Each of the purified homologous forms was mixed in the combination shown in Table 4, and the bispecific antibody of interest was produced by a method known to those skilled in the art (WO2015/046467).

TABLE 4

| No | Name of clone | Antibody 1 | Antibody 2 |
|---|---|---|---|
| 1 | 25F7//TR01H113 | 25F7-F760nN17 | TR01H113-F760nG3P17 |

(9-2) In Vitro Cytotoxic Activity of an Anti-Human LAG3/Anti-Human CD3 Bispecific Antibody on Regulatory T Cells Blood was collected using heparin from healthy donors. Each blood sample was diluted with PBS and then layered together with Ficoll-Paque Plus (GE healthcare) in a Leucosep tube (greiner bio-one). This was centrifuged at 1000×g for 10 minutes to separate the peripheral blood monocyte (PBMC) fraction. The obtained PBMCs were seeded into a 96-well round bottom plate (Corning) at 1×10$^6$ cells/well using RPMI 1640 (Nacalai Tesque) medium containing 10% FBS, and 100 Units/mL penicillin-100 μg/mL Streptomycin (GIBCO).

TRAB (25F7/TR01H113) was diluted with the medium at a final concentration of 1 μg/mL or 10 μg/mL, and added to the wells. The cells were cultured for four or six days in a CO$_2$ incubator set at 37° C. and 5% CO$_2$.

Four or six days later, the cells were transferred to tubes for FACS analysis, and centrifuged at 400×g for five minutes to remove the supernatant. Cell WASH (BD Biosciences) containing 0.2% BSA (Wako) was prepared, and this was used as the FACS Buffer. For complete removal of medium components, washing was performed by adding 2 mL of FACS Buffer to the cells from which the supernatant was removed and performing the centrifugation again at 400×g for five minutes to remove the supernatant.

FcR blocking reagent (Miltenyi Biotec) diluted ten-fold with the FACS Buffer, to which 1/1000 volume of eFluor780 (eBioscience) for staining dead cells was added, was prepared and used as the Staining Buffer. Solution produced by adding 5 μL of PerCP Mouse Anti-Human CD4 (BD Pharmingen), 2.5 μL of PE-Cy™7 Mouse Anti-Human CD45RA (BD Pharmingen), and 5 μL of PE Mouse Anti-Human CD25 to 50 μL of the Staining Buffer was placed into each tube. After incubation at 4° C. for one hour, 2 mL of FACS buffer was added, and the centrifugation was performed at 400×g for five minutes to remove the supernatant. Then, as a washing procedure, an additional 2 mL of FACS buffer was added, and the centrifugation was performed at 400×g for five minutes to remove the supernatant.

The cells were resuspended in 400 µL of FACS buffer and analyzed on a FACSVerse™ flow cytometer (BD).

Expression analysis was carried out using the FACS-Diva™ Software (BD). CD4-positive cells were gated from the cell population subjected for analysis, from which dead cells had been removed, and the expression of CD25 and CD45RA was analyzed. The CD25$^{high}$ CD45RA− fraction and the CD25− CD45RA+ fraction were regarded as regulatory T cells (Treg) and effector T cells (Teff), respectively. The Teff/Treg ratio was calculated from the proportion of Treg and Teff present in CD4-positive cells.

Figure 13:
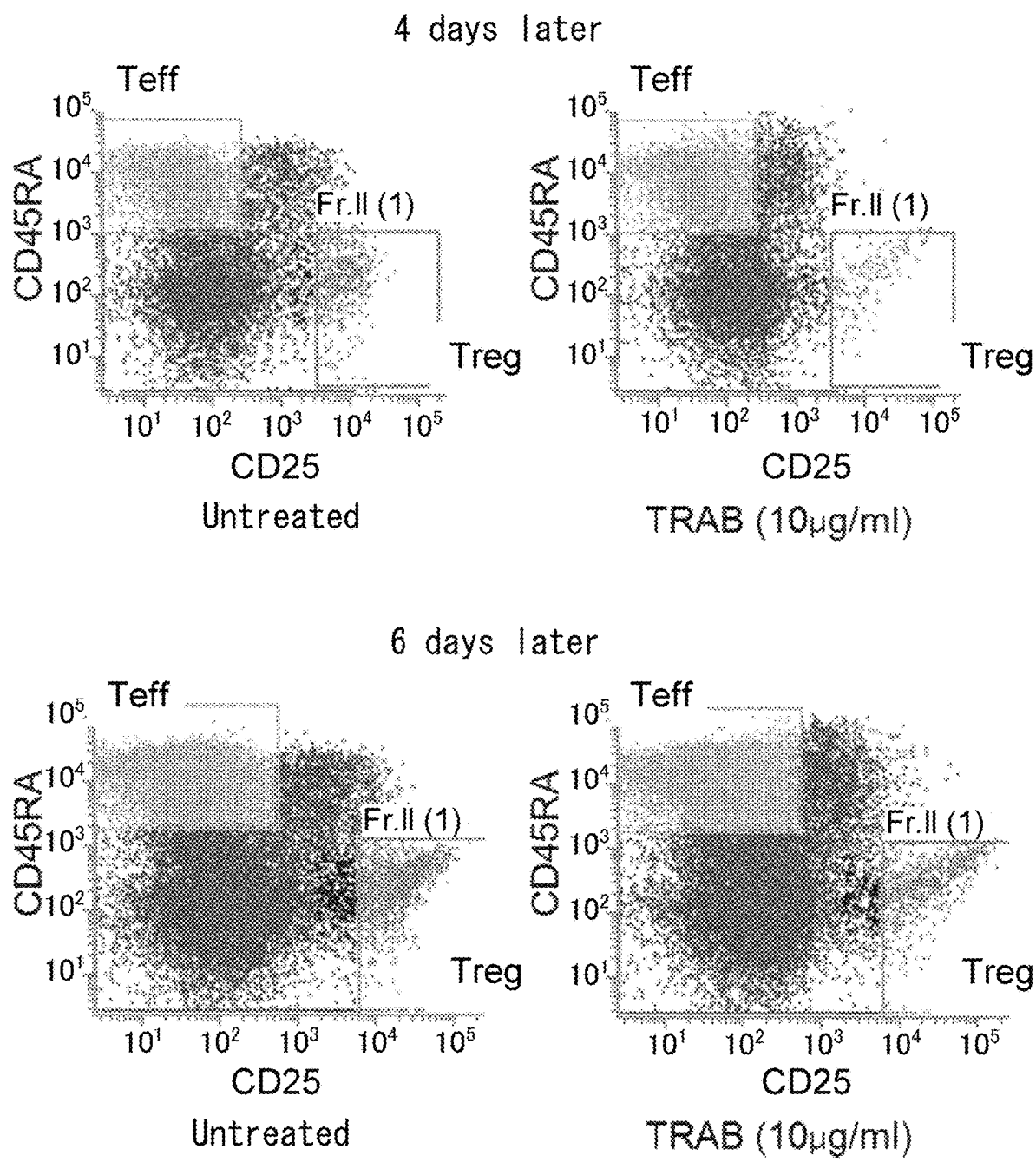
FIG. 13 presents graphs showing the results of analyzing CD4-positive cells based on the expression of CD25 and CD45RA, after a four- or six-day reaction of PBMC derived from a healthy person with an anti-human LAG3/anti-human CD3 bispecific antibody (TRAB).
Figure 14:
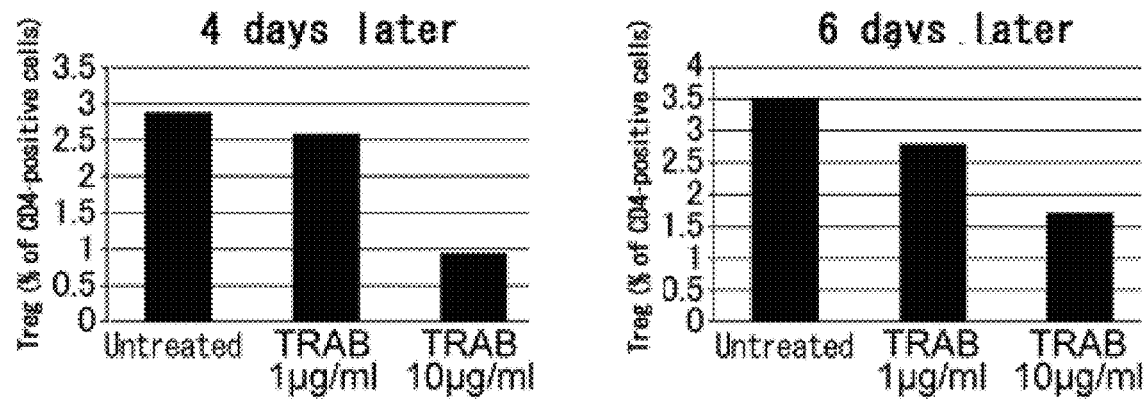
FIG. 14 presents graphs showing the proportion of regulatory T cells (Treg) in CD4-positive T cells, calculated based on the expression of CD25 and CD45RA, after a four- or six-day reaction of PBMC derived from a healthy person with an anti-human LAG3/anti-human CD3 bispecific antibody (TRAB).
Figure 15:
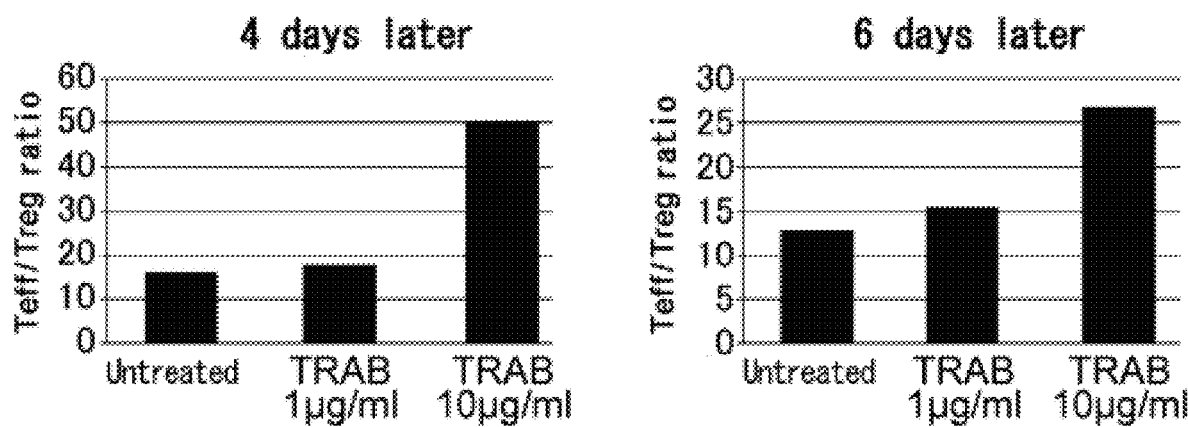
FIG. 15 presents graphs showing the ratio of effector T cells (Teff) to regulatory T cells (Treg) (Teff/Treg) in CD4-positive T cells, calculated based on the expression of CD25 and CD45RA, after a four- or six-day reaction of PBMC derived from a healthy person with an anti-human LAG3/anti-human CD3 bispecific antibody (TRAB).

The results of analyzing CD4-positive cells based on the expression of CD25 and CD45RA are shown (FIG. 13). Treatment with TRAB (25F7/TR01H113) at 1 µg/mL and 10 µg/mL showed decrease in Treg in a TRAB antibody dose-dependent manner, both at four and six days after the treatment (FIG. 14). Treatment with TRAB (25F7/TR01H113) at 1 µg/mL and 10 µg/mL increased the Teff/Treg ratios (FIG. 15).

[Reference Example 10] In Vitro Drug Efficacy Evaluation of an Anti-Human OX40/Anti-Human CD3 Bispecific Antibody (10-1) Expression and Purification of a Bispecific Antibody that Specifically Binds to Human OX40 and Human CD3

Genes encoding the variable regions of the anti-human OX40 antibody 12H3-F760nN17 (the heavy chain variable region 12H3VH is SEQ ID NO: 48, and the light chain variable region 12H3VL is SEQ ID NO: 49) were each inserted into human IgG1/kappa plasmids for expression in animals. Here, constant regions that have been modified so as to reduce binding to Fcγ receptors and to produce heterologous association of two heavy chains were used (the heavy chain constant region F760nN17 is SEQ ID NO: 33, and the light chain constant region k0 is SEQ ID NO: 34).

Genes encoding the variable regions of the anti-human CD3 antibody TR01H113-F760nG3P17 (the heavy chain variable region TR01H113 is SEQ ID NO: 40, and the light chain variable region L0011 is SEQ ID NO: 41) were each inserted into human IgG1/kappa plasmids for expression in animals. Here, constant regions that have been modified so as to reduce binding to Fcγ receptors and to produce heterologous association of two heavy chains were used (the heavy chain constant region F760nG3P17 is SEQ ID NO: 42, and the light chain constant region k0 is SEQ ID NO: 34).

Each of 12H3-F760nN17 and TR01H113-F760nG3P17 was expressed and purified by the method shown in Reference Example 2. Each of the purified homologous forms was mixed in the combination shown in Table 5, and the bispecific antibody of interest was produced by a method known to those skilled in the art (WO2015/046467).

TABLE 5

| No | Name of clone | Antibody 1 | Antibody 2 |
|---|---|---|---|
| 1 | 12H3//TR01H113 | 12H3-F760nN17 | TR01H113-F760nG3P17 |

(10-2) In Vitro Cytotoxic Activity of an Anti-Human OX40/Anti-Human CD3 Bispecific Antibody on Regulatory T Cells Blood was collected using heparin from two healthy donors. Each blood sample was diluted with PBS and then layered together with Ficoll-Paque™ Plus (GE healthcare) in a Leucosep tube (greiner bio-one). The centrifugation was performed at 1000×g for 10 minutes to separate the peripheral blood monocyte (PBMC) fraction. The obtained PBMCs were seeded into a 96-well round bottom plate (Corning) at 1×10$^6$ cells/well using RPMI 1640 (Nacalai Tesque) medium containing 10% FBS, and 100 Units/mL penicillin-100 µg/mL Streptomycin (GIBCO).

TRAB (12H3/TR01H113) was diluted with the medium at a final concentration of 1 µg/mL or 10 µg/mL, and was added to the wells. The cells were cultured for seven days in a CO$_2$ incubator set at 37° C. and 5% CO$_2$.

Seven days later, the cells were transferred to tubes for FACS analysis, and centrifuged at 400×g for five minutes to remove the supernatant. Cell WASH (BD Biosciences) containing 0.2% BSA (Wako) was prepared and used as the FACS Buffer. For complete removal of medium components, washing was performed by adding 2 mL of FACS Buffer to the cells from which the supernatant was removed and performing the centrifugation again at 400×g for five minutes to remove the supernatant.

FcR blocking reagent (Miltenyi Biotec) diluted ten-fold with the FACS Buffer, to which 1/1000 volume of eFluor780 (eBioscience) for staining dead cells was added, was prepared and used as the Staining Buffer. Solution produced by adding 5 µL of PerCP Mouse Anti-Human CD4 (BD Pharmingen), 2.5 µL of PE-Cy™ 7 Mouse Anti-Human CD45RA (BD Pharmingen), and 5 µL of PE Mouse Anti-Human CD25 to 50 µL of the Staining Buffer was placed into each tube. After incubation at 4° C. for one hour, 2 mL of FACS Buffer was added, and the centrifugation was performed at 400×g for five minutes to remove the supernatant. Then, as a washing procedure, 2 mL of FACS buffer was further added, and the centrifugation was performed at 400×g for five minutes to remove the supernatant. The cells were resuspended in 400 µL of FACS buffer and analyzed on a FACSVerse™ flow cytometer (BD).

Expression analysis was carried out using the FACS-Diva™ Software (BD). CD4-positive cells were gated from the cell population subjected to analysis, from which dead cells had been removed, and the expression of CD25 and CD45RA was analyzed. The CD25$^{high}$ CD45RA− fraction and the CD25− CD45RA+ fraction were regarded as regulatory T cells (Treg) and effector T cells (Teff), respectively. The Teff/Treg ratio was calculated from the proportion of Treg and Teff present in CD4-positive cells.

Figure 16:
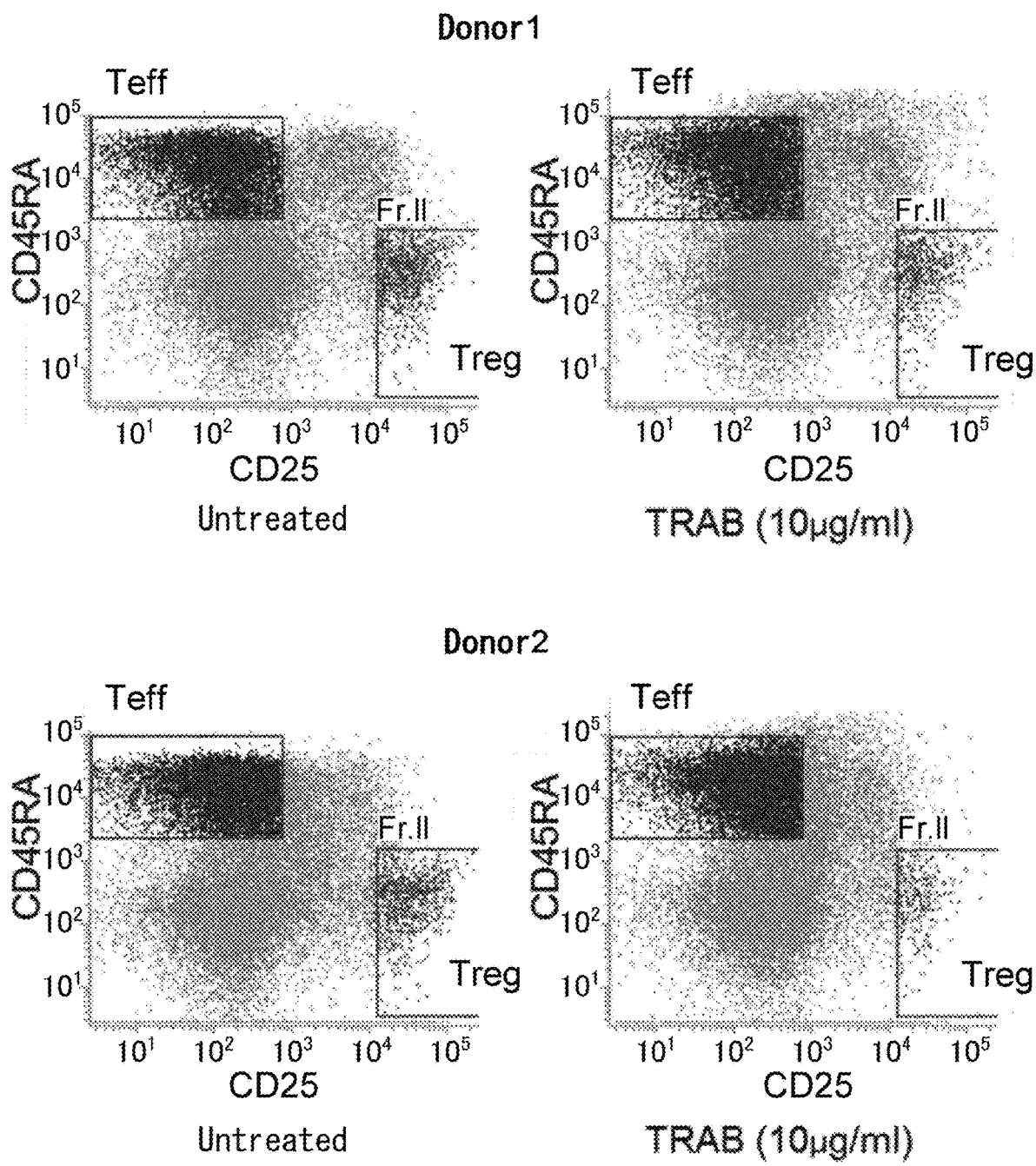
FIG. 16 presents graphs showing the results of analyzing CD4-positive cells based on the expression of CD25 and CD45RA, after a seven-day reaction of PBMC derived from a healthy person with an anti-human OX40/anti-human CD3 bispecific antibody (TRAB).
Figure 17:
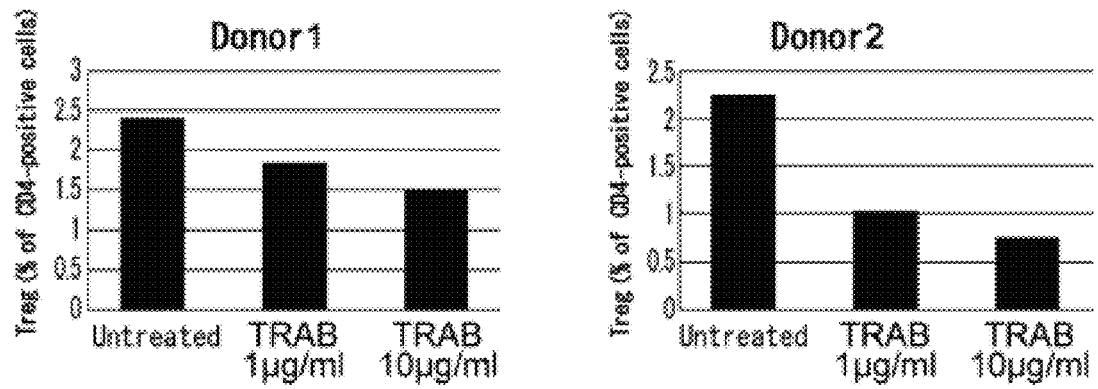
FIG. 17 presents graphs showing the proportion of regulatory T cells (Treg) in CD4-positive T cells, calculated based on the expression of CD25 and CD45RA, after a seven day reaction of PBMC derived from a healthy person with an anti-human OX40/anti-human CD3 bispecific antibody (TRAB).
Figure 18:
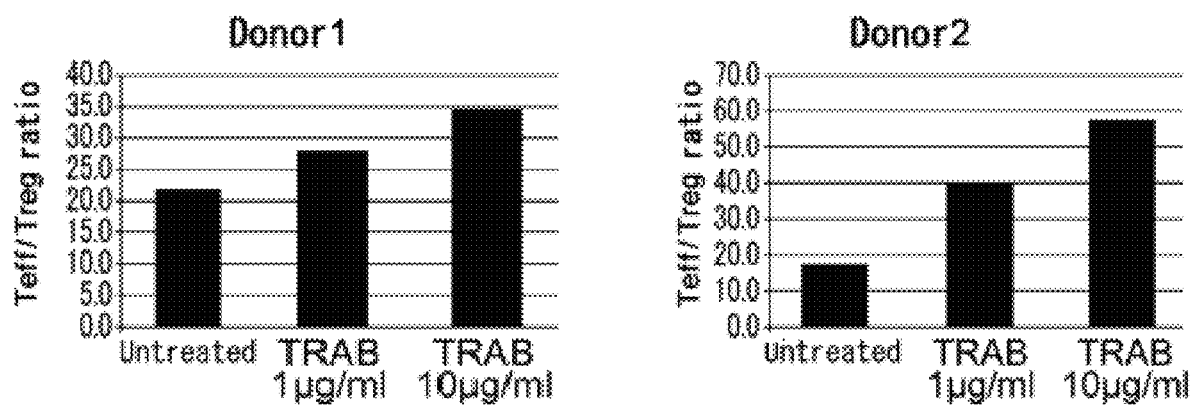
FIG. 18 presents graphs showing the ratio of effector T cells (Teff) to regulatory T cells (Treg) (Teff/Treg) in CD4-positive T cells, calculated based on the expression of CD25 and CD45RA, after a seven day reaction of PBMC derived from a healthy person with an anti-human OX40/anti-human CD3 bispecific antibody (TRAB).
Figure 19:
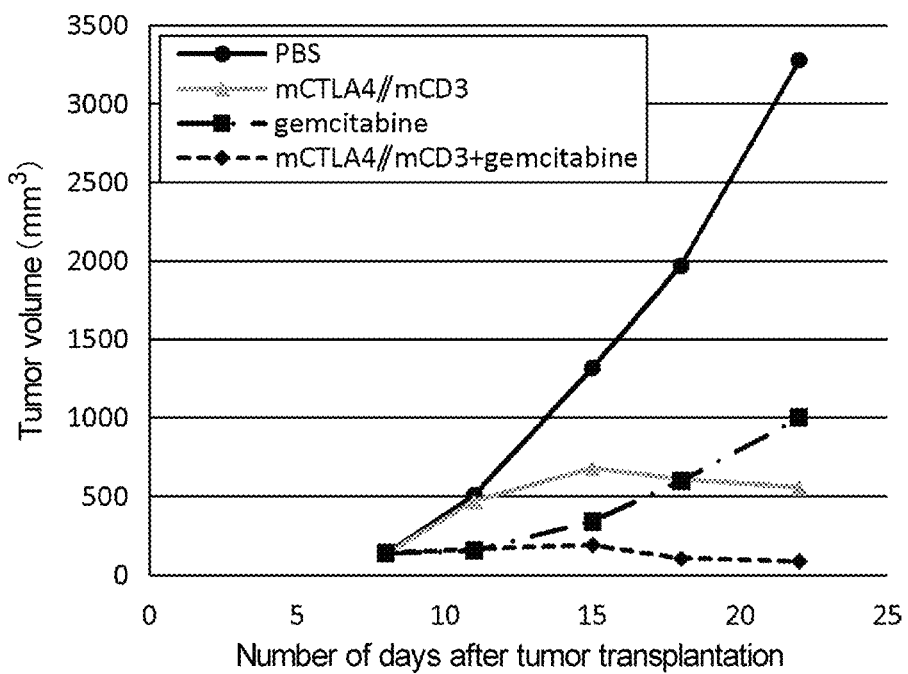
FIG. 19 presents a graph showing the results of verifying the effects of combined use of the anti-mouse CTLA4/anti-mouse CD3 antibody and gemcitabine in CT26.WT cell-transplanted models. It shows the changes in tumor volumes in CT26.WT cell line-transplanted mouse models to which the anti-mouse CTLA4/anti-mouse CD3 antibody and gemcitabine have been administered as a single agent or in combination. Each point shows the mean value of tumor volumes for n=5 per group. Parametric Tukey multiple comparison tests of the final measurement points indicated in the graph revealed that significant differences (p<0.05) were observed between the PBS-administered group vs. the mCTLA4/mCD3 antibody-administered group, the PBS-administered group vs. the gemcitabine-administered group, the PBS-administered group vs. the mCTLA4/mCD3 antibody+gemcitabine-administered group, and the gemcitabine-administered group vs. the mCTLA4/mCD3 antibody+gemcitabine-administered group.
Figure 20:
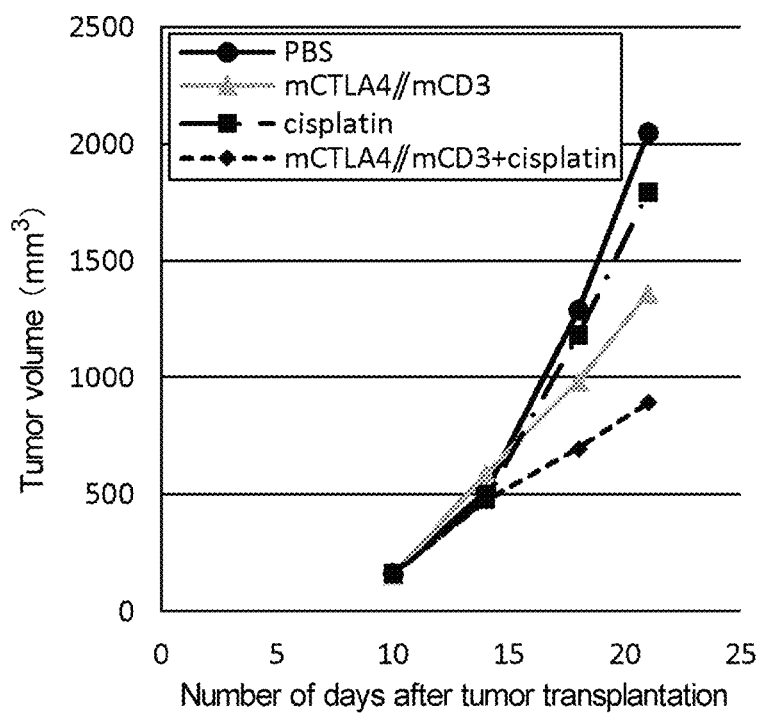
FIG. 20 presents a graph showing the results of verifying the effects of combined use of the anti-mouse CTLA4/anti-mouse CD3 antibody and cisplatin in LL/2 (LLC1) cell-transplanted models. It shows the changes in tumor volumes in LL/2 (LLC1) cell line-transplanted mouse models to which the anti-mouse CTLA4/anti-mouse CD3 antibody and cisplatin have been administered as a single agent or in combination. Each point shows the mean value of tumor volumes for n=5 per group. Parametric Tukey multiple comparison tests of the final measurement points indicated in the graph revealed that, while a significant difference (p<0.05) was observed between the PBS-administered group vs. the mCTLA4/mCD3 antibody+cisplatin-administered group, no significant difference was observed for each of the single agent-administered groups with respect to the PBS-administered group.
Figure 21:
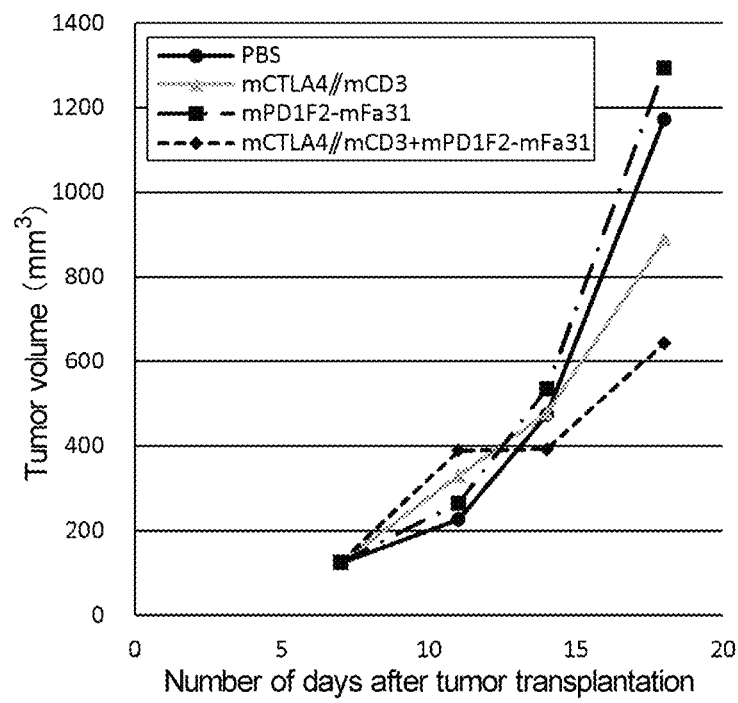
FIG. 21 presents a graph showing the results of verifying the effects of combined use of the anti-mouse CTLA4/anti-mouse CD3 antibody and the anti-mouse PD1 antibody in LL/2 (LLC1) cell-transplanted models. It shows the changes in tumor volumes in LL/2 (LLC1) cell line-transplanted mouse models to which the anti-mouse CTLA4/anti-mouse CD3 antibody and the anti-mouse PD1 antibody have been administered as a single agent or in combination. Each point shows the mean value of tumor volumes for n=5 per group. Parametric Tukey multiple comparison tests of the final measurement points indicated in the graph revealed that, while a significant difference (p<0.05) was observed between the PBS-administered group vs. the mCTLA4/mCD3 antibody+mPD1F2-mFa31 antibody-administered group, no significant difference was observed for each of the single agent-administered groups with respect to the PBS-administered group.
Figure 22:
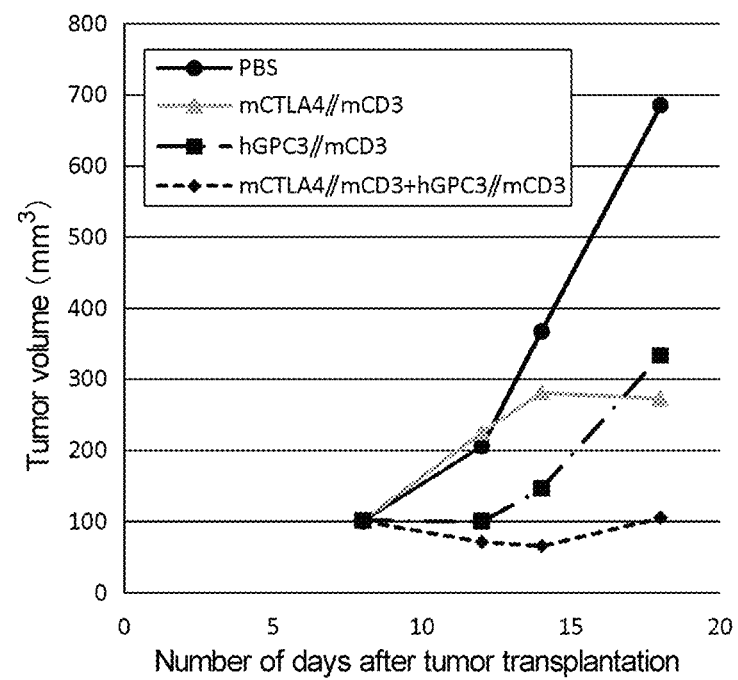
FIG. 22 presents a graph showing the results of verifying the effects of combined use of the anti-mouse CTLA4/anti-mouse CD3 antibody and the anti-human GPC3/anti-mouse CD3 antibody in LLC1/hGPC3 cell-transplanted models. It shows the changes in tumor volumes in LLC1/hGPC3 cell line-transplanted mouse models to which the anti-mouse CTLA4/anti-mouse CD3 antibody and the anti-human GPC3/anti-mouse CD3 antibody have been administered as a single agent or in combination. Each point shows the mean value of tumor volumes for n=5 per group. Parametric Tukey multiple comparison tests of the final measurement points indicated in the graph revealed that, while a significant difference (p<0.05) was observed between the PBS-administered group vs. the mCTLA4/mCD3 antibody+hGPC3/mCD3 antibody-administered group, no significant difference was observed for each of the single agent-administered groups with respect to the PBS-administered group.
Figure 23:
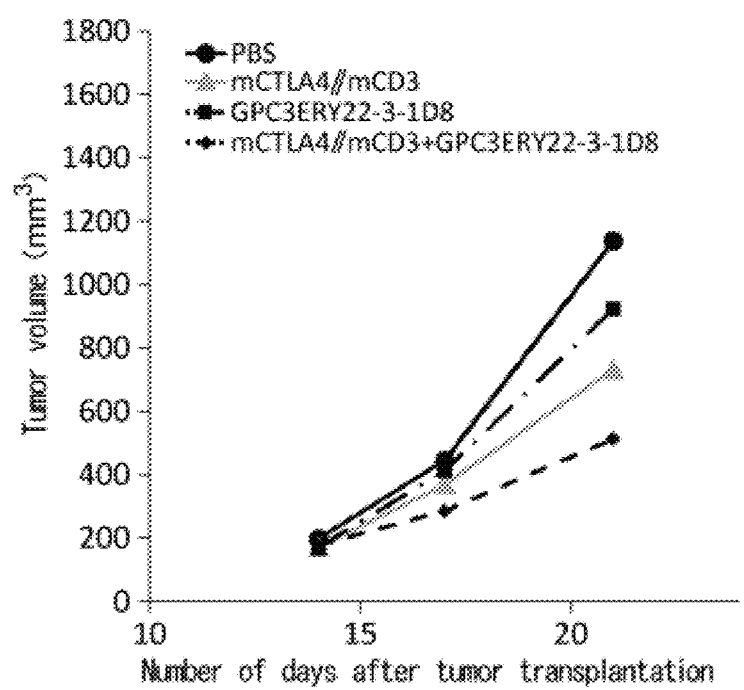
FIG. 23 presents a graph showing the results of verifying the effects of combined use of the anti-mouse CTLA4/anti-mouse CD3 antibody and the anti-mouse CD137/anti-human GPC3 antibody in CT26/hGPC3 cell-transplanted models. It shows the changes in tumor volumes in CT26/hGPC3 cell line-transplanted mouse models to which the anti-mouse CTLA4/anti-mouse CD3 antibody and the anti-mouse CD137/anti-human GPC3 antibody have been administered as a single agent or in combination. Each point shows the mean value of tumor volumes for n=5 per group.

The results of analyzing CD4-positive cells based on the expression of CD25 and CD45RA are shown (FIG. 16). Treatment of PBMCs derived from both donors with TRAB (12H3/TR01H113) at 1 µg/mL and 10 µg/mL showed decrease in Treg in a TRAB antibody dose-dependent manner (FIG. 17). Treatment with TRAB (12H3/TR01H113) at 1 µg/mL and 10 µg/mL increased the Teff/Treg ratios (FIG. 18).

[Reference Example 11] ADCC Activity of a Test Antibody Using Mouse FcgR4-Expressing Human NK Cell Line NK-92 as the Effector Cells Regarding anti-mouse CTLA4 antibodies, antibody concentration-dependent ADCC activities of test antibodies were measured, using the mouse FcgR4-expressing human NK cell line NK-92 (hereinafter referred to as mFcgR4-NK92) as effector cells by following the method described below.

(1) Preparation of mFcgR4-NK92 Solution

After washing mFcgR4-NK92 with RPMI-1640 (nacalai tesque) containing 10% FBS (hereinafter referred to as 10% FBS/RPMI), the cells were suspended in 10% FBS/RPMI at a cell density of $4 \times 10^5$ cells/ml. This cell suspension solution was used as the mFcgR4-NK92 solution in the subsequent experiments.

(2) Preparation of Target Cells

To $2 \times 10^6$ CHO/mouse CTLA4 cells which are CHO cells forced to express mouse CTLA4, 3.7 MBq of Cr-51 was added. The Cr-51-added cells were incubated in a 5% carbon dioxide gas incubator at 37° C. for one hour, then washed three times with 10% FBS/RPMI, and then suspended in 10% FBS/RPMI at a cell density of $2 \times 10^5$ cells/ml. The cell suspension was used as the target cells in the subsequent experiments.

(3) Chromium-Release Assay (ADCC Activity)

The ADCC activities were evaluated from the specific chromium release rate according to the chromium release method. First, antibody solutions prepared at each concentration (0, 0.04, 0.4, 4, and 40 µg/ml) were added to a 96-well U-bottomed plate at 50 µl per well. Next, the target cells prepared in (2) were seeded at 50 µl per well ($1 \times 10^4$ cells/well). Furthermore, 10% FBS/RPMI was added at 50 µl per well, and the plate was allowed to stand at room temperature for 15 minutes. The mFcgR4-NK92 solution prepared in (1) was added at 50 µl per well ($2 \times 10^4$ cells/well), the plate was left to stand in a 5% carbon dioxide gas incubator at 37° C. for four hours, and resultant was centrifuged. The radioactivity of 100 µl of culture supernatant in each well of the plate was measured using a gamma counter. The specific chromium release rate was determined based on the following equation.

$$\text{Chromium release rate (\%)} = (A-C) \times 100/(B-C)$$

In this equation, "A" represents the mean value of radioactivity (cpm) of 100 µl of culture supernatant in each well; "B" represents the mean value of radioactivity (cpm) of 100 µl of culture supernatant in a well where 50 µl of a 4% NP-40 aqueous solution (Nonidet P-40, Nacalai Tesque) and 100 µl of 10% FBS/RPMI had been added to the target cells; and "C" represents the mean value of radioactivity (cpm) of 100 µl of culture supernatant in a well where 150 µl of 10% FBS/RPMI had been added to the target cells. The examinations were performed in duplicate and the mean value for the specific chromium release rate (%) of the test antibody was calculated.

[Reference Example 12] Measurement of Cytotoxic Activity of a Test Antibody Using Mouse Splenocytes as Effector Cells Regarding the anti-mouse CTLA4/anti-mouse CD3 bispecific antibody (hUH02UL01/2C11-F760), antibody concentration-dependent cytotoxic activity of the test antibody was measured using mouse splenocytes as effector cells, and by following the method described below.

(1) Preparation of Mouse Splenocyte Solution

Ten mL of 10% FBS/RPMI was added to the spleen excised from a BALB/c mouse. The spleen was sliced into small pieces and passed through a cell strainer. After centrifugation (at 2,150 rpm for ten minutes at room temperature), a hemolysis procedure was performed using a Mouse Erythrocyte Lysing Kit (R&D Systems). After washing once with 10% FBS/RPMI, the cells were suspended in 10% FBS/RPMI at a cell density of $6 \times 10^6$ cells/ml. The cell suspension was used as the mouse splenocyte solution in the subsequent experiments.

(2) Cytotoxic Activity Evaluation Assay

Cytotoxic activity was evaluated by cell proliferation inhibition rate using the xCELLigence® Real-Time Cell Analyzer (Roche Diagnostics K.K.). CHO/mCTLA4 which is CHO forced to express mouse CTLA4 was used as the target cells. The cells were suspended in CHO-S-SFM II (Life technologies) containing 10% FBS, and were seeded in aliquots of 100 µl into an E-Plate 96 plate (Roche Diagnostics K.K.) at $5 \times 10^3$ cells/well. Measurement of living cells was started using the xCELLigence® Real-Time Cell Analyzer. On the following day, the plate was removed from the xCELLigence® Real-Time Cell Analyzer, and 50 µl of the respective antibodies prepared at each concentration (0.04, 0.4, 4, or 40 µg/ml) were added to the plate. After allowing this to stand at room temperature for 15 minutes, 50 µl of the mouse splenocyte solution prepared in (1) was added ($3 \times 10^5$ cells/well). By setting the plate into the xCELLigence® Real-Time Cell Analyzer again, measurement of living cells was started. The reaction was carried out in a 5% carbon dioxide gas incubator at 37° C., and from the Cell Index value obtained 72 hours after addition of the mouse splenocyte solution, the cell proliferation inhibition rate (%) was determined using the following equation. The Cell Index value used in the calculation was a normalized value where the Cell Index value immediately before antibody addition was defined as 1.

$$\text{Cell proliferation inhibition rate (\%)} = (A-B) \times 100/(A-1)$$

"A" represents the mean value of the Cell Index values in wells without antibody addition (containing only the target cells and human PBMC), and "B" represents the mean value of the Cell Index values in each well. The examinations were performed in duplicate.

[Reference Example 13] Production of an Anti-Mouse PD1 Antibody

An anti-mouse PD1 antibody (mPD1F2-mFa31) was produced. Heavy-chain variable region mPD1F2VH (SEQ ID NO: 50) and light-chain variable region mPD1F2VL (SEQ ID NO: 51) were used, and mouse heavy-chain constant region mFa31 (SEQ ID NO: 52) and wildtype mouse light-chain constant region mk1 (SEQ ID NO: 31) were used as the constant regions. In that case, the mouse heavy-chain constant region used was one which had been modified to decrease binding to Fcγ receptors.

The anti-mouse PD1 antibody was expressed using the following method. Cells of human embryonic kidney cell-derived FreeStyle™ 293-F strain (Invitrogen) were suspended and inoculated in the FreeStyle™ 293 Expression Medium (Invitrogen) at a cell density of $1.33 \times 10^6$ cells/mL. Prepared plasmids were introduced into the cells by a lipofection method. The cells were cultured for four days in a $CO_2$ incubator (37° C., 8% $CO_2$, 90 rpm). From the culture supernatants, antibodies were purified using Protein A Sepharose™ Fast Flow (Amersham Biosciences) by a method known to those skilled in the art. Absorbances at 280 nm of the purified antibody solutions were measured using a spectrophotometer. Concentrations of the purified antibodies were calculated from the determined values using an extinction coefficient calculated by the PACE method (Protein Science (1995) 4, 2411-2423).

[Reference Example 14] Production of an Anti-Mouse CTLA4/Anti-Mouse CD3 Bispecific Antibody and an Anti-Human GPC3/Anti-Mouse CD3 Bispecific Antibody (1) Production of an Anti-Mouse CTLA4/Anti-Mouse CD3 Bispecific Antibody An anti-mouse CTLA4/anti-mouse CD3 bispecific antibody (mCTLA4/mCD3), which is a combination of an anti-mouse CTLA4 antibody and an anti-mouse CD3 antibody, was produced. Heavy chain variable region hUH02 (SEQ ID NO: 28) and light chain variable region hUL01 (SEQ ID NO: 29) were used on the anti-mouse CTLA4 arm. In that case, the constant regions used were heavy chain constant region mF18mN4 (SEQ ID NO: 53), which had been modified to decrease binding to Fcγ receptors and enable heterologous association between the two heavy chains, and light chain constant region mk1 (SEQ ID NO: 31). Furthermore, heavy chain variable region 2C11VH (SEQ ID NO: 35) and light chain variable region 2C11VL (SEQ ID NO: 36) were used on the anti-mouse CD3 arm. In that case, the constant regions used were heavy chain constant region mF18mP4 (SEQ ID NO: 54), which had been modified to decrease binding to Fcγ receptors and enable heterologous association between the two heavy chains, and light chain constant region mk1 (SEQ ID NO: 31).

(2) Production of an Anti-Human GPC3/Anti-Mouse CD3 Bispecific Antibody

An anti-human GPC3/anti-mouse CD3 bispecific antibody (hGPC3/mCD3), which is a combination of an anti-human GPC3 antibody and an anti-mouse CD3 antibody, was produced. Heavy chain variable region H0000 (SEQ ID NO: 55) and light chain variable region GL4 (SEQ ID NO: 56) were used on the anti-human GPC3 arm. In that case, the constant regions used were heavy chain constant region mF18mN4 (SEQ ID NO: 53), which had been modified to decrease binding to Fcγ receptors and enable heterologous association between the two heavy chains, and light chain constant region mk1 (SEQ ID NO: 31). Furthermore, heavy chain variable region 2C11VH (SEQ ID NO: 35) and light chain variable region 2C11VL (SEQ ID NO: 36) were used on the anti-mouse CD3 arm. In that case, the constant regions used were heavy chain constant region mF18mP4 (SEQ ID NO: 54), which had been modified to decrease binding to Fcγ receptors and enable heterologous association between the two heavy chains, and light chain constant region mk1 (SEQ ID NO: 31).

(3) Antibody Expression

The antibodies of (1) and (2) above were expressed using the following method.

Cells of human embryonic kidney cell-derived FreeStyle™293-F strain (Invitrogen) were suspended and inoculated in the FreeStyle™ 293 Expression Medium (Invitrogen) at a cell density of $1.33 \times 10^6$ cells/mL. Prepared plasmids were introduced into the cells by a lipofection method. The cells were cultured for four days in a $CO_2$ incubator (37° C., 8% $CO_2$, 90 rpm). From the culture supernatants, antibodies were purified using the Hi Trap™ Protein G HP column (GE Healthcare) by a method known to those skilled in the art. Absorbances at 280 nm of the purified antibody solutions were measured using a spectrophotometer. Concentrations of the purified antibodies were calculated from the determined values using an extinction coefficient calculated by the PACE method (Protein Science (1995) 4: 2411-2423).

Each of the purified homologous forms was mixed in the combinations shown in Table 6, and the bispecific antibodies of interest were produced by a method known to those skilled in the art that utilizes differences in the charges of the constant regions (WO2015/046467).

TABLE 6

| No | Name of clone | Antibody 1 | Antibody 2 |
|---|---|---|---|
| 1 | mCTLA4//mCD3 | hUH02/hUL01-mF18mN4 | 2C11-mF18mP4 |
| 2 | hGPC3//mCD3 | H0000/GL4-mF18mN4 | 2C11-mF18mP4 |

[Reference Example 15] Production of an Anti-Human GPC3/Anti-Mouse CD137 Bispecific Antibody GPC3 ERY22-3-1D8, which is an anti-human GPC3/anti-mouse CD137 bispecific antibody, was produced. The H chains of GPC3 ERY22-3-1D8 comprise two types of H chains: GC33(2)H-G1dKnHSG3 (SEQ ID NO: 57) as the anti-human GPC3 arm H-chain constant region gene, prepared by introducing the H435R modification for simplifying purification known to those skilled in the art; and 1D8VH-G1dHlS (SEQ ID NO: 58) as the anti-mouse CD137 arm H chain constant region gene. As the L chains of GPC3 ERY22-3-1D8, GC33(2)L-k0 (SEQ ID NO: 59) and 1D8VL-k0 (SEQ ID NO: 60) were used on the anti-human GPC3 arm and the anti-mouse CD137 arm, respectively, to obtain the bispecific antibody of interest.

The antibody was expressed using the following method. Cells of human embryonic kidney cell-derived FreeStyle™ 293-F strain (Invitrogen) were suspended and inoculated in the FreeStyle™ 293 Expression Medium (Invitrogen) at a cell density of $1.33 \times 10^6$ cells/mL. Prepared plasmids were introduced into the cells by a lipofection method. The cells were cultured for four days in a $CO_2$ incubator (37° C., 8% $CO_2$, 90 rpm). The obtained culture supernatant was added to a MabSelect™ SuRe™ column (GE Healthcare), and the column was washed, followed by elution with 50 mM acetic acid. The antibody-containing fractions were added to a HisTrap™ HP column (GE Healthcare) or a Ni Sepharose™ FF column (GE Healthcare), and the column was washed, followed by elution with imidazole. The antibody-containing fractions were concentrated using an ultrafiltration membrane. Then, the concentrated solution was added to a Superdex® 200 column (GE Healthcare). Only the monomeric antibodies in the eluate were collected to obtain the purified antibodies.

TABLE 7

| Name of clone | H-chain gene 1 | L-chain gene 1 | H-chain gene 2 | L-chain gene 2 |
|---|---|---|---|---|
| GPC3 ERY22-3-1D8 | GC33 (2) H-G1dKnHSG3 | GC33 (2) L-k0 | 1D8VH-G1dHIS | 1D8VL-k0 |

[Example 1] Preparation of Syngeneic Tumor Cell-Engrafted Mouse Models (1) Cell Lines CT26.WT cells (ATCC No.: CRL-2638) or LL/2 (LLC1) cells (ATCC No.: CRL-1642) were used.

CT26/hGPC3 cell line that expresses human GPC3 in high levels was obtained by integrating the human GPC3 gene into the chromosome of the mouse colorectal cancer cell line CT26.WT by a method well known to those skilled in the art. The expression level of human GPC3 ($2.3 \times 10^5$/cell) was determined using the QIFI kit (Dako) by the manufacturer's recommended method.

CT26.WT cells were maintained and passaged in RPMI-1640 medium (manufactured by SIGMA) containing 10% FBS (manufactured by BOVOGEN), 0.5% D-glucose (manufactured by SIGMA), 1 mM Sodium Pyruvate (manufactured by ThermoFisher), and 10 mM HEPES (manufactured by SIGMA). The CT26/hGPC3 cell line was maintained and passaged in 10% FBS-containing RPMI-1640 (SIGMA, Cat. No. R8758) supplemented with 1 mM Sodium Pyruvate (Gibco, Cat. No. 11360-070), 10 mM HEPES (Sigma, Cat. No. H0887), 0.45% D-glucose (Sigma, Cat. No. G8769), and 200 µg/mL G-418 (Nacalai tesque, Cat. No. 09380-44).

The human GPC3 gene was integrated into the chromosome of the mouse lung cancer cell line LLC1 by a method well known to those skilled in the art to obtain an LLC1/hGPC3 cell line that expresses human GPC3 in high levels. The LL/2 (LLC1) cells and the LLC1/hGPC3 cell line were maintained and passaged in D-MEM (high glucose) medium (manufactured by SIGMA) containing 10% FBS (manufactured by BOVOGEN).

(2) Syngeneic Tumor Cell Engrafted Mouse Models

BALB/cA mice and C57BL/6N mice were purchased from Charles River Laboratories Japan, Inc. The CT26.WT cells or the CT26/hGPC3 cells were transplanted subcutaneously to BALB/cA mice, and the LL/2 (LLC1) cells or the LLC1/hGPC3 cells were transplanted subcutaneously to C57BL/6N mice. Models were established when the average volume of the transplanted tumors reached approximately 100 mm$^3$ to 200 mm$^3$.

The volume of the transplanted tumor was calculated using the following equation:

Tumor volume (mm$^3$)=major axis (mm)×minor axis (mm)×minor axis (mm)/2

[Example 2] Preparation of Pharmaceutical Agents to be Administered (1) The Pharmaceutical Agents to be Administered for Use in Test of Combined Use of an Anti-Mouse CTLA4/Anti-Mouse CD3 Bispecific Monoclonal Antibody and Gemcitabine As the pharmaceutical agents to be administered for the combined use test, the anti-mouse CTLA4/anti-mouse CD3 bispecific monoclonal antibody (mCTLA4/mCD3) was prepared at 0.125 mg/mL in PBS (−), and a pyrimidine analog (antimetabolite), gemcitabine (Gemzar: Eli Lilly Japan) was prepared at 12 mg/mL in physiological saline solution (Otsuka Pharmaceutical).

(2) The Pharmaceutical Agents to be Administered for Use in Test of Combined Use of an Anti-Mouse CTLA4/Anti-Mouse CD3 Bispecific Monoclonal Antibody and Cisplatin As the pharmaceutical agents to be administered for the combined use test, the anti-mouse CTLA4/CD3 bispecific monoclonal antibody (mCTLA4/mCD3) was prepared at 0.5 mg/mL in PBS (−), and, for a platinum compound, cisplatin (Briplatin: Bristol-Myers Co.), its stock solution (10 mg/20 mL) was administered as it was.

(3) The Pharmaceutical Agents to be Administered for Use in Examination of Combined Use of an Anti-Mouse CTLA4/Anti-Mouse CD3 Bispecific Monoclonal Antibody and an Anti-Mouse PD1 Monoclonal Antibody As the pharmaceutical agents to be administered for the combined use test, PBS (−) was used to prepare the anti-mouse CTLA4/CD3 bispecific monoclonal antibody (mCTLA4/mCD3) at 0.5 mg/mL and an immune checkpoint inhibitor, the anti-mouse PD1 monoclonal antibody (mPD1F2-mFa31) at 1.5 mg/mL.

(4) The Pharmaceutical Agents to be Administered for Use in Test of Combined Use of an Anti-Mouse CTLA4/Anti-Mouse CD3 Bispecific Monoclonal Antibody and an Anti-Human GPC3/Anti-Mouse CD3 Bispecific Monoclonal Antibody As the pharmaceutical agents to be administered for the combined use test, PBS (−) was used to prepare the anti-mouse CTLA4/anti-mouse CD3 bispecific monoclonal antibody (mCTLA4/mCD3) at 0.5 mg/mL and the anti-human GPC3/anti-mouse CD3 bispecific monoclonal antibody (hGPC3/mCD3) at 0.5 mg/mL.

(5) The Pharmaceutical Agents to be Administered for Use in Test of Combined Use of an Anti-Mouse CTLA4/Anti-Mouse CD3 Bispecific Monoclonal Antibody and an Anti-Mouse CD137/Anti-Human GPC3 Bispecific Antibody As the pharmaceutical agents to be administered for the combined use test, the anti-mouse CD137/human GPC3 bispecific antibody (GPC3 ERY22-3-1D8) and the anti-mouse CTLA4/anti-mouse CD3 bispecific antibody (mCTLA4/mCD3) were prepared at 0.05 mg/mL in 0.05% Tween 20/PBS.

[Example 3] Test of Combined Use of an Anti-Mouse CTLA4/Anti-Mouse CD3 Bispecific Monoclonal Antibody and Other Anticancer Agents 1-(1) Test of Combined Use of an Anti-Mouse CTLA4/Anti-Mouse CD3 Bispecific Monoclonal Antibody and Gemcitabine To evaluate the effects of combined use of the anti-mouse CTLA4/anti-mouse CD3 bispecific monoclonal antibody (mCTLA4/mCD3) and gemcitabine, the CT26.WT cell-transplanted model was used and given through the tail vein gemcitabine at 120 mg/kg eight days after transplantation and mCTLA3/mCD3 at 25 µg/mouse nine days after transplantation.

1-(2) the Pharmaceutical Agents to be Administered for Use in Test of Combined Use of an Anti-Mouse CTLA4/Anti-Mouse CD3 Bispecific Monoclonal Antibody and Cisplatin To evaluate the effects of combined use of the anti-mouse CTLA4/anti-mouse CD3 bispecific monoclonal antibody (mCTLA4/mCD3) and cisplatin, the LL/2 (LLC1) cell-transplanted model was used and given through the tail vein cisplatin at 5 mg/kg ten days after transplantation and mCTLA4/mCD3 at 100 µg/mouse eleven days after transplantation.

1-(3) the Pharmaceutical Agents to be Administered for Use in Test of Combined Use of an Anti-Mouse CTLA4/Anti-Mouse CD3 Bispecific Monoclonal Antibody and an Anti-Mouse PD1 Monoclonal Antibody To evaluate the effects of combined use of the anti-mouse CTLA4/CD3 bispecific monoclonal antibody (mCTLA4/mCD3) and the anti-mouse PD1 monoclonal antibody (mPD1F2-mFa31), the LL/2 (LLC1) cell-transplanted model was used and, seven days after transplantation, given through the tail vein mCTLA4/mCD3 at 100 µg/mouse and mPD1F2-mFa31 at 300 µg/mouse.

1-(4) the Pharmaceutical Agents to be Administered for Use in Test of Combined Use of an Anti-Mouse CTLA4/Anti- Mouse CD3 Bispecific Monoclonal Antibody and an Anti-Human GPC3/Anti-Mouse CD3 Bispecific Monoclonal Antibody To evaluate the effects of combined use of the anti-mouse CTLA4/CD3 bispecific monoclonal antibody (mCTLA4/mCD3) and the anti-human GPC3/anti-mouse CD3 bispecific monoclonal antibody (hGPC3/mCD3), the LLC1/hGPC3 cell-transplanted model was used and, eight days after transplantation, given mCTLA4/mCD3 and hGPC3/mCD3 each at 100 μg/mouse through the tail vein.

1-(5) Test of Combined Use of an Anti-Mouse CTLA4/Anti-Mouse CD3 Bispecific Monoclonal Antibody and an Anti-Mouse CD137/Anti-Human GPC3 Bispecific Antibody To evaluate the effects of combined use of the anti-mouse CTLA4/anti-mouse CD3 bispecific monoclonal antibody (mCTLA4/mCD3) and the anti-mouse CD137/anti-human GPC3 bispecific monoclonal antibody (GPC3 ERY22-3-1D8), the CT26/hGPC3 cell-transplanted model was used and, 14, 17, and 21 days after transplantation, given mCTLA4/mCD3 and GPC3 ERY22-3-1D8 each at 500 μg/kg through the tail vein.

The details of the pharmaceutical agent treatments described above in 1-(1) to 1-(5) are shown in Tables 8 to 12.

TABLE 8

CT26.WT cell-transplanted model (anti-mouse CTLA4/anti-mouse CD3 antibody and gemcitabine)

| Group | Number of animals | Pharmaceutical agent | Dose | Method of administration | Day of administration |
|---|---|---|---|---|---|
| 1 | 5 | PBS (—) | — | Tail vein | 8 days after transplantation |
| 2 | 5 | mCTLA4//mCD3 | 25 μg/mouse | Tail vein | 9 days after transplantation |
| 3 | 5 | gemcitabine | 120 mg/kg | Tail vein | 8 days after transplantation |
| 4 | 5 | mCTLA4//mCD3 gemcitabine | 25 μg/mouse 120 mg/kg | Tail vein Tail vein | 9 days after transplantation 8 days after transplantation |

TABLE 9

LL/2 (LLC1) cell-transplanted model (anti-mouse CTLA4/anti-mouse CD3 antibody and cisplatin)

| Group | Number of animals | Pharmaceutical agent | Dose | Method of administration | Day of administration |
|---|---|---|---|---|---|
| 1 | 5 | PBS (—) | — | Tail vein | 10 days after transplantation |
| 2 | 5 | mCTLA4//mCD3 | 100 μg/mouse | Tail vein | 11 days after transplantation |
| 3 | 5 | cisplatin | 5 mg/kg | Tail vein | 10 days after transplantation |
| 4 | 5 | mCTLA4//mCD3 cisplatin | 100 μg/mouse 5 mg/kg | Tail vein Tail vein | 11 days after transplantation 10 days after transplantation |

TABLE 10

LL/2 (LLC1) cell-transplanted model (anti-mouse CTLA4/anti-mouse CD3 antibody and anti-mouse PD1 antibody)

| Group | Number of animals | Pharmaceutical agent | Dose | Method of administration | Day of administration |
|---|---|---|---|---|---|
| 1 | 5 | PBS (—) | — | Tail vein | 7 days after transplantation |
| 2 | 5 | mCTLA4//mCD3 | 100 μg/mouse | Tail vein | 7 days after transplantation |
| 3 | 5 | mPD1F2-mFa31 | 300 μg/mouse | Tail vein | 7 days after transplantation |
| 4 | 5 | mCTLA4//mCD3 mPD1F2-mFa31 | 100 μg/mouse 300 μg/mouse | Tail vein Tail vein | 7 days after transplantation 7 days after transplantation |

TABLE 11

LLC1/hGPC3 cell-transplanted model (anti-mouse CTLA4/anti-mouse CD3 antibody and anti-human GPC3/anti-mouse CD3 antibody)

| Group | Number of animals | Pharmaceutical agent | Dose | Method of administration | Day of administration |
|---|---|---|---|---|---|
| 1 | 5 | PBS (—) | — | Tail vein | 8 days after transplantation |
| 2 | 5 | mCTLA4//mCD3 | 100 μg/mouse | Tail vein | 8 days after transplantation |
| 3 | 5 | hGPC3//mCD3 | 100 μg/mouse | Tail vein | 8 days after transplantation |

TABLE 11-continued

LLC1/hGPC3 cell-transplanted model (anti-mouse CTLA4/anti-mouse CD3 antibody and anti-human GPC3/anti-mouse CD3 antibody)

| Group | Number of animals | Pharmaceutical agent | Dose | Method of administration | Day of administration |
|---|---|---|---|---|---|
| 4 | 5 | mCTLA4//mCD3<br>hGPC3//mCD3 | 100 μg/mouse<br>100 μg/mouse | Tail vein<br>Tail vein | 8 days after transplantation<br>8 days after transplantation |

TABLE 12

CT26/hGPC3 cell-transplanted model (anti-mouse CTLA4/anti-mouse CD3 antibody and anti-mouse CD137/anti-human GPC3 antibody)

| Group | Number of animals | Pharmaceutical agent | Dose | Method of administration | Day of administration |
|---|---|---|---|---|---|
| 1 | 5 | 0.05% Tween 20 PBS | — | Tail vein | 14, 17, and 21 days after transplantation |
| 2 | 5 | mCTLA4//mCD3 | 500 μg/kg | Tail vein | 14, 17, and 21 days after transplantation |
| 3 | 5 | GPC3 ERY22-3-1D8 | 500 μg/kg | Tail vein | 14, 17, and 21 days after transplantation |
| 4 | 5 | mCTLA4//mCD3<br>GPC3 ERY22-3-1D8 | 500 μg/kg<br>500 μg/kg | Tail vein<br>Tail vein | 14, 17, and 21 days after transplantation<br>14, 17, and 21 days after transplantation |

2. Evaluation of Antitumor Effects in Combined Use Tests

Antitumor effects were evaluated from the tumor volumes calculated using the equation shown in (2) of Example 1. SAS preclinical package (SAS Institute Inc.) was used for statistical analyses. The evaluation results are shown in FIGS. 19 to 23. As a result of the evaluation, it was shown that tumor growth-suppressing effects of the anti-mouse CTLA4/anti-mouse CD3 bispecific monoclonal antibody were increased by using in combination with any one of gemcitabine, cisplatin, the anti-mouse PD1 antibody, the anti-human GPC3/anti-mouse CD3 antibody, and the anti-mouse CD137/anti-human GPC3 antibody.

The invention claimed is:

1. A method for treating colorectal cancer comprising administering to an individual in need thereof an effective amount of gemcitabine and an effective amount of an anti-CTLA4/CD3 bispecific antibody that comprises:
   (1) a first half that binds to CTLA4 and comprises a heavy chain variable region of SEQ ID NO: 28, a light chain variable region of SEQ ID NO: 29, a heavy chain constant region of SEQ ID NO: 53 and a light chain constant region of SEQ ID NO: 31; and
   (2) a second half that binds to CD3 and comprises a heavy chain variable region of SEQ ID NO: 35, a light chain variable region of SEQ ID NO: 36, a heavy chain constant region of SEQ ID NO: 54 and a light chain constant region of SEQ ID NO: 31,
   wherein gemcitabine is administered at a dose of 120 mg/kg and the anti-CTLA4/CD3 bispecific antibody is administered at a dose corresponding to 25 μg/mouse intravenously.

2. A method for treating non-small-cell lung cancer comprising administering to an individual in need thereof an effective amount of an anti-CTLA4/CD3 bispecific antibody and an effective amount of and anti-GPC3/CD3 bispecific antibody,
   wherein the anti-CTLA4/CD3 bispecific antibody comprises:
   (1) a first half that binds to CTLA4 and comprises a heavy chain variable region of SEQ ID NO: 28, a light chain variable region of SEQ ID NO: 29, a heavy chain constant region of SEQ ID NO: 53 and a light chain constant region of SEQ ID NO: 31; and
   (2) a second half that binds to CD3 and comprises a heavy chain variable region of SEQ ID NO: 35, a light chain variable region of SEQ ID NO: 36, a heavy chain constant region of SEQ ID NO: 54 and a light chain constant region of SEQ ID NO: 31,
   wherein the anti-GPC3/CD3 bispecific antibody comprises:
   (3) a first half that binds to GPC3 and comprises a heavy chain variable region of SEQ ID NO: 55, a light chain variable region of SEQ ID NO: 56, a heavy chain constant region of SEQ ID NO: 53 and a light chain constant region of SEQ ID NO: 31; and
   (4) a second half that binds to CD3 and comprises a heavy chain variable region of SEQ ID NO: 35, a light chain variable region of SEQ ID NO: 36, a heavy chain constant region of SEQ ID NO: 54 and a light chain constant region of SEQ ID NO: 31,
   wherein the anti-CTLA4/CD3 bispecific antibody and the anti-GPC3/CD3 bispecific antibody are administered each at a dose corresponding to 100 μg/mouse intravenously.

* * * * *

```
                        SEQUENCE LISTING

<160> NUMBER OF SEQ ID NOS: 60

<210> SEQ ID NO 1
<211> LENGTH: 330
<212> TYPE: PRT
<213> ORGANISM: Homo sapiens

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 2
<211> LENGTH: 326
<212> TYPE: PRT
<213> ORGANISM: Homo sapiens

<400> SEQUENCE: 2

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
```

```
            180                 185                 190
Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
            210                 215                 220

Pro Gln Val Tyr Thr Leu Pro Pro Ser Arg Glu Met Thr Lys Asn
225                 230                 235                 240

Gln Val Ser Leu Thr Cys Leu Val Lys Gly Phe Tyr Pro Ser Asp Ile
                    245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 3
<211> LENGTH: 377
<212> TYPE: PRT
<213> ORGANISM: Homo sapiens

<400> SEQUENCE: 3

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
                100                 105                 110

Arg Cys Pro Glu Pro Lys Ser Cys Asp Thr Pro Pro Cys Pro Arg
            115                 120                 125

Cys Pro Glu Pro Lys Ser Cys Asp Thr Pro Pro Cys Pro Arg Cys
            130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
            210                 215                 220
```

```
Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
            245                 250                 255

Ala Leu Pro Ala Pro Ile Glu Lys Thr Ile Ser Lys Thr Lys Gly Gln
        260                 265                 270

Pro Arg Glu Pro Gln Val Tyr Thr Leu Pro Pro Ser Arg Glu Glu Met
    275                 280                 285

Thr Lys Asn Gln Val Ser Leu Thr Cys Leu Val Lys Gly Phe Tyr Pro
290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 4
<211> LENGTH: 327
<212> TYPE: PRT
<213> ORGANISM: Homo sapiens

<400> SEQUENCE: 4

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220
```

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Arg Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 5
<211> LENGTH: 330
<212> TYPE: PRT
<213> ORGANISM: Artificial
<220> FEATURE:
<223> OTHER INFORMATION: an artificially synthesized sequence

<400> SEQUENCE: 5

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 6
<211> LENGTH: 326
<212> TYPE: PRT
<213> ORGANISM: Artificial
<220> FEATURE:
<223> OTHER INFORMATION: an artificially synthesized sequence

<400> SEQUENCE: 6

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285
```

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 7
<211> LENGTH: 377
<212> TYPE: PRT
<213> ORGANISM: Artificial
<220> FEATURE:
<223> OTHER INFORMATION: an artificially synthesized sequence

<400> SEQUENCE: 7

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

```
Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 8
<211> LENGTH: 327
<212> TYPE: PRT
<213> ORGANISM: Artificial
<220> FEATURE:
<223> OTHER INFORMATION: an artificially synthesized sequence

<400> SEQUENCE: 8

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300
```

-continued

```
Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 9
<211> LENGTH: 141
<212> TYPE: PRT
<213> ORGANISM: Homo sapiens

<400> SEQUENCE: 9

Asp Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 10
<211> LENGTH: 179
<212> TYPE: PRT
<213> ORGANISM: Homo sapiens

<400> SEQUENCE: 10

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160
```

Val Leu Val Ser Ala Leu Val Leu Met Ala Met Val Lys Arg Lys Asp
            165                 170                 175

Ser Arg Gly

<210> SEQ ID NO 11
<211> LENGTH: 173
<212> TYPE: PRT
<213> ORGANISM: Homo sapiens

<400> SEQUENCE: 11

Asp Lys Gln Leu Asp Ala Asp Val Ser Pro Lys Pro Thr Ile Phe Leu
1               5                   10                  15

Pro Ser Ile Ala Glu Thr Lys Leu Gln Lys Ala Gly Thr Tyr Leu Cys
            20                  25                  30

Leu Leu Glu Lys Phe Phe Pro Asp Val Ile Lys Ile His Trp Gln Glu
        35                  40                  45

Lys Lys Ser Asn Thr Ile Leu Gly Ser Gln Glu Gly Asn Thr Met Lys
    50                  55                  60

Thr Asn Asp Thr Tyr Met Lys Phe Ser Trp Leu Thr Val Pro Glu Lys
65                  70                  75                  80

Ser Leu Asp Lys Glu His Arg Cys Ile Val Arg His Glu Asn Asn Lys
                85                  90                  95

Asn Gly Val Asp Gln Glu Ile Ile Phe Pro Pro Ile Lys Thr Asp Val
            100                 105                 110

Ile Thr Met Asp Pro Lys Asp Asn Cys Ser Lys Asp Ala Asn Asp Thr
        115                 120                 125

Leu Leu Leu Gln Leu Thr Asn Thr Ser Ala Tyr Tyr Met Tyr Leu Leu
    130                 135                 140

Leu Leu Leu Lys Ser Val Val Tyr Phe Ala Ile Ile Thr Cys Cys Leu
145                 150                 155                 160

Leu Arg Arg Thr Ala Phe Cys Cys Asn Gly Glu Lys Ser
                165                 170

<210> SEQ ID NO 12
<211> LENGTH: 204
<212> TYPE: PRT
<213> ORGANISM: Homo sapiens

<400> SEQUENCE: 12

Lys Gln Leu Asp Ala Asp Val Ser Pro Lys Pro Thr Ile Phe Leu Pro
1               5                   10                  15

Ser Ile Ala Glu Thr Lys Leu Gln Lys Ala Gly Thr Tyr Leu Cys Leu
            20                  25                  30

Leu Glu Lys Phe Phe Pro Asp Ile Ile Lys Ile His Trp Gln Glu Lys
        35                  40                  45

Lys Ser Asn Thr Ile Leu Gly Ser Gln Glu Gly Asn Thr Met Lys Thr
    50                  55                  60

Asn Asp Thr Tyr Met Lys Phe Ser Trp Leu Thr Val Pro Glu Glu Ser
65                  70                  75                  80

Leu Asp Lys Glu His Arg Cys Ile Val Arg His Glu Asn Asn Lys Asn
                85                  90                  95

Gly Ile Asp Gln Glu Ile Ile Phe Pro Pro Ile Lys Thr Asp Val Thr
            100                 105                 110

Thr Val Asp Pro Lys Asp Ser Tyr Ser Lys Asp Ala Asn Asp Val Thr
        115                 120                 125

```
Thr Val Asp Pro Lys Tyr Asn Tyr Ser Lys Asp Ala Asn Asp Val Ile
    130                 135                 140
Thr Met Asp Pro Lys Asp Asn Trp Ser Lys Asp Ala Asn Asp Thr Leu
145                 150                 155                 160
Leu Leu Gln Leu Thr Asn Thr Ser Ala Tyr Tyr Met Tyr Leu Leu Leu
                165                 170                 175
Leu Leu Lys Ser Val Val Tyr Phe Ala Ile Ile Thr Cys Cys Leu Leu
            180                 185                 190
Gly Arg Thr Ala Phe Cys Cys Asn Gly Glu Lys Ser
            195                 200

<210> SEQ ID NO 13
<211> LENGTH: 177
<212> TYPE: PRT
<213> ORGANISM: Homo sapiens

<400> SEQUENCE: 13

Pro Ser Tyr Thr Gly Gly Tyr Ala Asp Lys Leu Ile Phe Gly Lys Gly
1               5                   10                  15
Thr Arg Val Thr Val Glu Pro Arg Ser Gln Pro His Thr Lys Pro Ser
            20                  25                  30
Val Phe Val Met Lys Asn Gly Thr Asn Val Ala Cys Leu Val Lys Glu
        35                  40                  45
Phe Tyr Pro Lys Asp Ile Arg Ile Asn Leu Val Ser Ser Lys Lys Ile
    50                  55                  60
Thr Glu Phe Asp Pro Ala Ile Val Ile Ser Pro Ser Gly Lys Tyr Asn
65                  70                  75                  80
Ala Val Lys Leu Gly Lys Tyr Glu Asp Ser Asn Ser Val Thr Cys Ser
                85                  90                  95
Val Gln His Asp Asn Lys Thr Val His Ser Thr Asp Phe Glu Val Lys
            100                 105                 110
Thr Asp Ser Thr Asp His Val Lys Pro Lys Glu Thr Glu Asn Thr Lys
        115                 120                 125
Gln Pro Ser Lys Ser Cys His Lys Pro Lys Ala Ile Val His Thr Glu
    130                 135                 140
Lys Val Asn Met Met Ser Leu Thr Val Leu Gly Leu Arg Met Leu Phe
145                 150                 155                 160
Ala Lys Thr Val Ala Val Asn Phe Leu Leu Thr Ala Lys Leu Phe Phe
                165                 170                 175
Leu

<210> SEQ ID NO 14
<211> LENGTH: 549
<212> TYPE: DNA
<213> ORGANISM: Homo sapiens

<400> SEQUENCE: 14
atggaacagg ggaagggcct ggctgtcctc atcctggcta tcattcttct tcaaggtact      60
ttggcccagt caatcaaagg aaaccacttg gttaaggtgt atgactatca agaagatggt     120
tcggtacttc tgacttgtga tgcagaagcc aaaaatatca catggtttaa agatgggaag     180
atgatcggct tcctaactga agataaaaaa aaatggaatc tgggaagtaa tgccaaggac     240
cctcgaggga tgtatcagtg taaaggatca cagaacaagt caaaaccact ccaagtgtat     300
tacagaatgt gtcagaactg cattgaacta atgcagccca ccatatctgg ctttctcttt     360
gctgaaatcg tcagcatttt cgtccttgct gttgggtct acttcattgc tggacaggat     420
```

-continued

```
ggagttcgcc agtcgagagc ttcagacaag cagactctgt tgcccaatga ccagctctac      480
cagcccctca aggatcgaga agatgaccag tacagccacc ttcaaggaaa ccagttgagg      540
aggaattga                                                              549
```

```
<210> SEQ ID NO 15
<211> LENGTH: 182
<212> TYPE: PRT
<213> ORGANISM: Homo sapiens

<400> SEQUENCE: 15
```

```
Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
            20                  25                  30

Val Tyr Asp Tyr Gln Glu Asp Gly Ser Val Leu Leu Thr Cys Asp Ala
        35                  40                  45

Glu Ala Lys Asn Ile Thr Trp Phe Lys Asp Gly Lys Met Ile Gly Phe
    50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Gln Asp Gly Val Arg Gln
    130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Asp Gln Tyr Ser His Leu Gln Gly
                165                 170                 175

Asn Gln Leu Arg Arg Asn
            180
```

```
<210> SEQ ID NO 16
<211> LENGTH: 516
<212> TYPE: DNA
<213> ORGANISM: Homo sapiens

<400> SEQUENCE: 16
atggaacata gcacgtttct ctctggcctg gtactggcta cccttctctc gcaagtgagc       60
cccttcaaga tacctataga ggaacttgag gacagagtgt ttgtgaattg caataccagc     120
atcacatggg tagagggaac ggtgggaaca ctgctctcag acattacaag actggacctg     180
ggaaaacgca tcctggaccc acgaggaata taggtgta atgggacaga tatatacaag       240
gacaaagaat ctaccgtgca agttcattat cgaatgtgcc agagctgtgt ggagctggat     300
ccagccaccg tggctggcat cattgtcact gatgtcattg ccactctgct ccttgctttg     360
ggagtcttct gctttgctgg acatgagact ggaaggctgt ctggggctgc cgacacacaa     420
gctctgttga ggaatgacca ggtctatcag cccctccgag atcgagatga tgctcagtac     480
agccaccttg aggaaactg ggctcggaac aagtga                                516
```

```
<210> SEQ ID NO 17
```

<211> LENGTH: 171
<212> TYPE: PRT
<213> ORGANISM: Homo sapiens

<400> SEQUENCE: 17

```
Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170
```

<210> SEQ ID NO 18
<211> LENGTH: 624
<212> TYPE: DNA
<213> ORGANISM: Homo sapiens

<400> SEQUENCE: 18

```
atgcagtcgg gcactcactg gagagttctg ggcctctgcc tcttatcagt tggcgtttgg      60
gggcaagatg gtaatgaaga atgggtggt attacacaga caccatataa agtctccatc     120
tctggaacca cagtaatatt gacatgccct cagtatcctg gatctgaaat actatggcaa     180
cacaatgata aaaacatagg cggtgatgag gatgataaaa acataggcag tgatgaggat     240
cacctgtcac tgaaggaatt ttcagaattg gagcaaagtg gttattatgt ctgctacccc     300
agaggaagca aaccagaaga tgcgaacttt tatctctacc tgagggcaag agtgtgtgag     360
aactgcatgg agatggatgt gatgtcggtg ccacaattg tcatagtgga catctgcatc     420
actgggggct tgctgctgct ggtttactac tggagcaaga atagaaaggc caaggccaag     480
cctgtgacac gaggagcggg tgctggcggc aggcaagggg acaaaacaa ggagaggcca     540
ccacctgttc ccaacccaga ctatgagccc atccggaaag ccagcgggga cctgtattct     600
ggcctgaatc agagacgcat ctga                                           624
```

<210> SEQ ID NO 19
<211> LENGTH: 207
<212> TYPE: PRT
<213> ORGANISM: Homo sapiens

<400> SEQUENCE: 19

```
Met Gln Ser Gly Thr His Trp Arg Val Leu Gly Leu Cys Leu Leu Ser
1               5                   10                  15
```

-continued

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
                195                 200                 205

<210> SEQ ID NO 20
<211> LENGTH: 4
<212> TYPE: PRT
<213> ORGANISM: Artificial
<220> FEATURE:
<223> OTHER INFORMATION: an artificially synthesized sequence

<400> SEQUENCE: 20

Gly Gly Gly Ser
1

<210> SEQ ID NO 21
<211> LENGTH: 4
<212> TYPE: PRT
<213> ORGANISM: Artificial
<220> FEATURE:
<223> OTHER INFORMATION: an artificially synthesized sequence

<400> SEQUENCE: 21

Ser Gly Gly Gly
1

<210> SEQ ID NO 22
<211> LENGTH: 5
<212> TYPE: PRT
<213> ORGANISM: Artificial
<220> FEATURE:
<223> OTHER INFORMATION: an artificially synthesized sequence

<400> SEQUENCE: 22

Gly Gly Gly Gly Ser
1               5

<210> SEQ ID NO 23
<211> LENGTH: 5

-continued

```
<212> TYPE: PRT
<213> ORGANISM: Artificial
<220> FEATURE:
<223> OTHER INFORMATION: an artificially synthesized sequence

<400> SEQUENCE: 23

Ser Gly Gly Gly Gly
1               5

<210> SEQ ID NO 24
<211> LENGTH: 6
<212> TYPE: PRT
<213> ORGANISM: Artificial
<220> FEATURE:
<223> OTHER INFORMATION: an artificially synthesized sequence

<400> SEQUENCE: 24

Gly Gly Gly Gly Gly Ser
1               5

<210> SEQ ID NO 25
<211> LENGTH: 6
<212> TYPE: PRT
<213> ORGANISM: Artificial
<220> FEATURE:
<223> OTHER INFORMATION: an artificially synthesized sequence

<400> SEQUENCE: 25

Ser Gly Gly Gly Gly Gly
1               5

<210> SEQ ID NO 26
<211> LENGTH: 7
<212> TYPE: PRT
<213> ORGANISM: Artificial
<220> FEATURE:
<223> OTHER INFORMATION: an artificially synthesized sequence

<400> SEQUENCE: 26

Gly Gly Gly Gly Gly Gly Ser
1               5

<210> SEQ ID NO 27
<211> LENGTH: 7
<212> TYPE: PRT
<213> ORGANISM: Artificial
<220> FEATURE:
<223> OTHER INFORMATION: an artificially synthesized sequence

<400> SEQUENCE: 27

Ser Gly Gly Gly Gly Gly Gly
1               5

<210> SEQ ID NO 28
<211> LENGTH: 116
<212> TYPE: PRT
<213> ORGANISM: Artificial
<220> FEATURE:
<223> OTHER INFORMATION: an artificially synthesized sequence

<400> SEQUENCE: 28

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Ser Gly
            20                  25                  30

Tyr Gly Trp Asn Trp Ile Arg Gln Pro Pro Gly Lys Gly Leu Glu Trp
```

```
                35                  40                  45
Ile Gly Phe Ile Tyr Tyr Glu Gly Ser Thr Tyr Tyr Asn Pro Ser Ile
             50                  55                  60
Lys Ser Arg Ile Ser Ile Thr Arg Asp Thr Ser Lys Asn Gln Phe Phe
 65                  70                  75                  80
Leu Gln Val Asn Ser Val Thr Glu Asp Thr Ala Thr Tyr Tyr Cys
                 85                  90                  95
Ala Arg Gln Thr Gly Tyr Phe Asp Tyr Trp Gly Gln Gly Thr Leu Val
            100                 105                 110
Thr Val Ser Ser
            115

<210> SEQ ID NO 29
<211> LENGTH: 113
<212> TYPE: PRT
<213> ORGANISM: Artificial
<220> FEATURE:
<223> OTHER INFORMATION: an artificially synthesized sequence

<400> SEQUENCE: 29

Asp Ile Val Met Thr Gln Ser Pro Asp Ser Leu Ala Val Ser Leu Gly
 1               5                  10                  15
Glu Arg Ala Thr Ile Asn Cys Lys Ser Ser Gln Ser Leu Phe Asn Ser
             20                  25                  30
Asn Ala Lys Thr Asn Tyr Leu Asn Trp Tyr Gln Gln Lys Pro Gly Gln
         35                  40                  45
Pro Pro Lys Leu Leu Ile Tyr Tyr Ala Ser Thr Arg His Thr Gly Val
     50                  55                  60
Pro Asp Arg Phe Ser Gly Ser Gly Ser Gly Thr Asp Phe Thr Leu Thr
 65                  70                  75                  80
Ile Ser Ser Leu Gln Ala Glu Asp Val Ala Val Tyr Tyr Cys Gln Gln
                 85                  90                  95
Trp Tyr Asp Tyr Pro Tyr Thr Phe Gly Ala Gly Thr Lys Val Glu Ile
            100                 105                 110
Lys

<210> SEQ ID NO 30
<211> LENGTH: 330
<212> TYPE: PRT
<213> ORGANISM: Artificial
<220> FEATURE:
<223> OTHER INFORMATION: an artificially synthesized sequence

<400> SEQUENCE: 30

Ala Lys Thr Thr Ala Pro Ser Val Tyr Pro Leu Ala Pro Val Cys Gly
 1               5                  10                  15
Asp Thr Thr Gly Ser Ser Val Thr Leu Gly Cys Leu Val Lys Gly Tyr
             20                  25                  30
Phe Pro Glu Pro Val Thr Leu Thr Trp Asn Ser Gly Ser Leu Ser Ser
         35                  40                  45
Gly Val His Thr Phe Pro Ala Val Leu Gln Ser Asp Leu Tyr Thr Leu
     50                  55                  60
Ser Ser Ser Val Thr Val Thr Ser Ser Thr Trp Pro Ser Gln Ser Ile
 65                  70                  75                  80
Thr Cys Asn Val Ala His Pro Ala Ser Ser Thr Lys Val Asp Lys Lys
                 85                  90                  95
Ile Glu Pro Arg Gly Pro Thr Ile Lys Pro Cys Pro Pro Cys Lys Cys
```

```
            100                 105                 110
Pro Ala Pro Asn Leu Leu Gly Gly Pro Asp Val Phe Ile Phe Pro Pro
            115                 120                 125

Lys Ile Lys Asp Val Leu Met Ile Ser Leu Ser Pro Ile Val Thr Cys
130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 31
<211> LENGTH: 107
<212> TYPE: PRT
<213> ORGANISM: Mus musculus

<400> SEQUENCE: 31

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 32
<211> LENGTH: 330
<212> TYPE: PRT
<213> ORGANISM: Mus musculus
```

```
<400> SEQUENCE: 32

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
    130                 135                 140

Val Val Val Asp Val Ser Glu Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 33
<211> LENGTH: 328
<212> TYPE: PRT
<213> ORGANISM: Artificial
<220> FEATURE:
<223> OTHER INFORMATION: an artificially synthesized sequence

<400> SEQUENCE: 33

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
```

```
                20              25              30
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Arg Gly Gly Pro Lys Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Tyr Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Glu Ser Leu Ser Leu Ser Pro
                325

<210> SEQ ID NO 34
<211> LENGTH: 107
<212> TYPE: PRT
<213> ORGANISM: Homo sapiens

<400> SEQUENCE: 34

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60
```

```
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 35
<211> LENGTH: 116
<212> TYPE: PRT
<213> ORGANISM: Cricetulus migratorius

<400> SEQUENCE: 35

Glu Val Gln Leu Val Glu Ser Gly Gly Gly Leu Val Gln Pro Gly Lys
 1               5                  10                  15

Ser Leu Lys Leu Ser Cys Glu Ala Ser Gly Phe Thr Phe Ser Gly Tyr
                20                  25                  30

Gly Met His Trp Val Arg Gln Ala Pro Gly Arg Gly Leu Glu Ser Val
            35                  40                  45

Ala Tyr Ile Thr Ser Ser Ile Asn Ile Lys Tyr Ala Asp Ala Val
        50                  55                  60

Lys Gly Arg Phe Thr Val Ser Arg Asp Asn Ala Lys Asn Leu Leu Phe
 65                  70                  75                  80

Leu Gln Met Asn Ile Leu Lys Ser Glu Asp Thr Ala Met Tyr Tyr Cys
                 85                  90                  95

Ala Arg Phe Asp Trp Asp Lys Asn Tyr Trp Gly Gln Gly Thr Met Val
            100                 105                 110

Thr Val Ser Ser
        115

<210> SEQ ID NO 36
<211> LENGTH: 107
<212> TYPE: PRT
<213> ORGANISM: Cricetulus migratorius

<400> SEQUENCE: 36

Asp Ile Gln Met Thr Gln Ser Pro Ser Ser Leu Pro Ala Ser Leu Gly
 1               5                  10                  15

Asp Arg Val Thr Ile Asn Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Asn Lys Leu Ala Asp Gly Val Pro Ser Arg Phe Ser Gly
        50                  55                  60

Ser Gly Ser Gly Arg Asp Ser Ser Phe Thr Ile Ser Ser Leu Glu Ser
 65                  70                  75                  80

Glu Asp Ile Gly Ser Tyr Tyr Cys Gln Gln Tyr Tyr Asn Tyr Pro Trp
                 85                  90                  95

Thr Phe Gly Pro Gly Thr Lys Leu Glu Ile Lys
            100                 105

<210> SEQ ID NO 37
<211> LENGTH: 328
<212> TYPE: PRT
<213> ORGANISM: Artificial
<220> FEATURE:
<223> OTHER INFORMATION: an artificially synthesized sequence

<400> SEQUENCE: 37
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Arg Gly Gly Pro Lys Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Lys Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Tyr Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 38
<211> LENGTH: 118
<212> TYPE: PRT
<213> ORGANISM: Artificial
<220> FEATURE:
<223> OTHER INFORMATION: an artificially synthesized sequence

<400> SEQUENCE: 38

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30
```

Thr Met His Trp Val Arg Gln Ala Pro Gly Lys Gly Leu Glu Trp Val
            35                  40                  45

Thr Phe Ile Ser Tyr Asp Gly Asn Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser
            115

<210> SEQ ID NO 39
<211> LENGTH: 110
<212> TYPE: PRT
<213> ORGANISM: Artificial
<220> FEATURE:
<223> OTHER INFORMATION: an artificially synthesized sequence

<400> SEQUENCE: 39

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Ser Ser
            100                 105                 110

<210> SEQ ID NO 40
<211> LENGTH: 122
<212> TYPE: PRT
<213> ORGANISM: Artificial
<220> FEATURE:
<223> OTHER INFORMATION: an artificially synthesized sequence

<400> SEQUENCE: 40

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Lys Ser Gln Asn Tyr Ala Thr Tyr Val Ala Glu
    50                  55                  60

Ser Val Lys Gly Arg Phe Thr Ile Ser Arg Ala Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Ala Ala Gly Tyr Gly Val Asp Ile Trp

```
                    100                 105                 110

Gly Gln Gly Thr Thr Val Thr Val Ser Ser
            115                 120

<210> SEQ ID NO 41
<211> LENGTH: 112
<212> TYPE: PRT
<213> ORGANISM: Artificial
<220> FEATURE:
<223> OTHER INFORMATION: an artificially synthesized sequence

<400> SEQUENCE: 41

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Pro Leu Val His Ser
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gly
                85                  90                  95

Thr Gln Val Pro Tyr Thr Phe Gly Gln Gly Thr Lys Leu Glu Ile Lys
                100                 105                 110

<210> SEQ ID NO 42
<211> LENGTH: 328
<212> TYPE: PRT
<213> ORGANISM: Artificial
<220> FEATURE:
<223> OTHER INFORMATION: an artificially synthesized sequence

<400> SEQUENCE: 42

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Arg Gly Gly Pro Lys Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Ala Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Lys Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Tyr Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn Arg Tyr Thr
305                 310                 315                 320

Gln Lys Ser Leu Ser Leu Ser Pro
                325

<210> SEQ ID NO 43
<211> LENGTH: 116
<212> TYPE: PRT
<213> ORGANISM: Artificial
<220> FEATURE:
<223> OTHER INFORMATION: an artificially synthesized sequence

<400> SEQUENCE: 43

Gln Val Gln Leu Gln Gln Ser Gly Pro Gln Leu Val Arg Pro Gly Ala
1               5                   10                  15

Ser Val Lys Ile Ser Cys Lys Ala Ser Gly Tyr Ser Phe Thr Ser Tyr
                20                  25                  30

Trp Met His Trp Val Asn Gln Arg Pro Gly Gln Gly Leu Glu Trp Ile
            35                  40                  45

Gly Met Ile Asp Pro Ser Tyr Ser Glu Thr Arg Leu Asn Gln Lys Phe
        50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Leu Tyr Gly Asn Tyr Phe Asp Tyr Trp Gly Gln Gly Thr Thr Leu
                100                 105                 110

Thr Val Ser Ser
        115

<210> SEQ ID NO 44
<211> LENGTH: 107
<212> TYPE: PRT
<213> ORGANISM: Artificial
<220> FEATURE:
<223> OTHER INFORMATION: an artificially synthesized sequence

<400> SEQUENCE: 44

Asp Ile Gln Met Thr Gln Ser Ser Ser Phe Ser Val Ser Leu Gly
1               5                   10                  15

Asp Arg Val Thr Ile Thr Cys Lys Ala Ser Glu Asp Ile Tyr Asn Arg
                20                  25                  30
```

```
Leu Ala Trp Tyr Gln Gln Lys Pro Gly Asn Ala Pro Arg Leu Leu Ile
             35                  40                  45

Ser Gly Ala Thr Ser Leu Glu Thr Gly Val Pro Ser Arg Phe Ser Gly
 50                  55                  60

Ser Gly Ser Gly Lys Asp Tyr Thr Leu Ser Ile Thr Ser Leu Gln Thr
 65                  70                  75                  80

Glu Asp Val Ala Thr Tyr Tyr Cys Gln Gln Tyr Trp Ser Thr Pro Tyr
                 85                  90                  95

Thr Phe Gly Gly Gly Thr Lys Leu Glu Val Lys
             100                 105

<210> SEQ ID NO 45
<211> LENGTH: 328
<212> TYPE: PRT
<213> ORGANISM: Artificial
<220> FEATURE:
<223> OTHER INFORMATION: an artificially synthesized sequence

<400> SEQUENCE: 45

Ala Ser Thr Lys Gly Pro Ser Val Phe Pro Leu Ala Pro Ser Ser Lys
1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 46
<211> LENGTH: 120
<212> TYPE: PRT
<213> ORGANISM: Artificial
<220> FEATURE:
<223> OTHER INFORMATION: an artificially synthesized sequence

<400> SEQUENCE: 46

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile Asn His Asn Gly Asn Thr Asn Ser Asn Pro Ser Leu Lys
    50                  55                  60

Ser Arg Val Thr Leu Ser Leu Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Phe Gly Tyr Ser Asp Tyr Glu Tyr Asn Trp Phe Asp Pro Trp Gly Gln
            100                 105                 110

Gly Thr Leu Val Thr Val Ser Ser
        115                 120

<210> SEQ ID NO 47
<211> LENGTH: 107
<212> TYPE: PRT
<213> ORGANISM: Artificial
<220> FEATURE:
<223> OTHER INFORMATION: an artificially synthesized sequence

<400> SEQUENCE: 47

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Asn Leu Glu Ile Lys
            100                 105

<210> SEQ ID NO 48
<211> LENGTH: 121
<212> TYPE: PRT

<213> ORGANISM: Artificial
<220> FEATURE:
<223> OTHER INFORMATION: an artificially synthesized sequence

<400> SEQUENCE: 48

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Lys Asp Tyr
                20                  25                  30

Thr Met His Trp Val Lys Gln Ser His Gly Lys Ser Leu Glu Trp Ile
            35                  40                  45

Gly Gly Ile Tyr Pro Asn Asn Gly Gly Ser Thr Tyr Asn Gln Asn Phe
        50                  55                  60

Lys Asp Lys Ala Thr Leu Thr Val Asp Lys Ser Ser Thr Ala Tyr
65                  70                  75                  80

Met Glu Phe Arg Ser Leu Thr Ser Glu Asp Ser Ala Val Tyr Tyr Cys
                85                  90                  95

Ala Arg Met Gly Tyr His Gly Pro His Leu Asp Phe Asp Val Trp Gly
            100                 105                 110

Ala Gly Thr Thr Val Thr Val Ser Pro
        115                 120

<210> SEQ ID NO 49
<211> LENGTH: 107
<212> TYPE: PRT
<213> ORGANISM: Artificial
<220> FEATURE:
<223> OTHER INFORMATION: an artificially synthesized sequence

<400> SEQUENCE: 49

Asp Ile Val Met Thr Gln Ser His Lys Phe Met Ser Thr Ser Leu Gly
1               5                   10                  15

Asp Arg Val Ser Ile Thr Cys Lys Ala Ser Gln Asp Val Gly Ala Ala
                20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
        50                  55                  60

Gly Gly Ser Gly Thr Asp Phe Thr Leu Thr Ile Ser Asn Val Gln Ser
65                  70                  75                  80

Glu Asp Leu Thr Asp Tyr Phe Cys Gln Gln Tyr Ile Asn Tyr Pro Leu
                85                  90                  95

Thr Phe Gly Gly Gly Thr Lys Leu Glu Ile Lys
            100                 105

<210> SEQ ID NO 50
<211> LENGTH: 118
<212> TYPE: PRT
<213> ORGANISM: Artificial
<220> FEATURE:
<223> OTHER INFORMATION: an artificially synthesized sequence

<400> SEQUENCE: 50

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Glu Trp Val
            35                  40                  45

```
Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Glu Asn Trp Gly Ser Tyr Phe Asp Leu Trp Gly Gln Gly Thr
            100                 105                 110

Thr Val Thr Val Ser Ser
            115
```

```
<210> SEQ ID NO 51
<211> LENGTH: 107
<212> TYPE: PRT
<213> ORGANISM: Artificial
<220> FEATURE:
<223> OTHER INFORMATION: an artificially synthesized sequence

<400> SEQUENCE: 51

Asp Ile Val Met Thr Gln Ser Pro Ser Thr Leu Ser Ala Ser Val Gly
 1               5                  10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Arg Ala Pro Lys Val Leu Ile
            35                  40                  45

Tyr Lys Ala Ser Thr Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Leu Glu Ile Lys
            100                 105
```

```
<210> SEQ ID NO 52
<211> LENGTH: 330
<212> TYPE: PRT
<213> ORGANISM: Artificial
<220> FEATURE:
<223> OTHER INFORMATION: an artificially synthesized sequence

<400> SEQUENCE: 52

Ala Lys Thr Thr Ala Pro Ser Val Tyr Pro Leu Ala Pro Val Cys Gly
 1               5                  10                  15

Asp Thr Thr Gly Ser Ser Val Thr Leu Gly Cys Leu Val Lys Gly Tyr
                20                  25                  30

Phe Pro Glu Pro Val Thr Leu Thr Trp Asn Ser Gly Ser Leu Ser Ser
            35                  40                  45

Gly Val His Thr Phe Pro Ala Val Leu Gln Ser Asp Leu Tyr Thr Leu
 50                  55                  60

Ser Ser Ser Val Thr Val Thr Ser Ser Thr Trp Pro Ser Gln Ser Ile
 65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Arg Arg Gly Pro Lys Val Phe Ile Phe Pro Pro
```

```
            115                 120                 125
Lys Ile Lys Asp Val Leu Met Ile Ser Leu Ser Pro Ile Val Thr Cys
        130                 135                 140

Val Val Val Asp Val Ser Glu Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 53
<211> LENGTH: 324
<212> TYPE: PRT
<213> ORGANISM: Artificial
<220> FEATURE:
<223> OTHER INFORMATION: an artificially synthesized sequence

<400> SEQUENCE: 53

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Lys
            100                 105                 110

Glu Val Ser Lys Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
```

```
        145                 150                 155                 160
Val His Thr Ala Gln Thr Gln Pro Arg Glu Glu Gln Phe Asn Ser Thr
                    165                 170                 175

Phe Arg Ser Val Ser Glu Leu Pro Ile Met His Gln Asp Trp Leu Asn
                180                 185                 190

Gly Lys Glu Phe Lys Cys Arg Val Asn Ser Ala Ala Phe Pro Ala Pro
            195                 200                 205

Ile Glu Lys Thr Ile Ser Lys Thr Lys Gly Arg Pro Lys Ala Pro Gln
        210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
                260                 265                 270

Pro Ile Met Asp Thr Asp Gly Ser Tyr Phe Val Tyr Ser Glu Leu Asn
            275                 280                 285

Val Gln Lys Ser Asn Trp Glu Ala Gly Asn Thr Phe Thr Cys Ser Val
        290                 295                 300

Leu His Glu Gly Leu His Asn His His Thr Glu Lys Ser Leu Ser His
305                 310                 315                 320

Ser Pro Gly Lys

<210> SEQ ID NO 54
<211> LENGTH: 324
<212> TYPE: PRT
<213> ORGANISM: Artificial
<220> FEATURE:
<223> OTHER INFORMATION: an artificially synthesized sequence

<400> SEQUENCE: 54

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
                20                  25                  30

Phe Pro Glu Pro Val Thr Val Thr Trp Asn Ser Gly Ser Leu Ser Ser
            35                  40                  45

Gly Val His Thr Phe Pro Ala Val Leu Gln Ser Asp Leu Tyr Thr Leu
        50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Lys
            100                 105                 110

Glu Val Ser Lys Val Phe Ile Phe Pro Pro Lys Pro Lys Asp Val Leu
        115                 120                 125

Thr Ile Thr Leu Thr Pro Lys Val Thr Cys Val Val Val Asp Ile Ser
        130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190
```

```
Gly Lys Glu Phe Lys Cys Arg Val Asn Ser Ala Ala Phe Pro Ala Pro
            195                 200                 205

Ile Glu Lys Thr Ile Ser Lys Thr Lys Gly Arg Pro Lys Ala Pro Gln
    210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Arg Thr Asp Gly Ser Tyr Phe Val Tyr Ser Lys Leu Asn
            275                 280                 285

Val Gln Lys Ser Asn Trp Glu Ala Gly Asn Thr Phe Thr Cys Ser Val
            290                 295                 300

Leu His Glu Gly Leu His Asn His His Thr Glu Lys Ser Leu Ser His
305                 310                 315                 320

Ser Pro Gly Lys

<210> SEQ ID NO 55
<211> LENGTH: 115
<212> TYPE: PRT
<213> ORGANISM: Artificial
<220> FEATURE:
<223> OTHER INFORMATION: an artificially synthesized sequence

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Ile Arg Gln Pro Pro Gly Gln Gly Leu Glu Trp Ile
        35                  40                  45

Gly Ala Ile Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115

<210> SEQ ID NO 56
<211> LENGTH: 112
<212> TYPE: PRT
<213> ORGANISM: Artificial
<220> FEATURE:
<223> OTHER INFORMATION: an artificially synthesized sequence

<400> SEQUENCE: 56

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Gln Gln Lys Pro Gly Gln Ala
        35                  40                  45
```

```
Pro Arg Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Asn
                 85                  90                  95

Thr His Val Pro Pro Thr Phe Gly Gln Gly Thr Lys Leu Glu Ile Lys
            100                 105                 110

<210> SEQ ID NO 57
<211> LENGTH: 450
<212> TYPE: PRT
<213> ORGANISM: Artificial
<220> FEATURE:
<223> OTHER INFORMATION: an artificially synthesized sequence

<400> SEQUENCE: 57

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Val His Ser
                 20                  25                  30

Asn Arg Asn Thr Tyr Leu His Trp Tyr Gln Gln Lys Pro Gly Gln Ala
             35                  40                  45

Pro Arg Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Asn
                 85                  90                  95

Thr His Val Pro Pro Thr Phe Gly Gln Gly Thr Lys Leu Glu Ile Lys
            100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Ala Ala Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Ala Ser Thr Tyr Arg Val Val Ser Val Leu Thr
    290                 295                 300
```

```
Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
            325                 330                 335

Lys Gly Gln Pro Arg Glu Pro Gln Val Cys Thr Leu Pro Pro Ser Arg
        340                 345                 350

Asp Glu Leu Thr Lys Asn Gln Val Ser Leu Trp Cys Leu Val Lys Gly
    355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
            405                 410                 415

Gly Asn Val Phe Ser Cys Ser Val Met His Glu Ala Leu His Asn Arg
        420                 425                 430

Tyr Thr Gln Lys Ser Leu Ser Leu Ser Pro His His His His His His
    435                 440                 445

His His
    450

<210> SEQ ID NO 58
<211> LENGTH: 441
<212> TYPE: PRT
<213> ORGANISM: Artificial
<220> FEATURE:
<223> OTHER INFORMATION: an artificially synthesized sequence

<400> SEQUENCE: 58

Gln Val Gln Leu Lys Glu Ala Gly Pro Gly Leu Val Gln Pro Thr Gln
1               5                   10                  15

Thr Leu Ser Leu Thr Cys Thr Val Ser Gly Phe Ser Leu Thr Ser Asp
            20                  25                  30

Gly Val His Trp Ile Arg Gln Pro Pro Gly Lys Gly Leu Glu Trp Met
        35                  40                  45

Gly Ile Ile Tyr Tyr Asp Gly Gly Thr Asp Tyr Asn Ser Ala Ile Lys
    50                  55                  60

Ser Arg Leu Ser Ile Ser Arg Asp Thr Ser Lys Ser Gln Val Phe Leu
65                  70                  75                  80

Lys Ile Asn Ser Leu Gln Thr Asp Asp Thr Ala Met Tyr Tyr Cys Ala
            85                  90                  95

Arg Ile His Phe Asp Tyr Trp Gly Gln Gly Val Met Val Thr Val Ser
        100                 105                 110

Ser Ala Ser Thr Lys Gly Pro Ser Val Phe Pro Leu Ala Pro Ser Ser
    115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
            165                 170                 175

Ser Leu Ser Ser Val Val Thr Val Pro Ser Ser Ser Leu Gly Thr Gln
        180                 185                 190

Thr Tyr Ile Cys Asn Val Asn His Lys Pro Ser Asn Thr Lys Val Asp
    195                 200                 205
```

```
Lys Lys Val Glu Pro Lys Ser Cys Asp Lys Thr His Thr Cys Pro Pro
            210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Ala Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Cys
            340                 345                 350

Glu Leu Thr Lys Asn Gln Val Ser Leu Ser Cys Ala Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Val Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro
        435                 440

<210> SEQ ID NO 59
<211> LENGTH: 222
<212> TYPE: PRT
<213> ORGANISM: Artificial
<220> FEATURE:
<223> OTHER INFORMATION: an artificially synthesized sequence

<400> SEQUENCE: 59

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Ile Arg Gln Pro Pro Gly Gln Gly Leu Glu Trp Ile
        35                  40                  45

Gly Ala Ile Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Arg Thr Val Ala Ala Pro Ser Val Phe Ile Phe Pro Pro
        115                 120                 125
```

```
Ser Asp Glu Gln Leu Lys Ser Gly Thr Ala Ser Val Val Cys Leu Leu
    130                 135                 140

Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
                165                 170                 175

Lys Asp Ser Thr Tyr Ser Leu Ser Ser Thr Leu Thr Leu Ser Lys Ala
                180                 185                 190

Asp Tyr Glu Lys His Lys Val Tyr Ala Cys Glu Val Thr His Gln Gly
            195                 200                 205

Leu Ser Ser Pro Val Thr Lys Ser Phe Asn Arg Gly Glu Cys
            210                 215                 220

<210> SEQ ID NO 60
<211> LENGTH: 213
<212> TYPE: PRT
<213> ORGANISM: Artificial
<220> FEATURE:
<223> OTHER INFORMATION: an artificially synthesized sequence

<400> SEQUENCE: 60

Asp Ile Val Leu Thr Gln Ser Pro Thr Thr Ile Ala Ala Ser Pro Gly
1               5                   10                  15

Glu Lys Val Thr Ile Thr Cys Arg Ala Ser Ser Ser Val Ser Tyr Met
                20                  25                  30

Tyr Trp Tyr Gln Gln Lys Ser Gly Ala Ser Pro Lys Leu Trp Ile Tyr
            35                  40                  45

Asp Thr Ser Lys Leu Ala Ser Gly Val Pro Asn Arg Phe Ser Gly Ser
        50                  55                  60

Gly Ser Gly Thr Ser Tyr Ser Leu Ala Leu Asn Thr Met Glu Thr Glu
65                  70                  75                  80

Asp Ala Ala Thr Tyr Tyr Cys Gln Gln Trp Ser Ser Thr Pro Leu Thr
                85                  90                  95

Phe Gly Ser Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
210
```